United States Patent
Finer et al.

(10) Patent No.: US 11,865,081 B2
(45) Date of Patent: Jan. 9, 2024

(54) ONCOLYTIC VIRAL DELIVERY OF THERAPEUTIC POLYPEPTIDES

(71) Applicant: Virogin Biotech Canada Ltd., Richmond (CA)

(72) Inventors: Mitchell H. Finer, Cambridge, MA (US); Luke Evnin, Cambridge, MA (US)

(73) Assignee: Virogin Biotech Canada Ltd., Richmond (CA)

( * ) Notice: Subject to any disclaimer, the term of this patent is extended or adjusted under 35 U.S.C. 154(b) by 422 days.

(21) Appl. No.: 16/958,371

(22) PCT Filed: Dec. 28, 2018

(86) PCT No.: PCT/US2018/067922
§ 371 (c)(1),
(2) Date: Jun. 26, 2020

(87) PCT Pub. No.: WO2019/133847
PCT Pub. Date: Jul. 4, 2019

(65) Prior Publication Data
US 2021/0085735 A1    Mar. 25, 2021

Related U.S. Application Data

(60) Provisional application No. 62/611,941, filed on Dec. 29, 2017.

(51) Int. Cl.
| | |
|---|---|
| *A61K 35/763* | (2015.01) |
| *A61P 35/00* | (2006.01) |
| *C07K 14/54* | (2006.01) |
| *C07K 16/28* | (2006.01) |
| *C12N 9/64* | (2006.01) |
| *A61K 9/00* | (2006.01) |

(52) U.S. Cl.
CPC ............ *A61K 35/763* (2013.01); *A61P 35/00* (2018.01); *C07K 14/5434* (2013.01); *C07K 14/5443* (2013.01); *C07K 16/2803* (2013.01); *C12N 9/6416* (2013.01); *A61K 9/0019* (2013.01); *C12Y 304/24035* (2013.01)

(58) Field of Classification Search
CPC .............. A61P 35/00; A61K 2039/505; C07K 16/2809; C07K 2317/31
USPC ............ 514/1, 2, 44; 530/300, 350; 435/6.1, 435/91.1, 471
See application file for complete search history.

(56) References Cited

U.S. PATENT DOCUMENTS

| | | |
|---|---|---|
| 4,476,116 A | 10/1984 | Anik |
| 5,059,538 A | 10/1991 | Nozaki et al. |
| 5,116,817 A | 5/1992 | Anik |
| 5,759,814 A | 6/1998 | Burke et al. |
| 5,804,413 A | 9/1998 | DeLuca |
| 5,811,097 A | 9/1998 | Allison et al. |
| 5,855,887 A | 1/1999 | Allison et al. |
| 5,898,031 A | 4/1999 | Crooke |
| 5,977,318 A | 11/1999 | Linsley et al. |
| 6,051,227 A | 4/2000 | Allison et al. |
| 6,071,742 A | 6/2000 | Tracy et al. |
| 6,107,094 A | 8/2000 | Crooke |
| 6,207,156 B1 | 3/2001 | Kuchroo et al. |
| 6,391,452 B1 | 5/2002 | Antonsen et al. |
| 6,455,677 B1 | 9/2002 | Park et al. |
| 6,469,155 B1 | 10/2002 | Fiume et al. |
| 6,506,559 B1 | 1/2003 | Fire et al. |
| 6,653,447 B1 | 11/2003 | Cosman et al. |
| 6,682,736 B1 | 1/2004 | Hanson et al. |
| 6,984,720 B1 | 1/2006 | Korman et al. |
| 7,056,704 B2 | 6/2006 | Tuschl et al. |
| 7,078,196 B2 | 7/2006 | Tuschl et al. |
| 7,109,003 B2 | 9/2006 | Hanson et al. |
| 7,132,281 B2 | 11/2006 | Hanson et al. |
| 7,282,564 B2 | 10/2007 | Mello et al. |
| 7,432,249 B2 | 10/2008 | Crooke |
| 7,432,250 B2 | 10/2008 | Crooke |
| 7,473,418 B2 | 1/2009 | Yu et al. |
| 7,514,252 B2 | 4/2009 | Chiocca et al. |
| 7,531,167 B2 | 5/2009 | Glorioso, III et al. |
| 7,538,095 B2 | 5/2009 | Fire et al. |
| 7,560,438 B2 | 7/2009 | Fire et al. |
| 8,129,167 B2 | 3/2012 | Cosman |
| 8,980,246 B2 | 3/2015 | Kirn |
| 9,157,071 B2 | 10/2015 | Capmadelli et al. |

(Continued)

FOREIGN PATENT DOCUMENTS

| | | |
|---|---|---|
| AU | 2012322999 B2 | 8/2017 |
| AU | 2017206231 B2 | 2/2019 |

(Continued)

OTHER PUBLICATIONS

Wang et al. (Cancer Immunology Research, vol. 2, No. 2, pp. 154-166 (2014)) (Year: 2014).*
Lee et al. (Clin. Cancer Res., vol. 15, No. 16, pp. 5126-5135 (2009)) (Year: 2009).*
Adamiak et al., "Herpes Simplex Virus Type 2 Glycoprotein G is Targeted by the Sulfated Oligo- and Polysaccharide Inhibitors of Virus Attachment to Cells," Journal of Virology, 81(24), 13424-13434 (2007).
Aghi et al., "Oncolytic herpes virus with defective ICP6 specifically replicates in quiescent cells with homozygous genetic mutations in p16.," Oncogene, 27: 4249-4254 (2008).

(Continued)

*Primary Examiner* — Jane J Zara
(74) *Attorney, Agent, or Firm* — COOLEY LLP

(57) ABSTRACT

Described herein are oncolytic viruses comprising one or more nucleic acids encoding an engager molecule. In some embodiments, the oncolytic viruses comprise one or more nucleic acids encoding an engager molecule and one or more therapeutic molecules. Pharmaceutical compositions containing the oncolytic virus and methods of treating cancer using the oncolytic viruses are further provided herein.

14 Claims, 31 Drawing Sheets

Specification includes a Sequence Listing.

(56) References Cited

U.S. PATENT DOCUMENTS

| | | |
|---|---|---|
| 9,226,977 B2 | 1/2016 | Kirn |
| 9,593,347 B2 | 3/2017 | Glorioso, III et al. |
| 9,919,062 B2 | 3/2018 | Kirn |
| 10,172,893 B2 | 1/2019 | Uchida et al. |
| 10,328,136 B2 | 6/2019 | Glorioso, III et al. |
| 10,576,115 B2 | 3/2020 | Uchida et al. |
| 10,604,574 B2 | 3/2020 | Evnin |
| 11,078,280 B2 | 8/2021 | Evnin et al. |
| 2001/0006640 A1 | 7/2001 | Grainger et al. |
| 2002/0031817 A1 | 3/2002 | Falduto et al. |
| 2002/0037575 A1 | 3/2002 | Speck |
| 2002/0039581 A1 | 4/2002 | Carreno et al. |
| 2002/0086014 A1 | 7/2002 | Korman et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2004/0265839 A1 | 12/2004 | Mello et al. |
| 2005/0100913 A1 | 5/2005 | Mello et al. |
| 2005/0201994 A1 | 9/2005 | Korman et al. |
| 2006/0024798 A1 | 2/2006 | Mello et al. |
| 2008/0044413 A1 | 2/2008 | Hammond et al. |
| 2008/0050342 A1 | 2/2008 | Fire et al. |
| 2008/0055443 A1 | 3/2008 | Okamoto et al. |
| 2008/0081373 A1 | 4/2008 | Fire et al. |
| 2008/0248576 A1 | 10/2008 | Fire et al. |
| 2009/0136452 A1 | 5/2009 | Zhou et al. |
| 2009/0291072 A1 | 11/2009 | Baeuerle et al. |
| 2010/0041737 A1 | 2/2010 | Naldini et al. |
| 2010/0104578 A1 | 4/2010 | Shafren |
| 2010/0233141 A1 | 9/2010 | Polach et al. |
| 2012/0034228 A1 | 2/2012 | Kufer et al. |
| 2013/0071430 A1 | 3/2013 | Nakamura et al. |
| 2013/0096186 A1 | 4/2013 | Glorioso, III et al. |
| 2013/0156808 A1 | 6/2013 | Jonjic |
| 2013/0287778 A1 | 10/2013 | Zugmaier et al. |
| 2014/0037584 A1 | 2/2014 | Stojdl |
| 2014/0193449 A1 | 7/2014 | Medin et al. |
| 2014/0294898 A1 | 10/2014 | Miller et al. |
| 2014/0370019 A1 | 12/2014 | Bruenker et al. |
| 2014/0377221 A1 | 12/2014 | Tufaro et al. |
| 2015/0017121 A1 | 1/2015 | Becher et al. |
| 2015/0165025 A1 | 6/2015 | Korman et al. |
| 2015/0231241 A1 | 8/2015 | Chang et al. |
| 2015/0299271 A1 | 10/2015 | Russell et al. |
| 2016/0000842 A1* | 1/2016 | Song ............... A61K 45/06 435/235.1 |
| 2016/0015749 A1 | 1/2016 | Gottschalk et al. |
| 2016/0168211 A1 | 6/2016 | Ahmed et al. |
| 2016/0250267 A1 | 9/2016 | Evnin |
| 2017/0000832 A1 | 1/2017 | Shafren et al. |
| 2017/0035819 A1 | 2/2017 | Uchida et al. |
| 2017/0107537 A1 | 4/2017 | Glorioso, III et al. |
| 2017/0137786 A1 | 5/2017 | Hemminki et al. |
| 2017/0157188 A1 | 6/2017 | Silvestre et al. |
| 2017/0189514 A1 | 7/2017 | Glorioso, III et al. |
| 2017/0216381 A1 | 8/2017 | Mohr et al. |
| 2017/0274025 A1 | 9/2017 | Uchida et al. |
| 2017/0274057 A1 | 9/2017 | Jonjic |
| 2018/0169241 A1 | 6/2018 | Cantwell |
| 2018/0169271 A1 | 6/2018 | Cantwell et al. |
| 2018/0215794 A1 | 8/2018 | Russell et al. |
| 2018/0311269 A1* | 11/2018 | Lobb ............... A61K 39/001113 |
| 2018/0318365 A1 | 11/2018 | Yeung et al. |
| 2018/0369304 A1 | 12/2018 | Brown et al. |
| 2019/0048082 A1 | 2/2019 | Evnin |
| 2019/0070233 A1 | 3/2019 | Yeung et al. |
| 2019/0201493 A1 | 7/2019 | Becher et al. |
| 2019/0262410 A1 | 8/2019 | Uchida et al. |
| 2021/0138007 A1 | 5/2021 | Uchida et al. |

FOREIGN PATENT DOCUMENTS

| | | |
|---|---|---|
| CA | 2476724 A1 | 9/2003 |
| CA | 2850575 A1 | 4/2013 |
| CN | 101104640 | 1/2008 |
| EP | 1591527 A1 | 11/2005 |
| EP | 2591796 A1 | 5/2013 |
| EP | 2766035 B1 | 3/2018 |
| EP | 3351261 A1 | 7/2018 |
| EP | 3441084 A1 | 2/2019 |
| JP | 2009-060907 A | 3/2009 |
| KR | 2003/0047667 A | 6/2003 |
| RU | 2536931 C2 | 12/2014 |
| WO | WO 1996/040915 A2 | 12/1996 |
| WO | WO 1997/020574 A1 | 6/1997 |
| WO | WO 1997/46570 A1 | 12/1997 |
| WO | WO 1998/42752 A1 | 10/1998 |
| WO | WO 1999/06583 A1 | 2/1999 |
| WO | WO 1999/32619 A1 | 7/1999 |
| WO | WO 1999/54440 A1 | 10/1999 |
| WO | WO 1999/57151 A2 | 11/1999 |
| WO | WO 2000/37504 A2 | 6/2000 |
| WO | WO 2001/014424 A2 | 3/2001 |
| WO | WO 2001/029058 A1 | 4/2001 |
| WO | WO 2001/068708 A2 | 9/2001 |
| WO | WO 2001/075164 A2 | 10/2001 |
| WO | WO 2003/086459 A1 | 10/2003 |
| WO | WO 2004/004771 A1 | 1/2004 |
| WO | WO 2004/035607 A2 | 4/2004 |
| WO | WO 2004/078928 A2 | 9/2004 |
| WO | WO 2004/081021 A2 | 9/2004 |
| WO | WO 2005/092380 A2 | 10/2005 |
| WO | WO 2006/017914 A1 | 2/2006 |
| WO | WO 2006/029219 A2 | 3/2006 |
| WO | WO 2006/133396 A2 | 12/2006 |
| WO | WO 2007/005874 A2 | 1/2007 |
| WO | WO 2007/077173 A1 | 7/2007 |
| WO | WO 2007/123737 A2 | 11/2007 |
| WO | WO 2007/137328 A1 | 12/2007 |
| WO | WO 2008/132601 A1 | 11/2008 |
| WO | WO 2008/141151 A2 | 11/2008 |
| WO | WO 2009/052623 A1 | 4/2009 |
| WO | WO 2009/100140 A1 | 8/2009 |
| WO | WO 2009/111892 A1 | 9/2009 |
| WO | WO 2009/144755 A1 | 12/2009 |
| WO | WO 2009/148488 A2 | 12/2009 |
| WO | WO 2009/150431 A1 | 12/2009 |
| WO | WO 2010/019570 A2 | 2/2010 |
| WO | WO 2010/036959 A2 | 4/2010 |
| WO | WO 2010/077634 A1 | 7/2010 |
| WO | WO 2010/089411 A2 | 8/2010 |
| WO | WO 2010/135242 A1 | 11/2010 |
| WO | WO 2011/127180 A1 | 10/2011 |
| WO | WO 2011/130749 A2 | 10/2011 |
| WO | WO 2011/159877 A2 | 12/2011 |
| WO | WO 2012/006181 A2 | 1/2012 |
| WO | WO 2012/020006 A2 | 2/2012 |
| WO | WO 2012/120125 A1 | 9/2012 |
| WO | WO 2012/145493 A1 | 10/2012 |
| WO | WO 2013/006490 A2 | 1/2013 |
| WO | WO 2013/053775 A1 | 4/2013 |
| WO | WO 2013/056716 A1 | 4/2013 |
| WO | WO 2013/079174 A1 | 6/2013 |
| WO | WO 2013/181634 A2 | 12/2013 |
| WO | WO 2014/047350 A1 | 3/2014 |
| WO | WO 2014/055442 A2 | 4/2014 |
| WO | WO 2014/138306 A1 | 9/2014 |
| WO | WO 2014/138314 A1 | 9/2014 |
| WO | WO 2015/066042 A1 | 5/2015 |
| WO | WO-2016008976 A1 | 1/2016 |
| WO | WO 2016/055432 A2 | 4/2016 |
| WO | WO 2016/115274 A8 | 7/2016 |
| WO | WO 2017/118864 A1 | 7/2017 |
| WO | WO 2017/118865 A1 | 7/2017 |
| WO | WO 2017/118866 A1 | 7/2017 |
| WO | WO 2017/118867 A1 | 7/2017 |
| WO | WO-2017118866 A1 * | 7/2017 ............ A61K 35/76 |
| WO | WO 2017/132552 A1 | 8/2017 |
| WO | WO 2017/156349 A1 | 9/2017 |
| WO | WO-2017197525 A1 | 11/2017 |
| WO | WO 2018/006005 A1 | 1/2018 |
| WO | WO 2018/026872 A1 | 2/2018 |
| WO | WO 2018/027316 A1 | 2/2018 |

(56) References Cited

FOREIGN PATENT DOCUMENTS

| WO | WO 2018/049248 A1 | 3/2018 | |
|----|----|----|----|
| WO | WO 2018/049261 A1 | 3/2018 | |
| WO | WO-2018041838 A1 * | 3/2018 | ........... A61K 35/761 |
| WO | WO 2018/085461 A1 | 5/2018 | |
| WO | WO 2018/118819 A2 | 6/2018 | |
| WO | WO 2018/118967 A1 | 6/2018 | |
| WO | WO 2018/127713 A1 | 7/2018 | |
| WO | WO 2019/133847 A1 | 7/2019 | |

OTHER PUBLICATIONS

Akimoto et al., "A new delivery system for 5-fluorouracil using prodrug and converting enzyme," J. Ophthalmol., 86(5): 581-586 (2002).

Anderson et al., "Pseudotyping of Glycoprotein D-Deficient Herpes Simplex Virus Type 1 with Vesicular Stomatitis Virus Glycoprotein G Enable Mutant Virus Attachment and Entry," Journal of Virology, 74(5): 2481-2487 (Mar. 2000).

Asano et al., "Humanization of the Bispecific Epidermal Growth Factor Receptor X CD3 Diabody and Its Efficacy as a Potential Clinical Reagent," Clin. Cancer Res., 12(13): 4036-4042 (Jul. 1, 2006).

Assi et al., "Gene Therapy for Brain Tumors: Basic Developments and Clinical Implementation," Neurosci. Lett. 527(2): 71-77 (2012).

Bae et al., "Fibroblast activation protein a identifies mesenchymal stromal cells from human bone marrow," British Journal of Haematology. 2008;142(5): 827-830.

Baek et al., "Bispecific Adapter-Mediated Retargeting of a Receptor-Restricted HSV-1 Vector to CEA-Bearing Tumor Cells," Molecular Therapy, 19(3): 507-514 (Mar. 2011).

Bennett et al., "Comparison of safety, delivery, and efficacy of two oncolytic herpes viruses (G207 and NV1020) for peritoneal cancer," Cancer Gene Therapy, 9: 935-945 (2002).

Broberg et al., "Immune Response to Herpes Simplex Virus and y134.5 Deleted HSV Vectors ," Current Gene Therapy, 5: 523-530 (2005).

Bruhl, "Depletion of CCR5-expressing cells with bispecific antibodies and chemokine toxins: a new strategy in the treatment of chronic inflammatory diseases and HIV." J. Immunol., (2001), 166, 2420-2426.

Busek et al., "Co-expression of the homologous proteases fibroblast activation protein and dipeptidyl peptidase-IV in the adult human Langerhans islets," Histochemistry and Cell Biology, 2015, 143: 497-504.

Busek et al., "Targeting fibroblast activation protein in cancer—Prospects and caveats," Frontiers in Bioscience, 2018, 23: 1933-1968.

Bzik et al., "Nucleotide Sequence of a Region of the Herpes Simplex Virus Type 1 gB Glycoprotein Gene: Mutations Affecting Rate of Virus Entry and Cell Fusion," Virology, 37: 185-190 (1984).

Cai et al., "Linker-Insertion Nonsense and Restriction-Site Deletion Mutations of the GB Glycoprotein Gene of Herpes Simplex Virus Type 1," Journal of Virology, 61(3): 714-721 (Mar. 1987).

Camacho et al., "Phase 1 clinical trial of anti-CTLA4 human monoclonal antibody CP-675,206 in patients (pts) with advanced solid malignancies," J. Clin. Oncol., 22(145): Abstract No. 2505 (2004) (antibody CP-675206), 4 pages.

Campadelli-Fiume et al., "Rethinking herpes simplex virus: the way to oncolytic agents," Rev. Med. Viral., 21: 213-226 (2011).

Cao et al., "A functional study of miR-124 in the developing neural tube," Genes & Development, 21: 531-536 (2007).

Cattaneo et al., "Reprogrammed viruses as cancer therapeutics: targeted, armed and shielded" Nature Reviews. Microbiology, 6(7): 529-540 (2008).

Cawood et al., "Use of Tissue-Specific MicroRNA to Control Pathology of Wild-Type Adenovirus without Attenuation of Its Ability to Kill Cancer Cells," PloS Pathogens, 5(5): 1-10 (May 2009).

Cheadle et al., "Cloning and expression of the variable regions of mouse myeloma protein MOPC315 in E. coli: recovery of active FV fragments.," Mol Immunol (1992) 29(1): 21-30.

Cocchi et al., "The Ectodomain of a Novel Member of the Immunoglobulin Subfamily Related to the Poliovirus Receptor Has the Attributes of a Bona Fide Receptor for Herpes Simplex Virus Types 1 and 2 in Human Cells," Journal of Virology, 72(12): 9992-10002 (Dec. 1998).

Cocchi et al., "The Herpes Simplex Virus JMP Mutant Enters Receptor-Negative J Cells through a Novel Pathway Independent of the Known Receptors nectin1, HveA, and nectin2," Journal of Virology, 78(9): 4720-4729 (May 2004).

Conner et al., "A strategy for systemic delivery of the oncolytic herpes virus HSV1716: redirected tropism by antibody-binding sites incorporated on the virion surface as a glycoprotein D fusion protein," Gene Therapy, 15: 1579-1592 (2008).

Connolly et al., "Potential Nectin-1 Binding Site on Herpes Simplex Virus Glycoprotein D," Journal of Virology, 79(2): 1282-1295 (Jan. 2005).

Connolly et al., Structure-Based Analysis of the Herpes Simplex Virus Glycoprotein D Binding Site Present on Herpevirus Entry Mediator HveA (HVEM), Journal of Virology 76(21):10894-10904 (Nov. 2002).

Currier et al., "Efficacy and Safety of the Oncolytic Herpes Simplex Virus rRp450 Alone and Combined With Cyclophosphamide," Molecular Therapy, 16(5): 879-885 (2008).

Dall'Acqua et al., "Contribution of domain interface residues to the stability of antibody CH3 domain homodimers," (Biochem. (1998) 37:9266-9273.

De Gruijl et al., "Arming oncolytic viruses to leverage antitumor immunity," Expert Opinion on Biological Therapy, (2015) 15:7, 959-971.

Deluca et al., "Nucleotide Sequences of Herpes Simplex Virus Type 1 (HSV-1) Affecting Virus Entry, Cell Fusion, and Production of Glycoprotein gB (VP7)," Virology, 122: 411-423 (1982).

Delwar et al., "Tumour-specific triple-regulated oncolytic herpes virus to target glioma," Oncotarget, 2016, vol. 7, No. 19, pp. 28658-28669.

Desai et al., "Incorporation of the Green Fluorescent Protein into the Herpes Simplex Virus Type 1 Capsid," Journal of Virology, 72(9): 7563-7568 (Sep. 1998).

Dmitrieva et al., "Chondroitinase ABC I-mediated spread and antitumor efficacy," Clin. Cancer Res., 17(6): 1362-1372 (2011).

Dolznig et al., "Characterization of cancer stroma markers: in silico analysis of an mRNA expression database for fibroblast activation protein and endosialin," Cancer Immunity, Aug. 2005, 5:10, 9 pages.

Doronina et al., "Site-specific release of nascent chains from ribosomes at a sense codon," Molecular and Cellular Biology, 28(13): 4227-4239 (2008).

Edge et al., "A let-7 MicroRNA-sensitive Vesicular Stomatitis Virus Demonstrates Tumor-specific Replication," Molecular Therapy, 16(8): 1437-1443 (Aug. 2008).

Eisenring et al., "IL-12 initiates tumor rejection via lymphoid tissue-inducer cells bearing the natural cytotoxicity receptor NKp46," Nat Immunol., 2010;11(11):1030-8.

Esko et al., "Animal Cell Mutants Defective in Glycosaminoglycan biosynthesis," Proc. Natl. Acad. Sci. USA, 82: 3197-3201 (May 1985).

European Patent Office, European Search Report in European U.S. Appl. No. 17/155,129 (dated May 30, 2017), 8 pages.

Fecci et al., "Systemic CTLA-4 Blockade Ameliorates Glioma-Induced Changes to the CD4+ T Cell Compartment without Affecting Regulatory T-Cell Function," Clin Cancer Res., 2007;13(7):2158-2167.

Frampton et al., "Equine Herpesvirus 1 Enters Cells by Two Different Pathways, and Infection Requires the Activation of the Cellular Kinase ROCK1," Journal of Virology, 81(20): 10879-10889 (2007).

Friedman et al., "Herpes Simplex Virus Oncolytic Therapy for Pediatric Malignancies "Molecular Therapy, 17(7): 1125-1135 (2009).

(56) References Cited

OTHER PUBLICATIONS

Fu et al., "Construction of an oncolytic herpes simplex virus that precisely targets hepatocellular carcinoma cells," Mol. Ther 20:339-46 (2012).
Fujioka et al., "Interleukin-18 protects mice against acute herpes simplex virus type 1 infection," Journal of Virology, 73(3): 2401-2409 (1999).
Fuller et al., "Anti-glycoprotein D Antibodies That Permit Adsorption but Block Infection by Herpes Simplex Virus 1 Prevent Virion-cell Fusion at the Cell Surface," Proc. Natl. Acad. Sci. USA, 84: 5454-5458 (Aug. 1987).
Fuller et al., "Neutralizing Antibodies Specific for Glycoprotein H of Herpes Simplex Virus Permit Viral Attachment to Cells but Prevent Penetration," Journal of Virology, 63(8): 3435-3443 (Aug. 1989).
Garin-Chesa et al., "Cell surface glycoprotein of reactive stromal fibroblasts as a potential antibody target in human epithelial cancers," PNAS, Sep. 1990, 87: 7235-7239.
Gaur et al., "Characterization of microRNA expression levels and their biological correlates in human cancer cell lines," Cancer Res., 67(6): 2456-2468 (2007).
GenBank® Accession No. NM_004431, Apr. 5, 2010, 4 pages.
GenBank® Accession No. NM_004448.2, 7, Feb. 26, 2018 pages.
GenBank® Accession No. NP_004422, Jan. 22, 2018, 5 pages.
GenBank® Accession No. NP_004439, Dec. 18, 2017, 32 pages.
Geraghty et al., "Entry of Alphaherpesviruses Mediated by Poliovirus Receptor-Related Protein 1 and Poliovirus Receptor," Science, 280: 1618-1620 (Jun. 5, 1998).
Gierasch et al., "Construction and Characterization of Bacterial Artificial Chromosomes Containing HSV-1 Strains 17 and KOS," Journal of Virological Methods, 135: 197-206 (2006).
Goscinski et al., "FAP-α and uPA Show Different Expression Patterns in Premalignant and Malignant Esophageal Lesions," Ultrastruct Pathol., (2008) 32:89-96.
Grandi et al., Design and application of oncolytic HSV vectors for glioblastoma therapy, Golemis; Protein-Protein Interactions: A Molecular Cloning Manual; Cold Spring Harbor Laboratory Press, 2002 Expert Rev. Neurother., 9(4): 505-517 (2009).
Grossman et al., "Survival of Patients with Newly Diagnosed Glioblastoma Treated with Radiation and Temozolomide in Research Studies in the United States," Clinical Cancer Research, 16: 2443-2449 (2010).
He et al., "Targeting Glioblastoma Stem Cells: Cell Surface Markers," Current Medicinal Chemistry, 19: 6050-6055 (2012).
Highlander et al., "Identification of mar Mutations in Herpes Simplex Virus Type 1 Glycoprotein B Which Alter Antigenic Structure and Function in Virus Penetration," Journal of Virology, 63(2): 730-738 (Feb. 1989).
Hodi et al., "Improved Survival with Ipilimumab in Patients with Metastatic Melanoma," The New England Journal of Medicine, 363(8): 711-723 (2010).
Hofheinz et al., "Stromal Antigen Targeting by a Humanised Monoclonal Antibody: An Early Phase II Trial of Sibrotuzumab in Patients with Metastatic Colorectal Cancer," Onkologie, 2003, 26(1):44-48.
Hong et al. "Ectopic matrix metalloproteinase 9 expression in human brain tumor cells enhances oncolytic HSV vector infection," Gene Therapy 17:1200-1205 (2010).
Hurwitz et al., "CTLA-4 blockade synergizes with tumor-derived granulocyte-macrophage colony-stimulating factor for treatment of an experimental mammary carcinoma," Proc. Natl. Acad. Sci. USA, 95(17): 10067-10071 (1998).
Iorio et al., "microRNA involvement in human cancer," Carcinogenesis, 33(6): 1126-1133 (2012).
Ishida et al., "Enhanced cytotoxicity with a novel system combining the paclitaxel-2'-ethylcarbonate prodrug and an HSV amplicon with an attenuated replication-competent virus, HF10 as a helper virus," Cancer Letters, 288: 17-27 (2010).
Jackson et al., "Insertion Mutations in Herpes Simplex Virus 1 Glycoprotein H Reduce Cell Surface Expression, Slow the Rate of Cell Fusion, or Abrogate Functions in Cell Fusion and Viral Entry," Journal of Virology, 84(4): 2038-2046 (Feb. 2010).
Kaji et al., "Virus-free induction of pluripotency and subsequent excision of reprogramming factors," Nature, 458(7239): 771-775 (2009).
Kambara et al., "An oncolytic HSV-1 mutant expressing ICP34.5 under control of a nestin promoter increases survival of animals even when symptomatic from a brain tumor," Cancer Res., 65(7): 2832-2839 (2005).
Karpowicz et al., "E-Cadherin Regulates Neural Stem Cell Self-Renewal," The Journal of Neuroscience, 29(121: 3885-3896 (2009).
Karsy et al., "Current Progress on Understanding MicroRNAs in Glioblastoma Multiforme.," Genes & Cancer, 3(1): 3-15 (2012).
Katoh et al., "Hedgehog signaling, epithelial-to-mesenchymal transition and miRNA (review)," International Journal of Molecular Medicine, 22: 271-275 (2008).
Kelly et al., "Attenuation of Vesicular Stomatitis Virus Encephalitis through MicroRNA Targeting," Journal of Virology, Feb. 2010, vol. 84, No. 3, pp. 1550-1562.
Kelly et al., "Engineering microRNA responsiveness to decrease virus pathogenicity," Nature Medicine, Nov. 2008, vol. 14, No. 11, pp. 1277-1283.
Kosovsky et al., "Herpes Simplex Virus 1 (HSV-1) Strain HSZP Glycoprotein B Gene: Comparison of Mutations among Strains Differing in Virulence," Virus Genes, 20(1): 27-33 (2000).
Krisky et al., "Rapid method for construction of recombinant HSV gene transfer vectors," Gene Therapy, 4: 1120-1125 (1997).
Krisky et al., "Deletion of multiple immediate early genes from herpes simplex virus reduces cytotoxicity and permits long-term gene expression in neurons," Gene Therapy 5:1593-1603 (1998).
Krummenacher et al., "Effects of Herpes Simplex Virus on Structure and Function of Nectin-1/HveC," Journal of Virology, 76(5): 2424-2433 (Mar. 2002).
Kuan et al., "Increased Binding Affinity Enhances Targeting of Glioma Xenografts by EGFRVIII-Specific scFv," Int. J. Cancer, 88: 962-969 (2000).
Kumar et al., "Impaired microRNA processing enhances cellular transformation and tumorigenesis," Nature Genetics, 39(5): 673-677 (2007).
Kwon et al., "Soluble V Domain of Nectin-1/HveC Enables Entry of Herpes Simplex Virus Type 1 (HSV-1) into HSY-Resistant Cells by Binding to Viral Glycoprotein D," Journal of Virology, 80(1): 138-148 (Jan. 2006).
Lakins et al., "Cancer-associated fibroblasts induce antigen-specific deletion of CD8 + T Cells to protect tumour cells," Nature Communications, 2018, 9(1):948, 9 pages.
Lavon et al., "Gliomas display a microRNA expression profile reminiscent of neural precursor cells," Neuro-Oncology, 12(5): 422-433 (2010).
Lee et al., "MicroRNA Regulation of Oncolytic Herpes Simplex Virus-1 for Selective Killing of Prostate Cancer Cells," Clin. Cancer Res., 15(16): 5126-5135 (2009).
Lee et al., "Transcriptional and Translational Dual-regulated Oncolytic Herpes Simplex Virus Type 1 for Targeting Prostate Tumors," Molecular Therapy, 2010; 18(5):929-935.
Ll et al., "Identification of Functional Domains in Herpes Simplex Virus 2 Glycoprotein B," Journal of Virology, 3792-3800 (Apr. 2006).
Ll et al., "MicroRNA-145 regulates oncolytic herpes simplex virus-1 for selective killing of human non-small cell lung cancer cells", Virology Journal 10(1): 241 (2013), 9 pages.
Ligas et al., "A Herpes Simplex Virus Mutant in Which Glycoprotein D Sequences Are Replaced by β-Galactosidase Sequences Binds to but Is Unable To Penetrate into Cells," Journal of Virology, 62(5): 1486-1494 (May 1988).
Lo et al., "Fibroblast activation protein augments progression and metastasis of pancreatic ductal adenocarcinoma," JCI Insight, 2017, 2(19):e92232, 11 pages.
Loffler, "A recombinant bispecific single-chain antibody, CD19 x CD3, induces rapid and high lymphoma-directed cytotoxicity by unstimulated T lymphocytes," Blood, 95(6)2098-2103 (2000).

(56) References Cited

OTHER PUBLICATIONS

Ma et al., "A novel HBV antisense RNA gene delivery system targeting hepatocellular carcinoma," World J Gastroenterol 9:463-467 (2003).
MacDonald et al., "Genome Sequence of Herpes Simplex Virus 1 Strain KOS," Journal of Virology, 86(11): 6371-6372 (Jun. 2012).
Mack, "A small bispecific antibody construct expressed as a functional single-chain molecule with high tumor cell cytotoxicity," PNAS 92:7021-7025 (1995).
Mack, "Biologic properties of a bispecific single-chain antibody directed against 17-1A (EpCAM) and CD3: tumor cell-dependent T cell stimulation and cytotoxic activity," J. Immunol. (1997), 158, 3965-3970.
Mammoto et al., "Role of Collagen Matrix in Tumor Angiogenesis and Glioblastoma Multiforme Progression," The American Journal of Pathology, 183(4): 1293-1305 (2013).
Manickan et al., "Genetic immunization against herpes simplex virus. Protection is mediated by CD4+ T lymphocytes.," The Journal of Immunology, 155: 259-265 (1995).
Markert et al., "Conditionally replicating herpes simplex virus mutant, G207 for the treatment of malignant glioma: results of a phase I trial.," Gene Therapy, 7: 867-874 (2000).
Mazzacurati et al., "Use of miRNA response sequences to block off-target replication and increase the safety of an unattenuated, glioblastoma-targeted oncolytic HSV.," Molecular Therapy, 23(1): 99-107 (2015).
McKee et al., "Degradation of fibrillar collagen in a human melanoma xenograft improves the efficacy of an oncolytic herpes simplex virus vector."Cancer Research, 66(5): 2509-2513 (2006).
Menotti et al., "Construction of a Fully Retargeted Herpes Simplex Virus 1 Recombinant Capable of Entering Cells Solely via Human Epidermal Growth Factor Receptor 2," Journal of Virology, 82(20): 10153-10161 (Oct. 2008).
Menotti, L., et al., "Inhibition of human tumor growth in mice by an oncolytic herpes simplex virus designed to target solely HER-2-positive cells," PNAS 106:9039-9044 (2009).
Miao et al., "EphA2 promotes infiltrative invasion of glioma stem cells in vivo through cross-talk with Akt and regulates stem cell properties," Oncogene, 34(5): 558-567 (2015).
Miest et al., "New viruses for cancer therapy: meeting clinical needs," Nature Reviews. Microbiology, 12(1): 23-34 (2014).
Miller et al., "Development of a Syngenic Murine 816 Cell Line-Derived Melanoma Susceptible to Destruction by Neuroattenuated HSV-1," Molecular Therapy, 3(2): 160-168 (Feb. 2001).
Milne et al., "Glycoprotein D Receptor-Dependent, Low-pH-Independent Endocytic Entry of Herpes Simplex Virus Type 1," Journal of Virology, 79(11): 6655-6663 (Jun. 2005).
Mohyeldin et al., "Gene and viral therapy for glioblastoma: a review of clinical trials and future directions," The Cancer Journal, 18(1): 82-88 (2012).
Mok et al., "Matrix Metalloproteinases-1 and -8 Improve the Distribution and Efficacy of an Oncolytic Virus," Cancer Res., 67(22): 10664-10668 (2007).
Mokyr et al., Realization of the Therapeutic Potential of CTLA-4 Blockade in Low-Dose Chemotherapy-treated Tumor-bearing Mice[1], Cancer Res., 58:5301-5304 (1998).
Montgomery et al., "Herpes Simplex Virus-1 Entry into Cells Mediated by a Novel Member of the TNF/NGF Receptor Family," Cell 87:427-436 (1996).
Muggeridge, "Characterization of Cell-cell Fusion Mediated by Herpes Simplex Virus 2 glycoproteins gB, gD, gH and gL in Transfected Cells," Journal of General Virology, 81: 2017-2027 (2000).
Mullokandov et al. "High-throughput assessment of microRNA activity and function using microRNA sensor and decoy libraries," Nature methods 9:840-846 (2012).
Nakano et al., "Mechanism of HSV infection through soluble adapter-mediated virus bridging to the EGF receptor," Virology, 413: 12-18 (2011).
Navaratnarajah et al., "Targeted Entry of Enveloped Viruses: Measles and Herpes Simplex Virus," Curr. Opin. Viral., 2(1): 43-49 (2012).
Navid et al., "Anti-GD2 Antibody Therapy for GD2-expressing Tumors," Curr Cancer Drug Targets. 2010; 10(2):200-209.
NCBI, "Chain A, Glycoprotein B From Herpes Simplex Virus Type 1" Database Entrez-Nucleotide, Accession No. 4L1R_A (Jun. 26, 2013). Retrieved on Mar. 5, 2018, 5 pages.
NCBI, "ephrin type-A receptor 2 isoform 2 [*Homo sapiens*]," NCBI Reference Sequence: NP_001316019.1 (Sep. 12, 2020). 3 pages.
NCBI, "glycoprotein B [Human herpesvirus 1]," Database Entrez-Nucleotide, Accession No. AAA91805 (Mar. 8, 1996). Retrieved on Mar. 5, 2018, 1 page.
NCBI, "glycoprotein B [Human herpesvirus 1]," Database Entrez-Nucleotide, Accession No. AAF70301 (May 16, 2000). Retrieved on Mar. 5, 2018, 1 page.
NCBI, "glycoprotein B [Human herpesvirus 2]," Database Entrez-Nucleotide, Accession No. ABU45427 (Nov. 29, 2007). Retrieved on Mar. 5, 2018, 2 pages.
NCBI, "Herpes Simplex Virus Type 1 Gene for Glycoprotein gH," Database GenBank Accession No. X03896 (Jul. 26, 2016). Retrieved on Mar. 5, 2018, 3 pages.
NCBI, "*Homo sapiens* EPH receptor A2 (EPHA2), transcript variant 2, mRNA," NCBI Reference Sequence: NM_001329090.1 (May 12, 2019). 5 pages.
NCBI, "*Homo sapiens* erb-b2 receptor tyrosine kinase 2 (ERBB2), transcript variant 2, mRNA," NCBI Reference Sequence: NM_001005862.2 (May 18, 2020). 6 pages.
NCBI, "*Homo sapiens* erb-b2 receptor tyrosine kinase 2 (ERBB2), transcript variant 3, mRNA," NCBI Reference Sequence: NM_001289936.1 (May 18, 2020). 7 pages.
NCBI, "*Homo sapiens* erb-b2 receptor tyrosine kinase 2 (ERBB2), transcript variant 4, mRNA," NCBI Reference Sequence: NM_001289937.2 (Sep. 27, 2020). 8 pages.
NCBI, "*Homo sapiens* erb-b2 receptor tyrosine kinase 2 (ERBB2), transcript variant 5, mRNA," NCBI Reference Sequence: NM_001289938.2 (Sep. 27, 2020). 5 pages.
NCBI, "*Homo sapiens* fibroblast activation protein alpha (FAP), transcript variant 1, mRNA," NCBI Reference Sequence: NM_004460.5 (Sep. 7, 2020). 6 pages.
NCBI, "*Homo sapiens* fibroblast activation protein alpha (FAP), transcript variant 2, mRNA," NCBI Reference Sequence: NM_001291807.2 (May 2, 2019). 5 pages.
NCBI, "Human Herpesvirus 1 Complete Genome," Database GenBank Accession No. X14112 (Oct. 23, 2008). Retrieved on Mar. 5, 2018, 70 pages.
NCBI, "Human Herpesvirus 1 Strain KOS Glycoprotein B Gene," Database GenBank Accession No. AF311740 (Jan. 24, 2001). Retrieved on Mar. 5, 2018, 2 pages.
NCBI, "prolyl endopeptidase FAP isoform 1 [*Homo sapiens*]," NCBI Reference Sequence: NP_004451.2 (Sep. 7, 2020). 4 pages.
NCBI, "prolyl endopeptidase FAP isoform 2 [*Homo sapiens*]," NCBI Reference Sequence: NP_001278736.1 (Sep. 13, 2020). 3 pages.
NCBI, "receptor tyrosine-protein kinase erbB-2 isoform b [*Homo sapiens*]," NCBI Reference Sequence: NP_001005862.1 (Sep. 27, 2020). 3 pages.
NCBI, "receptor tyrosine-protein kinase erbB-2 isoform c [*Homo sapiens*]," NCBI Reference Sequence: NP_001276865.1 (Sep. 27, 2020). 3 pages.
NCBI, "receptor tyrosine-protein kinase erbB-2 isoform d precursor [*Homo sapiens*]," NCBI Reference Sequence: NP_001276866.1 (Sep. 27, 2020). 4 pages.
NCBI, "receptor tyrosine-protein kinase erbB-2 isoform e [*Homo sapiens*]," NCBI Reference Sequence: NP_001276867.1 (Sep. 27, 2020). 3 pages.
Nduom et al., "Glioblastoma Cancer Stem-like Cells—Implications for Pathogenesis and Treatment," Cancer., 18(1): 100-106 (2012).
Nicola and Straus, "Cellular and Viral Requirements for Rapid Endocytic Entry of Herpes Simplex Virus," Journal of Virology, 78(14): 7508-7517 (Jul. 2004).
Nicola et al., "Roles for Endocytosis and Low pH in Herpes Simplex Virus Entry into HeLa and Chinese Hamster Ovary Cells," Journal of Virology, 77(9): 5324-5332 (May 2003).

(56) References Cited

OTHER PUBLICATIONS

Niedermeyer et al., "Expression of the fibroblast activation protein during mouse embryo development," Intl. J. Dev. Biol. 2001, 45(2): 445-447.
O'Day et al., "Efficacy and safety of ipilimumab monotherapy in patients with pretreated advanced melanoma: a multicenter single-arm phase II study," Annals of Oncology, 2010 21:1712-1717.
Ocana et al., "A new regulatory loop in cancer-cell invasion," Molecular Biology Organization, 9(6): 521-522 (2008).
Omidfar et al., "Production of a Novel Camel Single-Domain Antibody Specific for the Type III Mutant EGFR," Tumor Biology, 25: 296-305 (2004).
Omidfar et al., "Production and Characterization of a New Antibody Specific for the Mutant EGF Receptor, EGFRvIII, in Camelus bactrianus," Tumor Biology, 25:179-187 (2004).
Opalinska et al., "Nucleic-Acid Therapeutics: Basic Principles and Recent Applications," Nature Reviews, 1: 503-514 (2002).
Parker et al., "Oncolytic viral therapy of malignant glioma," Neurotherapeutics: The Journal of the American Society for Experimental NeuroTherapeutics, 6: 558-569 (2009).
Patriarca et al., "Epithelial cell adhesion molecule expression (CD326) in cancer: a short review," Cancer Treatment Reviews, 38: 68-75 (2012).
Payne et al., "The pathobiology of collagens in glioma," Mol. Cancer Res., 11: 1129-1140 (2013).
Pertel et al., "Cell Fusion Induced by Herpes Simplex Virus Glycoproteins gB, gD, and gH-gL Requires a gD Receptor but Not Necessarily Heparan Sulfate," Virology, 279: 313-324 (2001).
Ploessl et al., "Dinutuximab: An Anti-GD2 Monoclonal Antibody for High-Risk Neuroblastoma," Ann Pharmacother. 2016; 50(5): 416-422.
Rauch et al., "Mutations in Herpes Simplex Virus Glycoprotein D Distinguish Entry of Free Virus from Cell-Cell Spread," Journal of Virology, 74(24): 11437-11446 (Dec. 2000).
Riddick et al., "Integration and analysis of genome-scale data from gliomas," Nature Reviews—Neurology, 7: 439-450 (2011).
Saharkhiz-Langroodi and Holland, Identification of the Fusion-from-without Determinants of Herpes Simplex Virus Type 1 Glycoprotein B, Virology 227, 153-159 (1997).
Santos et al., "Targeting fibroblast activation protein inhibits tumor stromagenesis and growth in mice," J Clin Invest (2009) 119(12): 3613-3625.
Schaffer et al., "Temperature-Sensitive Mutants of Herpes Simplex Virus Type 1: Isolation, Complementation and Partial Characterization," Virology, 52: 57-71 (1973).
Scott et al., "A Phase I Dose-Escalation Study of Sibrotuzumab in Patients with Advanced or Metastatic Fibroblast Activation Protein-positive Cancer," Clin Cancer Res., May 2003, 9(5): 1639-1647.
Sethi et al., "Protection of Mice from Fatal Herpes Simplex Virus Type 1 Infection by Adoptive Transfer of Cloned Virus-specific and H-2-restricted Cytotoxic T Lymphocytes," J. Gen. Viral., 64: 443-447 (1983).
Shi et al., "hsa-mir-181a and hsa-mir-181b function as tumor suppressors in human glioma cells," Brain Research, 1236: 185-193 (2008).
Shogan et al., "Virucidal Activity of a GT-Rich Oligonucleotide against Herpes Simplex Virus Mediated by Glycoprotein B," Journal of Virology, 80(10): 4740-4747 (May 2006).
Silber et al., "miR-124 and miR-137 inhibit proliferation of glioblastoma multiforme cells and induce differentiation of brain tumor stem cells," BMC Medicine, 6(14): 1-17 (2008).
Simmons et al., "Local secretion of anti-CTLA-4 enhances the therapeutic efficacy of a cancer immunotherapy with reduced evidence of systemic autoimmunity," Cancer Immunol Immunother., 2008;57(8):1263-1270.
Slavuljica et al., "Recombinant mouse cytomegalovirus expressing a ligand for the NKG2d receptor is attenuated and has improved vaccine properties," J. Clin. Invest., 120(12): 4532-4545 (Dec. 2010).
Smith, "Relationship Between the Envelope and the Infectivity of Herpes Simplex Virus," Herpes Virus Envelopes, 814-816 (1964).
Stamenkovic et al., "Extracellular matrix remodelling: the role of matrix metalloproteinases," Journal of Pathology, 2003, 200: 448-464.
Struyf et al., "Mutations in the N-Terminal Domains of Nectin-1 and Nectin-2 Reveal Differences in Requirements for Entry of Various Alphaherpesviruses and for Nectin-Nectin Interactions," Journal of Virology, 76(24): 12940-12950 (Dec. 2002).
Szymczak et al., "Development of 2A peptide-based strategies in the design of multicistronic vectors," Expert Opin. Biol. Ther., 5(5): 627-638 (2005).
Tischer et al., "Two-step red-mediated recombination for versatile high-efficiency markerless DNA manipulation in *Escherichia coli.*," BioTechniques, 40(2): 191-196 (2006).
Tocchi et al., "Functional interactions between matrix metalloproteinases and glycosaminoglycans," FEBS Journal (2013) 280:2332-2341.
Todo, "Oncolytic Virus Therapy Using Genetically Engineered Herpes Simplex Viruses," Cell, 15(3): 151-159 (2002).
Topalian et al., "Safety, Activity, and Immune Correlates of Anti-PD-1 Antibody in Cancer," The New England Journal of Medicine, 366(26): 2443-2454 (2012).
Tran et al., "Immune targeting of fibroblast activation protein triggers recognition of multipotent bone marrow stromal cells and cachexia," J Exp Med., 2013, 210(6): 1125-1135.
Triozzi et al., "Phase I Study of the Intratumoral Administration of Recombinant Canarypox Viruses Expressing B7.1 and Interleukin 12 in Patients with Metastatic Melanoma," Clin Cancer Res 2005;11(11):4168-4175.
Tsvitov et al., "Characterization of Soluble Glycoprotein D-mediated Herpes Simplex Virus Type 1 Infection," Virology, 360: 477-491 (2007).
Turner et al., "Glycoproteins gB, gD, and gHgL of Herpes Simplex Virus Type 1 Are Necessary and Sufficient To Mediate Membrane Fusion in a Cos Cell Transfection System," Journal of Virology, 72(1): 873-875 (Jan. 1998).
Uchida et al., "A Double Mutation in Glycoprotein gB Compensates for Ineffective gD-Dependent initiation of Herpes Simplex Virus Type 1 Infection," Journal of Virology, 84(23): 12200-12209 (Dec. 2010).
Uchida et al., "Co-engineering of HSV-1 gB and gD Enables Efficient Retargeted Infection," 29th Annual Meeting of the American Society for Virology, slides of oral presentation, 38 pages, Bozeman, MT (Jul. 17-21, 2010).
Uchida et al., "Co-engineering of HSV-1 Glycoproteins B and D Enables Highly Efficient Retargeted Infection," 29th Annual Meeting of the American Society for Virology, abstract, 1 page, Bozeman, MT (Jul. 17-21, 2010).
Uchida et al., "Effective Treatment of an Orthotopic Xenograft Model of Human Glioblastoma Using an EGFR-retargeted Oncolytic Herpes Simplex Virus," Molecular Therapy 21(3):561-569 (2012).
Uchida et al., "Fully Retargeted HSV-1 Infection Directed by Re-Engineered Glycoprotein D (gD) Is Augmented by Hyperactive gB Mutations," Molecular Therapy, 18(Supp. 1): S249, Abstract 640 (May 2010).
Uchida et al., "Generation of Herpes virus Entry Mediator (HVEM)-Restricted Herpes Simplex Virus Type 1 Mutant Viruses: Resistance of HVEM-Expressing Cells and Identification of Mutations That Rescue Nectin-1 Recognition," Journal of Virology, 83(7): 2951-2961 (Apr. 2009).
Uchida et al., "Hyperactive gB Mutations Augment Fully Retargeted HSV Infection," 13 Annual Meeting of the American Society of Gene & Cell Therapy, slides of oral presentation, 34 pages, Washington, DC (May 19-22, 2010).
Uchida et al., "Hyperactive gB Mutations Augment Fully Retargeted HSV Infection," 35th Annual International Herpes Virus Workshop, poster presentation, 1 page, Salt Lake City, UT (Jul. 24-29, 2010).
Uchida et al., "Hyperactive Glycoprotein B (gB) Mutations Augment Fully Retargeted Herpes Simplex Virus (HSV) Infection," 101"Annual Meeting of the American Association for Cancer Research, poster presentation, 1 page, Washington, DC (Apr. 18, 2010).

(56) References Cited

OTHER PUBLICATIONS

Uchida et al., "Hyperactive Glycoprotein B Mutations Augment Fully Retargeted HSV Infection," 35th Annual International Herpes Virus Workshop, abstract, 1 page, Salt Lake City, UT (Jul. 24-29, 2010).
Uchida et al., "Identification of Mutations in HSV-1 Envelope Glycoprotein B That Enhance Retargeted Infection," Proceedings of the American Association for Cancer Research, 51: 139, Abstract 584 (Apr. 2010).
Uchida et al., "Novel Mutations in gB and gH Circumvent the Requirement for Known gD Receptors in Herpes Simplex Virus 1 Entry and Cell-to-Cell Spread," Journal of Virology, 87(3): 1430-1442 (Feb. 2013).
Ushijima et al., "Determination and Analysis of the DNA Sequence of Highly Attenuated Herpes Simplex Virus Type 1 Mutant HF10, a Potential Oncolylic Virus," Microbes and Infection, 9: 142-149 (2007).
Varghese et al., "Oncolytic herpes simplex virus vectors for cancer virotherapy," Cancer Gene Therapy, 9(12): 967-978 (2002).
Verhaak et al., "An integrated genomic analysis identifies clinically relevant subtypes of glioblastoma characterized by abnormalities in PDGFRA, IDH1, EGFR and NF1," Cancer Cell, 17: 98-110 (2010).
Visvanathan et al., "The microRNA miR-124 antagonizes the antineural REST/SCP1 pathway during embryonic CNS development," Genes & Development, 21: 744-749 (2007).
Voeks et al., "Gene therapy for prostate cancer delivered by ovine adenovirus and mediated by purine nucleoside phosphorylase and fludarabine in mouse models," Gene Therapy, 9(12): 759-768 (2002).
Wakimoto et al., "Effects of innate immunity on herpes simplex virus and its ability to kill tumor cells," Gene Therapy, 10: 983-990 (2003).
Warner et al., "A Cell Surface Protein with Herpesvirus Entry Activity (HveB) Confers Susceptibility to Infection by Mutants of Herpes Simplex Virus Type 1, Herpes Simples Virus Type 2, and Pseudorabies Virus," Virology, 246: 179-189 (1998).
Wikstrand et al., "Monoclonal Antibodies against EGFRvIII Are Tumor Specific and React with Breast and Lung Carcinomas and Malignant Gliomas, " Cancer Research, 55: 3140-3148 (Jul. 15, 1995).
Wong et al., "Targeted oncolytic herpes simplex viruses for aggressive cancers," Current Pharmaceutical Biotechnology, 13: 1786-1794 (2012).
Xia et al., "Loss of Brain-enriched miR-124 MicroRNA Enhances Stem-like Traits and Invasiveness of Glioma Cells," The Journal of Biological Chemistry, 287(13): 9962-9971 (2012).
Yan et al. "Effective small RNA destruction by the expression of a short tandem target mimic in *Arabidopsis*," The Plant Cell 24:415-427 (2012).
Yin et al., "The treatment of glioblastomas: A systematic update on clinical Phase III trials," Critical Reviews in Oncology/Hematology, 87: 265-282 (2013).
Yu et al., "T-cell Engager-armed Oncolytic Vaccinia Virus Significantly Enhances Antitumor Therapy," Molecular Therapy, Jan. 2014, vol. 22, No. 1, pp. 102-111.
Yun, "Overcoming the extracellular matrix barrier to improve intratumoral spread and therapeutic potential of oncolytic virotherapy," Current Opinion in Molecular Therapeutics, 10(4): 356-361 (2008).
Zaharoff et al., "Intratumoral Immunotherapy of Established Solid Tumors with Chitosan/IL-12," J Immunother. 2010;33(7):697-705.
Zhang et al., "MicroRNA-128 inhibits glioma cells proliferation by targeting transcription factor E2F3a," J. Mol Med., 87: 43-51 (2009).
Zhong et al., "Induction, Selection and Expansion of Acute Myeloid Leukemia Reactive Autologous T Cells for Adoptive Immunotherapy," Blood, Nov. 2005, 106(11):1061.
Zhou and Roizman, "Construction and properties of a herpes simplex virus 1 designed to enter cells solely via the IL-13α2 receptor, " PNAS 103(14):5508-5513 (2006).

Partial Supplementary European Search Report for European Application No. 17821384.9, dated Dec. 19, 2019, 18 pages.
Extended European Search Report for European Application No. 17821384.9, dated Mar. 25, 2020, 18 pages.
Extended European Search Report issued by the European Patent Office for Application No. 14859119.1, dated Apr. 19, 2017, 10 pages.
International Preliminary Report on Patentability issued by the International Searching Authority for Application No. PCT/US2011/032923, dated Oct. 16, 2012, 8 pages.
International Preliminary Report on Patentability issued by the International Searching Authority for Application No. PCT/US2014/062676, dated May 3, 2016, 5 pages.
International Search Report and Written Opinion issued by the International Searching Authority for Application No. PCT/US17/40354, dated Nov. 20, 2017, 16 pages.
International Search Report and Written Opinion issued by the International Searching Authority for Application No. PCT/US2011/032923, dated Mar. 28, 2012 12 pages.
International Search Report and Written Opinion issued by the International Searching Authority for Application No. PCT/US2014/062676, dated Dec. 23, 2014, 9 pages.
International Search Report and Written Opinion issued by the International Searching Authority for Application No. PCT/US2017/015417, dated May 19, 2017, 15 pages.
Extended European Search Report and Search Opinion for European Application No. 20184441.2, dated Jan. 12, 2021, 7 pages.
Extended European Search Report for European Application No. 18893898.9, dated Oct. 29, 2021, 8 pages.
Henke et al., "microRNA-122 stimulates translation of hepatitis C virus RNA," EMBO J. (2008) 27:3300-3310.
International Search Report and Written Opinion, dated Mar. 14, 2019, for International Application No. PCT/US2018/067922 (13 total pages).
Liu B.L., et al., "ICP34.5 Deleted Herpes Simplex Virus with Enhanced Oncolytic, Immune Stimulating, and Anti-Tumour Properties," Gene Therophy, 2003, pp. 292-303.
Pleshkan et al., "Fibroblast Activation Protein (FAP) as a Possible Target of an Antitumor Strategy," Molecular Genetics, Microbiology and Virology, 2016, vol. 31, No. 3, pp. 125-134.
Ruizhi G. et al., "The therapeutic effect of an oncolytic adenovirus which caryying gene SIRPα-Fc for human cholangiocarcinoma," Modern Oncology, Feb. 2015, vol. 23, No. 03, pp. 310-314 (with English abstract).
Scaria et al., "Host-virus interaction: a new role for microRNAs," Retrovirology 2006, 3:68, pp. 1-9.
U.S. Appl. No. 61/562,738, inventor Jonjic, filed Nov. 22, 2011.
Walters et al., "AB928, a dual antagonist of the $A_2aR$ and $A_2bR$ adenosine receptors for the treatment of cancer," Journal for Immuno Therapy of Cancer 2017, 5(Suppl 2):87, Abstract P498, p. 240.
Walters, M., "32nd Annual Meeting and Pre-Conference Program of the Society for Immunotherapy of Cancer (SITC 2017): Part Two: Nov. 20117, ABS P498", Journal for Immunotherapy of Cancer, vol. 5, No. S2, (Nov. 2017), doi: 10.1186/s40425-017-0288-4, pp. 117-244.
Yu F. et al., Cancer Associated Fibroblasts-Targeted Oncolytic Virus Results in Enhanced Antitumor Activity in Mouse Model, Molecular Therapy, May 2015, vol. 23(1), S246, Abstract No. 620, https://doi.org/10.1016/S1525-0016(16)34229-0.
Zhang et al., "Abstract 3669: IDH mutant glial cell resistance to natural killer cell cytotoxicity," Cancer Research, 74, 3669 (Oct. 1, 2014).
Jenkins et al., "Deletion of the Herpes simplex 1 internal repeat sequences affects pathogenicity in the mouse," Frontiers in Bioscience, Oct. 1996, 1:a59-68.
Junejo et al., "Deletions and Duplication in Internal Inverted Repeat Sequence of Long Region/Unique Sequence of Long Region (IRL/UL) of Herpes Simplex Virus Type-i (HSV-i) Genome are not Evidently Associated with Intracranial and Foot-Pad Pathogenicity in Mouse Model," J. Pak. Med. Assoc., 1995, 45(4), pp. 95-98.
Wollman et al., "Oncolytic Virus Therapy for Glioblastoma Multiforme: Concepts and Candidates," Cancer J., Jan.-Feb. 2012;18(1):69-81.

(56) References Cited

OTHER PUBLICATIONS

Argnani, R., et al., "Replication-competent herpes simplex vectors: design and applications," Gene Therapy (2005), vol. 12, pp. S170-S177.

Banerjee, et al., "Herpes Simplex Virus: The Hostile Guest that Takes Over Your Home," Frontiers in Microbiology, 11:733, pp. 1-18 (2020).

Champion, B., et al., "Targeting T-cells to human cancer associated fibroblasts using an oncolytic virus expressing a FAP-specific T-cell engager," Journal of ImmunoTherapy of Cancer, Nov. 7, 2017, vol. 5(Suppl. 2), pp. 197, P404.

Chen, S-H. et al., "Neither LAT nor Open Reading Frame P Mutations Increase Expression of Spliced or Intron-Containing ICP0 Transcripts in Mouse Ganglia Latently Infected with Herpes Simplex Virus", Journal of Virology, vol. 76, No. 10, pp. 4764-4772 (May 2002).

Cheng, J., et al., "Novel transcription regulatory sequences and factors of the immune evasion protein ICP47 (US12) of herpes simplex viruses," Virology Journal (2020), vol. 17:101, doi: 10.1186/s12985-020-01365-3, 11 pages.

De Sostoa Pomés, J., et al., "Arming oncolytic adenovirus with FAP-targeting bispecific T-cell engager to improve antitumor efficacy," Annals of Oncology, Dec. 1, 2017, vol. 28 (Suppl 11), pp. xi18, 61P.

International Preliminary Report on Patentability, dated Jan. 10, 2019, for International Application No. PCT/US2017/040354, 9 pages.

International Preliminary Report on Patentability, dated Jul. 9, 2020, for International Application No. PCT/US2018/067922, 10 pages.

Invitation to Pay Additional Fees and, Where Applicable, Protest Fee, dated Sep. 15, 2017, for International Application No. PCT/US17/40354 (3 pages).

Manservigi, R., et al., "HSV Recombinant Vectors for Gene Therapy," The Open Virology Journal, 2010, vol. 4, pp. 123-156.

Russell, T., et al., Engineering herpes simplex viruses by infection-transfection methods including recombination site targeting by CRISP/Cas9 nucleases, Journal of Virological Methods, 2015, vol. 213, pp. 18-25.

Russell, T., et al., "Lytic Promoters Express Protein during Herpes Simplex Virus Latency," PLOS Pathogens, doi: 10.1371/journal.ppat.1005729 (Jun. 2016), 20 pages.

Todo, T., "Oncolytic virus therapy using genetically engineered herpes simplex viruses", Frontiers in Bioscience (Landmark Ed.), 13(6): 2060-2064 (Jan. 2008).

\* cited by examiner

FIG. 1

CD19-CD3 BiTE (SEQ ID NO: 44)

Signal peptide 1: SEQ ID NO: 2
Light chain CD19: SEQ ID NO: 16
Heavy chain CD19: SEQ ID NO: 18

Light chain CD3: SEQ ID NO: 20
Heavy chain CD3: SEQ ID NO: 22
3X G4S linker: SEQ ID NO: 8

1X G4S linker: SEQ ID NO: 6
G2S linker: SEQ ID NO: 10
His-tag: SEQ ID NO: 12

FIG. 2

CD19-CD3-IL15 BiTE (SEQ ID NO: 53)

Signal peptide 1: SEQ ID NO: 2
Light chain CD19: SEQ ID NO: 16
Heavy chain CD19: SEQ ID NO: 18

Light chain CD3: SEQ ID NO: 20
Heavy chain CD3: SEQ ID NO: 23
Human IL15: SEQ ID NO: 24

3X G4S linker: SEQ ID NO: 8
1X G4S linker: SEQ ID NO: 6
G2S linker: SEQ ID NO: 10
T2A v4: SEQ ID NO: 14

FIG. 3

CD19-CD3-IL12 BiTE (SEQ ID NO: 54)

Signal peptide 1: SEQ ID NO: 2
Light chain CD19: SEQ ID NO: 16
Heavy chain CD19: SEQ ID NO: 18
His-tag: SEQ ID NO: 12

Light chain CD3: SEQ ID NO: 20
Heavy chain CD3: SEQ ID NO: 22
Human IL12 p35: SEQ ID NO: 28
Human IL12 p40: SEQ ID NO: 26

3X G4S linker: SEQ ID NO: 8
1X G4S linker: SEQ ID NO: 6
G2S linker: SEQ ID NO: 10
T2A v4: SEQ ID NO: 14

FIG. 4

CD19-CD3-CXCL10 BiTE (SEQ ID NO: 55)

Signal peptide 1: SEQ ID NO: 2
Light chain CD19: SEQ ID NO: 16
Heavy chain CD19: SEQ ID NO: 18

Light chain CD3: SEQ ID NO: 20
Heavy chain CD3: SEQ ID NO: 22
Human CXCL10: SEQ ID NO: 30
His-tag: SEQ ID NO: 12

3X G4S linker: SEQ ID NO: 8
1X G4S linker: SEQ ID NO: 6
G2S linker: SEQ ID NO: 10
T2A v4: SEQ ID NO: 14

FIG. 5

SIRP1α-CD3 (SL) BiTE (SEQ ID NO: 46)

[sequence diagram with annotated regions: Signal peptide, SIRP1α, Light chain CD3, Heavy chain CD3]

Signal peptide 2: SEQ ID NO: 4  
SIRP1α: SEQ ID NO: 32

Light chain CD3: SEQ ID NO: 20  
Heavy chain CD3: SEQ ID NO: 22

G2S linker: SEQ ID NO: 10  
His-tag: SEQ ID NO: 12

FIG. 6

SIRP1α-CD3 (LL) BiTE (SEQ ID NO: 48)

[sequence diagram with annotated regions: Signal peptide, SIRP1α, G4S Linker, Heavy chain CD3, Light chain CD3, His-tag]

Signal peptide 2: SEQ ID NO: 4  
SIRP1α: SEQ ID NO: 32

Light chain CD3: SEQ ID NO: 20  
Heavy chain CD3: SEQ ID NO: 22

1X G4S linker: SEQ ID NO: 6  
G2S linker: SEQ ID NO: 10  
His-tag: SEQ ID NO: 12

FIG. 7

SIRP1α-CD3-IL15 (SL) BiTE (SEQ ID NO: 56)

Signal peptide 2: SEQ ID NO: 4
SIRP1α: SEQ ID NO: 32
Heavy chain CD3: SEQ ID NO: 22

Light chain CD3: SEQ ID NO: 20
Multiple G2S linker: SEQ ID NO: 10
His-tag: SEQ ID NO: 12

T2A v4: SEQ ID NO: 14
Human IL15: SEQ ID NO: 24

FIG. 8

SIRP1α-CD3-IL15 (LL) BiTE (SEQ ID NO: 57)

Signal peptide 2: SEQ ID NO: 4
SIRP1α: SEQ ID NO: 32
G4S Linker: SEQ ID NO: 6

Light chain CD3: SEQ ID NO: 20
Heavy chain CD3: SEQ ID NO: 22
Multiple G2S linker: SEQ ID NO: 10

His-tag: SEQ ID NO: 12
Human IL15: SEQ ID NO: 24
T2A v4: SEQ ID NO: 14

FIG. 9

SIRP1α-CD3-IL12 (SL) BiTE (SEQ ID NO: 58)

Signal peptide 2: SEQ ID NO: 4
SIRP1α: SEQ ID NO: 32
Heavy chain CD3: SEQ ID NO: 22

Light chain CD3: SEQ ID NO: 20
Multiple G2S linker: SEQ ID NO: 10
His-tag: SEQ ID NO: 12

T2A v4: SEQ ID NO: 14
Human IL12, p35: SEQ ID NO: 28
IL12, p40: SEQ ID NO: 26

FIG. 10

SIRP1α-CD3-IL12 (LL) BiTE (SEQ ID NO: 59)

Signal peptide 2: SEQ ID NO: 4
SIRP1α: SEQ ID NO: 32
G4S Linker: SEQ ID NO: 6

Light chain CD3: SEQ ID NO: 20
Heavy chain CD3: SEQ ID NO: 22
Multiple G2S Linker: SEQ ID NO: 10

His-tag: SEQ ID NO: 12
Human IL12, p35: SEQ ID NO: 28
IL12, p40: SEQ ID NO: 26
T2A v4: SEQ ID NO: 14

FIG. 11

SIRP1α-CD3-CXCL10 (SL) BiTE (SEQ ID NO: 60)

Signal peptide 2: SEQ ID NO: 4
SIRP1α: SEQ ID NO: 32
Heavy chain CD3: SEQ ID NO: 22

Light chain CD3: SEQ ID NO: 20
Multiple G2S linker: SEQ ID NO: 10
His-tag: SEQ ID NO: 12

T2A v4: SEQ ID NO: 14
Human CXCL10: SEQ ID NO: 30

FIG. 12

SIRP1α-CD3-CXCL10 (LL) BiTE (SEQ ID NO: 61)

Signal peptide 2: SEQ ID NO: 4
SIRP1α: SEQ ID NO: 32
G4S Linker: SEQ ID NO: 6

Light chain CD3: SEQ ID NO: 20
Heavy chain CD3: SEQ ID NO: 22
Multiple G2S linker: SEQ ID NO: 10

T2A v4: SEQ ID NO: 14
His-tag: SEQ ID NO: 12
Human CXCL10: SEQ ID NO: 30

FIG. 13

PDL1-CD3 BiTE (SEQ ID NO: 50)

Signal peptide 1: SEQ ID NO: 2
Multiple G2S linker: SEQ ID NO: 10
G4S linker: SEQ ID NO: 6

Light chain CD3: SEQ ID NO: 20
Heavy chain CD3: SEQ ID NO: 22
Light Chain PDL1: SEQ ID NO: 36

Heavy chain PDL1: SEQ ID NO: 38
3X G4S linker: SEQ ID NO: 8
His-tag: SEQ ID NO: 12

FIG. 14

PDL1-CD3-IL15 BiTE (SEQ ID NO: 62)

Signal peptide 1: SEQ ID NO: 2
Multiple G2S linker: SEQ ID NO: 10
G4S linker: SEQ ID NO: 6

Light chain CD3: SEQ ID NO: 20
Heavy chain CD3: SEQ ID NO: 22
Light Chain PDL1: SEQ ID NO: 36
Heavy chain PDL1: SEQ ID NO: 38

Human IL15: SEQ ID NO: 24
3X G4S linker: SEQ ID NO: 8
His-tag: SEQ ID NO: 12
T2A v4: SEQ ID NO: 14

FIG. 15

PDL1-CD3-IL12 BiTE (SEQ ID NO: 63)

Signal peptide 1: SEQ ID NO: 2
Multiple G2S linker: SEQ ID NO: 10
G4S linker: SEQ ID NO: 6
3X G4S linker: SEQ ID NO: 8

Light chain CD3: SEQ ID NO: 20
Heavy chain CD3: SEQ ID NO: 22
IL12, p40: SEQ ID NO: 26
IL12, p35: SEQ ID NO: 28

Light Chain PDL1: SEQ ID NO: 36
Heavy chain PDL1: SEQ ID NO: 38
T2A v4: SEQ ID NO: 14
His-tag: SEQ ID NO: 12

FIG. 16

PDL1-CD3-CXCL10 BiTE (SEQ ID NO: 64)

Signal peptide 1: SEQ ID NO: 2
Multiple G2S linker: SEQ ID NO: 10
G4S linker: SEQ ID NO: 6
3X G4S linker: SEQ ID NO: 8

Light chain CD3: SEQ ID NO: 20
Heavy chain CD3: SEQ ID NO: 22
Light Chain PDL1: SEQ ID NO: 36
Heavy chain PDL1: SEQ ID NO: 38

Human CXCL10: SEQ ID NO: 30
His-tag: SEQ ID NO: 12
T2A v4: SEQ ID NO: 14

FIG. 17

PDL1-CD3-Fc BiTE (SEQ ID NO: 52)

Signal peptide 1: SEQ ID NO: 2
Multiple G2S linker: SEQ ID NO: 10
G4S linker: SEQ ID NO: 6

Light chain CD3: SEQ ID NO: 20
Heavy chain CD3: SEQ ID NO: 22
PD-L1 Light Chain Fv: SEQ ID NO: 36
PD-L1 Heavy chain Fv: SEQ ID NO: 38

3X G4S linker: SEQ ID NO: 8
Heavy chain Fc: SEQ ID NO: 40
His-tag: SEQ ID NO: 12

FIG. 18A

SIRP1α-CD3-MMP9 (SL) BiTE (SEQ ID NO: 65)

Signal peptide 2: SEQ ID NO: 4
SIRP1α: SEQ ID NO: 32
Heavy chain CD3: SEQ ID NO: 22

Light chain CD3: SEQ ID NO: 20
Multiple G2S linker: SEQ ID NO: 10
His-tag: SEQ ID NO: 12

T2A v4: SEQ ID NO: 14
Human MMP9: SEQ ID NO: 34

FIG. 18B

SIRP1α-CD3-MMP9 (LL) BiTE (SEQ ID NO: 66)

Signal peptide 2: SEQ ID NO: 4
SIRP1α: SEQ ID NO: 32
G4S Linker: SEQ ID NO: 6

Light chain CD3: SEQ ID NO: 20
Heavy chain CD3: SEQ ID NO: 22
Multiple G2S linker: SEQ ID NO: 10

His-tag: SEQ ID NO: 12
T2A v4: SEQ ID NO: 14
Human MMP9: SEQ ID NO: 34

FIG. 27A
FIG. 27B
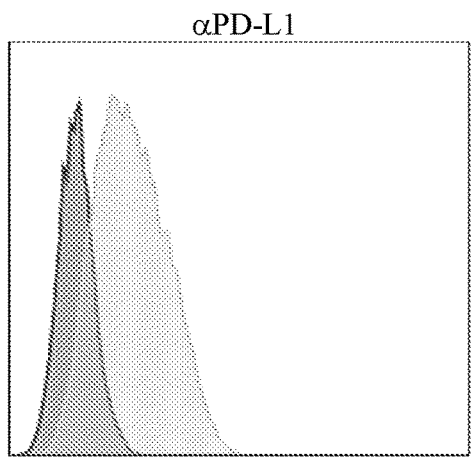
αPD-L1
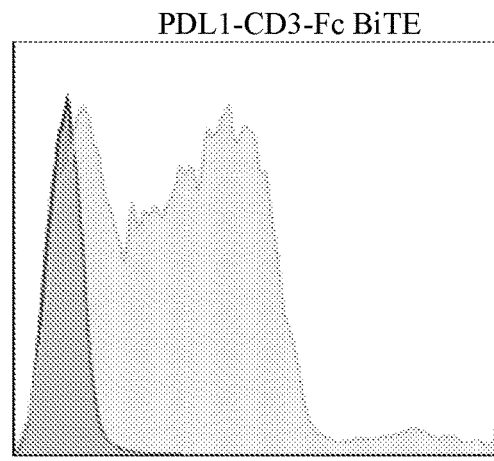
PDL1-CD3-Fc BiTE
FIG. 27C
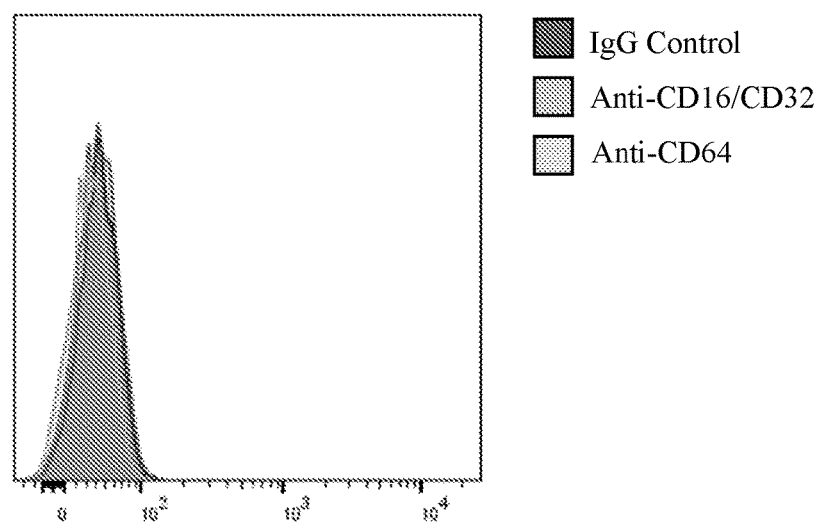
- IgG Control
- Anti-CD16/CD32
- Anti-CD64

αHis tag

1: 100 ng ONCR085 (purified)
2: 50 ng ONCR085 (purified)
3: 25 ng ONCR085 (purified)
4: 12.5 ng ONCR085 (purified)
5: ONCR085 concentrated viral sup (10 µL)
6: ONCR085 concentrated viral sup (5 µL)
7: ONCR087 concentrated viral sup (10 µL)
8: ONCR087 concentrated viral sup (5 µL)

ONCR085 = SIRP1α-CD3 BiTE-SL
ONCR087 = SIRP1α-CD3 BiTE-LL

αHis tag

1: 100 ng ONCR089 (purified)
2: 50 ng ONCR089 (purified)
3: 25 ng ONCR089 (purified)
4: 12.5 ng ONCR089 (purified)
5: ONCR089 concentrated viral sup (10 μL)
6: ONCR089 concentrated viral sup (5 μL)

ONCR089 = PDL1-Fc-CD3

FIG. 37

SIRP1α-CD3-PDL1-Fc (SL) (SEQ ID NO: 68)

Signal peptide : SEQ ID NO: 4
SIRP1α: SEQ ID NO: 32
Heavy chain CD3: SEQ ID NO: 22

Light chain CD3: SEQ ID NO: 20
Multiple G2S linker: SEQ ID NO: 10
His-tag: SEQ ID NO: 12
3X G4S linker: SEQ ID NO: 8

T2A v4: SEQ ID NO: 14
Light chain anti-PDL1: SEQ ID NO: 36
Heavy chain anti-PDL1: SEQ ID NO: 38
IgG1 Fc: SEQ ID NO: 40

FIG. 38

SIRP1α-CD3-PDL1-Fc (LL) (SEQ ID NO: 70)

Signal peptide: SEQ ID NO: 4
SIRP1α: SEQ ID NO: 32
Heavy chain CD3: SEQ ID NO: 22
Light chain CD3: SEQ ID NO: 20

Multiple G2S linker: SEQ ID NO: 10
His-tag: SEQ ID NO: 12
G4S linker: SEQ ID NO: 6
3x G4S linker: SEQ ID NO: 8

T2A v4: SEQ ID NO: 14
Light chain anti-PDL1: SEQ ID NO: 36
Heavy chain anti-PDL1: SEQ ID NO: 38
IgG1 Fc: SEQ ID NO: 40

FIG. 40A

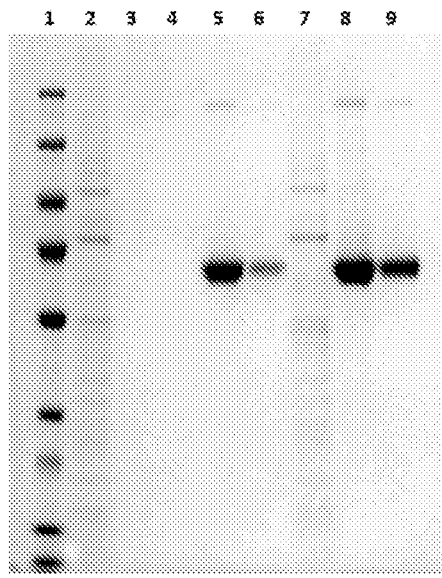

1: Protein Ladder
2: SIRP1α-CD3/PDL1-Fc (SL) Protein A column flow-through
3: SIRP1α-CD3/PDL1-Fc (SL) Protein A column elution fraction 1
4: SIRP1α-CD3/PDL1-Fc (SL) Protein A column elution fraction 2
5: SIRP1α-CD3/PDL1-Fc (SL) Protein A column elution fraction 3
6: SIRP1α-CD3/PDL1-Fc (SL) Protein A column elution fraction 4
7: SIRP1α-CD3/PDL1-Fc (LL) Protein A column flow-through
8: SIRP1α-CD3/PDL1-Fc (LL) Protein A column elution fraction 1
9: SIRP1α-CD3/PDL1-Fc (LL) Protein A column elution fraction 2

FIG. 40B

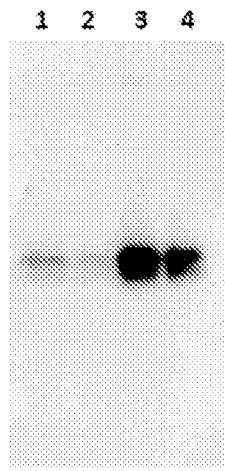

1: SIRP1α-CD3/PDL1-Fc (SL) Protein A column flow-through (10 µL)
2: SIRP1α-CD3/PDL1-Fc (SL) Protein A column flow-through (5 µL)
3: SIRP1α-CD3/PDL1-Fc (LL) Protein A column flow-through (10 µL)
4: SIRP1α-CD3/PDL1-Fc (LL) Protein A column flow-through (5 µL)

αHis tag western blot

FIG. 41A
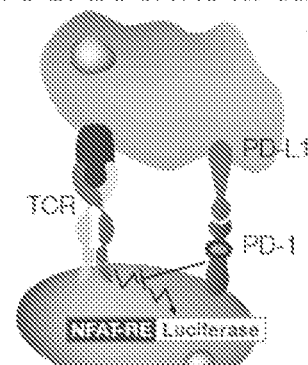
FIG. 41B
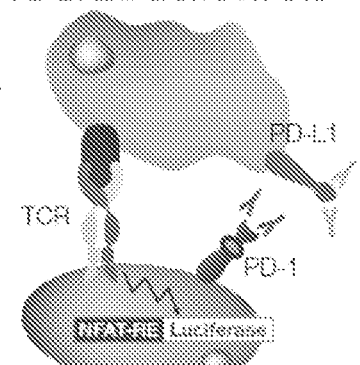
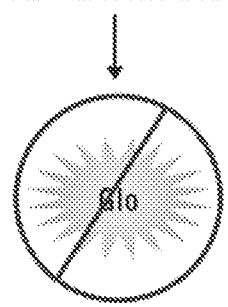
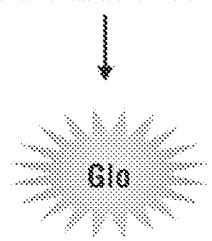
FIG. 41C
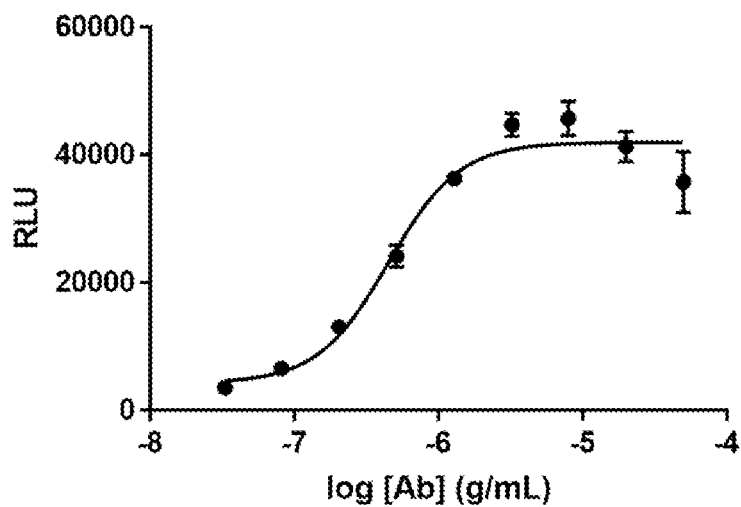

ONCOLYTIC VIRAL DELIVERY OF THERAPEUTIC POLYPEPTIDES

CROSS-REFERENCE TO RELATED APPLICATIONS

This application is a national phase filing under 35 U.S.C. § 371 of International Patent Application No. PCT/US2018/067922, filed Dec. 28, 2018, which claims the benefit of priority to U.S. Provisional Application No. 62/611,941, filed Dec. 29, 2017, the disclosures of which are each incorporated herein by reference in their entireties.

DESCRIPTION OF THE TEXT FILED SUBMITTED ELECTRONICALLY

The contents of the text filed submitted electronically herewith are incorporated herein by reference in their entirety: A computer readable format copy of the Sequence Listing (file name: ONCR_011_001WO_ST25.txt; date generated: Dec. 21, 2018; file size: 208 kilobytes).

BACKGROUND OF THE INVENTION

Patients with certain hematologic and solid tumors remain in need of new therapies. The use of bispecific antibodies to direct cytotoxic T cells to tumor cells, and chimeric antigen receptors (CARs) to engineer antigen specificity onto an immune effector cell are being demonstrated to provide a therapeutic benefit. Also, oncolytic virus technologies are useful additions to the current standard of care of solid tumors, expected to have a safety profile and the ability to infect, replicate in, and lyse tumor cells. However, the antitumor efficacy of the bispecific antibodies, CARs and oncolytic virus are suboptimal, demonstrating the continued need for further advances of oncology, antibodies, and oncolytic virus therapy.

SUMMARY OF THE INVENTION

In some embodiments, the present disclosure provides an oncolytic virus comprising a first recombinant nucleic acid encoding a polypeptide comprising an effector domain specific for an antigen expressed on an effector cell and an targeting domain specific for an antigen expressed on a target cell, wherein the target antigen is fibroblast activation protein (FAP). In some embodiments, the present disclosure provides an oncolytic virus comprising one or more micro RNA (miR) target sequences inserted into a locus of one or more genes required for viral replication, and further comprising a first nucleic acid sequence encoding a polypeptide comprising an effector domain specific for an antigen expressed on an effector cell and a targeting domain that binds to a target antigen expressed on a target cell, wherein the target antigen is fibroblast activation protein (FAP). In some embodiments, the one or more miR target sequences is recognized by miR-10b, miR-17, miR-21, miR-106a, miR-125b, miR-145, miR-146a, miR-146b, miR-155, miR-96, miR-182, miR-183, miR-221, miR-222, or miR-1247-5p. In some embodiments, the one or more miR target sequences is recognized by a plurality of microRNAs selected from miR-10b, miR-17, miR-21, miR-106a, miR-125b, miR-145, miR-146a, miR-146b, miR-155, miR-96, miR-182, miR-183, miR-221, miR-222, and miR-1247-5p.

In some embodiments, the oncolytic virus is derived from herpes simplex virus-1 (HSV-1). In some embodiments, the oncolytic virus is capable of preferential replication in a tumor cell.

In some embodiments, the recombinant nucleic acid further comprises a second nucleic acid sequence encoding an immune modulator polypeptide selected from the group consisting of a cytokine, a costimulatory molecule, an immune checkpoint polypeptide, an anti-angiogenesis factor, and a matrix metalloprotease (MMP). In some embodiments, the cytokine is selected from IL-15, IL-12, CXCL10, and CCL4. In some embodiments, the immune checkpoint polypeptide comprises i) an inhibitor of PD-1, PDL-1, CTLA-4, LAG3, TIM3, neuropilin, or CCR4; ii) an agonist of GITR, OX-40, or CD28; or iii) a combination of i) and ii). In some embodiments, the MMP is MMP9. In some embodiments, the cytokine is selected from IL-15, IL-12, CCL4, and CXCL10.

In some embodiments, the engager polypeptide is a bipartite polypeptide and is comprised of an antibody, an antibody domain, a human immunoglobulin heavy chain variable domain, a dual-variable-domain antibody (DVD-Ig), a Tandab, a diabody, a flexibody, a dock-and-lock antibody, a Scorpion polypeptide, a single chain variable fragment (scFv), a Bill, a DuoBody, an Fc-engineered IgG, an Fcab, a Mab2, or DART polypeptide.

In some embodiments, the first and second nucleic acid sequences are expressed from a single promoter sequence. In some embodiments, the recombinant nucleic acid is a multicistronic sequence. In some embodiments, the multicistronic sequence is a bicistronic sequence or a tricistronic sequence. In some embodiments, the multicistronic sequence comprises a picornavirus-2a-like sequence, and wherein the first and second nucleic acid sequences are expressed from a single promoter sequence present in the recombinant nucleic acid. In some embodiments, the first and second nucleic acids have a size of 7.2-38 kb.

In some embodiments, the effector cell is a T cell or an NKT cell, an NK cell, or a macrophage. In some embodiments, the antigen expressed on the effector cell is CD3 CD4, CD5, CD8, CD16, CD28, CD40, CD134, CD137, or NKG2D.

In some embodiments, the present disclosure provides an oncolytic virus comprising a first recombinant nucleic acid encoding a polypeptide comprising an effector domain specific for an antigen expressed on an effector cell and a targeting domain specific for an antigen expressed on a target cell, wherein the effector cell antigen is CD3 and the target antigen is fibroblast activation protein (FAP). In some embodiments, the engager molecule comprises a polypeptide sequence that is at least 90%, 95%, 96%, 97%, 98%, or 99% identical to SEQ ID NO: 75. In some embodiments, the engager molecule comprises the polypeptide sequence of SEQ ID NO: 75. In some embodiments, the engager molecule consists of the polypeptide sequence of SEQ ID NO: 75. In some embodiments, the first recombinant nucleic acid is at least 95%, 96%, 97%, 98%, or 99% identical to SEQ ID NO: 74. In some embodiments, the first recombinant nucleic acid comprises SEQ ID NO: 74. In some embodiments, the first recombinant nucleic acid consists of SEQ ID NO: 74.

In some embodiments, the oncolytic virus further comprises a second recombinant nucleic acid encoding a therapeutic molecule. In some embodiments, the therapeutic molecule is IL-12, IL-15, CXCL10, or MMP9. In some embodiments, the therapeutic molecule is IL-12 and wherein the recombinant nucleic acid sequence encodes a polypeptide sequence that is at least 90%, 95%, 96%, 97%, 98%, or 99% identical to SEQ ID NO: 54. In some embodiments, the therapeutic molecule is IL-15 and wherein the recombinant nucleic acid sequence encodes a polypeptide sequence that is at least 90%, 95%, 96%, 97%, 98%, or 99% identical to SEQ ID NO: 53. In some embodiments, the therapeutic molecule is CXCL10 and wherein the recombinant nucleic acid sequence encodes a polypeptide sequence that is at least 90%, 95%, 96%, 97%, 98%, or 99% identical to SEQ ID NO: 55. In some embodiments, the therapeutic molecule is CCL4 and wherein the recombinant nucleic acid sequence encodes a polypeptide sequence that is at least 90%, 95%, 96%, 97%, 98%, or 99% identical to SEQ ID NO: 80. In some embodiments, the therapeutic molecule is MMP9 and wherein the recombinant nucleic acid sequence encodes a polypeptide sequence that is at least 90%, 95%, 96%, 97%, 98%, or 99% identical to SEQ ID NO: 34.

In some embodiments, the oncolytic virus further comprises one or more additional recombinant nucleic acid sequences encoding two or more therapeutic molecules. In some embodiments, the two or more therapeutic molecules comprise two or more of CCL4, CXCL20, and IL-12. In some embodiments, the two or more therapeutic molecules comprise each of CCL4, CXCL20, and IL-12.

In some embodiments, the oncolytic virus is a pseudo-typed oncolytic virus. In some embodiments, the pseudo-typed oncolytic virus comprises one or more modified glycoproteins involved in viral entry into a host cell. In some embodiments, the one or more modified glycoproteins comprise one or more amino acid mutations. In some embodiments, the pseudotyped oncolytic virus comprises a non-viral protein present on the viral surface. In some embodiments, the non-viral protein binds to a protein expressed on the cell-surface of a target cell. In some embodiments, the protein expressed on the cell-surface of the target cell is not associated with a cancer. In some embodiments, the pseudotyped oncolytic virus possesses an altered tropism relative to a non-pseudotyped virus. In some embodiments, the pseudotyped oncolytic virus yields reduced toxicity and/or reduced entry of non-tumor cells or tissue relative to a non-pseudotyped virus. In some embodiments, the pseudotyped oncolytic virus yields increased toxicity and/or increased entry of tumor cells or cancerous tissue relative to a non-pseudotyped virus.

In some embodiments, the oncolytic virus is administered to the subject intravenously. In some embodiments, the oncolytic virus is selected from or is derived from an adenovirus, a herpes simplex virus 1 (HSV1), a myxoma virus, a reovirus, a poliovirus, a vesicular stomatitis virus (VSV), a measles virus (MV), a lassa virus (LASV), or a Newcastle disease virus (NDV).

In some embodiments, the present disclosure provides a pharmaceutical composition comprising an oncolytic virus described herein. In some embodiments, the composition is capable of being administered intravenously. In some embodiments, the oncolytic virus induces an immune response. In some embodiments, the immune response is selectively cytotoxic to a target cell. In some embodiments, the target cell is derived from a solid tumor or a hematologic cancer.

In some embodiments, the present disclosure provides a method of treating a cancer in a subject in need thereof, comprising administering a therapeutically effective amount of an oncolytic virus described herein or a pharmaceutical composition thereof. In some embodiments, the method further comprises administering one or more additional therapies to the subject in need thereof. In some embodiments, the one or more additional therapies comprise surgery, radiation, chemotherapy, immunotherapy, hormone therapy, or a combination thereof.

In some embodiments, the present disclosure provides a method of treating one or more tumors in a subject in need thereof comprising administering a therapeutically effective amount of an oncolytic virus described herein or a pharmaceutical composition thereof to a patient, wherein the one or more tumors express a tumor antigen.

In some embodiments, the present disclosure provides a method of delivering an engager polypeptide and a therapeutic polypeptide to a tumor site comprising administering to a patient in need thereof an oncolytic virus described herein or a pharmaceutical composition thereof.

BRIEF DESCRIPTION OF THE DRAWINGS

FIG. 1 illustrates an amino acid sequence of a CD19-CD3 bipartite polypeptide comprising a first single chain variable fragment (scFv) directed against CD19 linked to a second scFv directed against CD3.

FIG. 2 illustrates an amino acid sequence of a CD19-CD3-IL15 construct encoded by a bicistronic gene. The first gene encodes a bipartite polypeptide comprising a first scFv directed against CD19 linked to a second scFv directed against CD3. A second gene encoding IL-15 is linked to the bipartite gene sequence by a T2A self-cleaving polypeptide linker.

FIG. 3 illustrates an amino acid sequence of a CD19-CD3-IL12 construct encoded by a multicistronic gene. The first gene encodes a bipartite polypeptide comprising a first scFv directed against CD19 linked to a second scFv directed against CD3. A second gene encoding the p35 subunit of IL-12 is linked to the bipartite gene sequence by a T2A self-cleaving polypeptide linker and a third gene encoding the p40 subunit of IL-12 is linked by a T2A self-cleaving polypeptide linker.

FIG. 4 illustrates an amino acid sequence of a CD19-CD3-CXCL10 construct encoded by a bicistronic gene. The first gene encodes a bipartite polypeptide comprising a first scFv directed against CD19 linked to a second scFv directed against CD3. A second gene encoding CXCL10 is linked to the bipartite gene sequence by a T2A self-cleaving polypeptide linker.

FIG. 5 illustrates an amino acid sequence of a SIRP1α-CD3 bipartite polypeptide comprising a first protein comprising the first 120 amino acids of SIRP1a linked by a single amino acid linker to an scFv directed against CD3.

FIG. 6 illustrates an amino acid sequence of a SIRP1α-CD3-LL bipartite polypeptide comprising a first protein comprising the first 120 amino acids of SIRP1α linked by a G4S motif linker to an scFv directed against CD3.

FIG. 7 illustrates an amino acid sequence of a SIRP1α-CD3-IL15 construct encoded by a bicistronic gene. The first gene encodes a bipartite polypeptide comprising the first 120 amino acids of SIRP1α linked by a single amino acid linker to an scFv directed against CD3. A second gene encoding IL-15 is linked to the bipartite gene sequence by a T2A self-cleaving polypeptide linker.

FIG. 8 illustrates an amino acid sequence of a SIRP1α-CD3-IL15-LL construct encoded by a bicistronic gene. The first gene encodes a bipartite polypeptide comprising the first 120 amino acids of SIRP1α linked by a G4S motif linker to an scFv directed against CD3. A second gene encoding IL-15 is linked to the bipartite gene sequence by a T2A self-cleaving polypeptide linker.

FIG. 9 illustrates an amino acid sequence of a SIRP1α-CD3-IL12 construct encoded by a multicistronic gene. The first gene encodes a bipartite polypeptide comprising the first 120 amino acids of SIRP1α linked by a single amino acid linker to an scFv directed against CD3. A second gene encoding the p35 subunit of IL-12 is linked to the bipartite gene sequence by a T2A self-cleaving polypeptide linker and a third gene encoding the p40 subunit of IL-12 is linked by a T2A self-cleaving polypeptide linker.

FIG. 10 illustrates an amino acid sequence of a SIRP1α-CD3-IL12-LL construct encoded by a multicistronic gene. The first gene encodes a bipartite polypeptide comprising the first 120 amino acids of SIRP1α linked by a G4S motif linker to an scFv directed against CD3. A second gene encoding the p35 subunit of IL-12 is linked to the bipartite gene sequence by a T2A self-cleaving polypeptide linker and a third gene encoding the p40 subunit of IL-12 is linked by a T2A self-cleaving polypeptide linker.

FIG. 11 illustrates an amino acid sequence of a SIRP1α-CD3-CXCL10 construct encoded by a bicistronic gene. The first gene encodes a bipartite polypeptide comprising the first 120 amino acids of SIRP1α linked by a single amino acid linker to an scFv directed against CD3. A second gene encoding CXCL10 is linked to the bipartite gene sequence by a T2A self-cleaving polypeptide linker.

FIG. 12 illustrates an amino acid sequence of a SIRP1α-CD3-CXCL10-LL construct encoded by a bicistronic gene. The first gene encodes a bipartite polypeptide comprising the first 120 amino acids of SIRP1α linked by a G4S motif linker to an scFv directed against CD3. A second gene encoding CXCL10 is linked to the bipartite gene sequence by a T2A self-cleaving polypeptide linker.

FIG. 13 illustrates an amino acid sequence of a PDL1-CD3 bipartite polypeptide comprising a first scFv directed against PDL1 linked to a second scFv directed against CD3.

FIG. 14 illustrates an amino acid sequence of a PDL1-CD3-IL15 construct encoded by a bicistronic gene. The first gene encodes a bipartite polypeptide comprising a first scFv directed against PDL1 linked to a second scFv directed against CD3. A second gene encoding IL-15 is linked to the bipartite gene sequence by a T2A self-cleaving polypeptide linker.

FIG. 15 illustrates an amino acid sequence of a PDL1-CD3-IL12 construct encoded by a multicistronic gene. The first gene encodes a bipartite polypeptide comprising a first scFv directed against PDL1 linked to a second scFv directed against CD3. A second gene encoding the p35 subunit of IL-12 is linked to the bipartite gene sequence by a T2A self-cleaving polypeptide linker and a third gene encoding the p40 subunit of IL-12 is linked by a T2A self-cleaving polypeptide linker.

FIG. 16 illustrates an amino acid sequence of a PDL1-CD3-CXCL10 construct encoded by a bicistronic gene. The first gene encodes a bipartite polypeptide comprising a first scFv directed against PDL1 linked to a second scFv directed against CD3. A second gene encoding CXCL10 is linked to the bipartite gene sequence by a T2A self-cleaving polypeptide linker.

FIG. 17 illustrates an amino acid sequence of a PDL1-CD3-Fc tripartite polypeptide comprising a first scFv directed against CD3, linked by a G4S motif linker to a second scFv directed against PDL1, which is in turn linked to the CH2-CH3 domain of human IgG1 by an IgG1 hinge.

FIG. 18 illustrates an amino acid sequence of a SIRP1α-CD3-MMP9-SL construct encoded by a bicistronic gene (FIG. 18A) and an amino acid sequence of a SIRP1α-CD3-MMP9-LL construct encoded by a bicistronic gene (FIG. 18B).

FIG. 27A-FIG. 27C illustrate the binding of PDL1-Fc-CD3 tripartite T cell engagers to U251 cells. The binding of the PDL1-Fc-CD3 constructs (FIG. 27B) is compared to the binding of an anti-PDL1 antibody (FIG. 27A). Binding was not mediated by FcγRs, as U251 cells do not express FcγRI, FcγRII, or FcγRIII (FIG. 27C).

FIG. 37 illustrates an amino acid sequence of a SIRP1α-CD3-PDL1-Fc (SL) construct encoded by a bicistronic gene wherein the first gene encodes an anti-PDL1 scFv linked to an IgG1 Fc domain and the second gene encodes a bipartite polypeptide comprising the first 120 amino acids of SIRP1α linked by a single amino acid linker to an scFv directed against CD3.

FIG. 38 illustrates an amino acid sequence of a SIRP1α-CD3-PDL1-Fc (LL) construct encoded by a bicistronic gene wherein the first gene encodes an anti-PDL1 scFv linked to an IgG1 Fc domain and the second gene encodes a bipartite polypeptide comprising the first 120 amino acids of SIRP1α linked by a G4S motif linker to an scFv directed against CD3.

FIG. 40 illustrates purification of the SIRP1α-CD3 BiTE (SL), SIRP1α-CD3 BiTE (LL), and the anti-PDL1-Fc compounds from supernatants of transfected 293 T cells. FIG. 40A shows purification of anti-PDL1-Fc compounds assessed by Coomassie. FIG. 40B illustrates purification of SIRP1α-CD3 BiTE compounds as assessed by Western Blot using an anti-His detection antibody.

FIG. 41 shows results of a PD1/PDL1 blockade assay. A schematic of the assay is shown in FIG. 41A-FIG. 41B. The results of the PD1/PDL1 blockade assay using the anti-PDL1-Fc compound produced from 293 cells transfected are shown in FIG. 41C.

DETAILED DESCRIPTION OF THE INVENTION

Figure 19A:
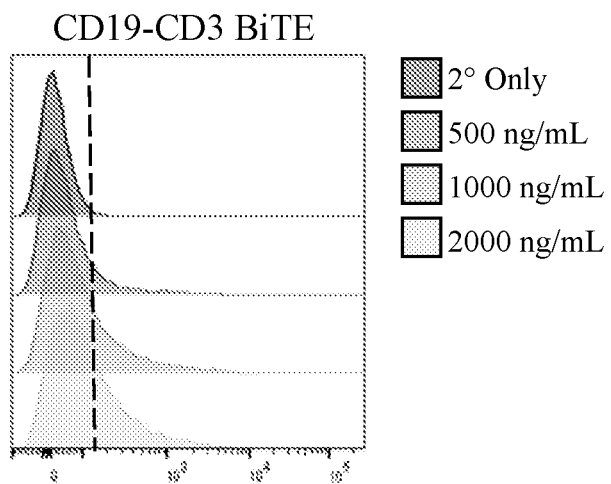
FIG. 19A-FIG. 19C illustrate the binding of CD19-CD3 BiTE constructs (FIG. 19A), SIRP1α-CD3 BiTE constructs (FIG. 19B), and PDL1-CD3-Fc tripartite T cell engagers (FIG. 19C) CD3$^+$ T cells.

The present disclosure provides novel engineered oncolytic viruses, in particular oncolytic viruses that produce multipartite polypeptides and/or other therapeutic polypeptides for the treatment of cancers including solid tumors (e.g., advanced solid tumors) and hematologic malignancies. In some embodiments, the multipartite and/or therapeutic polypeptides produced by the oncolytic viruses described herein mediate and/or enhance the anti-tumor effects of the oncolytic viruses, such as by effector cell-mediated lysis of target cells (e.g., tumor cells). The oncolytic viruses described herein may have multiple (e.g. dual) modes of action, including effector cell-mediated cytolysis of target cells as a result of the expression of multipartite polypeptides, and viral-mediated destruction of target cells. The present disclosure further provides therapeutic compositions comprising the engineered oncolytic viruses and methods of use in the treatment of solid tumors and hematologic malignancies.

Overview

In some embodiments, the present invention provides oncolytic viruses, compositions thereof, and methods of use for the treatment of cancer. The oncolytic viruses provided herein comprise recombinant nucleic acids that encode engager polypeptides and/or other therapeutic molecules. Typically, the engager polypeptides function as effector cell engagers and generally comprise a first domain directed against a cell surface molecule expressed on an effector cell (e.g., an effector domain) and a second domain directed against a target cell antigen (e.g., a targeting domain) or other cell-surface molecule (e.g., an activation domain). In some embodiments, the engager molecules encoded by the oncolytic viruses described herein are bipartite, tripartite or multipartite polypeptides (e.g., comprising one or multiple engager domains, one or multiple targeting domains, or one or multiple activation domains, and optionally one or multiple other functional domains). In some embodiments, the oncolytic viruses described herein are further engineered by pseudotyping or other recombinant technology in order to modulate the tropism of the virus to result in a viral infection specific for tumor cells and/or surrounding tumor stroma and/or for other beneficial purposes.

Also provided are methods of treating cancer, comprising the step of delivering to human subject in need thereof a therapeutically effective amount of the oncolytic viruses described herein or pharmaceutical compositions thereof. Such methods optionally include the step of delivering to the human subject an additional cancer therapy, such as surgery, radiation, chemotherapy, immunotherapy, hormone therapy, or a combination thereof.

Definitions

As used herein, the singular forms "a," "an," or "the" include plural references unless the context clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 30%, 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein the specification, "subject" or "subjects" or "individuals" include, but are not limited to, mammals such as humans or non-human mammals, including domesticated, agricultural or wild, animals, as well as birds, and aquatic animals. In some embodiments, subjects are livestock such as cattle, sheep, goats, cows, swine, and the like; poultry such as chickens, ducks, geese, turkeys, and the like; and domesticated animals such as dogs and cats. In some embodiments (e.g., particularly in research contexts) subjects are rodents (e.g., mice, rats, hamsters), rabbits, primates, or swine such as inbred pigs and the like. In particular embodiments, the subject is a human. "Patients" are subjects suffering from or at risk of developing a disease, disorder, or condition or otherwise in need of the compositions and methods provided herein. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, "treating" or "treatment" refers to any indicia of success in the treatment or amelioration of a disease or condition, particularly cancer. Treating or treatment may be performed in vitro and/or in vivo, and may comprise delivering an oncolytic virus, or composition thereof, described herein to a patient or subject in need thereof. In some embodiments, treating includes, for example, reducing, delaying or alleviating the severity of one or more symptoms of the disease or condition, and/or reducing the frequency with which symptoms of a disease, defect, disorder, or adverse condition are experienced by a subject or patient. Herein, "treat or prevent" is used herein to refer to a method that results in some level of treatment or amelioration of the disease or condition, and contemplates a range of results directed to that end, including but not restricted to prevention of the condition entirely.

As used herein, "preventing" refers to the prevention of a disease or condition, e.g., tumor formation, in a patient or subject and may also be referred to as "prophylactic treatment." Prevention of disease development can refer to complete prevention of the symptoms of disease, a delay in disease onset, or a lessening of the severity of the symptoms in a subsequently developed disease. As a non-limiting illustrative example, if an individual at risk of developing a tumor or other form of cancer is treated with the methods of the present invention and does not later develop the tumor or other form of cancer, then the disease has been prevented, at least over a period of time, in that individual.

The terms "therapeutically effective amount" and "therapeutically effective dose" are used interchangeably herein and refer to the amount of an oncolytic virus or composition thereof that is sufficient to provide a beneficial effect or to otherwise reduce a detrimental non-beneficial event (e.g. an amount or dose sufficient to treat a disease). The exact amount or dose of an oncolytic virus comprised within a therapeutically effective amount or therapeutically effective dose will depend on variety of factors including: the purpose of the treatment; the weight, sex, age, and general health of the subject or patient; the route of administration; the timing of administrations; and the nature of the disease to be treated. The therapeutically effective amount for a given subject or patient is ascertainable by one skilled in the art using known techniques (see, e.g. Lieberman, Pharmaceutical Dosage Forms (vols. 1-3, 1992); Lloyd, *The Art, Science and Technology of Pharmaceutical Compounding* (1999); and Pickar, *Dosage Calculations* (1999)).

"Pseudotype" refers to a virus particle, wherein a portion of the virus particle (e.g., the envelope or capsid) comprises one or more heterologous proteins, such as viral proteins derived from a heterologous virus or non-viral proteins, and/or one or more modified viral coat proteins. Non-viral proteins (also referred to as "targeting moieties") may include antibodies and antigen-binding fragments thereof.

The term "targeting moiety" refers herein to a heterologous protein linked to a virus particle that is capable of binding to a protein on the cell surface of a selected cell type in order to direct interaction between the virus particle and the selected cell type. The targeting moiety may be covalently or non-covalently linked and is generally linked to an envelope protein, e.g., E1, E2, or E3. Representative targeting moieties include antibodies, antigen binding fragments thereof, and receptor ligands. A viral "envelope" protein, or "Env" protein, refers to any polypeptide sequence that resides on the surface lipid bilayer of a virion and functions to mediate the adsorption to and viral entry of host cells susceptible to infection.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In some embodiments, the vector is a virus (i.e., a viral vector or oncolytic viral vector) and the transferred nucleic acid sequence is a recombinant nucleic acid sequence encoding an engager molecule and/or a therapeutic molecule. A viral vector may sometimes be referred to as a "recombinant virus" or a "virus." The terms "oncolytic virus" and "oncolytic vector" are used interchangeably herein.

"Nucleic acid genome" or "viral genome" refers to the nucleic acid component of a virus particle, which encodes the genome of the virus particle including any proteins required for replication and/or integration of the genome. In some embodiments, a viral genome acts as a viral vector and may comprise a heterologous gene operably linked to a promoter. The promoter may be either native or heterologous to the gene and may be viral or non-viral in origin. The viral genomes described herein may be based on any virus, may be an RNA or DNA genome, and may be either single stranded or double stranded. Preferably, the nucleic acid genome is from the family Rhabdoviridae.

"Retroviral vectors," as used herein, refer to viral vectors based on viruses of the Retroviridae family. In their wild-type (WT) form, retroviral vectors typically contain a nucleic acid genome.

The term "antibody fragment or derivative thereof" includes polypeptide sequences containing at least one CDR and capable of specifically binding to a target antigen. The term further relates to single chain antibodies, or fragments thereof, synthetic antibodies, antibody fragments, such as a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, nanobody), etc., or a chemically modified derivative of any of these. In some embodiments, antibodies or their corresponding immunoglobulin chain(s) are further modified by using, for example, amino acid deletion(s), insertion(s), substitution(s), addition(s), and/or recombination(s) and/or any other modification(s) (e.g. posttranslational and chemical modifications, such as glycosylation and phosphorylation), either alone or in combination. Methods for introducing such modifications in the DNA sequence underlying the amino acid sequence of an immunoglobulin chain are well known to the person skilled in the art.

The term "single-chain" as used in accordance with the present disclosure refers to the covalent linkage of two or more polypeptide sequences, preferably in the form of a co-linear amino acid sequence encoded by a single nucleic acid molecule.

The terms "binding to" and "interacting with" are used interchangeably herein and refer to the interaction of at least two "antigen-interaction-sites" with each other. An "antigen-interaction-site" refers to a motif of a polypeptide (e.g., an antibody or antigen binding fragment thereof) capable of specific interaction with an antigen or a group of antigens. The binding/interaction is also understood to define a "specific interaction" or "specific binding."

The terms "specific binding" or "specific interaction" refer to an antigen-interaction-site that is capable of specifically interacting with and/or binding to at least two amino acids of a target molecule as defined herein. The term relates to the ability of the antigen-interaction-site to discriminate between the specific regions (e.g. epitopes) of the target molecules defined herein such that it does not, or essentially does not, cross-react with polypeptides of similar structures. In some embodiments, the epitopes are linear. In some embodiments, the epitopes are conformational epitopes, a structural epitope, or a discontinuous epitope consisting of two regions of the human target molecules or parts thereof. In context of this disclosure, a conformational epitope is defined by two or more discrete amino acid sequences separated in the primary sequence which come together on the surface of the folded protein. Specificity and/or cross-reactivity of a panel of antigen bindings construct under investigation can be tested, for example, by assessing binding of the panel of the constructs to the polypeptide of interest as well as to a number of more or less (structurally and/or functionally) closely related polypeptides under conventional conditions (See e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999). Only those constructs that bind to the polypeptide/protein of interest and do not, or essentially do not, bind to any of the other polypeptides are considered specific for the polypeptide/protein of interest. Examples of specific interactions of an antigen-interaction-site with a specific antigen include the interaction of ligands which induce a signal upon binding to its specific receptor, the specificity of a ligand for its receptor, such as cytokines that bind to specific cytokine receptors, and the binding of an antigen binding site of an antibody to an antigenic epitope, among others.

In some instances, the specific interaction of the antigen-interaction-site with a specific antigen results in the initiation of a signal, e.g. due to the induction of a change of the conformation of the antigen, oligomerization of the antigen, etc. In some embodiments, specific binding encompasses a "key-lock-principle." Therefore in some embodiments, specific motifs in the amino acid sequence of the antigen-interaction-site interact with specific motifs in the antigen and bind to each other as a result of their primary, secondary or tertiary structure, or as the result of secondary modifications of said structure. In some embodiments, the specific interaction of the antigen-interaction-site with its specific antigen results in a simple binding of the site to the antigen.

Oncolytic Viruses

Oncolytic viruses are able to infect, replicate in, and lyse tumor cells, and are further capable of spreading to other tumor cells in successive rounds of replication. While past oncolytic virus therapy has shown promise in preclinical models and clinical studies, anti-tumor efficacy of these oncolytic virus, such as vaccinia, has been suboptimal. For example, these viruses demonstrated limited viral spread throughout the tumor and/or limited activation of anti-tumor T cell responses within the tumor. Therefore, the present disclosure provides oncolytic viruses that 1) facilitate tumor infiltration and activation of effector cells (e.g., T cells), and/or 2) effectively lyse tumor cells that are not infected the virus (also known as by-stander killing).

In some embodiments, the oncolytic viruses described herein have one or more of the following advantageous properties:

(a) the viruses are oncolytic and have a particularly high oncolytic activity compared to other previously described oncolytic viruses;

(b) the viruses replicate preferentially in tumor cells and have a particularly high replication capability compared to other oncolytic viruses;

(c) the viruses infect actively dividing cells as well as resting cells;

(d) the viruses induce a strong innate, humoral, and cellular immune response;

(e) the viruses replicate purely cytoplasmatically, i.e., they cannot integrate into the host cell genome or recombine into replication-competent viruses;

(f) one or more of the native viral glycoproteins are interchangeable with a heterologous envelope protein.

Pseudotyped Oncolytic Viruses

In some embodiments, the present invention provides pseudotyped oncolytic viruses. In general, viruses have natural host cell populations that they infect most efficiently. For example, retroviruses have limited natural host cell ranges, while adenoviruses and adeno-associated viruses are able to efficiently infect a relatively broader range of host cells, although some cell types are refractory to infection by these viruses. The proteins on the surface of a virus (e.g., envelope proteins or capsid proteins) mediate attachment to and entry into a susceptible host cell and thereby determine the tropism of the virus, i.e., the ability of a particular virus to infect a particular cell or tissue type. In some embodiments, the oncolytic viruses described herein comprise a single type of protein on the surface of the virus. For example, retroviruses and adeno-associated viruses have a single protein coating their membrane. In some embodiments, the oncolytic viruses described herein comprise more than one type of protein on the surface of the virus. For example, adenoviruses are coated with both an envelope protein and fibers that extend away from the surface of the virus.

The proteins on the surface of the virus can bind to cell-surface molecules such as heparin sulfate, thereby localizing the virus to the surface of the potential host cell. The proteins on the surface of the virus can also mediate interactions between the virus and specific protein receptors expressed on a host cell that induce structural changes in the viral protein in order to mediate viral entry. Alternatively, interactions between the proteins on the surface of the virus and cell receptors can facilitate viral internalization into endosomes, wherein acidification of the endosomal lumen induces refolding of the viral coat. In either case, viral entry into potential host cells requires a favorable interaction between at least one molecule on the surface of the virus and at least one molecule on the surface of the cell.

In some embodiments, the oncolytic viruses described herein comprise a viral coat (e.g., a viral envelop or viral capsid), wherein the proteins present on the surface of the viral coat (e.g., viral envelop proteins or viral capsid proteins) modulate recognition of a potential target cell for viral entry. In some instances, this process of determining a potential target cell for entry by a virus is referred to as host tropism. In some embodiments, the host tropism is cellular tropism, wherein viral recognition of a receptor occurs at a cellular level, or tissue tropism, wherein viral recognition of cellular receptors occurs at a tissue level. In some instances, the viral coat of a virus recognizes receptors present on a single type of cell. In other instances, the viral coat of a virus recognizes receptors present on multiple cell types (e.g., 2, 3, 4, 5, 6 or more different cell types). In some instances, the viral coat of a virus recognizes cellular receptors present on a single type of tissue. In other instances, the viral coat of a virus recognizes cellular receptors present on multiple tissue types (e.g., 2, 3, 4, 5, 6 or more different tissue types).

In some embodiments, the oncolytic viruses described herein are pseudotyped in order to limit or control the viral tropism (i.e., to reduce the number of different cell or tissue types that the oncolytic virus is capable of infecting). In some embodiments, the pseudotyped oncolytic viruses described herein are pseudotyped in order to expand the viral tropism (i.e., to increase the number of different cell or tissue types that the pseudotyped oncolytic virus is capable of infecting).

In some embodiments, a pseudotyped oncolytic virus comprises a viral coat comprising one or more amino acid mutations in one or more endogenous viral coat proteins (e.g., one or more amino acid insertions, deletions, and/or substitutions). In some embodiments, a pseudotyped virus comprises a viral coat comprising one or more heterologous viral proteins, or wherein one or more of the endogenous viral coat proteins have been replaced or modified. In some embodiments, a pseudotyped oncolytic virus comprises a viral coat that has been modified to incorporate coat proteins from a heterologous virus. In some embodiments, a pseudotyped oncolytic viruses comprises a viral coat wherein the viral coat of a first virus is exchanged with a viral coat of second, wherein the viral coat of the second virus is allows the pseudotyped oncolytic virus to infect a particular cell or tissue type.

In some embodiments, a pseudotyped oncolytic virus comprises a viral coat comprising one or more heterologous, non-viral proteins, such as a targeting moiety. In some embodiments, the non-viral targeting moiety may include antibodies, antigen-binding fragments thereof, and/or receptor ligands. In some embodiments, the viral coat of a pseudotyped oncolytic virus comprises one or more chimeric proteins. In some embodiments, the chimeric proteins are comprised of parts of an endogenous viral protein necessary for incorporation into the virion, as well proteins or nucleic acids designed to interact with specific host cell proteins (e.g., targeting moieties).

The non-viral targeting moieties may be any moiety capable of binding to a corresponding receptor or ligand on the surface of a selected cell type, thereby directing the interaction between the virus particle and the selected cell type. In some instances, any cell surface biological material known in the art (e.g., a protein, lipid, or carbohydrate) or yet to be identified that is differentially expressed or otherwise present on a particular cell or tissue type (e.g., a tumor or tumor cell, or tumor associated stroma or stromal cell) may be used as a potential target for the oncolytic viruses the present invention. In particular embodiments, the cell surface material is a protein. In some embodiments, the targeting moiety binds cell surface antigens indicative of a disease, such as a cancer (e.g., breast, lung, ovarian, prostate, colon, lymphoma, leukemia, melanoma, and others); an autoimmune disease (e.g. myasthenia gravis, multiple sclerosis, systemic lupus erythymatosis, rheumatoid arthritis, diabetes mellitus, and others); an infectious disease, including infection by HIV, HCV, HBV, CMV, and HPV; and a genetic disease including sickle cell anemia, cystic fibrosis, Tay-Sachs, J3-thalassemia, neurofibromatosis, polycystic kidney disease, hemophilia, etc. In certain embodiments, the targeting moiety targets a cell surface antigen specific to a particular cell or tissue type, e.g., cell-surface antigens present in neural, lung, kidney, muscle, vascular, thyroid, ocular, breast, ovarian, testis, or prostate tissue.

Exemplary antigens and cell surface molecules for targeting include, e.g. P-glycoprotein, Her2/Neu, erythropoietin (EPO), epidermal growth factor receptor (EGFR), vascular endothelial growth factor receptor (VEGF-R), cadherin, carcinoembryonic antigen (CEA), CD4, CD8, CD19, CD20, CD33, CD34, CD45, CD117 (c-kit), CD133, HLA-A, HLA-B, HLA-C, chemokine receptor 5 (CCR5), ABCG2 transporter, ovarian cancer antigen CA125, immunoglobulins, integrins, prostate specific antigen (PSA), prostate stem cell antigen (PSCA), dendritic cell-specific intercellular adhesion molecule 3-grabbing nonintegrin (DC-SIGN), thyroglobulin, granulocyte-macrophage colony stimulating factor (GM-CSF), myogenic differentiation promoting factor-1 (MyoD-1), Leu-7 (CD57), LeuM-1, cell proliferation-associated human nuclear antigen defined by the monoclonal antibody Ki-67 (Ki-67), viral envelope proteins, HIV gp120, transferrin receptor, etc.

In some embodiments, the viral coat comprises a capsid. In some instances, the capsid is assembled from oligomeric protein subunits termed protomers. In some embodiments, the capsid is assembled from one type of protomer or protein, or is assembled from two, three, four, or more types of protomers or proteins. In some embodiments, the viral coat comprises a viral envelope. In some instances, the viral envelope comprises a phospholipid bilayer and proteins such as proteins obtained from a host membrane. In some embodiments, the viral envelope further comprises glycoproteins for recognition and attachment to a receptor expressed by a host cell. In some embodiments, the pseudotyped oncolytic viruses described herein comprise one or more heterologous glycoproteins (GPs) or one or more endogenous GPs that have been modified (i.e., by amino acid mutation). In some embodiments, the pseudotyped oncolytic viruses described herein comprise one or more GPs derived from VSV. In some embodiments, the pseudotyped oncolytic viruses described herein comprise one or more GPs derived from lyssavirus, lymphocytic choriomeningitis virus, alphavirus GPs (e.g., RRV and SFV GPs), sindbis virus, filovirus, and baculovirus (e.g., GP64).

In some embodiments, the pseudotyped oncolytic viruses described herein demonstrate i) altered tropism relative to non-pseudotyped virus; and/or ii) reduction or elimination of a non-beneficial effect, such as infectivity of healthy cells or tissue; and/or iii) increase of a beneficial effect, such as infectivity of cancerous cells or tissue. For example, in some embodiments a pseudotyped virus demonstrates reduced toxicity or reduced infection of non-tumor cells or non-tumor tissue as compared to a non-pseudotyped virus. In some embodiments, a pseudotyped virus is capable of infecting a cell or tissue type that the corresponding non-pseudotyped virus is not capable of infecting. In some embodiments, a pseudotyped virus is capable of preferentially infecting a cell or tissue type compared to a non-pseudotyped virus.

Figure 36:
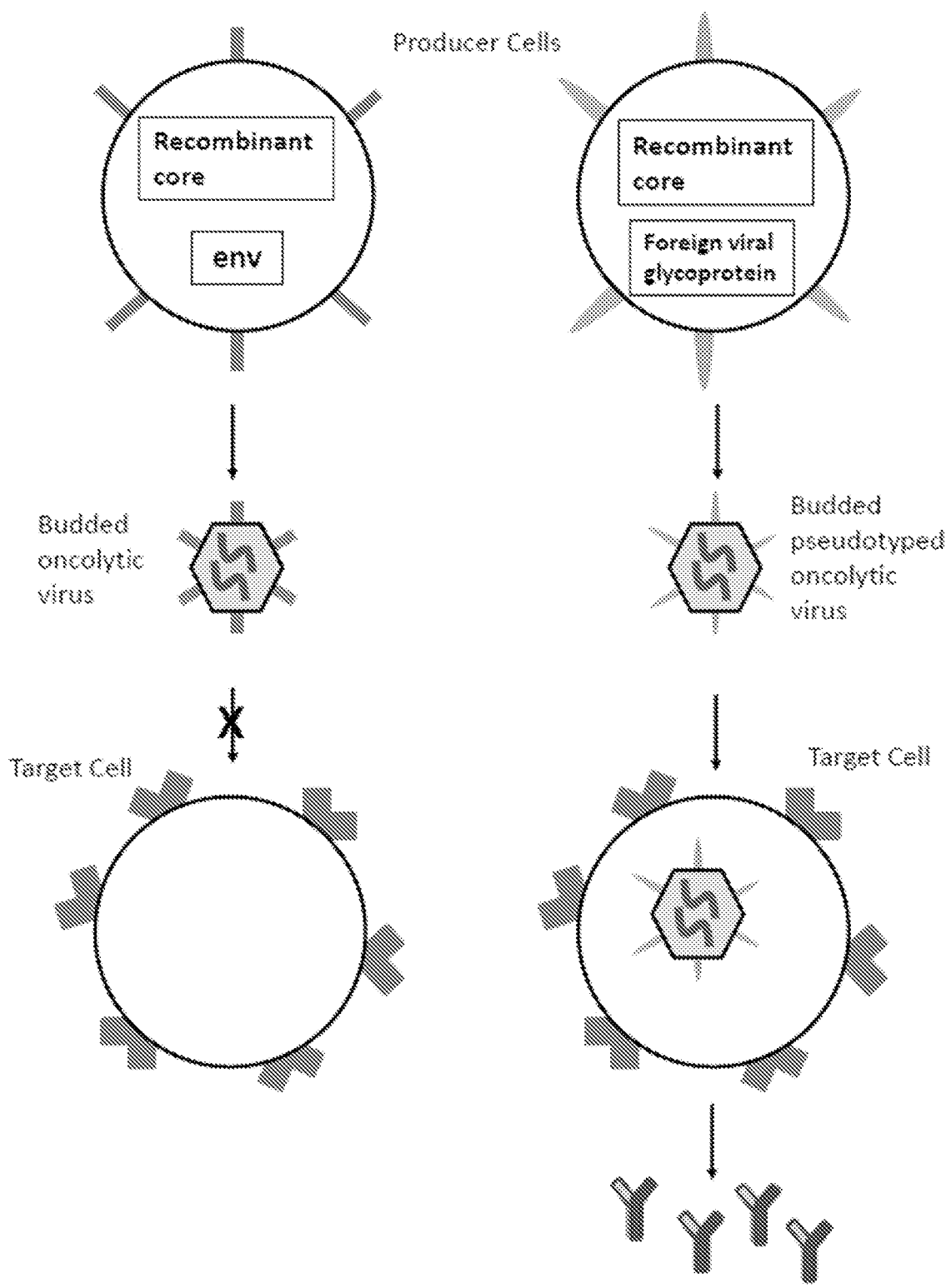
FIG. 36 illustrates a cartoon representation of the production of a pseudotyped oncolytic virus and a recombinant oncolytic virus and infection of a target cell by the respective pseudotyped oncolytic virus and the recombinant oncolytic virus.

In some embodiments, the pseudotyped oncolytic viruses provided herein are capable of selectively entering, replicating in, and/or lysing tumor cells. Such an embodiment is illustrated in FIG. 36, wherein the pseudotyped oncolytic virus gains entry to the target cell due to the incorporation of viral glycoproteins derived from a different (i.e., heterologous) virus that allow for entry of the pseudotyped oncolytic virus into the target cell. In contrast, the non-pseudotyped oncolytic virus is unable to gain entry into the target cell due to the non-permissive nature of the envelope proteins. In some instances, the ability of a pseudotyped oncolytic virus to selectively enter, replicate in, and/or lyse a tumor cells is due to a reduced or otherwise ineffective cellular interferon (IFN) response. In some embodiments, the pseudotyped oncolytic viruses produce an engager molecule and/or a therapeutic molecule, such as an immune modulating polypeptide, that interferes or impairs the cellular IFN response, thereby enhancing the replication of the pseudotyped or engineered virus.

The pseudotyped oncolytic viruses described herein may be derived from a variety of viruses, non-limiting examples of which include vaccinia virus, adenovirus, herpes simplex virus 1 (HSV1), myxoma virus, reovirus, poliovirus, vesicular stomatitis virus (VSV), measles virus (MV), lassa virus (LASV) and Newcastle disease virus (NDV). In some embodiments, the pseudotyped oncolytic viruses described herein can infect substantially any cell type. An exemplary lentivirus for use in oncolytic therapy is Simian immunodeficiency virus coated with the envelope proteins, G-protein (GP), from VSV. In some instances, this virus is referred to as VSV G-pseudotyped lentivirus, and is known to infect an almost universal set of cells.

In some embodiments, the present invention provides recombinant vesicular stomatitis viruses (VSV) and VSV vectors. The VSV genome includes five genes, l, m, n, p and g, which encode the proteins L, M, N, P and G and are essential for the reproduction of the virus. N is a nucleoprotein which packages the VSV genomic RNA. The VSV genome is replicated as RNA-protein complex and L and P together form a polymerase complex which replicates the VSV genome and transcribes the VSV mRNA. M is a matrix protein which provides structural support between the lipid envelope and nucleocapsid and is important for particle sprouting at the cell membrane. G is the envelope protein which is incorporated in the viral envelope and is essential for the infectivity and tropism of the virus.

In some embodiments, the pseudotyped oncolytic viruses of the present invention are VSV viruses pseudotyped against healthy brain cells, i.e., neurons and exhibit considerably reduced toxicity. Since neurotropism is a dose-limiting factor in all applications of oncolytic VSV, the use of the vector according to some embodiments of the present invention is that they are used for all tumors types of solid tumors.

In some embodiments, the pseudotyped VSV vectors have one or more key attributes including: (i) the VSV is not cell-toxic; (ii) the vectors are concentrated by ultracentrifugation without loss of infectivity; and (iii) the vectors show a tropism for tumor cells, whereas neurons and other non-tumor cells are infected inefficiently. To increase the safety during the use of replicable viruses in therapeutic uses, some embodiments of the present invention provide a vector system which ensures that replication, oncolysis and the production of VSV viruses takes place only in cells which are infected by at least two replication-deficient, mutually complementing vectors.

In some embodiments, the genetic material (e.g., the viral coat protein or the core genetic material) for generating a pseudotyped oncolytic virus is obtained from a DNA virus, an RNA virus, or from both virus types. In some embodiments, a DNA virus is a single-stranded (ss) DNA virus, a double-stranded (ds) DNA virus, or a DNA virus that contains both ss and ds DNA regions. In some embodiments, an RNA virus is a single-stranded (ss) RNA virus or a double-stranded (ds) RNA virus. In some embodiments, an ssRNA virus is further classified into a positive-sense RNA virus or a negative-sense RNA virus.

In some instances, the genetic material for generating a pseudotyped oncolytic virus is obtained from a dsDNA virus of any one of the following families: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, or Tectiviridae.

In some cases, the genetic material for generating a pseudotyped oncolytic virus is obtained from a ssDNA virus of any one of the following families: Anelloviridae, Bacillariodnaviridae, Bidnaviridae, Circoviridae, Geminiviridae, Inoviridae, Microviridae, Nanoviridae, Parvoviridae, or Spiraviridae.

In some embodiments, the genetic material for generating a pseudotyped oncolytic virus is obtained from a DNA virus that contains both ssDNA and dsDNA regions. In some cases, the DNA virus is from the group pleolipoviruses. In some cases, the pleolipoviruses include *Haloarcula hispanica* pleomorphic virus 1, Halogeometricum pleomorphic virus 1, Halorubrum pleomorphic virus 1, Halorubrum pleomorphic virus 2, Halorubrum pleomorphic virus 3, or Halorubrum pleomorphic virus 6.

In some cases, the genetic material for generating a pseudotyped oncolytic virus is obtained from a dsRNA virus of any one of the following families: Birnaviridae, Chrysoviridae, Cystoviridae, Endornaviridae, Hypoviridae, Megavirnaviridae, Partitiviridae, Picobirnaviridae, Reoviridae, Rotavirus or Totiviridae.

In some instances, the genetic material for generating a pseudotyped oncolytic virus is obtained from a positive-sense ssRNA virus of any one of the following families: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae Leviviridae, Luteoviridae, Marnaviridae, Mesoniviridae, Narnaviridae, Nodaviridae, Permutotetraviridae, Picornaviridae, Potyviridae, Roniviridae, Secoviridae, Togaviridae, Tombusviridae, Tymoviridae, or Virgaviridae.

In some cases, the genetic material for generating a pseudotyped oncolytic virus is obtained from a negative-sense ssRNA virus of any one of the following families: Bornaviridae, Filoviridae, Paramyxoviridae, Rhabdoviridae, Nyamiviridae, Arenaviridae, Bunyaviridae, Ophioviridae, or Orthomyxoviridae.

In some instances, the genetic material for generating a pseudotyped oncolytic virus is obtained from oncolytic DNA viruses that comprise capsid symmetry that is isocahedral or complex. In some cases, isosahedral oncolytic DNA viruses are naked or comprise an envelope. Exemplary families of oncolytic DNA viruses include the Adenoviridae (for example, Adenovirus, having a genome size of 36-38 kb), Herpesviridae (for example, HSV1, having a genome size of 120-200 kb), and Poxviridae (for example, Vaccinia virus and myxoma virus, having a genome size of 130-280 kb).

In some cases, the genetic material for generating a pseudotyped oncolytic virus is obtained from oncolytic RNA viruses include those having icosahedral or helical capsid symmetry. In some cases, icosahedral oncolytic viruses are naked without envelope and include Reoviridae (for example, Reovirus, having a genome of 22-27 kb) and Picornaviridae (for example, Poliovirus, having a genome size of 7.2-8.4 kb). In other cases, helical oncolytic RNA viruses are enveloped and include Rhabdoviridae (for example, VSV, having genome size of 13-16 kb) and Paramyxoviridae (for example MV and NDV, having genome sizes of 16-20 kb).

In some instances, the genetic material for generating a pseudotyped oncolytic virus is obtained from a virus such as Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat Lyssavirus, Aviadenovirus, avian erythroblastosis virus, avian infectious bronchitis virus, avian leukemia virus, avian 23apulose virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus. BK virus, Black Creek Canal virus, bluetongue virus, Bolivian hemorrhagic fever virus. Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine 23apulose virus, bovine mammillitis virus, bovine papillomavirus, bovine 23apulos stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charieville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV eastern equine encephalitis virus, eastern equine encephalomyelitis virus, EB virus. Ebola virus, Ebola-like virus, echo virus, echovirus, echovirus 10, echovirus 28, echovirus 9, ectromelia virus, FEE virus, HA virus, ETA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, fetid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden 24apulo virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, 24apulo virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus. Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, mucid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus. Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis 27apulose virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Tatera.pox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilvuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

Methods of Producing Pseudotyped Oncolytic Viruses

In some instances, a pseudotyped oncolytic virus described herein is generated using methods well known in the art. In some instances, the methods involve one or more transfection steps and one or more infection steps. In some instances, a cell line such as a mammalian cell line, an insect cell line, or a plant cell line is infected with a pseudotyped oncolytic virus described herein to produce one or more viruses. Exemplary mammalian cell lines include: 293A cell line, 293FT cell line, 293F cells, 293 H cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, I-REx™ Jurkat cell line, Per. C6 cells, T-REx™-293 cell line, T-REx™-CHO cell line, T-REx™-HeLa cell line, 3T6, A549, A9, AtT-20, BALB/3T3, BHK-21, BHL-100, BT, Caco-2, Chang, Clone 9, Clone M-3, COS-1, COS-3, COS-7, CRFK, CV-1, D-17, Daudi, GH1, GH3, H9, HaK, HCT-15, HL-60, HT-1080, HT-29, HUVEC, I-10, IM-9, JEG-2, Jensen, K-562, KB, KG-1, L2, LLC-WRC 256, McCoy, MCF7, VERO, WI-38, WISH, XC, or Y-1. Exemplary insect cell lines include *Drosophila* S2 cells, Sf9 cells, Sf21 cells, High Five™ cells, or expresSF+® cells. Exemplary plant cell lines include algae cells such as for example *Phaeocystis pouchetii*.

Any method known to one skilled in the art is used for large scale production of recombinant oncolytic vectors and vector constructs, such as pseudotyped oncolytic vectors. For example, master and working seed stocks can be prepared under GMP conditions in qualified primary CEFs or by other methods. In some instances, cells are plated on large surface area flasks, grown to near confluency, and infected at selected MOI. The produced virus can then be purified. In some cases, cells are harvested and intracellular virus is released by mechanical disruption. In some embodiments, cell debris is removed by large-pore depth filtration and/or host cell DNA is digested with an endonuclease. In some cases, virus particles are subsequently purified and concentrated by tangential-flow filtration, followed by diafiltration. The resulting concentrated virus can formulated by dilution with a buffer containing one or more stabilizers, filled into vials, and lyophilized. Compositions and formulations can be stored for later use. In some embodiments, a lyophilized virus is reconstituted by addition of one or more diluents.

MicroRNA-Attenuated Oncolytic Viruses

In some embodiments, the present invention provides oncolytic viruses, wherein one or more micro-RNA (miR) target sequences are inserted into a locus of one or more viral genes required for viral replication. The terms "microRNA" and "miRNA" and "miR" are used interchangeably herein and refer to small non-coding endogenous RNAs that regulate gene expression by directing their target messenger RNAs (mRNA) for degradation or translational repression. miRs are differentially expressed in a broad array of disease states, including multiple types of cancer. In some aspects, cancer cells of a given cancer type or tissue demonstrate differential expression of miRs compared to non-cancerous control cells. As used herein, the term "oncomiR" refers to miRs that are associated (either positively or negatively) with carcinogenesis, malignant transformation, and/or metastasis. In some aspects, the expression level of a particular oncomiR is associated with the development or maintenance of a particular cancer. Such miRs are referred to herein as "oncogenic miRs." In some embodiments, the expression of a particular oncomiR is associated with the prevention and/or delay of carcinogenesis and/or metastasis. Such oncomiRs are referred to herein as "tumor-suppressor miRs" or "tumor-suppressive miRs," as their expression prevents or suppresses the development of cancer.

One aspect of the invention comprises a recombinant oncolytic virus (or viral vector) comprising a plurality of copies of one or more tumor-suppressive miRNA target sequences inserted into a locus of one or more viral genes required for viral replication. In certain embodiments, a recombinant oncolytic virus may comprise tumor-suppressive miRNA target sequences inserted into a locus of at least one, at least two, at least three, at least four, at least five, at least six, at least seven, at least eight, at least nine, or at least ten viral genes required for viral replication. Tumor-suppressor miRNAs expressed in normal (non-cancerous) cells can bind to such target sequences and suppress expression of the viral gene containing the miRNA target sequence, thereby limiting viral replication in healthy, non-cancerous cells. Such recombinant oncolytic viruses and/or vectors are referred to herein as "miR-attenuated" or "replication-restricted" as they result in reduced or attenuated viral replication in cell that express a tumor-suppressive miR capable of binding to the incorporated tumor-suppressive miR target sequence compared to cells that do not express, or have reduced expression of, the tumor-suppressive miR. By incorporating tumor-suppressive miRNAs into key genes required for viral replication, viral replication can be conditionally suppressed in normal diploid cells expressing the tumor-suppressive miRNAs and can proceed normally in cells that do not express the tumor-suppressive miRNAs. In such embodiments, healthy, non-cancerous cells are protected from the normal cells from lytic effects of infection by the recombinant viral vector. Exemplary miR-attenuated oncolytic viruses are described in PCT Publication No. WO 2017/132552, which is incorporated by reference in its entirety. In some embodiments, one or more target sequences for miR-1, miR-9, miR-10b, miR-17, miR-21, miR-30a, miR-96, miR-106a, miR-122, miR-124, miR-125b, miR-126, miR-127, miR-128, miR-133a, miR-137, miR-143, miR-145, miR-146a, miR-146b, miR-148a, miR-150, miR-155, miR-182, miR-183, miR-204, miR-206, miR-208a, miR-208b, miR-218, miR-219a, miR-221, miR-222, miR-378g, miR-378i, miR-499, miR-885, miR-1247-5p, or miR-4284.

Engager Molecules

In some embodiments, the oncolytic viruses described herein comprise a polynucleotide sequence that encodes an engager molecule, e.g., an engager polypeptide. The engager molecules of the present invention comprise at least two domains each capable of binding to a different cell surface molecule.

In some embodiments, the engager molecule is a bipartite polypeptide (i.e., comprises 2 domains each binding to a different cell surface protein). In some embodiments, the engager molecule is a tripartite or multipartite polypeptide (i.e., comprises 3 or more domains each binding to a different cell surface protein). In such embodiments, the engager molecule comprises one or more effector domains and one or more activation or targeting domains. In some embodiments, the engager molecules further comprise one or more dimerization or trimerization domains. In some embodiments, the engager molecule is a tripartite polypeptide comprising (i) an effector domain, (ii) an activation or targeting domain, and (iii) an additional domain e.g., an additional effector domain, an additional activation domain, an additional targeting domain, a therapeutic molecule domain (such as a cytokine, a co-stimulatory domain, an immune checkpoint inhibitor, or an anti-angiogenic factor, described infra), or a combination thereof. In some embodiments, the engager is a first polypeptide provided within the oncolytic virus with a second polypeptide having one or more other domains, e.g., one or more of a cytokine, a co-stimulatory domain, a domain that inhibits negative regulatory molecules of T-cell activation, or a combination thereof. In some embodiments, the first polypeptide and the second polypeptide are encoded in the same vector (e.g., viral vector). In some embodiments, the first polypeptide and the second polypeptide are encoded in different vectors (e.g., viral vectors). In specific embodiments, the cytokine is IL-15, IL-2, and/or IL-7. In other specific embodiments, the co-stimulatory domain is CD27, CD80, CD83, CD86, CD134, or CD137. In other specific embodiments, the domain that inhibits negative regulatory molecules of T-cell activation is PD-1, PDL1, CTLA4, or B7-H4.

In some embodiments, the engager molecules of the present invention are in one of the following formats: DVD-Ig, Fab-scFv-Fc, Morrison heterodimer (2+1), Fc-DART, Azymertric™ bispecific Abs, Binanbody, multi-DARPin, an antibody, an antibody domain, a human immunoglobulin heavy chain variable domain, a dual-variable-domain antibody (DVD-Ig), a Tandab, a diabody, a flexibody, a dock-and-lock antibody, a single chain variable fragment (scFv), a BiTE, a DuoBody, an Fc-engineered IgG, an Fcab, a Mab2, or DART polypeptide.

In some embodiments, the engager molecule comprises an antibody or an antigen-binding fragment thereof e.g., a single chain variable fragment (scFv), an Fab, an Fv, a minibody, or a diabody. In some embodiments, the engager molecule is a is a trifunctional antibody, an Fab₂, a bi-specific scFv such as a bi-specific T-cell engager (BiTE), a bivalent minibody, a bispecific diabody, a DuoBody, or an Mab2. In certain embodiments, the engager molecule is a bipartite T cell engager (BiTE) or a tripartite T cell engager (TiTE). In some embodiments, these antibody-derived fragments or derivatives may be modified by chemical, biochemical, or molecular biological methods. In some instances, the antibodies or antigen-binding fragments thereof used in the construction of the engager molecules described herein are humanized or deimmunized constructs. Methods for the humanization and/or deimmunization of polypeptides and, in particular, antibody constructs are known to the person skilled in the art. Corresponding methods are known in the art and described, inter alia, in laboratory manuals (see Sambrook et al., Molecular Cloning: A Laboratory Manual; Cold Spring Harbor Laboratory Press, 2nd edition 1989 and 3rd edition 2001; Gerhardt et al., Methods for General and Molecular Bacteriology, ASM Press, 1994; Lefkovits, Immunology Methods Manual: The Comprehensive Sourcebook of Techniques; Academic Press, 1997; Golemis, Protein-Protein Interactions: A Molecular Cloning Manual; Cold Spring Harbor Laboratory Press, 2002). In some embodiments, the domains of the engager molecule comprise a ligand, a peptide, a peptide that recognize and interacts with a cell surface receptor.

In some embodiments, two or more of the domains of an engager molecule are linked by a linker. In some instances, the linker is of any suitable length, and such a parameter is routinely optimized in the art. For example, linkers are of a length and sequence sufficient to ensure that each of the domains can, independently from one another, retain their differential binding specificities. The term "peptide linker" refers to an amino acid sequence by which the amino acid sequences of a first domain and a second domain of a defined construct are linked together. In some instance, one technical feature of such peptide linker is that said peptide linker does not comprise any polymerization activity and/or does not promote formation of secondary structures. Such peptide linkers are known in the art and described, for example, in Dall'Acqua et al. (Biochem. (1998) 37, 9266-9273); Cheadle et al. (Mol Immunol (1992) 29, 21-30); and Raag and Whitlow (FASEB (1995) 9(1), 73-80). In some embodiments, the peptide linkers of the present invention comprise less than 5 amino acids, less than 4 amino acids, less than 3 amino acids, less than 2 amino acids, or 1 amino acid. In some embodiments, the peptide linker is a single amino acid linker. In such embodiments, the single amino acid is typically a glycine (Gly). In some embodiments, peptide linkers that also do not promote any secondary structures are preferred. Methods for preparing fused, operatively-linked constructs and their expression in mammalian or bacterial cells are well-known in the art (See e.g., International PCT Publication No. WO 99/54440; Ausubel, Current Protocols in Molecular Biology, Green Publishing Associates and Wiley Interscience, N.Y. 1989 and 1994; and Sambrook et al., Molecular Cloning: A Laboratory Manual, Cold Spring Harbor Laboratory Press, Cold Spring Harbor, New York, 2001).

In some embodiments, the engager molecule is a single chain bi-specific antibody construct comprising two antibody-derived binding domains. In such embodiments, one of the binding domains comprises variable regions (or parts thereof) of the heavy chain ($V_H$) and light chain ($V_L$) of an antibody capable of specifically binding to/interacting with a first cell surface molecule and the second binding domain comprises variable regions (or parts thereof) of the heavy chain ($V_H$) and light chain ($V_L$) of an antibody capable of specifically binding to/interacting with a second cell surface molecule. In particular embodiments, each of the two antibody-derived binding domains comprise at least one complementary determining region (CDR), particularly a CDR3. In some embodiments, the single chain bi-specific antibody construct is a diabody. In some embodiments, the single chain bispecific antibody construct is a single chain bispecific scFv, wherein the two scFvs are connected by a peptide or linker sequence. In some embodiments, a single chain bispecific scFv further comprises a signal peptide to allow for secretion from cells. Bispecific single chain molecules are known in the art and are described in International PCT Publication No. WO 99/54440; Mack, J. Immunol. (1997), 158, 3965-3970; Mack, PNAS, (1995), 92, 7021-7025; Kufer, Cancer Immunol Immunother, (1997), 45, 193-197; Loftier, Blood, (2000), 95, 6, 2098-2103; and Bruhl, J. Immunol., (2001), 166, 2420-2426.

In some embodiments, the molecular format of the polynucleotide encoding a single chain bi-specific scFv polypeptide comprises a nucleic acid sequence encoding a signal peptide (such as the signal sequences of SEQ ID NO: 2 or 4) followed by two or more scFv regions (e.g., a first scFv and a second scFv) each comprising one $V_H$ and one $V_L$ chain linked together. In specific embodiments, the two or more antibody-derived regions are scFvs and are linked by a peptide linker to form a single chain bi-specific scFv construct. In some embodiments, the bi-specific scFv is a tandem bi-scFv or a diabody. Single chain bispecific scFvs can be arranged in different formats from N-terminus to C-terminus, including the following, wherein "L" is a linker:
$V_H1$-L-$V_L1$-L-$V_H2$-L-$V_L2$;    $V_L1$-L-$V_H1$-L-$V_H2$-L-$V_L2$;
$V_H1$-L-$V_L1$-L-$V_L2$-L-$V_H2$;    $V_L1$-L-$V_H1$-L-$V_L2$-L-$V_H2$;
$V_H2$-L-$V_L2$-L-$V_H1$-L-$V_L1$;    $V_L2$-L-$V_H2$-L-$V_H1$-L-$V_L1$;
$V_H2$-L-$V_L2$-Ly-$V_L1$-L-$V_H1$;    $V_L2$-L-$V_H2$-L-$V_L1$-L-$V_H1$;
$V_H1$-L-$V_H2$-L-$V_L2$-L-$V_L1$; $V_L2$-L-$V_L1$-L-$V_H1$-L-$V_H2$; $V_H2$-L-$V_H1$-L-$V_L1$-L-$V_L2$; or $V_L1$-L-$V_L2$-L-$V_H2$-L-$V_H1$.

In some embodiments, the engager molecules of the present invention specifically bind to/interact with a particular conformational/structural epitope(s) of cell-surface molecules. Accordingly, specificity in some instances is determined experimentally by methods known in the art and methods as disclosed and described herein. Such methods comprise, but are not limited to Western blots, enzyme-linked immunosorbent assay (ELISA), radioimmunoassay (RIA), radioimmunoprecipitation (RIP), electrochemiluminescence (ECL), immunoradiometric assay (IRMA), enzyme immunoassay (EIA), and peptide scans.

In some embodiments, the engager polypeptides comprise an effector domain and a targeting domain or an activation domain. In some embodiments, the respective domains are in any order from N-terminus to C-terminus. For example, in some embodiments, the engager molecule comprises an N-terminal effector domain and a C-terminal targeting domain. In some embodiments, the engager molecule may comprise an N-terminal targeting domain and a C-terminal effector domain. In some embodiments, the engager molecule may comprise an N-terminal effector domain and a C-terminal activation domain. In some embodiments, the engager molecule may comprise an N-terminal activation domain and a C-terminal effector domain. In some embodiments, the engager molecule comprises multiple (e.g., 2, 3, 4, 5 or more) targeting domains to allow targeting of multiple antigens on target cells. In some embodiments, the engager molecule comprises multiple (e.g., 2, 3, 4, 5 or more) effector domains. In some embodiments, the engager molecule comprises multiple (e.g., 2, 3, 4, 5 or more) activation domains. In some embodiments of the disclosure, the engager molecule comprises additional domains for the isolation and/or preparation of recombinantly produced constructs, such as a tag or a label. The tag or label may be a short peptide sequence, such as a histidine tag (SEQ ID NO: 12), or may be a tag or label that is capable of being imaged, such as fluorescent or radioactive label.

In some embodiments, the engager polypeptides comprise an effector domain and a targeting domain or an activation domain. An "effector domain" recognizes and binds to a molecule present on the surface of an effector cell. As used herein, the term "effector cell" refers to any mammalian cell type that is capable of mediating an immune response, including facilitating the death of a target cell. In particular embodiments, the effector cells of the present invention are immune cells, such as a T cell, a B cell, an innate lymphocyte, a natural killer (NK) cell, a natural killer T cell (NKT), a granulocyte (e.g., a neutrophil, basophil, mast cell, or eosinophil), a macrophage, a monocyte, or a dendritic cell. Exemplary effector cell types include T cells, NK cells, NKT cells, and macrophages. The skilled artisan will recognize that the nature of the cell surface molecule recognized by the effector domain may vary according to the nature of the effector cell, although different groups of effector cells may share expression of certain types of cell surface molecules. For example, T cells express different surface receptors than NK cells or macrophages. As an illustrative example, CD3 is a receptor expressed by T-cells that is not expressed by NK cells or macrophages, whereas CD1, CD16, NKG2D, and/or NKp30 are receptors expressed by NK cells that are not expressed by T cells. Therefore, in some instances, engager molecules that activate T-cells have a different effector domain than engager molecules that activate NK cells, macrophages, NKT cells, or other types of effector cells.

In some embodiments, the effector cell is a T cell. The T-cell repertoire is comprised of numerous sub-types of T cell, cytotoxic T cells (Tc or CTL), memory T cells, helper T cells (e.g., Th1, Th2, Th17, Th9, and/or Th22 cells), suppressor T cells (e.g., regulator T cells (Tregs)), mucosal-associated invariant T cells, and γδ T cells. In some instances, one or more surface receptors expressed by one T cell subtype are not expressed by another T cell subtype. In some instances, one or more surface receptors expressed by one T cell subtype are expressed by at least one other T cell subtype. In some instances, one or more surface receptors expressed by one T cell subtype are generally expressed by all, or most, T cell subtypes. For example, CD3 is a signaling component of the T cell receptor (TCR) complex and is expressed in multiple T cell subtypes.

In some embodiments, the effector cell is a T cell and the effector domain of the engager molecule binds to one or more components of CD3 (e.g., CD3γ, CD3δ, CD3ε or CD3ξ), CD2, CD4, CD5, CD6, CD7, CD8, CD25, CD27, CD28, CD30, CD38, CD40, CD57, CD69, CD70, CD73, CD81, CD82, CD96, CD134, CD137, CD152, CD278 and/or LIGHT (also known as TNFSF14). In some embodiments, the effector cell is an NKT-cell and the effector domain of the engager molecule binds to one or more components of CD3 or an invariant TCR. In some embodiments, the effector cell is an NK cell and the effector domain of the engager molecule binds to CD16, CD94/NKG2 (e.g., NKG2D), NKp30, NKp44, NKp46, or killer activation receptors (KARs). Additional cell-surface molecules that can be expressed on lymphocytes and can be bound by effector domains of engager molecules include CD48, expressed by T cells and NK cells.

In some embodiments, binding of an effector domain to a molecule present on the surface of an effector cell results in activation of the effector cell. In some embodiments, activation of an effector cell results in one or more of the following: (i) increased proliferation of the effector cell; (ii) changes in the expression or activity of one or more cell surface proteins of the effector cell; (iii) change in expression or activity of one or more intracellular proteins expressed by the effector cell; (iv) changes in the amount or nature of factors produced and/or secreted by the effector cell, such as cytokines, chemokines or reactive oxygen species; (v) changes in the morphology of the effector cell; (vi) changes in the chemotactic potential of the effector cell, such as through increased or decreased expression of one or more chemokine receptors; (vii) changes in the functional activity of the effector cell, such as increased cytolytic activity and/or increased phagocytic activity; and/or (viii) increased cytotoxicity against a target cell. Activation of an effector cell, or population of effector cells, can be determined by any means known in the art. For example, changes in proliferation, protein expression, production, or secretion can be determined by flow cytometry, Western blot, ELISA, immunohistochemistry, immunoprecipitation, or immunofluorescence and changes in cell morphology can be determined by numerous types of microscopy known in the art.

In some embodiments, the engager polypeptides comprise an effector domain and an activation domain. An "activation domain" of an engager molecule binds to a protein expressed on the cell-surface and results in cell activation. In some embodiments, the cell-surface protein recognized by the activation domain and the cell-surface protein recognized by the effector domain are both expressed on an effector cell. However, the cell-surface protein recognized by the activation domain is distinct from the cell-surface protein recognized by the effector domain. In particular embodiments, the activation domain binds to a cell surface protein that is a negative regulator of effector cell function (e.g., an immune checkpoint molecule or other inhibitory molecule). Exemplary cell-surface antigen for targeting by an activation domain include 2B4, A2aR, B7H3 (CD276), B7H4, CD2, CD28, CD30, CD40, CD47, CD70, CD80, CD86, CD137, CD160, CD226, DR3, GALS, GITR, HAVCR2, HVEM, IDO1, IDO2, ICOS, LAIR1, LIGHT, MARCO, PS, SLAM, TIGHT, VISTA, VTCN1, PD1, PDL1, PDL2, CTLA4, TIM2, LAG3, BTLA, KIR, TIGIT, OX40, FITR, CD27, SLAMF7, and CD200. In certain embodiments, engager molecules comprising an activation domain and an effector domain enhance the activation of the effector cell and thereby facilitate the destruction of one or more bystander target cells by the effector cell.

In some embodiments, the engager polypeptides comprise an effector domain and a targeting domain. A "targeting domain" of an engager molecule binds to a cell-surface molecule expressed by a target cell. As used herein, the term "target cell" refers to a mammalian cell that should be killed, attacked, destroyed, and/or controlled. In particular, target cells are cells that are in some way altered compared to a normal cell of the same cell type, such as a cancerous cell, a bacterially-infected cell, a virally-infected cell, a fungally-infected cell, and/or an autoimmune cell. In particular embodiments, the target cells of the present invention are cancerous cells (e.g., tumor cells). In some embodiments, binding of an engager molecule to a target cell and an effector cell brings the effector cell in close proximity to the target cell and thereby facilitates the destruction of the target cell by the effector cell. Destruction (i.e., death) of a target cell can be determined by any means known in the art, such as flow cytometry (e.g., by AnnexinV, propidium iodide, or other means), cell counts, and/or microscopy to determine the cellular morphology of the target cells.

In some embodiments, the targeting domain of an engager molecule brings a target cell (e.g., tumor cell) into the vicinity of an effector cell via interaction between the targeting domain and surface antigens expressed by the target cell (e.g., target cell antigens). In some embodiments, the target-cell antigen is a tumor antigen. In some embodiments, a tumor antigen is a tumor-specific antigen (TSA), and is expressed only by tumor cells. In some embodiments, the target cell antigen is a tumor-associated antigen (TAA), and is expressed by tumor cells and one or more types of normal cells or non-tumor cells. In some cases, TSA is also present in one or more types of normal cells or non-tumor cells, but is predominantly expressed by tumor cells. In some instances, a tumor antigen (e.g., TSA or TAA) is present in one cancer type. In some instances, a tumor antigen is present in multiple cancer types. In one embodiment, a tumor antigen is expressed on a blood cancer cell. In another embodiment, a tumor antigen is expressed on a cell of a solid tumor. In some embodiments, the solid tumor is a glioblastoma, a non-small cell lung cancer, a lung cancer other than a non-small cell lung cancer, breast cancer, prostate cancer, pancreatic cancer, liver cancer, colon cancer, stomach cancer, a cancer of the spleen, skin cancer, a brain cancer other than a glioblastoma, a kidney cancer, a thyroid cancer, or the like. In more specific embodiments, a tumor antigen is expressed by a tumor cell in an individual.

In certain embodiments, the targeting domain of an engager molecule specifically binds a tumor-associated antigen (TAA) or a tumor-specific antigen (TSA). In certain embodiments, the targeting domain comprises an antibody or an antibody fragment or an antigen-binding fragment or portion thereof, such as for example, a monoclonal antibody, Fv, a scFv, Fab, minibody, or diabody that is specific for a TAA or TSA. In certain embodiments, the targeting domain of the engager is an scFv that is specific for a TAA or TSA. In a specific embodiment, the TAA or TSA is expressed on a cancer cell. In one embodiment, the TAA or TSA is expressed on a blood cancer cell. In another embodiment, the TAA or TSA is expressed on a cell of a solid tumor. In some embodiments, the solid tumor is a glioblastoma, a non-small cell lung cancer, a lung cancer other than a non-small cell lung cancer, breast cancer, prostate cancer, pancreatic cancer, liver cancer, colon cancer, stomach cancer, a cancer of the spleen, skin cancer, a brain cancer other than a glioblastoma, a kidney cancer, a thyroid cancer, or the like. In more specific embodiments, the TAA or TSA is expressed by a tumor cell in an individual.

Exemplary tumor antigens (e.g., TSAs or TAAs) include, but are not limited to, 5T4, 8H9, ABCG2, absent in melanoma 2 (AIM2), acetylglucosaminyltransferase-V (GnT-V, β1,6-N), alphafetoprotein (AFP), the transferrin receptor, antigen recognized by T cells (ART)-1, ART4, B7-H3, B7-H4, B7-H6, BCMA, BMI1 polycomb ring finger oncogene (BMI1), CA-125 (also known as MUC16), carbonic anhydrase (CA)-6, CA-9 (also known as CAIX), cadherin, calcium binding tyrosine-(Y)-phosphorylation regulated (CABYR), cancer/testis antigen 2 (CTAG2), carcinoembryonic antigen (CEA), cathepsin B, caveolin-1 (Cav-1), CCR8, CD10 (also known as neprilysin, membrane metallo-endopeptidase (MME), neutral endopeptidase (NEP), and common acute lymphoblastic leukemia antigen (CALLA)), CD117 (c-kit), CD123, CD133, CD138, CD15, CD171, CD19, CD20, CD21, CD22, CD30, CD33, CD38, CD4, CD44, CD44v6, CD44v7/8, CD45, CD70, CD74, CD79b, CD8, CEACAM5, cell proliferation-associated human nuclear antigen defined by the monoclonal antibody Ki-67 (Ki-67), chemokine receptor 5 (CCR5), CD74, CSAG family member 2 (CSAG2), chondroitin sulfate proteoglycan 4 (CSPG4, also known as MCSP), cyclin B, cyclooxygenase-2 (COX-2), cysteine-rich secretory protein 3 (CRISP3), dendritic cell-specific intercellular adhesion molecule 3-grabbing nonintegrin (DC-SIGN), dihydrofolate reductase (DHFR), EGP2, EGP40, enhancer of zeste homolog 2 (EZH2), EpCAM, EPH receptor A2 (EphA2), EphA2/epithelial kinase (EphA2/Eck), epidermal growth factor receptor variant III (EGFRvIII), epithelial calcium-dependent adhesion (E-cadherin), epithelial tumor antigen (ETA), ERBB3, ErbB3/4, ERBB4, erythropoietin (EPO), fibroblast activation protein (FAP), far upstream binding element 1 (FUBP1), FAR, folate binding proteins (FBP including Folate receptor alpha (FRα)), ferritin heavy polypeptide 1 testis-specific expression (FTHL17), fetal AchR, FGFR3, fos-related antigen 1 (Fra-1/Fos1 1), G antigen 1 (GAGE1), Ganglioside/GD2, GD3, glioma-associated oncogene homolog 1 (Gli1), glycoprotein 100 (GP100), Glypican-3, GPA33, granulocyte-macrophage colony stimulating factor (GM-CSF), H60, HIV gp120, HLA-A, HLA-A2, HLA-AI, HLA-B, HLA-C, HMW-MAA, human epidermal growth factor receptor 2 (Her2/Neu), human Ku heterodimer proteins subunits (u70/80), human LI cell adhesion molecule (LICAM), IL-15R, IL-1R2, IL-1Ra, immunoglobulins, integrins, interleukin-13 receptor subunit alpha-2 (IL-13Rα2), kappa light chain, lactate dehydrogenase C (LDHC), lambda light chain, LAMP-1 (also known as CD107b), layilin (LAYN), Leu-7 (CD57), LeuM-1, Lewis-Y, LIV-1, Livin (also known as BIRC7), melanoma antigen family A (MAGEA) 1, MAGEA3, MAGEA4, melanoma antigen family B 6 (MAGEB6), melanoma antigen recognized by T cells (MART-1), Mesothelin, mitogen-activated protein kinase 1 (MAPK1), mucin (MUC)-1, multidrug resistance protein 3 (MRP-3), myogenic differentiation promoting factor-1 (MyoD-1), sodium-dependent phosphate transport protein 2A (NaPi2a), neural cell adhesion molecule (NCAM), necrotic regions of tumors, nectin 4, Nestin, New York esophageal squamous cell carcinoma 1 (NY-ESO-1), NKG2D ligands (including the murine NKG2D ligands Rae-1α, Rae-1β, Rae-1γ, and Rae-1δ, and human NKG2D ligands MHC Class I polypeptide-related sequence A (MICA) and MICB, and ULBP1, ULBP2, ULBP3, ULBP4, ULBP5, and ULBP6), NLR family, nuclear proliferation-associated antigen of antibody Ki67 (Ki67), oligodendrocyte transcription factor (OLIG2), oncofetal variants of fibronectin, p53, P-Cadherin, PDZ binding kinase (PB), P-glycoprotein, preferentially expressed antigen in melanoma (PRAME), prospero homeobox protein 1 (PROX1), prostate specific antigen (PSA), prostate stem cell antigen (PSCA), prostate stem cell antigen (PSCA), PSC1, PSMA, pyrin domain containing 4 (NLRP4), Ras, ROR1, SART2, SART3, sex determining region Y-box (SOX)-2, SOX10, SOX11, SLITRK6, sperm protein associated with the nucleus X-linked family member A1 (SPANXA1), squamous cell carcinoma antigen recognized by T cells (SART)-1, synovial sarcoma X breakpoint 2 (SSX2), SSX4, SSX5, STEAP1, Survivin, TAG72, TEM1, TEM8, tenascin, testis specific 10 (TSGA10), testis-specific serine kinase 6 (TSSK6), thyroglobulin, TMEM97, TRP-2, tubby like protein (TULP2), tyrosinase, tyrosine related protein (TRP)-1, urokinase-type plasminogen activator receptor (UPAR), VEGF receptors (including VEGFR-R2, also known as KDR), VEGF, viral envelope proteins, v-raf murine sarcoma viral oncogene homolog B1 (BRAE), Wilms' tumor protein 1 (WT-1), X antigen family member 2 (XAGE2), zinc finger protein 165 (ZNF165), αvβ6 integrin, and β-catenin.

Ephrin Type-A Receptor 2 (EphA2)

In some embodiments, the target antigen is ephrin type-A receptor 2 (EPHA2, also known as ARCC2, CTPA, CTPP1, and ECK). The EPHA2 protein is a member of the ephrin receptor subfamily of the protein-tyrosine kinase family. Receptors in this subfamily generally comprise a single kinase domain and an extracellular region comprising a Cys-rich domain and 2 fibronectin type III repeats; embodiments of the antibodies of the disclosure target any of these domains. Exemplary human EphA2 nucleic sequences are provided in GenBank® Accession No. NM_004431.5 and NM_001329090.1, and exemplary human EphA2 polypeptide sequences are in GenBank® Accession No. NP_004422.2 and NP_001316019.1.

The Eph family, the largest group among tyrosine kinase receptor families, is comprised of the EphA (EphA1-10) or EphB (EphB1-6) subclasses of receptors classified by sequence homology and binding affinity for Ephrin (Eph receptor interacting protein) ligands. The human EphA2 gene is located on chromosome 1, encodes a receptor tyrosine kinase of 976 amino acids with an apparent molecular weight of 130 kDa and has a 90% amino acid sequence homology to the mouse EphA2. The Eph family contains an extracellular conserved N-terminal ligand-binding domain followed by a cysteine-rich domain with an epidermal growth factor-like motif and two fibronectin type-III repeats. The extracellular motif is followed by a membrane spanning region and a cytoplasmic region that encompasses a juxtamembrane region, a tyrosine kinase domain, a sterile alpha motif (SAM), and a post synaptic domain (disc large and zona occludens protein (PDZ) domain-binding motif). EphA2 shows 25-35% sequence homologies with other Eph receptors, and the tyrosine residues are conserved within the juxtamembrane and kinase domain.

EphA2 mRNA expression is observed in the skin, bone marrow, thymus, uterus, testis, prostate, urinary bladder, kidney, small intestine, colon, spleen, liver, lung, and brain. EphA2 expression in the colon, skin, kidney and lung is increased over ten-fold relative to the bone marrow. EphA2 is also expressed during gastrulation in the ectodermal cells and early embryogenesis in the developing hind brain. In the skin, EphA2 is present in keratinocytes of epidermis and hair follicles but not in dermal cells (fibroblasts, vascular cells and inflammatory cells). EphA2 is also expressed in proliferating mammary glands in female mice at puberty and differentially expressed during the estrous cycle. EphA2 is also overexpressed in several cancers, such as breast cancer, gastric cancer, melanoma, ovarian cancer, lunch cancer, gliomas, urinary bladder cancer, prostate cancer, esophageal cancer, renal cancer, colon cancer, and vulvar cancers. In particular, a high level of EphA2 is detected in malignant cancer-derived cell lines and advanced forms of cancer. In light of the EphA2 overexpression in pre-clinical models and clinical specimens of many different types of cancer, the increased level of EphA2 expression is informative in both the prediction of cancer outcomes and in the clinical management of cancer. The differential expression of EphA2 in normal cells compared to cancer cells also signifies its importance as a therapeutic target.

Human Epidermal Growth Factor Receptor 2 (HER2)

In some embodiments, the target antigen is human Epidermal Growth Factor Receptor 2 (HER2, also referred to as ERBB2, NEU, NGL, HER2, TKR1, CD340, HER-2, MLN 19, HER-2/neu). HER2 is a member of the epidermal growth factor receptor family having tyrosine kinase activity and is encoded by the HER2 gene in the epidermal growth factor receptor (EFR/ErbB) family. Dimerization of the receptor results in the autophosphorylation of tyrosine residues within the cytoplasmic domain of the receptors and initiates a variety of signaling pathways leading to cell proliferation and tumorigenesis. Amplification or overexpression of HER2 is associated with a multitude of different cancers and can serve as a prognostic and predictive biomarker. For example, amplification or overexpression of HER2 occurs in approximately 15-30% of breast cancers and 10-30% of gastric/gastroesophageal cancers. Overexpression of the HER2 protein and amplification of the HER2 gene was found in 23% and 27%, respectively, of 200 resected tumors in a gastric cancer study. Further, in a study of 260 gastric cancers, HER2 overexpression was an independent negative prognostic factor and HER2 staining intensity correlated with tumor size, serosal invasion, and lymph node metastases. Additional studies have reported HER2 overexpression in 0-83% of esophageal cancers, with a tendency towards higher rates of positivity in adenocarcinoma (10-83%) compared to squamous cell carcinomas (0-56%). HER2 overexpression has also been seen in ovarian cancers, endometrial cancers, bladder cancer, lung cancer, colon cancer, and head and neck cancer. For example, overexpression of HER2 has been reported in 20-30% patients with ovarian cancer. In endometrial serous carcinoma, the reported rates of HER2 overexpression range between 14% and 80% with HER2 amplification ranging from 21% to 47%.

Exemplary human HER2 nucleic sequences are provided in GenBank® Accession Nos. NM_004448.3, NM_001005862.2, NM_001289936.1, NM_001289937.1, and NM_001289938.1. Exemplary human HER2 polypeptide sequences are provided in in GenBank® Accession Nos. NP_004439.2, NP_001005862.1, NP_001276865.1, NP_001276866.1, and NP_001276867.1.

Disialoganglioside GD2

In some embodiments, the target antigen is the disialoganglioside GD2. GD2 is a sialic acid-containing glycosphingolipid expressed primarily on the cell surface. The function of this carbohydrate antigen is not completely understood; however, it is thought to play an important role in the attachment of tumor cells to extracellular matrix proteins. GD2 expression in normal fetal and adult tissues is primarily restricted to the central nervous system, peripheral nerves, and skin melanocytes, although GD2 expression has been described in the stromal component of some normal tissues and white pulp of the spleen. In malignant cells, GD2 is uniformly expressed in neuroblastomas and most melanomas and to a variable degree in a variety of other tumors, including bone and soft-tissue sarcomas, small cell lung cancer, and brain tumors. GD2 is present and concentrated on cell surfaces, with the two hydrocarbon chains of the ceramide moiety embedded in the plasma membrane and the oligosaccharides located on the extracellular surface, where they present points of recognition for extracellular molecules or surfaces of neighboring cells. Because of the relatively tumor-selective expression combined with its localization on the cell surface, GD2 is an attractive target for tumor-specific antibody therapy. Exemplary antigen binding domains for targeting GD2 are known in the art, for example those described in Navid et al., Curr Cancer Drug Targets. 2010; 10(2):200-209, and the monoclonal Dinutuximab antibody (Ploessl et al., Ann Pharmacother. 2016; (50(5): 416-422).

Fibroblast Activation Protein (FAP)

In some embodiments, the target antigen is fibroblast activation protein (FAP, also known as FAPA, SIMP, DPPIV, and FAPalpha). FAP is a 170 kDa membrane-bound gelatinase expressed during embryonic development (Niedermeyer et al., *Intl J Dev Biol.* 2001; 45(2): 445-7 and in adults in pancreatic alpha cells (Busek et al., Histochemistry and Cell Biology. 2015; 143(5): 497-504), in multipotent bone marrow stromal cells (Bae et al., British Journal of Haematology. 2008; 142(5): 827-30), and uterine stroma (Dolznig et al, Cancer Immunity. 2005; 5:10). FAP expression is seen on activated stromal fibroblasts of more than 90% of all human carcinomas (Pure et al., Oncogene. 2018; 37 (32): 4343-4357; Busek et al., Frontiers in Bioscience. 2018; 23: 1933-1968).

Exemplary human FAP nucleic sequences are provided in GenBank® Accession Nos. NM_001291807.2 and NM_004460.5. Exemplary human FAP polypeptide sequences are provided in in GenBank® Accession Nos. NP_001278736.1 and NP_004451.2. Exemplary antigen binding domains for targeting FAP are known in the art, including the monoclonal antibody sibrotuzumab (Scott et al., Clin Cancer Res. 2003; 9(5):1639-47; Hofheinz et al., Onkologie. 2003; 26(1):44-8) as well as those described in Tran et al., J Exp Med. 2013 Jun. 3; 210(6):1125-35; Garin-Chesa et al., PNAS 1990; 87(18): 7235-7239; Santos et al., J Clin Invest 119:3613-25 (2009); Goscinski et al., Ultrastruct Pathol 32:89-96 (2008); Lo et al., JCI Insight, 2017; 2(19); Lakins et al., Nat Commun, 2018; 9(1):948; U.S. Pat. No. 6,455,677; US Patent Application Publication No. 2014-0370019; International PCT Publication Nos. WO 1999/057151, 2001/068708, WO 2007/077173, WO 2012/020006, WO WO 2014/055442, and WO 2016/055432. Exemplary anti-FAP scFv sequences are provided in SEQ ID NO: 73.

Therapeutic Molecules

In some embodiments, the oncolytic viruses described herein comprise a nucleic acid sequence that encodes an engager molecule and one or more additional nucleic acid sequences that encode one or more therapeutic molecules. As used herein, a "therapeutic molecule" refers to a molecule that enhances the therapeutic efficacy of an oncolytic virus described herein. In general, the therapeutic molecules described herein are proteins, nucleic acids, or a combination thereof. Exemplary therapeutic molecules include cytokines, chemokines, antibodies or antigen binding fragments thereof, proteases, RNA polynucleotides, and DNA polynucleotides.

In some embodiments, the therapeutic molecule is capable of increasing or enhancing the therapeutic efficacy of an oncolytic virus described herein by stimulating, or activating, a cellular immune response. In some embodiments, the therapeutic molecule is capable of increasing or enhancing the therapeutic efficacy of an oncolytic virus described herein by antagonizing a suppressive or regulatory immune response. In some embodiments, reduction of a suppressive immune response occurs in a tumor microenvironment. In some instances, reduction of a suppressive immune response by the therapeutic molecule enhances the oncolytic effects of an oncolytic virus described herein. In some embodiments, the therapeutic molecule further reduces immunoregulatory T cell activity in a subject treated with an oncolytic virus described herein. In some embodiments, the therapeutic molecule modulates or impairs the production level of a protein at a nucleic acid level or at a protein level, or disrupts a protein function.

In some embodiments, the nucleic acid sequence encoding the engager molecule and the nucleic acid sequence encoding one or more therapeutic molecules are comprised within the same vector or virus. In some embodiments, the nucleic acid sequence encoding the engager molecule and the nucleic acid sequence encoding one or more therapeutic molecules are comprised in different vectors or viruses. In some embodiments, the vector is a viral vector. In some embodiments, the therapeutic molecule is a polypeptide. In some instances, the polypeptide is an immune modulator polypeptide. In some cases, the immune modulator polypeptide is a cytokine, a co-stimulatory domain, a domain that inhibits negative regulatory molecules of T-cell activation (e.g., an immune checkpoint inhibitor), or a combination thereof.

In some embodiments, the immune modulator polypeptide modulates the activity of one or more cell types, such as regulatory T cells (Tregs), myeloid-derived suppressor cells (MDSCs), dendritic cells, and/or T cells. Exemplary Treg modulatory polypeptides include CCR4, Helios, TIGIT, GITR, neuropilin, neuritin, CD103, CTLA-4, ICOS, and Swap70. Exemplary MDSC modulatory polypeptides include TGF-βR1, GM-CSF, INFγ, interleukins such as IL-β, IL-1F2, IL-6, IL-10, IL-12, IL-13, IL-6, IL-6Ra, IL-6/IL-6R complex, TGF-β1, M-CSF, Prostaglandin E2/PGE2, Prostaglandin E Synthase 2, S100A8, and VEGF. Exemplary dendritic-cell directed modulatory polypeptides include GM-CSF and/or IL-13. Exemplary T cell-directed modulatory polypeptides include IL-12, OX-40, GITR, CD28, or IL-28, or an antibody that agonizes a pathway comprising IL-12, OX-40, GITR, CD28, or IL-28.

In other embodiments, the therapeutic polypeptides modulate the fibrotic stroma. Exemplary fibrotic stromal polypeptides include fibroblast activation protein-alpha (FAP). In some embodiments, the therapeutic polypeptide is a protease. In particular embodiments, the protease is capable of altering the extracellular matrix, particularly the extracellular matrix within a tumor microenvironment. Exemplary proteases include matrixmetalloproteases (MMP), such as MMP9, collagenases, and elastases.

Cytokines as Therapeutic Molecules

In some cases, the immune modulator polypeptide is a cytokine. Cytokines are a category of small proteins between about 5-20 kDa that are involved in cell signaling and include chemokines, interferons (INF), interleukins (IL), and tumor necrosis factors (TNF), among others. Chemokines play a role as a chemoattractant to guide the migration of cells and are classified into four subfamilies: CXC, CC, CX3C, and XC. Exemplary chemokines include chemokines from the CC subfamily, such as CCL1, CCL2 (MCP-1), CCL3, CCL4, CCL5 (RANTES), CCL6, CCL7, CCL8, CCL9 (or CCL10), CCL11, CCL12, CCL13 CCL14, CCL15, CCL16, CCL17, CCL18, CCL19, CCL20, CCL21, CCL22, CCL23, CCL24, CCL25, CCL26, CCL27, and CCL28; the CXC subfamily, such as CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily, such as XCL1 and XCL2; and the CX3C subfamily, such as CX3CL1.

Interferons (IFNs) comprise Type I IFNs (e.g. IFN-α, IFN-β, IFN-ε, IFN-κ, and IFN-ω), Type II IFNs (e.g. IFN-γ), and Type III IFNs. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21. Interleukins are a broad class of cytokine that promote the development and differentiation of immune cells, including T and B cells, and other hematopoietic cells. Exemplary interleukins include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31 IL-32, IL-33, IL-35, and IL-36. Tumor necrosis factors (TNFs) are a group of cytokines that modulate apoptosis. In some instances, there are about 19 members within the TNF family, including, not limited to, TNFα, lymphotoxin-alpha (LT-α), lymphotoxin-beta (LT-β), T cell antigen gp39 (CD40L, also called CD154), CD27L, CD30L, FASL, 4-1BBL, OX40L, and TNF-related apoptosis inducing ligand (TRAIL).

In some embodiments, an oncolytic virus comprises a nucleic acid sequence that encodes an engager and an additional nucleic acid sequence that encodes a cytokine In some embodiments, the cytokine selected from IL-15, IL-12, CXCL0, and CCL4.

Co-Stimulatory Domains as Therapeutic Molecules

In some embodiments, the immune modulator polypeptide is a co-stimulatory domain. In some cases, the co-stimulatory domain enhances antigen-specific cytotoxicity. In some cases, the co-stimulatory domain further enhances cytokine production. In some embodiments, the co-stimulatory domain comprises CD27, CD28, CD70, CD80, CD83, CD86, CD134 (OX-40), CD134L (OX-40L), CD137 (41BB), CD137L (41BBL), or CD224.

In some embodiments, an oncolytic virus comprises a nucleic acid sequence that encodes an engager and an additional nucleic acid sequence that encodes a co-stimulatory domain. In some embodiments, the co-stimulatory domain is selected from CD27, CD28, CD80, CD83, CD86, CD134, CD134L, CD137, CD137L, or CD224.

Immune Checkpoint Polypeptides as Therapeutic Molecules

In some embodiments, the immune modulator polypeptide is an immune checkpoint polypeptide. In some embodiments, the immune modulator polypeptide is an immune checkpoint inhibitor polypeptide that inhibits a negative regulatory molecule of T-cell activation. Immune checkpoint inhibitor bind to immune checkpoint molecules, which are a group of molecules on the cell surface of CD4 and CD8 T cells. In some instances, these molecules effectively serve as "brakes" to down-modulate or inhibit an anti-tumor immune response. An immune checkpoint inhibitor refers to any molecule that modulates or inhibits the activity of an immune checkpoint molecule. In some instances, immune checkpoint inhibitors include antibodies, antibody-derivatives (e.g., Fab fragments, scFvs, minobodies, diabodies), antisense oligonucleotides, siRNA, aptamers, or peptides.

Exemplary immune checkpoint molecules include, but are not limited to, programmed death-ligand 1 (PDL1, also known as B7-H1, CD274), PD-L2 (B7-DC, CD273), programmed death 1 (PD-1), CTLA-4, LAG3, TIM3 (HAVCR2), A2aR, B7H1, B7H3 (CD276), B7H4 (VTCN1), BTLA, CD27, CD70, GAL9, HVEM, IDO1, IDO2, KIR, LAIR1, LIGHT, TIGIT, and VISTA.

In some embodiments, an oncolytic virus comprises a nucleic acid sequence that encodes an engager molecule and an additional nucleic acid sequence that encodes an immune checkpoint inhibitor. In some embodiments, the immune checkpoint inhibitor reduces the expression or activity of one or more immune checkpoint molecules. In some embodiments, the immune checkpoint inhibitor reduces the interaction between an immune checkpoint molecule and its ligand (e.g., reduced the interaction between PD-1 and PDL1). In some embodiments, the immune checkpoint inhibitor inhibits one or more of PDL1, PD-1, CTLA-4, PD-L2, LAG3, TIM3 (HAVCR2), A2aR, B7H1, B7H3 (CD276), B7H4 (VTCN1), BTLA, CD27, CD70, GAL9, HVEM, IDO1, IDO2, KIR, LAIR1, LIGHT, TIGIT, and VISTA.

In some embodiments, the immune checkpoint inhibitor is an inhibitor of PDL1. In some embodiments, the immune checkpoint inhibitor is an antibody (e.g., a monoclonal antibody or antigen-binding fragments thereof, or a humanized or chimeric antibody or antigen-binding fragments thereof) against PDL1. In some embodiments, the inhibitor of PDL1 reduces the expression or activity of PDL1. In some embodiments, the inhibitor of PDL1 reduces the interaction between PD-1 and PDL1. Exemplary inhibitors of PDL1 include anti-PDL1 antibodies, RNAi molecules (e.g., anti-PDL1 RNAi), antisense molecules (e.g., an anti-PDL1 antisense RNA), or dominant negative proteins (e.g., a dominant negative PDL1 protein). Exemplary anti-PDL1 antibodies includes clone EH12; MPDL3280A (Genentech, RG7446); anti-mouse PDL1 antibody Clone 10F.9G2 (BioXcell, Cat #BE0101); anti-PDL1 monoclonal antibody MDX-1105 (BMS-936559 and BMS-935559 from Bristol-Meyers Squibb; MSB0010718C; mouse anti-PDL1 Clone 29E.2A3; and AstraZeneca's MEDI4736. In some embodiments, the anti-PDL1 antibody is an anti-PDL1 antibody disclosed in International PCT Publication Nos. WO 2013/079174; WO 2010/036959; WO 2013/056716; WO 2007/005874; WO 2010/089411; WO 2010/077634; WO 2004/004771; WO 2006/133396; WO 2013/09906; WO 2012/145493; WO 2013/181634; U.S. Patent Application Publication No. 20140294898; or Chinese Patent Application Publication No. CN 101104640.

In some embodiments, the PDL1 inhibitor is a nucleic acid inhibitor of PDL1 expression. In some embodiments, the PDL1 inhibitor is one disclosed in International PCT Publication Nos. WO 2011/127180 or WO 2011/000841.

In some embodiments, an oncolytic virus comprises a nucleic acid sequence that encodes an engager molecule and an additional nucleic acid sequence that encodes PDL1 inhibitor selected from EH12, Genentech's MPDL3280A (RG7446); Anti-mouse PDL1 antibody Clone 10F.9G2 (Cat #BE0101) from BioXcell; anti-PDL1 monoclonal antibody MDX-1105 (BMS-936559) and BMS-935559 from Bristol-Meyer's Squibb; MSB0010718C; mouse anti-PDL1 Clone 29E. 2A3; and AstraZeneca's MEDI4736.

In some embodiments, the immune checkpoint inhibitor is an inhibitor of PD-L2. In some embodiments, the inhibitor of PD-L2 is an antibody (e.g., a monoclonal antibody or fragments, or a humanized or chimeric antibody or fragments thereof) against PD-L2. In some embodiments, the inhibitor of PD-L2 reduces the expression or activity of PD-L2. In other embodiments, the inhibitor of PD-L2 reduces the interaction between PD-1 and PD-L2. Exemplary inhibitors of PD-L2 include antibodies (e.g., an anti-PD-L2 antibody), RNAi molecules (e.g., an anti-PD-L2 RNAi), antisense molecules (e.g., an anti-PD-L2 antisense RNA), or dominant negative proteins (e.g., a dominant negative PD-L2 protein). In some embodiments, the PD-L2 inhibitor is GlaxoSmithKline's AMP-224 (Amplimmune). In some embodiments, the PD-L2 inhibitor is rHIgM12B7. In some embodiments, an oncolytic virus comprises a nucleic acid sequence that encodes an engager molecule and an additional nucleic acid sequence that encodes a PD-L2 inhibitor. In some embodiments, the PD-L2 inhibitor is selected from AMP-224 (Amplimmune) or rHIgM12B7.

In some embodiments, the immune checkpoint inhibitor is an inhibitor of PD1. In some embodiments, the inhibitor of PDL1 is an antibody (e.g., a monoclonal antibody or fragments, or a humanized or chimeric antibody or fragments thereof) against PD-1. Exemplary antibodies against PD-1 include: anti-mouse PD-1 antibody Clone J43 (Cat #BE0033-2) from BioXcell; anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda, pembrolizumab, lambrolizumab); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011), CureTech Ltd.

In some embodiments, an oncolytic virus comprises a nucleic acid sequence that encodes an engager molecule and an additional nucleic acid sequence that encodes a PD1 inhibitor selected from ANB011; antibody MDX-1106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011).

In some embodiments, the immune checkpoint inhibitor is an inhibitor of CTLA-4. In some embodiments, the inhibitor of CTLA-4 is an antibody (e.g., a monoclonal antibody or fragments, or a humanized or chimeric antibody or fragments thereof) against CTLA-4. In one embodiment, the anti-CTLA-4 antibody blocks the binding of CTLA-4 to CD80 (B7-1) and/or CD86 (B7-2) expressed on antigen presenting cells. Exemplary antibodies against CTLA-4 include ipilimumab (also known as Yervoy®, MDX-010, BMS-734016 and MDX-101, Bristol Meyers Squibb); anti-CTLA4 antibody clone 9H10 from Millipore; tremelimumab (CP-675,206, ticilimumab, Pfizer); and anti-CTLA4 antibody clone BNI3 from Abcam.

In some embodiments, the anti-CTLA-4 antibody is one disclosed in any of International PCT Publication Nos. WO 2001/014424; WO 2004/035607; WO 2003/086459; WO 2012/120125; WO 2000/037504; WO 2009/100140; WO 2006/09649; WO 2005/092380; WO 2007/123737; WO 2006/029219; WO 2010/0979597; WO 2006/12168; WO 1997/020574 U.S. Patent Application Publication No. 2005/0201994; or European Patent Application Publication No. EP 1212422. Additional CTLA-4 antibodies are described in U.S. Pat. Nos. 5,811,097; 5,855,887; 5,977,318; 6,051,227; 6,682,736; 6,984,720; 7,109,003; 7,132,281; International PCT Publication Nos. WO 01/14424 and WO 00/37504; and in U.S. Patent Application Publication Nos. 2002/0039581 and 2002/086014. In some embodiments, the anti-CTLA-4 antibody is one disclosed in any of International PCT Publication Nos. WO 1998/42752; U.S. Pat. Nos. 6,682,736 and 6,207,156; Hurwitz et al, Proc. Natl. Acad. Sci. USA, 95(17): 10067-10071 (1998); Camacho et al, J Clin Oncol, 22(145): Abstract No. 2505 (2004) (antibody CP-675206); Mokyr et al, Cancer Res., 58:5301-5304 (1998). In some embodiments, the CTLA-4 inhibitor is a CTLA-4 ligand as disclosed in International PCT Publication No. WO 1996/040915.

In some embodiments, the CTLA-4 inhibitor is a nucleic acid inhibitor of CTLA-4 expression, such as an RNAi molecule. In some embodiments, anti-CTLA4 RNAi molecules take the form of those described in any of International PCT Publication Nos. WO 1999/032619 and WO 2001/029058; U.S. Patent Application Publication Nos. 2003/0051263, 2003/0055020, 2003/0056235, 2004/0265839, 2005/0100913, 2006/0024798, 2008/0050342, 2008/0081373, 2008/0248576, and 2008/055443; and/or U.S. Pat. Nos. 6,506,559; 7,282,564; 7,538,095; and 7,560, 438. In some instances, the anti-CTLA4 RNAi molecules are double stranded RNAi molecules, such as those disclosed in European Patent No. EP 1309726. In some instances, the anti-CTLA4 RNAi molecules are double stranded RNAi molecules, such as those described in U.S. Pat. Nos. 7,056,704 and 7,078,196. In some embodiments, the CTLA4 inhibitor is an aptamer, such as those described in International PCT Publication No. WO 2004/081021, such as Del 60 or M9-14 del 55. Additionally, in some embodiments, the anti-CTLA4 RNAi molecules of the present invention are RNA molecules, such as those described in U.S. Pat. Nos. 5,898,031, 6,107,094, 7,432,249, and 7,432,250, and European Application No. EP 0928290.

In some embodiments, an oncolytic virus comprises a nucleic acid sequence that encodes an engager molecule, and an additional nucleic acid sequence that encodes a CTLA-4 inhibitor. In some embodiments, the CTLA-4 inhibitor is selected from ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA4 antibody clone BNI3 from Abcam.

In some embodiments, the immune checkpoint inhibitor is an inhibitor of LAG3 (CD223). In some embodiments, the inhibitor of LAG3 is an antibody (e.g., a monoclonal antibody or fragments, or a humanized or chimeric antibody or fragments thereof) against LAG3. In additional embodiments, an antibody against LAG3 blocks the interaction of LAG3 with major histocompatibility complex (MEC) class II molecules. Exemplary antibodies against LAG3 include: anti-Lag-3 antibody clone eBioC9B7W (C9B7W) from eBioscience; anti-Lag3 antibody LS-B2237 from LifeSpan Biosciences; IMP321 (ImmuFact) from Immutep; anti-Lag3 antibody BMS-986016; and the LAG-3 chimeric antibody A9H12. In some embodiments, the anti-LAG3 antibody is an anti-LAG3 antibody disclosed in International PCT Publication Nos. WO 2010/019570; WO 2008/132601; or WO 2004/078928.

In some embodiments, an oncolytic virus comprises a nucleic acid sequence that encodes an engager molecule and an additional nucleic acid sequence that encodes LAG3 inhibitor. In some embodiments, the LAG3 inhibitor is selected from anti-Lag-3 antibody clone eBioC9B7W (C9B7W) from eBioscience; anti-Lag3 antibody LS-B2237 from LifeSpan Biosciences; IMP321 (ImmuFact) from Immutep; anti-Lag3 antibody BMS-986016; and the LAG-3 chimeric antibody A9H12.

In some embodiments, the immune checkpoint inhibitor is an inhibitor of TIM3. In some embodiments, the inhibitor of TIM3 is an antibody (e.g., a monoclonal antibody or fragments, or a humanized or chimeric antibody or fragments thereof) against TIM3 (also known as HAVCR2). In additional embodiments, an antibody against TIM3 blocks the interaction of TIM3 with galectin-9 (Ga19). In some embodiments, the anti-TIM3 antibody is an anti-TIM3 antibody disclosed in International PCT Publication Nos. WO 2013/006490; WO 2011/55607; WO 2011/159877; or WO 2001/17057. In another embodiment, a TIM3 inhibitor is a TIM3 inhibitor disclosed in International PCT Publication No. WO 2009/052623. In some embodiments, an oncolytic virus comprises a nucleic acid sequence that encodes an engager molecule and an additional nucleic acid sequence that encodes TIM3 inhibitor. In some embodiments, the TIM3 inhibitor is an antibody that blocks the interaction of TIM3 with Ga19.

In some embodiments, the immune checkpoint inhibitor is an inhibitor of B7-H3. In some embodiments, the inhibitor of B7-H3 is an antibody (e.g., a monoclonal antibody or fragments, or a humanized or chimeric antibody or fragments thereof) against B7-H3. In some embodiments, the inhibitor of B7-H3 is MGA271 (MacroGenics). In some embodiments, an oncolytic virus comprises a nucleic acid sequence that encodes an engager molecule and an additional nucleic acid sequence that encodes a B7-H3 inhibitor. In some embodiments, the B7-H3 inhibitor is MGA271.

In some embodiments, the immune checkpoint polypeptide is an agonist of a cell surface molecule expressed on an effector cell (i.e., an immune checkpoint activator). In some embodiments, immune checkpoint activators include antibodies, antibody-derivatives (e.g., Fab fragments, scFvs, minobodies, diabodies), antisense oligonucleotides, siRNA, aptamers, or peptides. In some embodiments, the immune checkpoint activator activates a cell surface molecule selected from 2B4, CD16 (FcγRIII), CD28, CD30, CD40, CD80, CD86, CD137, CD160, CD226, CD276, DR3, GITR, inducible T cell costimulatory (ICOS), macrophage receptor with collageneous structure (MARCO), OX-40, phosphatidylserine (PS) receptor, SLAM receptors (including CD2), and CD16 (FcγRIII). In some embodiments, an oncolytic virus comprises a nucleic acid sequence that encodes an engager molecule and an additional nucleic acid sequence that encodes an immune checkpoint activator. In some embodiments, the immune checkpoint activator increases the expression or activity of one or more activating cell surface molecules. In some embodiments, the immune activator activates one or more of 2B4, CD16 (FcγRIII), CD28, CD30, CD40, CD80, CD86, CD137, CD160, CD226, CD276, DR3, GITR, ICOS, MARCO, OX-40, PS receptor, SLAM receptors (including CD2), and CD16 (FcγRIII).

Anti-Angiogenic Factors as Therapeutic Molecules

In some embodiments, the therapeutic molecule is a polypeptide such as an anti-angiogenic factor. Angiogenesis or neovascularization is the formation of new microvessels from an established vascular network. In some instances, the angiogenic process involves communications from multiple cell types such as endothelial cells (EC) and circulating endothelial progenitor cells, pericytes, vascular smooth muscle cells, stromal cells, including stem cells, and parenchymal cells. These communications or interactions occur through secreted factors such as VEGF, fibroblast growth factor (FGF), platelet-derived growth factor (PDGF), or angiopoietins. In some instances, an anti-angiogenic factor is a polypeptide that disrupts one or more of the interactions of the cell types: endothelial cells (EC) and circulating endothelial progenitor cells, pericytes, vascular smooth muscle cells, stromal cells, including stem cells, and parenchymal cells. In some instances, an anti-angiogenic factor is a polypeptide that disrupts one or more of the interactions of secreted factors such as VEGF, fibroblast growth factor (FGF), platelet-derived growth factor (PDGF) or angiopoietins.

In other embodiments, provided are oncolytic viruses comprising nucleic acids that encode therapeutic polypeptides that modulate regulatory T cells. In some instances, regulatory T cells maintain the tolerance to self-antigens and in some instances abrogate autoimmune. In some cases, Treg suppresses or downregulates induction and proliferation of effector T cells. Exemplary Treg modulatory polypeptides include CCR4, Helios, TIGIT, GITR, neuropilin, neuritin, CD103, CTLA-4, ICOS, and Swap70.

In other embodiments, provided are oncolytic viruses comprising nucleic acids that encode therapeutic polypeptides that modulate myeloid-derived suppressor cells (MDSCs). MDSCs are a heterogenous population of immune cells from the myeloid lineage (a cluster of different cell types that originate from bone marrow stem cells), to which also includes dendritic cells, macrophages and neutrophils. In some instances, myeloid cells interact with T cells to regulate the T cell's function. Exemplary MDSC modulatory polypeptides include TGF-βR1, GM-CSF, IFN-γ, Interleukins (e.g., IL-β, IL-1F2, IL-6, IL-10, IL-12, IL-13, IL-6, IL-6Rα, IL-6/IL-6R complex, TGF-β1, M-CSF, Prostaglandin E2/PGE2, Prostaglandin E Synthase 2, S100A8, and VEGF.

In other embodiments, provided are oncolytic viruses comprising nucleic acids that encode therapeutic polypeptides that modulate the fibrotic stroma. In some embodiments, fibrosis occurs in response to inflammation, either chronic or recurrent. Over time, the repeated bouts of inflammation irritate and scar the tissue, causing buildups of fibrous tissue. In some instances, if enough fibrous material develops, it turns into stromal fibrosis.

Nucleic Acid Polymers as Therapeutic Molecules

In some embodiments, the therapeutic molecule is a nucleic acid polymer. In some instances, the nucleic acid polymer is a RNA polymer. In some instances, the RNA polymer is an antisense polymer those sequence is complementary to a microRNA (miRNA or miR) target sequence. In some instances, the RNA polymer is a microRNA polymer. In some instances, the RNA polymer comprises a DNA-directed RNAi (ddRNAi) sequence, which enables in vivo production of short hairpin RNAs (shRNAs).

In some embodiments, a microRNA polymer is a short non-coding RNA that is expressed in different tissue and cell types which suppresses the expression of a target gene. For example, miRNAs are transcribed by RNA polymerase II as part of the capped and polyadenylated primary transcripts (pri-miRNAs). In some instances, the primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. In some instances, the mature miRNA is incorporated into a RNA-induced silencing complex (RISC), which recognizes target mRNAs through imperfect base pairing with the miRNA and in some instances results in translational inhibition or destabilization of the target mRNA.

In some instances, dysregulated microRNA expression is correlated with one or more types of cancer. In some embodiments, the microRNA is referred to as an oncomiR. In some instances, the dysregulated microRNA expression is an elevated expression. In some instances, the elevated expression level of microRNA correlates to one or more types of cancer. For example, overexpression of microRNA-155 (miR-155) has been observed in cancers such as Burkitt lymphoma, or laryngeal squamous cell carcinoma (LSCC) and overexpression of microRNA-21 (miR-21) has been observed in breast cancer. In some embodiments, exemplary microRNAs with an elevated expression level include, but are not limited to, miR-10 family (e.g., miR-10b), miR-17, miR-21, miR-106 family (e.g., miR-106a), miR-125 family (e.g., miR-125b), miR-145, miR-146 family (e.g., miR-146a, miR-146b), miR-155, miR-96, miR-182, miR-183, miR-221, miR-222, and miR-1247-5p.

In some instances, the nucleic acid polymer is an antisense polymer those sequence complements an oncomiR. In some instances, the nucleic acid polymer is an antisense polymer those sequence complements an oncomiR that is characterized with an overexpression. In some instances, the nucleic acid polymer is an antisense polymer those sequence complements a microRNA target sequence. In some instances, the nucleic acid polymer is an antisense polymer those sequence complements a microRNA target sequence that is characterized with an overexpression. In some instances, the therapeutic molecule is an antisense polymer those sequence complements a microRNA target sequence. In some instances, the therapeutic molecule is an antisense polymer those sequence complements a microRNA target sequence that is characterized with an overexpression. In some instances, the overexpression level is relative to the endogenous expression level of the microRNA.

In some instances, the dysregulated microRNA expression is a reduced expression. In some instances, the reduced expression level of microRNA correlates to one or more types of cancer. For example, a depleted level of miR-31 has been observed in both human and mouse metastatic breast cancer cell lines. In some embodiments, exemplary microRNAs with reduced expression levels include, but are not limited to, miR-31, miR-34 family (e.g., miR34a, miR-34b, and miR-34c), miR-101, miR-126, miR-145, miR-196a, and the miR-200 family.

In some instances, the nucleic acid polymer is an oncomiR. In some instances, the oncomiR is equivalent to an endogenous oncomiR wherein the endogenous oncomiR is characterized with a reduced expression level. In some instances, the nucleic acid polymer is a microRNA polymer. In some instances, the therapeutic molecule is a microRNA polymer. In some instances, the microRNA is equivalent to an endogenous microRNA polymer wherein the endogenous microRNA is characterized with a reduced expression level.

As described above, in some instances the RNA polymer comprises a DNA-directed RNAi (ddRNAi) sequence. In some instances, a ddRNAi construct encoding a shRNA is packaged into a viral vector such as a viral vector of a oncolytic virus described herein. In some instances upon entry into the target cell (e.g., a tumor cell), the viral genome is processed to produce the encoded shRNAs. The shRNAs are then processed by endogenous host systems and enter the RNAi pathway to modulate or silence the desired gene target. In some instances, the gene target is a gene that is overexpressed in a cancer type. In some instances, the gene target is a gene that is overexpressed in a solid tumor. In some instances, the gene target is a gene that is overexpressed in a hematologic cancer. Exemplary genes that are overexpressed in cancer include, but are not limited to, TP53, human epidermal growth factor receptor 2 (HER2), mucin 1-cell surface associated (MUC1), human pituitary tumour-transforming gene 1 (hPPTG1), prostate and breast cancer overexpressed gene 1 protein (PBOV1), and the like.

In some instances, the nucleic acid polymer comprises a ddRNAi sequence. In some instances, the nucleic acid polymer is comprises a ddRNAi sequence which targets a gene that is overexpressed in a cancer. In some instances, the therapeutic molecule comprises a ddRNAi sequence. In some instances, the therapeutic molecule comprises a ddRNAi sequence which targets a gene that is overexpressed in a cancer.

Exemplary Oncolytic Viruses and Engager Molecules

In some embodiments, the oncolytic viruses described herein comprise a polynucleotide sequence encoding an engager molecule. In some embodiments, the engager molecule is a bi-specific antibody construct comprising an effector domain and a targeting domain. In some embodiments, the engager molecule is a bi-specific antibody construct comprising an effector domain and an activation domain. In some embodiments, the engager molecule is a tripartite polypeptide comprising (i) an effector domain, (ii) an activation or targeting domain, and (iii) an additional domain e.g., an additional effector domain, an additional activation domain, an additional targeting domain, a therapeutic molecule domain (such as a cytokine, a co-stimulatory domain, an immune checkpoint inhibitor, or an anti-angiogenic factor), or a combination thereof.

In some embodiments, the oncolytic viruses described herein comprise a first polynucleotide sequence encoding an engager molecule and a second polynucleotide encoding a therapeutic molecule. In some embodiments, the first polypeptide and the second polynucleotide sequences are comprised in the same vector (e.g., in the same oncolytic virus). In some embodiments, the first polypeptide and the second polypeptide are encoded in different vectors (e.g., in different oncolytic viruses).

In some embodiments, the oncolytic viruses described herein comprise a first polynucleotide sequence encoding an engager molecule comprising an effector domain and a targeting domain. In some such embodiments, the effector domain binds to one or more components of CD3. In some such embodiments, the targeting domain binds to a target antigen selected from FAP and CD19. In some embodiments, the oncolytic viruses described herein comprise a first polynucleotide sequence encoding an engager molecule comprising an effector domain and an activation domain. In some such embodiments, the effector domain binds to one or more components of CD3. In some such embodiments, the activation domain binds to a cell-surface molecule selected from CD47, PD1, and PDL1. In some embodiments, the oncolytic viruses described herein comprise a first polynucleotide sequence encoding an engager molecule comprising an effector domain and a targeting or activation domain and a second polynucleotide sequence encoding a therapeutic molecule. In some such embodiments, the therapeutic molecule is selected from a cytokine, a co-stimulatory domain, and an immune checkpoint inhibitor. In some embodiments, the cytokine is selected from IL-15, IL-2, IL-7, IL-12, CCL4, and CXCL10. In some embodiments, the co-stimulatory molecule is selected from a molecule that binds to and activates a cell-surface molecule selected from CD27, CD80, CD83, CD86, CD134, or CD137. In some embodiments, the immune checkpoint inhibitor molecule is selected from a molecule that binds to and inhibits a cell surface molecule selected from PD-1, PDL1, CTLA4, and B7-H4.

In some embodiments, the oncolytic viruses described herein comprise a polynucleotide sequence encoding an engager molecule comprising an effector domain, wherein the effector domain comprises an anti-CD3 scFv. In some embodiments, the anti-CD3 scFv comprises a light chain variable fragment comprising an amino acid sequence that is at least 80%, at least, 85%, at least 90%, at least 95%, at least 96%, at least 97%, at least 98%, or at least 99% identical to SEQ ID NO: 20 or 77 and a heavy chain variable fragment comprising an amino acid sequence that is at least 80%, at least, 85%, at least 90%, at least 95%, at least 96%, at least 97%, at least 98%, or at least 99% identical to SEQ ID NO: 22 or 76. In some embodiments, the anti-CD3 scFv comprises a light chain variable fragment comprising an amino acid sequence that is 100% identical to SEQ ID NO: 20 or 77 and a heavy chain variable fragment that is 100% identical to SEQ ID NO: 22 or 76. In some embodiments, the anti-CD3 scFv comprises a light chain variable fragment comprising SEQ ID NO: 20 or 77 and a heavy chain variable fragment comprising SEQ ID NO: 22 or 76. In some embodiments, the anti-CD3 scFv comprises a light chain variable fragment consisting of SEQ ID NO: 20 or 77 and a heavy chain variable fragment consisting of SEQ ID NO: 22 or 76.

In some embodiments, the anti-CD3 scFv comprises a light chain variable fragment and a heavy chain variable fragment, wherein the nucleic acid sequence encoding the light chain variable fragment is at least 80%, at least, 85%, at least 90%, at least 95%, at least 96%, at least 97%, at least 98%, or at least 99% identical to SEQ ID NO: 19 and wherein the nucleic acid sequence encoding the heavy chain variable fragment is at least 80%, at least, 85%, at least 90%, at least 95%, at least 96%, at least 97%, at least 98%, or at least 99% identical to SEQ ID NO: 21. In some embodiments, the nucleic acid sequence encoding the light chain variable fragment is 100% identical to the nucleic acid sequence of SEQ ID NO: 19 and the nucleic acid sequence encoding the heavy chain variable fragment is 100% identical SEQ ID NO: 21. In some embodiments, the nucleic acid sequence encoding the light chain variable fragment comprises SEQ ID NO: 19 and the nucleic acid sequence encoding the heavy chain variable fragment comprises SEQ ID NO: 21. In some embodiments, the nucleic acid sequence encoding the light chain variable fragment consists of SEQ ID NO: 19 and the nucleic acid sequence encoding the heavy chain variable fragment consists of SEQ ID NO: 21.

In some embodiments, the oncolytic viruses described herein comprise a polynucleotide sequence encoding an engager molecule comprising a targeting domain, wherein the targeting domain comprises an anti-CD19 scFv. In some embodiments, the anti-CD19 scFv comprises a light chain variable fragment comprising an amino acid sequence that is at least 80%, at least, 85%, at least 90%, at least 95%, at least 96%, at least 97%, at least 98%, or at least 99% identical to SEQ ID NO: 16 and a heavy chain variable fragment comprising an amino acid sequence that is at least 80%, at least, 85%, at least 90%, at least 95%, at least 96%, at least 97%, at least 98%, or at least 99% identical to SEQ ID NO: 18. In some embodiments, the anti-CD19 scFv comprises a light chain variable fragment comprising an amino acid sequence that is 100% identical to SEQ ID NO: 16 and a heavy chain variable fragment that is 100% identical to SEQ ID NO: 18. In some embodiments, the anti-CD19 scFv comprises a light chain variable fragment comprising SEQ ID NO: 16 and a heavy chain variable fragment comprising SEQ ID NO: 18. In some embodiments, the anti-CD19 scFv comprises a light chain variable fragment consisting of SEQ ID NO: 16 and a heavy chain variable fragment consisting of SEQ ID NO: 18.

In some embodiments, the anti-CD19 scFv comprises a light chain variable fragment and a heavy chain variable fragment, wherein the nucleic acid sequence encoding the light chain variable fragment is at least 80%, at least, 85%, at least 90%, at least 95%, at least 96%, at least 97%, at least 98%, or at least 99% identical to SEQ ID NO: 15 and the nucleic acid sequence encoding the heavy chain variable fragment is at least 80%, at least 85%, at least 90%, at least 95%, at least 96%, at least 97%, at least 98%, or at least 99% identical to SEQ ID NO: 17. In some embodiments, the nucleic acid sequence encoding the light chain variable fragment is 100% identical to SEQ ID NO: 15 and the nucleic acid sequence encoding the heavy chain variable fragment is 100% identical to SEQ ID NO: 17. In some embodiments, the nucleic acid sequence encoding the light chain variable fragment nucleic acid sequence comprises SEQ ID NO: 15 and the nucleic acid sequence encoding the heavy chain variable fragment comprises SEQ ID NO: 17. In some embodiments, the nucleic acid sequence encoding the light chain variable fragment nucleic acid sequence consists of SEQ ID NO: 15 and the nucleic acid sequence encoding the heavy chain variable fragment nucleic acid sequence consists of SEQ ID NO: 17.

In some embodiments, the oncolytic viruses described herein comprise a polynucleotide sequence encoding an engager molecule comprising a targeting domain, wherein the targeting domain comprises an anti-FAP scFv. In some embodiments, the anti-FAP scFv comprises a light chain variable fragment comprising an amino acid sequence that is at least 80%, at least, 85%, at least 90%, at least 95%, at least 96%, at least 97%, at least 98%, or at least 99% identical to SEQ ID NO: 71 and a heavy chain variable fragment comprising an amino acid sequence that is at least 80%, at least, 85%, at least 90%, at least 95%, at least 96%, at least 97%, at least 98%, or at least 99% identical to SEQ ID NO: 72. In some embodiments, the anti-FAP scFv comprises a light chain variable fragment comprising an amino acid sequence that is 100% identical to SEQ ID NO: 71 and a heavy chain variable fragment that is 100% identical to SEQ ID NO: 72. In some embodiments, the anti-FAP scFv comprises a light chain variable fragment comprising the amino acid sequence of SEQ ID NO: 71 and a heavy chain variable fragment comprising the amino acid sequence of SEQ ID NO: 72. In some embodiments, the anti-FAP scFv comprises a light chain variable fragment consisting of the amino acid sequence of SEQ ID NO: 71 and a heavy chain variable fragment consisting of the amino acid sequence of SEQ ID NO: 72. In some embodiments, the amino acid sequence of the anti-FAP scFv is at least 80%, at least, 85%, at least 90%, at least 95%, at least 96%, at least 97%, at least 98%, or at least 99% identical to SEQ ID NO: 75. In some embodiments, the amino acid sequence of the anti-FAP scFv is 100% identical to SEQ ID NO: 75. In some embodiments, the amino acid sequence of the anti-FAP scFv comprises SEQ ID NO: 75. In some embodiments, the amino acid sequence of the anti-FAP scFv consists of SEQ ID NO: 75.

In some embodiments, the polynucleotide sequence encoding the anti-FAP scFv comprises a nucleic acid sequence that is at least 80%, at least, 85%, at least 90%, at least 95%, at least 96%, at least 97%, at least 98%, or at least 99% identical to SEQ ID NO: 74. In some embodiments, the polynucleotide sequence encoding the anti-FAP scFv comprises a nucleic acid sequence that is 100% identical to SEQ ID NO: 74. In some embodiments, the polynucleotide sequence encoding the anti-FAP scFv comprises SEQ ID NO: 74. In some embodiments, the polynucleotide sequence encoding the anti-FAP scFv consists of SEQ ID NO: 74.

In some embodiments, the oncolytic viruses described herein comprise a polynucleotide sequence encoding an engager molecule comprising an activation domain, wherein the activation domain comprises an anti-PDL1 scFv. In some embodiments, the anti-PDL1 scFv comprises a light chain variable fragment comprising an amino acid sequence that is at least 80%, at least, 85%, at least 90%, at least 95%, at least 96%, at least 97%, at least 98%, or at least 99% identical to SEQ ID NO: 36 and a heavy chain variable fragment comprising an amino acid sequence that is at least 80%, at least, 85%, at least 90%, at least 95%, at least 96%, at least 97%, at least 98%, or at least 99% identical to SEQ ID NO: 38. In some embodiments, the anti-PDL1 scFv comprises a light chain variable fragment comprising an amino acid sequence that is 100% identical to SEQ ID NO: 36 and a heavy chain variable fragment that is 100% identical to SEQ ID NO: 38. In some embodiments, the anti-PDL1 scFv comprises a light chain variable fragment comprising the amino acid sequence of SEQ ID NO: 36 and a heavy chain variable fragment comprising the amino acid sequence of SEQ ID NO: 38. In some embodiments, the anti-PDL1 scFv comprises a light chain variable fragment consisting of the amino acid sequence of SEQ ID NO: 36 and a heavy chain variable fragment consisting of the amino acid sequence of SEQ ID NO: 38.

In some embodiments, the anti-PDL1 scFv comprises a light chain variable fragment and a heavy chain variable fragment, wherein the nucleic acid sequence encoding the light chain variable fragment is at least 80%, at least, 85%, at least 90%, at least 95%, at least 96%, at least 97%, at least 98%, or at least 99% identical to SEQ ID NO: 35 and the nucleic acid sequence encoding the heavy chain variable fragment is at least 80%, at least, 85%, at least 90%, at least 95%, at least 96%, at least 97%, at least 98%, or at least 99% identical to SEQ ID NO: 37. In some embodiments, the nucleic acid sequence encoding the light chain variable fragment nucleic acid sequence is 100% identical to SEQ ID NO: 35 and the nucleic acid sequence encoding the heavy chain variable fragment is 100% identical to SEQ ID NO: 37. In some embodiments, the nucleic acid sequence encoding the light chain variable fragment comprises SEQ ID NO: 35 and the nucleic acid sequence encoding the heavy chain variable fragment comprises SEQ ID NO: 37. In some embodiments, the nucleic acid sequence encoding the light chain variable fragment consists of SEQ ID NO: 35 and the nucleic acid sequence encoding the heavy chain variable fragment nucleic acid sequence consists of SEQ ID NO: 37.

In some embodiments, the oncolytic viruses described herein comprise a polynucleotide sequence encoding an engager molecule comprising an activation domain comprising a SIRP1α polypeptide fragment. In some embodiments, the SIRP1α polypeptide fragment comprises an amino acid sequence that is at least 80%, at least, 85%, at least 90%, at least 95%, at least 96%, at least 97%, at least 98%, or at least 99% identical to SEQ ID NO: 32. In some embodiments, the SIRP1α polypeptide fragment comprises an amino acid sequence that is 100% identical to SEQ ID NO: 32. In some embodiments, the SIRP1α polypeptide fragment comprises SEQ ID NO: 32. In some embodiments, the SIRP1α polypeptide fragment consists of SEQ ID NO: 32.

In some embodiments, the nucleic acid sequence encoding the SIRP1α polypeptide fragment is at least 80%, at least, 85%, at least 90%, at least 95%, at least 96%, at least 97%, at least 98%, or at least 99% identical to SEQ ID NO: 31. In some embodiments, the nucleic acid sequence encoding the SIRP1α polypeptide fragment is 100% identical to SEQ ID NO: 31. In some embodiments, the nucleic acid sequence encoding the SIRP1α polypeptide fragment comprises SEQ ID NO: 31. In some embodiments, the nucleic acid sequence encoding the SIRP1α polypeptide fragment consists of SEQ ID NO: 31.

In some embodiments, the oncolytic viruses described herein comprise a first nucleic acid sequence encoding an engager molecule and a second nucleic acid sequence encoding a therapeutic molecule. In some embodiments, the therapeutic molecule is IL-15 and comprises an amino acid sequence that is at least 80%, at least 85%, at least 90%, at least 95%, at least 96%, at least 97%, at least 98%, or at least 99% identical to SEQ ID NO: 24. In some embodiments, the therapeutic molecule is IL-15 and comprises an amino acid sequence that is 100% identical to SEQ ID NO: 24. In some embodiments, the therapeutic molecule is IL-15 and comprises the amino acid sequence of SEQ ID NO: 24. In some embodiments, the therapeutic molecule is IL-15 and consists of the amino acid sequence of SEQ ID NO: 24. In some embodiments, the therapeutic molecule is IL-15 and is encoded by a nucleic acid sequence that is at least 80%, at least 85%, at least 90%, at least 95%, at least 96%, at least 97%, at least 98%, or at least 99% identical to SEQ ID NO: 23. In some embodiments, the therapeutic molecule is IL-15 and is encoded by a nucleic acid sequence that 100% identical to SEQ ID NO: 23. In some embodiments, the therapeutic molecule is IL-15 and is encoded by a nucleic acid sequence comprising SEQ ID NO: 23. In some embodiments, the therapeutic molecule is IL-15 and is encoded by a nucleic acid sequence consisting of SEQ ID NO: 23.

In some embodiments, the oncolytic viruses described herein comprise a first nucleic acid sequence encoding an engager molecule and a second nucleic acid sequence encoding a therapeutic molecule. In some embodiments, the therapeutic molecule is IL-12 p35 and/or IL-12 p40 and comprises an amino acid sequence that is at least 80%, at least 85%, at least 90%, at least 95%, at least 96%, at least 97%, at least 98%, or at least 99% identical to SEQ ID NO: 26 or SEQ ID NO: 28, respectively. In some embodiments, the therapeutic molecule is IL-12 p35 and/or IL-12 p40 and comprises an amino acid sequence that is 100% identical to SEQ ID NO: 26 or SEQ ID NO: 28, respectively. In some embodiments, the therapeutic molecule is IL-12 p35 and/or IL-12 p40 and comprises the amino acid sequence of SEQ ID NO: 26 or SEQ ID NO: 28, respectively. In some embodiments, the therapeutic molecule is IL-12 p35 and/or IL-12 p40 and consists of the amino acid sequence of SEQ ID NO: 26 or SEQ ID NO: 28, respectively. In some embodiments, the therapeutic molecule is IL-12 p35 and/or IL-12 p40 and is encoded by a nucleic acid sequence that is at least 80%, at least 85%, at least 90%, at least 95%, at least 96%, at least 97%, at least 98%, or at least 99% identical to SEQ ID NO: 25 or SEQ ID NO: 27, respectively. In some embodiments, the therapeutic molecule is IL-12 p35 and/or IL-12 p40 and is encoded by a nucleic acid sequence that 100% identical to SEQ ID NO: 25 or SEQ ID NO: 27, respectively. In some embodiments, the therapeutic molecule is IL-12 p35 and/or IL-12 p40 and is encoded by a nucleic acid sequence comprising SEQ ID NO: 25 or SEQ ID NO: 27, respectively. In some embodiments, the therapeutic molecule is IL-12 p35 and/or IL-12 p40 and is encoded by a nucleic acid sequence consisting of SEQ ID NO: 25 or SEQ ID NO: 27, respectively.

In some embodiments, the oncolytic viruses described herein comprise a first nucleic acid sequence encoding an engager molecule and a second nucleic acid sequence encoding a therapeutic molecule. In some embodiments, the therapeutic molecule is CXCL10 and comprises an amino acid sequence that is at least 80%, at least 85%, at least 90%, at least 95%, at least 96%, at least 97%, at least 98%, or at least 99% identical to SEQ ID NO: 30. In some embodiments, the therapeutic molecule is CXCL10 and comprises an amino acid sequence that is 100% identical to SEQ ID NO: 30. In some embodiments, the therapeutic molecule is CXCL10 and comprises the amino acid sequence of SEQ ID NO: 30. In some embodiments, the therapeutic molecule is CXCL10 and consists of the amino acid sequence of SEQ ID NO: 30. In some embodiments, the therapeutic molecule is CXCL10 and is encoded by a nucleic acid sequence that is at least 80%, at least 85%, at least 90%, at least 95%, at least 96%, at least 97%, at least 98%, or at least 99% identical to SEQ ID NO: 29. In some embodiments, the therapeutic molecule is CXCL10 and is encoded by a nucleic acid sequence that 100% identical to SEQ ID NO: XX29X. In some embodiments, the therapeutic molecule is CXCL10 and is encoded by a nucleic acid sequence comprising SEQ ID NO: 29. In some embodiments, the therapeutic molecule is CXCL10 and is encoded by a nucleic acid sequence consisting of SEQ ID NO: 29.

In some embodiments, the oncolytic viruses described herein comprise a first nucleic acid sequence encoding an engager molecule and a second nucleic acid sequence encoding a therapeutic molecule. In some embodiments, the therapeutic molecule is CCL4 and comprises an amino acid sequence that is at least 80%, at least 85%, at least 90%, at least 95%, at least 96%, at least 97%, at least 98%, or at least 99% identical to SEQ ID NO: 80. In some embodiments, the therapeutic molecule is CCL4 and comprises an amino acid sequence that is 100% identical to SEQ ID NO: 80. In some embodiments, the therapeutic molecule is CCL4 and comprises the amino acid sequence of SEQ ID NO: 80. In some embodiments, the therapeutic molecule is CCL4 and consists of the amino acid sequence of SEQ ID NO: 80.

In some embodiments, the oncolytic viruses described herein comprise a first nucleic acid sequence encoding an engager molecule and a second nucleic acid sequence encoding a therapeutic molecule. In some embodiments, the therapeutic molecule is MMP9 and comprises an amino acid sequence that is at least 80%, at least 85%, at least 90%, at least 95%, at least 96%, at least 97%, at least 98%, or at least 99% identical to SEQ ID NO: 34. In some embodiments, the therapeutic molecule is MMP9 and comprises an amino acid sequence that is 100% identical to SEQ ID NO: 34. In some embodiments, the therapeutic molecule is MMP9 and comprises the amino acid sequence of SEQ ID NO: 34. In some embodiments, the therapeutic molecule is MMP9 and consists of the amino acid sequence of SEQ ID NO: 34. In some embodiments, the therapeutic molecule is MMP9 and is encoded by a nucleic acid sequence that is at least 80%, at least 85%, at least 90%, at least 95%, at least 96%, at least 97%, at least 98%, or at least 99% identical to SEQ ID NO: 33. In some embodiments, the therapeutic molecule is MMP9 and is encoded by a nucleic acid sequence that 100% identical to SEQ ID NO: 33. In some embodiments, the therapeutic molecule is MMP9 and is encoded by a nucleic acid sequence comprising SEQ ID NO: 33. In some embodiments, the therapeutic molecule is MMP9 and is encoded by a nucleic acid sequence consisting of SEQ ID NO: 33.

In some embodiments, the oncolytic viruses described herein comprise a polynucleotide sequence encoding an engager molecule comprising an effector domain comprising an scFv that binds to CD3 and targeting domain comprising an scFv that binds to CD19, referred to herein as a CD19-CD3 BiTE, or a CD19 BiTE. A schematic of an exemplary CD19-CD3 BiTE is shown in FIG. 1 (SEQ ID NO: 44). In such embodiments, the anti-CD3 scFv and the anti-CD19 scFv are linked together by a G45 linker (SEQ ID NO: 6). In some embodiments, the oncolytic viruses described herein comprise a first nucleic acid sequence encoding a CD19-CD3 BiTE and a second nucleic acid sequence encoding a therapeutic molecule such as IL-15, IL-12, CXCL10, or CCL4. In some embodiments, the nucleic acid sequences encoding the CD19-CD3 BiTE and the therapeutic molecule are separate nucleic acid sequences and the CD19-CD3 BiTE and the therapeutic molecule are encoded as separate proteins. In some embodiments, the oncolytic viruses described herein comprise a bicistronic or multicistronic nucleic acid sequence, wherein a first nucleic acid sequence encodes a CD19-CD3 BiTE and a second nucleic acid sequence encodes a therapeutic molecule such as IL-15 (FIG. 2, SEQ ID NO: 53), IL-12 (FIG. 3, SEQ ID NO: 54), or CXCL10 (FIG. 4, SEQ ID NO: 55). In such embodiments, the CD19-CD3 BiTE (e.g., SEQ ID NO: 44) is linked to the therapeutic molecule, e.g., IL-15 (SEQ ID NO: 24), IL-12 p35 (SEQ ID NO: 28), IL-12 p40 (SEQ ID NO: 26), and/or CXCL10 (SEQ ID NO: 30), by a T2A self-cleaving peptide linker (SEQ ID NO: 14).

In some embodiments, the oncolytic viruses described herein comprise a polynucleotide sequence encoding an engager molecule comprising an effector domain comprising an scFv that binds to CD3 and an activation domain comprising an scFv that binds to FAP, referred to herein as a FAP-CD3 BiTE, or a FAP BiTE (SEQ ID NO: 75). In such embodiments, the anti-CD3 scFv and the anti-FAP scFv are linked together by a G45 linker (SEQ ID NO: 6). In some embodiments, the oncolytic viruses described herein comprise a first nucleic acid sequence encoding a FAP-CD3 BiTE and a second nucleic acid sequence encoding a therapeutic molecule such as IL-15, IL-12, CXCL10, or CCL4. In some embodiments, the nucleic acid sequences encoding the FAP-CD3 BiTE and the therapeutic molecule are separate nucleic acid sequences and the FAP-CD3 BiTE and the therapeutic molecule are encoded as separate proteins. In some embodiments, the oncolytic viruses described herein comprise a bicistronic or multicistronic nucleic acid sequence, wherein a first nucleic acid sequence encodes a FAP-CD3 BiTE and a second nucleic acid sequence encodes a therapeutic molecule such as IL-15, IL-12, CXCL10, or CCL4. In some such embodiments, the encoded FAP-CD3 BiTE (e.g., SEQ ID NO: 74) is linked to the therapeutic molecule, e.g., IL-15 (SEQ ID NO: 24), IL-12 p35 (SEQ ID NO: 28), IL-12 p40 (SEQ ID NO: 26), CXCL10 (SEQ ID NO: 30), and/or CCL4 (SEQ ID NO: 80) by a T2A self-cleaving peptide linker (SEQ ID NO: 14).

In some embodiments, the oncolytic viruses described herein comprise a polynucleotide sequence encoding an engager molecule comprising an effector domain comprising an scFv that binds to CD3 and an activation domain comprising a SIRP1α polypeptide fragment that binds to CD47 (SEQ ID NO: 32), referred to herein as an SIRP1α-CD3 BiTE or a SIRP1α BiTE. A schematic of an exemplary SIRP1α-CD3 BiTE is shown in FIG. 5 (SIRP1α-CD3 (SL), SEQ ID NO: 46) and FIG. 6 (SIRP1α-CD3 (LL), SEQ ID NO: 48). In some embodiments, the anti-CD3 scFv and the SIRP1α peptide fragment are linked together by a single amino acid linker, or a "short linker" (SL) (e.g., SIRP1α-CD3 (SL) as shown in FIG. 5). In some embodiments, the anti-CD3 scFv and the SIRP1α peptide fragment are linked together by G45 linker, or a "long linker" (LL) (e.g., SIRP1α-CD3 (LL) as shown in FIG. 6). In some embodiments, the oncolytic viruses described herein comprise a first nucleic acid sequence encoding a SIRP1α-CD3 BiTE and a second nucleic acid sequence encoding a therapeutic molecule such as IL-15, IL-12, CXCL10, or CCL4. In some embodiments, the nucleic acid sequences encoding the SIRP1α-CD3 BiTE and the therapeutic molecule are separate nucleic acid sequences and the FAP-CD3 BiTE and the therapeutic molecule are encoded as separate proteins. In some embodiments, the oncolytic viruses described herein comprise a bicistronic or multicistronic nucleic acid sequence, wherein a first nucleic acid sequence encodes a SIRP1α-CD3 BiTE and a second nucleic acid sequence encodes a therapeutic molecule such as IL-15 (FIG. 7, SEQ ID NO: 56 and FIG. 8, SEQ ID NO: 57), IL-12 (FIG. 9, SEQ ID NO: 58 and FIG. 10, SEQ ID NO: 59), or CXCL10 (FIG. 11, SEQ ID NO: 60 and FIG. 12, SEQ ID NO: 61). In such embodiments, the SIRP1α-CD3 BiTE (e.g., SEQ ID NO: 46 or SEQ ID NO: 48) is linked to the therapeutic molecule, e.g., IL-15 (SEQ ID NO: 24), IL-12 p35 (SEQ ID NO: 28), IL-12 p40 (SEQ ID NO: 26), and/or CXCL10 (SEQ ID NO: 30), by a T2A self-cleaving peptide linker (SEQ ID NO: 14).

In some embodiments, the oncolytic viruses described herein comprise a bicistronic or multicistronic nucleic acid sequence, wherein a first nucleic acid sequence encodes a SIRP1α-CD3 BiTE and a second nucleic acid sequence encodes a therapeutic molecule such as MMP9 (FIG. 18A, SEQ ID NO: 65 and FIG. 18B, SEQ ID NO: 66). In such embodiments, the SIRP1α-CD3 BiTE (e.g., SEQ ID NO: 65 or 66) is linked to the MMP9 polypeptide (SEQ ID NO: 34) by a T2A self-cleaving peptide linker (SEQ ID NO: 14). In some embodiments, the oncolytic viruses described herein comprise a bicistronic or multicistronic nucleic acid sequence, wherein a first nucleic acid sequence encodes a SIRP1α-CD3 BiTE and a second nucleic acid sequence encodes a therapeutic molecule comprising an anti-PDL1 scFv linked to an IgG1 Fc domain (e.g., comprises an IgG1 CH2-CH3-Hinge, SEQ ID NO: 40), such as the SIRP1α-CD3-PDL1-Fc (SL) construct shown in FIG. 37 (SEQ ID NO: 68) or the SIRP1α-CD3-PDL1-Fc (LL) construct show in FIG. 38 (SEQ ID NO: 70).

In some embodiments, the oncolytic viruses described herein comprise a polynucleotide sequence encoding an engager molecule comprising an effector domain comprising an scFv that binds to CD3 and an activation domain comprising an scFv that binds to PDL1, referred to herein as an PDL1-CD3 BiTE or a PDL1 BiTE. Exemplary PDL1-CD3 BiTEs are shown in FIG. 13 (SEQ ID NO: 50). In some embodiments, the anti-CD3 scFv and the anti-PDL1 scFv are linked together by G45 linker (SEQ ID NO: 6). In some embodiments, the oncolytic viruses described herein comprise a first nucleic acid sequence encoding a PDL1-CD3 BiTE and a second nucleic acid sequence encoding a therapeutic molecule such as IL-15, IL-12, CXCL10, or CCL4. In some embodiments, the nucleic acid sequences encoding the PDL1-CD3 BiTE and the therapeutic molecule are separate nucleic acid sequences and the PDL1-CD3 BiTE and the therapeutic molecule are encoded as separate proteins. In some embodiments, the oncolytic viruses described herein comprise a bicistronic or multicistronic nucleic acid sequence, wherein a first nucleic acid sequence encodes a PDL1-CD3 BiTE and a second nucleic acid sequence encodes a therapeutic molecule such as IL-15 (FIG. 14, SEQ ID NO: 62), IL-12 (FIG. 15, SEQ ID NO: 63), or CXCL10 (FIG. 16, SEQ ID NO: 64). In such embodiments, the SIRP1α-CD3 BiTE (e.g., SEQ ID NO: 50) is linked to the therapeutic molecule, e.g., IL-15 (SEQ ID NO: 24), IL-12 p35 (SEQ ID NO: 28), IL-12 p40 (SEQ ID NO: 26), and/or CXCL10 (SEQ ID NO: 30), by a T2A self-cleaving peptide linker (SEQ ID NO: 14).

In some embodiments, oncolytic viruses described herein comprise a polynucleotide sequence encoding an engager molecule wherein the engager molecule is a tripartite engager molecule and comprises an effector domain comprising an scFv that binds to CD3, an activation domain comprising an scFv that binds to PDL1, and a third domain comprising an IgG1 Fc domain (e.g., comprises an IgG1 CH2-CH3-Hinge, SEQ ID NO: 40) and capable of binding to one or more FcγRs, referred to herein as an PDL1-CD3-Fc tripartite T cell engager, or TiTE, or a PDL1 TiTE. A schematic of an exemplary PDL1-CD3-Fc TiTE is shown in FIG. 17 (SEQ ID NO: 52).

The amino acid sequences of exemplary engager molecules and therapeutic molecules are shown in Table 1.

TABLE 1

| Amino acid sequences of exemplary engager molecules | | |
|---|---|---|
| BiTE | Amino Acid Sequence | SEQ ID |
| CD19-CD3 | MEFGLSWVFLVALFRGVQCDIQLTQSPASLAVSLGQRATISCKASQSVDYDGDSYLN WYQQIPGQPPKLLIYDASNLVSGIPPRFSGSGSGTDFTLNIHPVEKVDAATYHCQQS TEDPWTFGGGTKLEIKGGGGSGGGGSGGGGSQVQLQQSGAELVRPGSSVKISCKASG YAFSSYWMNWVKQRPGQGLEWIGQIWPGDGDTNYNGKFKGKATLTADESSSTAYMQL SSLASEDSAVYFCARRETTTVGRYYYAMDYWGQGTTVTVSSGGGGSDIKLQQSGAEL ARPGASVKMSCKTSGYTFTRYTMHWVKQRPGQGLEWIGYINPSRGYTNYNQKFKDKA TLTTDKSSSTAYMQLSSLTSEDSAVYYCARYYDDHYCLDYWGQGTTLTVSSVEGGSG GSGGSGGSGGVDDIQLTQSPAIMSASPGEKVTMTCRASSSVSYMNWYQQKSGTSPKR WIYDTSKVASGVPYRFSGSGSGTSYSLTISSMEAEDAATYYCQQWSSNPLTFGAGTK LELKHHHHHH- | 44 |
| SIRP1α-CD3-SL | METDTLLLWVLLLWVPGSTGDEEELQIIQPDKSVLVAAGETATLRCTITSLFPVGPI QWFRGAGPGRVLIYNQRQGPFPRVTTVSDTTKRNNMDFSIRIGNITPADAGTYYCIK FRKGSPDDVEFKSGAGTELSVRAKPSASDIKLQQSGAELARPGASVKMSCKTSGYTF TRYTMHWVKQRPGQGLEWIGYINPSRGYTNYNQKFKDKATLTTDKSSSTAYMQLSSL TSEDSAVYYCARYYDDHYCLDYWGQGTTLTVSSVEGGSGGSGGSGGSGGVDDIQLTQ SPAIMSASPGEKVTMTCRASSSVSYMNWYQQKSGTSPKRWIYDTSKVASGVPYRFSG SGSGTSYSLTISSMEAEDAATYYCQQWSSNPLTFGAGTKLELKHHHHHH- | 46 |
| SIRP1α-CD3-LL | METDTLLLWVLLLWVPGSTGDEEELQIIQPDKSVLVAAGETATLRCTITSLFPVGPI QWFRGAGPGRVLIYNQRQGPFPRVTTVSDTTKRNNMDFSIRIGNITPADAGTYYCIK FRKGSPDDVEFKSGAGTELSVRAKPSASGGGGSDIKLQQSGAELARPGASVKMSCKT SGYTFTRYTMHWVKQRPGQGLEWIGYINPSRGYTNYNQKFKDKATLTTDKSSSTAYM QLSSLTSEDSAVYYCARYYDDHYCLDYWGQGTTLTVSSVEGGSGGSGGSGGSGGVDD IQLTQSPAIMSASPGEKVTMTCRASSSVSYMNWYQQKSGTSPKRWIYDTSKVASGVP YRFSGSGSGTSYSLTISSMEAEDAATYYCQQWSSNPLTFGAGTKLELKHHHHHH- | 48 |
| PDL1-CD3 | MEFGLSWVFLVALFRGVQCDIKLQQSGAELARPGASVKMSCKTSGYTFTRYTMHWVK QRPGQGLEWIGYINPSRGYTNYNQKFKDKATLTTDKSSSTAYMQLSSLTSEDSAVYY CARYYDDHYCLDYWGQGTTLTVSSVEGGSGGSGGSGGSGGVDDIQLTQSPAIMSASP GEKVTMTCRASSSVSYMNWYQQKSGTSPKRWIYDTSKVASGVPYRFSGSGSGTSYSL TISSMEAEDAATYYCQQWSSNPLTFGAGTKLELKGGGGSDIQMTQSPSSLSASVGDR VTITCRASQDVSTAVAWYQQKPGKAPKLLIYSASFLYSGVPSRFSGSGSGTDFTLTI SSLQPEDFATYYCQQYLYHPATFGQGTKVEIKRGGGGSGGGGSGGGGSEVQLVESGG GLVQPGGSLRLSCAASGFTFSDSWIHWVRQAPGKGLEWVAWISPYGGSTYYADSVKG | 50 |

TABLE 1-continued

Amino acid sequences of exemplary engager molecules

| BiTE | Amino Acid Sequence | SEQ ID |
|---|---|---|
| | RFTISADTSKNTAYLQMNSLRAEDTAVYYCARRHWPGGFDYWGQGTLVTVSAHHHHH H- | |
| PDIA-CD3-Fc | MEFGLSWVFLVALFRGVQCDIKLQQSGAELARPGASVKMSCKTSGYTFTRYTMHWVK QRPGQGLEWIGYINPSRGYTNYNQKFKDKATLTTDKSSSTAYMQLSSLTSEDSAVYY CARYYDDHYCLDYWGQGTTLTVSSVEGGSGGSGGSGGSGGVDDIQLTQSPAIMSASP GEKVTMTCRASSSVSYMNWYQQKSGTSPKRWIYDTSKVASGVPYRFSGSGSGTSYSL TISSMEAEDAATYYCQQWSSNPLTFGAGTKLELKGGGGSDIQMTQSPSSLSASVGDR VTITCRASQDVSTAVAWYQQKPGKAPKLLIYSASFLYSGVPSRFSGSGSGTDFTLTI SSLQPEDFATYYCQQYLYHPATFGQGTKVEIKRGGGGSGGGGSGGGGSEVQLVESGG GLVQPGGSLRLSCAASGFTFSDSWIHWVRQAPGKGLEWVAWISPYGGSTYYADSVKG RFTISADTSKNTAYLQMNSLRAEDTAVYYCARRHWPGGFDYWGQGTLVTVSAVDEAK SCDKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLSPG HHHHHH- | 52 |
| CD19-CD3-IL15 | MEFGLSWVFLVALFRGVQCDIQLTQSPASLAVSLGQRATISCKASQSVDYDGDSYLN WYQQIPGQPPKLLIYDASNLVSGIPPRFSGSGSGTDFTLNIHPVEKVDAATYHCQQS TEDPWTFGGGTKLEIKGGGGSGGGGSGGGGSQVQLQQSGAELVRPGSSVKISCKASG YAFSSYWMNWVKQRPGQGLEWIGQIWPGDGDTNYNGKFKGKATLTADESSSTAYMQL SSLASEDSAVYFCARRETTTVGRYYYAMDYWGQGTTVTVSSGGGGSDIKLQQSGAEL ARPGASVKMSCKTSGYTFTRYTMHWVKQRPGQGLEWIGYINPSRGYTNYNQKFKDKA TLTTDKSSSTAYMQLSSLTSEDSAVYYCARYYDDHYCLDYWGQGTTLTVSSVEGGSG GSGGSGGSGGVDDIQLTQSPAIMSASPGEKVTMTCRASSSVSYMNWYQQKSGTSPKR WIYDTSKVASGVPYRFSGSGSGTSYSLTISSMEAEDAATYYCQQWSSNPLTFGAGTK LELKHHHHHHRRKREGRGSLLTCGDVEENPGPMRISKPHLRSISIQCYLCLLLNSHF LTEAGIHVFILGCFSAGLPKTEANWVNVISDLKKIEDLIQSMHIDATLYTESDVHPS CKVTAMKCFLLELQVISLESGDASIHDTVENLIILANNSLSSNGNVTESGCKECEEL EEKNIKEFLQSFVHIVQMFINTS- | 53 |
| CD19-CD3-IL12 | MEFGLSWVFLVALFRGVQCDIQLTQSPASLAVSLGQRATISCKASQSVDYDGDSYLN WYQQIPGQPPKLLIYDASNLVSGIPPRFSGSGSGTDFTLNIHPVEKVDAATYHCQQS TEDPWTFGGGTKLEIKGGGGSGGGGSGGGGSQVQLQQSGAELVRPGSSVKISCKASG YAFSSYWMNWVKQRPGQGLEWIGQIWPGDGDTNYNGKFKGKATLTADESSSTAYMQL SSLASEDSAVYFCARRETTTVGRYYYAMDYWGQGTTVTVSSGGGGSDIKLQQSGAEL ARPGASVKMSCKTSGYTFTRYTMHWVKQRPGQGLEWIGYINPSRGYTNYNQKFKDKA TLTTDKSSSTAYMQLSSLTSEDSAVYYCARYYDDHYCLDYWGQGTTLTVSSVEGGSG GSGGSGGSGGVDDIQLTQSPAIMSASPGEKVTMTCRASSSVSYMNWYQQKSGTSPKR WIYDTSKVASGVPYRFSGSGSGTSYSLTISSMEAEDAATYYCQQWSSNPLTFGAGTK LELKHHHHHHRRKREGRGSLLTCGDVEENPGPMWPPGSASQPPPSPAAATGLHPAAR PVSLQCRLSMCPARSLLLLVATLVLLDHLSLARNLPVATPDPGMFPCLHHSQNLLRAV SNMLQKARQTLEFYPCTSEEIDHEDITKDKTSTVEACLPLELTKNESCLNSRETSFI TNGSCLASRKTSFMMALCLSSIYEDLKMYQVEFKTMNAKLLMDPKRQIFLDQNMLAV IDELMQALNFNSETVPQKSSLEEPDFYKTKIKLCILLHAFRIRAVTIDRVMSYLNAS RRKREGRGSLLTCGDVEENPGPPMCHQQLVISWFSLVFLASPLVAIWELKKDVYVVE LDWYPDAPGEMVVLTCDTPEEDGITWTLDQSSEVLGSGKTLTIQVKEFGDAGQYTCH KGGEVLSHSLLLLHKKEDGIWSTDILKDQKEPKNKTFLRCEAKNYSGRFTCWWLTTI STDLTFSVKSSRGSSDPQGVTCGAATLSAERVRGDNKEYEYSVECQEDSACPAAEES LPIEVMVDAVHKLKYENYTSSFFIRDIIKPDPPKNLQLKPLKNSRQVEVSWEYPDTW STPHSYFSLTFCVQVQGKSKREKKDRVFTDKTSATVICRKNASISVRAQDRYYSSSW SEWASVPCS- | 54 |
| CD19-CD3-CXCL10 | MEFGLSWVFLVALFRGVQCDIQLTQSPASLAVSLGQRATISCKASQSVDYDGDSYLN WYQQIPGQPPKLLIYDASNLVSGIPPRESGSGSGTDFTLNIHPVEKVDAATYHCQQS TEDPWTFGGGTKLEIKGGGGSGGGGSGGGGSQVQLQQSGAELVRPGSSVKISCKASG YAFSSYWMNWVKQRPGQGLEWIGQIWPGDGDTNYNGKFKGKATLTADESSSTAYMQL SSLASEDSAVYFCARRETTTVGRYYYAMDYWGQGTTVTVSSGGGGSDIKLQQSGAEL ARPGASVKMSCKTSGYTFTRYTMHWVKQRPGQGLEWIGYINPSRGYTNYNQKFKDKA TLTTDKSSSTAYMQLSSLTSEDSAVYYCARYYDDHYCLDYWGQGTTLTVSSVEGGSG GSGGSGGSGGVDDIQLTQSPAIMSASPGEKVTMTCRASSSVSYMNWYQQKSGTSPKR WIYDTSKVASGVPYRFSGSGSGTSYSLTISSMEAEDAATYYCQQWSSNPLTFGAGTK LELKHHHHHHRRKREGRGSLLTCGDVEENPGPMNQTAILICCLIFLTLSGIQGVPLS RTVRCTCISISNQPVNPRSLEKLEIIPASQFCPRVEIIATMKKKGEKRCLNPESKAI KNLLKAVSKERSKRSP- | 55 |
| SIRP1α-CD3-IL15 (SL) | METDTLLLWVLLLWVPGSTGDEEELQIIQPDKSVLVAAGETATLRCTITSLFPVGPI QWFRGAGPGRVLIYNQRQGPFPRVTTVSDTTKRNNMDFSIRIGNITPADAGTYYCIK FRKGSPDDVEFKSGAGTELSVRAKPSASDIKLQQSGAELARPGASVKMSCKTSGYTF TRYTMHWVKQRPGQGLEWIGYINPSRGYTNYNQKFKDKATLTTDKSSSTAYMQLSSL TSEDSAVYYCARYYDDHYCLDYWGQGTTLTVSSVEGGSGGSGGSGGSGGVDDIQLTQ SPAIMSASPGEKVTMTCRASSSVSYMNWYQQKSGTSPKRWIYDTSKVASGVPYRFSG SGSGTSYSLTISSMEAEDAATYYCQQWSSNPLTFGAGTKLELKHHHHHHRRKREGRG SLLTCGDVEENPGPMRISKPHLRSISIQCYLCLLLNSHFLTEAGIHVFILGCFSAGL PKTEANWVNVISDLKKIEDLIQSMHIDATLYTESDVHPSCKVTAMKCFLLELQVISL | 56 |

TABLE 1-continued

Amino acid sequences of exemplary engager molecules

| BiTE | Amino Acid Sequence | SEQ ID |
|---|---|---|
| | ESGDASIHDTVENLIILANNSLSSNGNVTESGCKECEELEEKNIKEFLQSFVHIVQM FINTS- | |
| SIRP1α-CD3-IL15 (LL) | METDTLLLWVLLLWVPGSTGDEEELQIIQPDKSVLVAAGETATLRCTITSLFPVGPI QWFRGAGPGRVLIYNQRQGPFPPRVTTVSDTTKRNNMDFSIRIGNITPADAGTYYCIK FRKGSPDDVEFKSGAGTELSVRAKPSASGGGGSDIKLQQSGAELARPGASVKMSCKT SGYTFTRYTMHWVKQRPGQGLEWIGYINPSRGYTNYNQKFKDKATLTTDKSSSTAYM QLSSLTSEDSAVYYCARYYDDHYCLDYWGQGTTLTVSSVEGGSGGSGGSGGSGGVDD IQLTQSPAIMSASPGEKVTMTCRASSSVSYMNWYQQKSGTSPKRWIYDTSKVASGVP YRFSGSGSGTSYSLTISSMEAEDAATYYCQQWSSNPLTFGAGTKLELKHHHHHHRRK REGRGSLLTCGDVEENPGPMRISKPHLRSISIQCYLCLLLNSHFLTEAGIHVFILGC FSAGLPKTEANWVNVISDLKKIEDLIQSMHIDATLYTESDVHPSCKVTAMKCFLLEL QVISLESGDASIHDTVENLIILANNSLSSNGNVTESGCKECEELEEKNIKEFLQSFV HIVQMFINTS- | 57 |
| SIRP1α-C3-IL12) (SL) | METDTLLLWVLLLWVPGSTGDEEELQIIQPDKSVLVAAGETATLRCTITSLFPVGPI QWFRGAGPGRVLIYNQRQGPFPPRVTTVSDTTKRNNMDFSIRIGNITPADAGTYYCIK FRKGSPDDVEFKSGAGTELSVRAKPSASDIKLQQSGAELARPGASVKMSCKTSGYTF TRYTMHWVKQRPGQGLEWIGYINPSRGYTNYNQKFKDKATLTTDKSSSTAYMQLSSL TSEDSAVYYCARYYDDHYCLDYWGQGTTLTVSSVEGGSGGSGGSGGSGGVDDIQLTQ SPAIMSASPGEKVTMTCRASSSVSYMNWYQQKSGTSPKRWIYDTSKVASGVPYRFSG SGSGTSYSLTISSMEAEDAATYYCQQWSSNPLTFGAGTKLELKHHHHHHRRKREGRG SLLTCGDVEENPGPMWPPGSASQPPPSPAAATGLHPAARPVSLQCRLSMCPARSLLL VATLVLLDHLSLARNLPVATPDPGMFPCLHHSQNLLRAVSNMLQKARQTLEFYPCTS EEIDHEDITKDKTSTVEACLPLELTKNESCLNSRETSFITNGSCLASRKTSFMMALC LSSIYEDLKMYQVEFKTMNAKLLMDPKRQIFLDQNMLAVIDELMQALNFNSETVPQK SSLEEPDFYKTKIKLCILLHAFRIRAVTIDRVMSYLNASRRKREGRGSLLTCGDVEE NPGPPMCHQQLVISWFSLVFLASPLVAIWELKKDVYVVELDWYPDAPGEMVVLTCDT PEEDGITWTLDQSSEVLGSGKTLTIQVKEFGDAGQYTCHKGGEVLSHSLLLLHKKED GIWSTDILKDQKEPKNKTFLRCEAKNYSGRFTCWWLTTISTDLTFSVKSSRGSSDPQ GVTCGAATLSAERVRGDNKEYEYSVECQEDSACPAAEESLPIEVMVDAVHKLKYENY TSSFFIRDIIKPDPPKNLQLKPLKNSRQVEVSWEYPDTWSTPHSYFSLTFCVQVQGK SKREKKDRVFTDKTSATVICRKNASISVRAQDRYYSSSWSEWASVPCS- | 58 |
| SIRP1α-CD3-IL12 (LL) | METDTLLLWVLLLWVPGSTGDEEELQIIQPDKSVLVAAGETATLRCTITSLFPVGPI QWFRGAGPGRVLIYNQRQGPFPPRVTTVSDTTKRNNMDFSIRIGNITPADAGTYYCIK FRKGSPDDVEFKSGAGTELSVRAKPSASGGGGSDIKLQQSGAELARPGASVKMSCKT SGYTFTRYTMHWVKQRPGQGLEWIGYINPSRGYTNYNQKFKDKATLTTDKSSSTAYM QLSSLTSEDSAVYYCARYYDDHYCLDYWGQGTTLTVSSVEGGSGGSGGSGGSGGVDD IQLTQSPAIMSASPGEKVTMTCRASSSVSYMNWYQQKSGTSPKRWIYDTSKVASGVP YRFSGSGSGTSYSLTISSMEAEDAATYYCQQWSSNPLTFGAGTKLELKHHHHHHRRK REGRGSLLTCGDVEENPGPMWPPGSASQPPPSPAAATGLHPAARPVSLQCRLSMCPA RSLLLVATLVLLDHLSLARNLPVATPDPGMFPCLHHSQNLLRAVSNMLQKARQTLEF YPCTSEEIDHEDITKDKTSTVEACLPLELTKNESCLNSRETSFITNGSCLASRKTSF MMALCLSSIYEDLKMYQVEFKTMNAKLLMDPKRQIFLDQNMLAVIDELMQALNFNSE TVPQKSSLEEPDFYKTKIKLCILLHAFRIRAVTIDRVMSYLNASRRKREGRGSLLTC GDVEENPGPPMCHQQLVISWFSLVFLASPLVAIWELKKDVYVVELDWYPDAPGEMVV LTCDTPEEDGITWTLDQSSEVLGSGKTLTIQVKEFGDAGQYTCHKGGEVLSHSLLLL HKKEDGIWSTDILKDQKEPKNKTFLRCEAKNYSGRFTCWWLTTISTDLTFSVKSSRG SSDPQGVTCGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYFSLTFCV QVQGKSKREKKDRVFTDKTSATVICRKNASISVRAQDRYYSSSWSEWASVPCS- | 59 |
| SIRP1α-CD3-CXCL10 (SL) | METDTLLLWVLLLWVPGSTGDEEELQIIQPDKSVLVAAGETATLRCTITSLFPVGPI QWFRGAGPGRVLIYNQRQGPFPPRVTTVSDTTKRNNMDFSIRIGNITPADAGTYYCIK FRKGSPDDVEFKSGAGTELSVRAKPSASDIKLQQSGAELARPGASVKMSCKTSGYTF TRYTMHWVKQRPGQGLEWIGYINPSRGYTNYNQKFKDKATLTTDKSSSTAYMQLSSL TSEDSAVYYCARYYDDHYCLDYWGQGTTLTVSSVEGGSGGSGGSGGSGGVDDIQLTQ SPAIMSASPGEKVTMTCRASSSVSYMNWYQQKSGTSPKRWIYDTSKVASGVPYRFSG SGSGTSYSLTISSMEAEDAATYYCQQWSSNPLTFGAGTKLELKHHHHHHRRKREGRG SLLTCGDVEENPGPMNQTAILICCLIFLTLSGIQGVPLSRTVRCTCISISNQPVNPR SLEKLEIIPASQFCPRVEIIATMKKKGEKRCLNPESKAIKNLLKAVSKERSKRSP- | 60 |
| SIRP1α-CD3-CXCL10 (LL) | METDTLLLWVLLLWVPGSTGDEEELQIIQPDKSVLVAAGETATLRCTITSLFPVGPI QWFRGAGPGRVLIYNQRQGPFPPRVTTVSDTTKRNNMDFSIRIGNITPADAGTYYCIK FRKGSPDDVEFKSGAGTELSVRAKPSASGGGGSDIKLQQSGAELARPGASVKMSCKT SGYTFTRYTMHWVKQRPGQGLEWIGYINPSRGYTNYNQKFKDKATLTTDKSSSTAYM QLSSLTSEDSAVYYCARYYDDHYCLDYWGQGTTLTVSSVEGGSGGSGGSGGSGGVDD IQLTQSPAIMSASPGEKVTMTCRASSSVSYMNWYQQKSGTSPKRWIYDTSKVASGVP YRFSGSGSGTSYSLTISSMEAEDAATYYCQQWSSNPLTFGAGTKLELKHHHHHHRRK REGRGSLLTCGDVEENPGPMNQTAILICCLIFLTLSGIQGVPLSRTVRCTCISISNQ PVNPRSLEKLEIIPASQFCPRVEIIATMKKKGEKRCLNPESKAIKNLLKAVSKERSK RSP- | 61 |
| PDL1-CD3-IL15 | MEFGLSWVFLVALFRGVQCDIKLQQSGAELARPGASVKMSCKTSGYTFTRYTMHWVK QRPGQGLEWIGYINPSRGYTNYNQKFKDKATLTTDKSSSTAYMQLSSLTSEDSAVYY | 62 |

TABLE 1-continued

Amino acid sequences of exemplary engager molecules

| BiTE | Amino Acid Sequence | SEQ ID |
|---|---|---|
| | CARYYDDHYCLDYWGQGTTLTVSSVEGGSGGSGGSGGSGGVDDIQLTQSPAIMSASP<br>GEKVTMTCRASSSVSYMNWYQQKSGTSPKRWIYDTSKVASGVPYRFSGSGSGTSYSL<br>TISSMEAEDAATYYCQQWSSNPLTFGAGTKLELKGGGGSDIQMTQSPSSLSASVGDR<br>VTITCRASQDVSTAVAWYQQKPGKAPKLLIYSASFLYSGVPSRFSGSGSGTDFTLTI<br>SSLQPEDFATYYCQQYLYHPATFGQGTKVEIKRGGGGSGGGGSGGGGSEVQLVESGG<br>GLVQPGGSLRLSCAASGFTFSDSWIHWVRQAPGKGLEWVAWISPYGGSTYYADSVKG<br>RFTISADTSKNTAYLQMNSLRAEDTAVYYCARRHWPGGFDYWGQGTLVTVSAHHHHH<br>HRRKREGRGSLLTCGDVEENPGPMRISKPHLRSISIQCYLCLLLNSHFLTEAGIHVF<br>ILGCFSAGLPKTEANWVNVISDLKKIEDLIQSMHIDATLYTESDVHPSCKVTAMKCF<br>LLELQVISLESGDASIHDTVENLIILANNSLSSNGNVTESGCKECEELEEKNIKEFL<br>QSFVHIVQMFINTS- | |
| PDL1-CD3-<br>IL12 | MEFGLSWVFLVALFRGVQCDIKLQQSGAELARPGASVKMSCKTSGYTFTRYTMHWVK<br>QRPGQGLEWIGYINPSRGYTNYNQKFKDKATLTTDKSSSTAYMQLSSLTSEDSAVYY<br>CARYYDDHYCLDYWGQGTTLTVSSVEGGSGGSGGSGGSGGVDDIQLTQSPAIMSASP<br>GEKVTMTCRASSSVSYMNWYQQKSGTSPKRWIYDTSKVASGVPYRFSGSGSGTSYSL<br>TISSMEAEDAATYYCQQWSSNPLTFGAGTKLELKGGGGSDIQMTQSPSSLSASVGDR<br>VTITCRASQDVSTAVAWYQQKPGKAPKLLIYSASFLYSGVPSRFSGSGSGTDFTLTI<br>SSLQPEDFATYYCQQYLYHPATFGQGTKVEIKRGGGGSGGGGSGGGGSEVQLVESGG<br>GLVQPGGSLRLSCAASGFTFSDSWIHWVRQAPGKGLEWVAWISPYGGSTYYADSVKG<br>RFTISADTSKNTAYLQMNSLRAEDTAVYYCARRHWPGGFDYWGQGTLVTVSAHHHHH<br>HRRKREGRGSLLTCGDVEENPGPMWPPGSASQPPPSPAAATGLHPAARPVSLQCRLS<br>MCPARSLLLVATLVLLDHLSLARNLPVATPDPGMFPCLHHSQNLLRAVSNMLQKARQ<br>TLEFYPCTSEEIDHEDITKDKTSTVEACLPLELTKNESCLNSRETSFITNGSCLASR<br>KTSFMMALCLSSIYEDLKMYQVEFKTMNAKLLMDPKRQIFLDQNMLAVIDELMQALN<br>FNSETVPQKSSLEEPDFYKTKIKLCILLHAFRIRAVTIDRVMSYLNASRRKREGRGS<br>LLTCGDVEENPGPPMCHQQLVISWFSLVFLASPLVAIWELKKDVYVVELDWYPDAPG<br>EMVVLTCDTPEEDGITWTLDQSSEVLGSGKTLTIQVKEFGDAGQYTCHKGGEVLSHS<br>LLLLHKKEDGIWSTDILKDQKEPKNKTFLRCEAKNYSGRFTCWWLTTISTDLTFSVK<br>SSRGSSDPQGVTCGAATLSAERVRGDNKEYEYSVECQEDSACPAAEESLPIEVMVDA<br>VHKLKYENYTSSFFIRDIIKPDPPKNLQLKPLKNSRQVEVSWEYPDTWSTPHSYFSL<br>TFCVQVQGKSKREKKDRVFTDKTSATVICRKNASISVRAQDRYYSSSWSEWASVPCS | 63 |
| PDL1-CD3-<br>CXCL10 | MEFGLSWVFLVALFRGVQCDIKLQQSGAELARPGASVKMSCKTSGYTFTRYTMHWVK<br>QRPGQGLEWIGYINPSRGYTNYNQKFKDKATLTTDKSSSTAYMQLSSLTSEDSAVYY<br>CARYYDDHYCLDYWGQGTTLTVSSVEGGSGGSGGSGGSGGVDDIQLTQSPAIMSASP<br>GEKVTMTCRASSSVSYMNWYQQKSGTSPKRWIYDTSKVASGVPYRFSGSGSGTSYSL<br>TISSMEAEDAATYYCQQWSSNPLTFGAGTKLELKGGGGSDIQMTQSPSSLSASVGDR<br>VTITCRASQDVSTAVAWYQQKPGKAPKLLIYSASFLYSGVPSRFSGSGSGTDFTLTI<br>SSLQPEDFATYYCQQYLYHPATFGQGTKVEIKRGGGGSGGGGSGGGGSEVQLVESGG<br>GLVQPGGSLRLSCAASGFTFSDSWIHWVRQAPGKGLEWVAWISPYGGSTYYADSVKG<br>RFTISADTSKNTAYLQMNSLRAEDTAVYYCARRHWPGGFDYWGQGTLVTVSAHHHHH<br>HRRKREGRGSLLTCGDVEENPGPMNQTAILICCLIFLTLSGIQGVPLSRTVRCTCIS<br>ISNQPVNPRSLEKLEIIPASQFCPRVEIIATMKKKGEKRCLNPESKAIKNLLKAVSK<br>ERSKRSP- | 64 |
| SIRP1α-<br>CD3-MMP9<br>(SL) | METDTLLLWVLLLWVPGSTGDEEELQIIQPDKSVLVAAGETATLRCTITSLFPVGPI<br>QWFRGAGPGRVLIYNQRQGPFPRVTTVSDTTKRNNMDFSIRIGNITPADAGTYYCIK<br>FRKGSPDDVEFKSGAGTELSVRAKPSASDIKLQQSGAELARPGASVKMSCKTSGYTF<br>TRYTMHWVKQRPGQGLEWIGYINPSRGYTNYNQKFKDKATLTTDKSSSTAYMQLSSL<br>TSEDSAVYYCARYYDDHYCLDYWGQGTTLTVSSVEGGSGGSGGSGGSGGVDDIQLTQ<br>SPAIMSASPGEKVTMTCRASSSVSYMNWYQQKSGTSPKRWIYDTSKVASGVPYRFSG<br>SGSGTSYSLTISSMEAEDAATYYCQQWSSNPLTFGAGTKLELKHHHHHHRRKREGRG<br>SLLTCGDVEENPGPMSLWQPLVLVLLVLGCCFAAPRQRQSTLVLFPGDLRTNLTDRQ<br>LAEEYLYRYGYTRVAEMRGESKSLGPALLLLQKQLSLPETGELDSATLKAMRTPRCG<br>VPDLGRFQTFEGDLKWHHHNITYWIQNYSEDLPRAVIDDAFARAFALWSAVTPLTFT<br>RVYSRDADIVIQFGVAEHGDGYPFDGKDGLLAHAFPPGPGIQGDAHFDDDELWSLGK<br>GVVVPTRFGNADGAACHFPFIFEGRSYSACTTDGRSDGLPWCSTTANYDTDDRFGFC<br>PSERLYTRDGNADGKPCQFPFIFQGQSYSACTTDGRSDGYRWCATTANYDRDKLFGF<br>CPTRADSTVMGGNSAGELCVFPFTFLGKEYSTCTSEGRGDGRLWCATTSNFDSDKKW<br>GFCPDQGYSLFLVAAHEFGHALGLDHSSVPEALMYPMYRFTEGPPLHKDDVNGIRHL<br>YGPRPEPEPRPPTTTTPQPTAPPTVCPTGPPTVHPSERPTAGPTGPPSAGPTGPPTA<br>GPSTATTVPLSPVDDACNVIFDAIAEIGNQLYLFKDGKYWRFSEGRGSRPQGPFLI<br>ADKWPALPRKLDSVFEEPLSKKLFFFSGRQVWVYTGASVLGPRRLDKLGLGADVAQV<br>TGALRSGRGKMLLFSGRRLWRFDVKAQMVDPRSASEVDRMFPGVPLDTHDVFQYREK<br>AYFCQDRFYWRVSSRSELNQVDQVGYVTYDILQCPED- | 65 |
| SIRP1α-<br>CD3-MMP9<br>(LL) | METDTLLLWVLLLWVPGSTGDEEELQIIQPDKSVLVAAGETATLRCTITSLFPVGPI<br>QWFRGAGPGRVLIYNQRQGPFPRVTTVSDTTKRNNMDFSIRIGNITPADAGTYYCIK<br>FRKGSPDDVEFKSGAGTELSVRAKPSASGGGGSDIKLQQSGAELARPGASVKMSCKT<br>SGYTFTRYTMHWVKQRPGQGLEWIGYINPSRGYTNYNQKFKDKATLTTDKSSSTAYM<br>QLSSLTSEDSAVYYCARYYDDHYCLDYWGQGTTLTVSSVEGGSGGSGGSGGSGGVDD<br>IQLTQSPAIMSASPGEKVTMTCRASSSVSYMNWYQQKSGTSPKRWIYDTSKVASGVP<br>YRFSGSGSGTSYSLTISSMEAEDAATYYCQQWSSNPLTFGAGTKLELKHHHHHHRRK<br>REGRGSLLTCGDVEENPGPMSLWQPLVLVLLVLGCCFAAPRQRQSTLVLFPGDLRTN<br>LTDRQLAEEYLYRYGYTRVAEMRGESKSLGPALLLLQKQLSLPETGELDSATLKAMR | 66 |

TABLE 1-continued

Amino acid sequences of exemplary engager molecules

| BiTE | Amino Acid Sequence | SEQ ID |
|---|---|---|
| | TPRCGVPDLGRFQTFEGDLKWHHHNITYWIQNYSEDLPRAVIDDAFARAFALWSAVT<br>PLTFTRVYSRDADIVIQFGVAEHGDGYPFDGKDGLLAHAFPPGPGIQGDAHFDDDEL<br>WSLGKGVVVPTRFGNADGAACHFPFIFEGRSYSACTTDGRSDGLPWCSTTANYDTDD<br>RFGFCPSERLYTRDGNADGKPCQFPFIFQGQSYSACTTDGRSDGYRWCATTANYDRD<br>KLFGFCPTRADSTVMGGNSAGELCVFPFTFLGKEYSTCTSEGRGDGRLWCATTSNFD<br>SDKKWGFCPDQGYSLFLVAAHEFGHALGLDHSSVPEALMYPMYRFTEGPPLHKDDVN<br>GIRHLYGPRPEPEPRPPTTTTPQPTAPPTVCPTGPPTVHPSERPTAGPTGPPSAGPT<br>GPPTAGPSTATTVPLSPVDDACNVNIFDAIAEIGNQLYLEKDGKYWRFSEGRGSRPQ<br>GPFLIADKWPALPRKLDSVFEEPLSKKLFFFSGRQVWVYTGASVLGPRRLDKLGLGA<br>DVAQVTGALRSGRGKMLLFSGRRLWRFDVKAQMVDPRSASEVDRMFPGVPLDTHDVF<br>QYREKAYFCQDRFYWRVSSRSELNQVDQVGYVTYDILQCPED- | |
| SIRP1α-<br>CD3-PDL1-<br>Fc(SL) | METDRLLLWVLLLWVPGSTGDYPYDVPDYAGAQPADDIQMTQSPSSLSASVGDRVTI<br>TCRASQDVSTAVAWYQQKPGKAPKLLIYSASFLYSGVPSRFSGSGSGTDFTLTISSL<br>QPEDFATYYCQQYLYHPATFGQGTKVEIKRGGGGSGGGGSGGGGSEVQLVESGGGLV<br>QPGGSLRLSCAASGETFSDSWIHWVRQAPGKGLEWVAWISPYGGSTYYADSVKGRFT<br>ISADTSKNTAYLQMNSLRAEDTAVYYCARRHWPGGFDYWGQGTLVTVSAVDEAKSCD<br>KTHTCPPCPAPELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPAPIEKT<br>ISKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGKVD<br>EQKLISEEDLNRRKREGRGSLLTCGDVEENPGPMETDRLLLWVLLLWVPGSTGDEEE<br>LQIIQPDKSVLVAAGETATLRCTITSLFPVGPIQWFRGAGPGRVLIYNQRQGPFPRV<br>TTVSDTTKRNNMDFSIRIGNITPADAGTYYCIKFRKGSPDDVEFKSGAGTELSVRAK<br>PSASDIKLQQSGAELARPGASVKMSCKTSGYTFTRYTMHWVKQRPGQGLEWIGYINP<br>SRGYTNYNQKFKDKATLTTDKSSSTAYMQLSSLTSEDSAVYYCARYYDDHYCLDYWG<br>QGTTLTVSSVEGGSGGSGGSGGSGGVDDIQLTQSPAIMSASPGEKVTMTCRASSSVS<br>YMNWYQQKSGTSPKRWIYDTSKVASGVPYRFSGSGSGTSYSLTISSMEAEDAATYYC<br>QQWSSNPLTFGAGTKLELKHHHHHH- | 68 |
| SIRP1α-<br>CD3-PDL1-<br>Fc(LL) | METDRLLLWVLLLWVPGSTGDYPYDVPDYAGAQPADDIQMTQSPSSLSASVGDRVTI<br>TCRASQDVSTAVAWYQQKPGKAPKLLIYSASFLYSGVPSRFSGSGSGTDFTLTISSL<br>QPEDFATYYCQQYLYHPATFGQGTKVEIKRGGGGSGGGGSGGGGSEVQLVESGGGLV<br>QPGGSLRLSCAASGETFSDSWIHWVRQAPGKGLEWVAWISPYGGSTYYADSVKGRFT<br>ISADTSKNTAYLQMNSLRAEDTAVYYCARRHWPGGFDYWGQGTLVTVSAVDEAKSCD<br>KTHTCPPCPAPELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPAPIEKT<br>ISKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGKVD<br>EQKLISEEDLNRRKREGRGSLLTCGDVEENPGPMETDRLLLWVLLLWVPGSTGDEEE<br>LQIIQPDKSVLVAAGETATLRCTITSLFPVGPIQWFRGAGPGRVLIYNQRQGPFPRV<br>TTVSDTTKRNNMDFSIRIGNITPADAGTYYCIKFRKGSPDDVEFKSGAGTELSVRAK<br>PSASGGGGSDIKLQQSGAELARPGASVKMSCKTSGYTFTRYTMHWVKQRPGQGLEWI<br>GYINPSRGYTNYNQKFKDKATLTTDKSSSTAYMQLSSLTSEDSAVYYCARYYDDHYC<br>LDYWGQGTTLTVSSVEGGSGGSGGSGGSGGVDDIQLTQSPAIMSASPGEKVTMTCRA<br>SSSVSYMNWYQQKSGTSPKRWIYDTSKVASGVPYRFSGSGSGTSYSLTISSMEAEDA<br>ATYYCQQWSSNPLTFGAGTKLELKHHHHHH- | 70 |
| FAP-CD3 | MYRMQLLSCIALSLALVTNSQVQLQQSGAELARPGASVNLSCKASGYTFTNNGINWL<br>KQRTGQGLEWIGEIYPRSTNTLYNEKFKGKATLTADRSSNTAYMELRSLTSEDSAVY<br>FCARTLTAPFAFWGQGTLVTVSAGSTSGSGKPGSGEGSTKGQIVLTQSPAIMSASPG<br>EKVTMTCSASSGVNFMHWYQQKSGTSPKRWIFDTSKLASGVPARFSGSGSGTSYSLT<br>ISSMEAEDAATYYCQQWSFNPPTFGGGTKLEIKRGGGGSEVQLVESGGGLVQPGKSL<br>KLSCEASGETFSGYGMHWVRQAPGRGLESVAYITSSSINTKYADAVKGRFTVSRDNA<br>KNLLFLQMNILKSEDTAMYYCARFDWDKNYWGQGTMVTVSSGGGGSGGGGSGGGGSD<br>IQMTQSPSSLPASLGDRVTINCQASQDISNYLNWYQQKPGKAPKLLIYYTNKLADGV<br>PSRFSGSGSGRDSSETISSLESEDIGSYYCQQYYNYPWTFGPGTKLEIKRHHHHHH | 75 |

In some embodiments, the oncolytic viruses described herein comprise a nucleic acid sequence selected from SEQ ID NOs: 43, 45, 47, 49, 51, 67, and 69. In some embodiments, the oncolytic viruses described herein comprise a nucleic acid sequence that is at least 80%, at least, 85%, at least 90%, at least 95%, at least 96%, at least 97%, at least 98%, or at least 99% identical to a nucleic acid sequence selected from SEQ ID NOs: 43, 45, 47, 49, 51, 67, and 69. In some embodiments, the oncolytic viruses described herein comprise a nucleic acid sequence that is 100% identical to a nucleic acid sequence selected from SEQ ID NOs: 43, 45, 47, 49, 51, 67, and 69. In some embodiments, the oncolytic viruses described herein consist of a nucleic acid sequence selected from SEQ ID NOs: 43, 45, 47, 49, 51, 67, and 69.

In some embodiments, the oncolytic viruses described herein comprise a nucleic acid sequence encoding an engager molecule and/or therapeutic molecule that is at least 80%, at least, 85%, at least 90%, at least 95%, at least 96%, at least 97%, at least 98%, or at least 99% identical to an amino acid sequence selected from SEQ ID NOs: 44, 46, 48, 50, and 52. In some embodiments, the oncolytic viruses described herein comprise a nucleic acid sequence encoding an engager molecule that is 100% identical to an amino acid sequence selected from SEQ ID NOs: 44, 46, 48, 50, and 52. In some embodiments, the oncolytic viruses described herein comprise a nucleic acid sequence encoding an engager molecule comprising an amino acid sequence selected from SEQ ID NOs: 44, 46, 48, 50, and 52. In some embodiments, the oncolytic viruses described herein comprise a nucleic acid sequence encoding an engager molecule consisting of an amino acid sequence selected from SEQ ID NOs: 44, 46, 48, 50, and 52.

In some embodiments, the oncolytic viruses described herein comprise a nucleic acid sequence encoding an engager molecule and a therapeutic molecule. In some embodiments, the recombinant nucleic acid sequences encode an engager molecule and a therapeutic molecule comprising an amino acid sequence is at least 80%, at least, 85%, at least 90%, at least 95%, at least 96%, at least 97%, at least 98%, or at least 99% identical to an amino acid sequence selected from SEQ ID NOs: 53-66, 68 and 70. In some embodiments, the recombinant nucleic acid sequences encode an engager molecule and a therapeutic molecule comprising an amino acid sequence that is 100% identical to an amino acid sequence selected from SEQ ID NOs: 53-66, 68 and 70. In some embodiments, the recombinant nucleic acid sequences encode an engager molecule and a therapeutic molecule comprising an amino acid sequence consisting of an amino acid sequence selected from SEQ ID NOs: 53-66, 68 and 70.

TABLE 2

| \multicolumn{3}{c}{Nucleic sequences of exemplary engager molecules} | | |
| --- | --- | --- |
| BiTE | Nucleic Acid Sequence | SEQ ID |
| CD19-CD3 | ATGGAGTTCGGCCTGAGCTGGGTGTTCCTGGTGGCCCTGTTCAGGGGCGTGCAGTGC<br>GACATCCAGCTGACCCAGAGCCCCGCCAGCCTGGCCGTGAGCCTGGGCCAGAGGGCC<br>ACCATCAGCTGCAAGGCCAGCCAGAGCGTGGACTACGACGGCGACAGCTACCTGAAC<br>TGGTACCAGCAGATCCCCGGCCAGCCCCCCAAGCTGCTGATCTACGACGCCAGCAAC<br>CTGGTGAGCGGCATCCCCCCCAGGTTCAGCGGCAGCGGCAGCGGCACCGACTTCACC<br>CTGAACATCCACCCCGTGGAGAAGGTGGACGCCGCCACCTACCACTGCCAGCAGAGC<br>ACCGAGGACCCCTGGACCTTCGGCGGCGGCACCAAGCTGGAGATCAAGGGCGGCGGC<br>GGCAGCGGCGGCGGCGGCAGCGGCGGCGGCGGCAGCCAGGTGCAGCTGCAGCAGAGC<br>GGCGCCGAGCTGGTGAGGCCCGGCAGCAGCGTGAAGATCAGCTGCAAGGCCAGCGGC<br>TACGCCTTCAGCAGCTACTGGATGAACTGGGTGAAGCAGAGGCCCGGCCAGGGCCTG<br>GAGTGGATCGGCCAGATCTGGCCCGGCGACGGCGACACCAACTACAACGGCAAGTTC<br>AAGGGCAAGGCCACCCTGACCGCCGACGAGAGCAGCAGCACCGCCTACATGCAGCTG<br>AGCAGCCTGGCCAGCGAGGACAGCGCCGTGTACTTCTGCGCCAGGAGGGAGACCACC<br>ACCGTGGGCAGGTACTACTACGCCATGGACTACTGGGGCCAGGGCACCACCGTGACC<br>GTGAGCAGCGGCGGCGGCGGCAGCGACATCAAGCTGCAGCAGAGCGGCGCCGAGCTG<br>GCCAGGCCCGGCGCCAGCGTGAAGATGAGCTGCAAGACCAGCGGCTACACCTTCACC<br>AGGTACACCATGCACTGGGTGAAGCAGAGGCCCGGCCAGGGCCTGGAGTGGATCGGC<br>TACATCAACCCCAGCAGGGGCTACACCAACTACAACCAGAAGTTCAAGGACAAGGCC<br>ACCCTGACCACCGACAAGAGCAGCAGCACCGCCTACATGCAGCTGAGCAGCCTGACC<br>AGCGAGGACAGCGCCGTGTACTACTGCGCCAGGTACTACGACGACCACTACTGCCTG<br>GACTACTGGGGCCAGGGCACCACCCTGACCGTGAGCAGCGTGGAGGGCGGCAGCGGC<br>GGCAGCGGCGGCAGCGGCGGCAGCGGCGGCGTGGACGACATCCAGCTGACCCAGAGC<br>CCCGCCATCATGAGCGCCAGCCCCGGCGAGAAGGTGACCATGACCTGCAGGGCCAGC<br>AGCAGCGTGAGCTACATGAACTGGTACCAGCAGAAGAGCGGCACCAGCCCCAAGAGG<br>TGGATCTACGACACCAGCAAGGTGGCCAGCGGCGTGCCCTACAGGTTCAGCGGCAGC<br>GGCAGCGGCACCAGCTACAGCCTGACCATCAGCAGCATGGAGGCCGAGGACGCCGCC<br>ACCTACTACTGCCAGCAGTGGAGCAGCAACCCCCTGACCTTCGGCGCCGGCACCAAG<br>CTGGAGCTGAAGCACCACCACCACCACTAG | 43 |
| SIRP1a-CD3 (SL) | ATGGAGACCGATACCCTGCTCTTGTGGGTTTTGCTTCTTTGGGTGCCAGGATCTACA<br>GGTGATGAAGAAGAATTGCAGATCATCCAACCAGACAAATCCGTACTCGTGGCCGCA<br>GGAGAGACCGCTACCCTCAGATGTACCATCACTTCTCTCTTCCCCGTTGGCCCCATC<br>CAGTGGTTTCGAGGCGCAGGACCAGGACGAGTGCTTATTTACAATCAACGACAGGGC<br>CCATTCCCAAGAGTGACAACAGTATCCGATACCACCAAGCGCAATAATATGGACTTT<br>AGCATTAGAATCGGCAACATAACACCCGCTGACGCCGGTACATACTATTGTATTAAA<br>TTTCGAAAGGGCTCACCAGACGACGTGGAATTTAAGTCAGGGGCCGGAACCGAACTC<br>TCAGTTAGAGCAAAACCTTCTGCTAGCGACATCAAGCTGCAGCAGAGCGGCGCCGAG<br>CTGGCCAGGCCCGGCGCCAGCGTGAAGATGAGCTGCAAGACCAGCGGCTACACCTTC<br>ACCAGGTACACCATGCACTGGGTGAAGCAGAGGCCCGGCCAGGGCCTGGAGTGGATC<br>GGCTACATCAACCCCAGCAGGGGCTACACCAACTACAACCAGAAGTTCAAGGACAAG<br>GCCACCCTGACCACCGACAAGAGCAGCAGCACCGCCTACATGCAGCTGAGCAGCCTG<br>ACCAGCGAGGACAGCGCCGTGTACTACTGCGCCAGGTACTACGACGACCACTACTGC<br>CTGGACTACTGGGGCCAGGGCACCACCCTGACCGTGAGCAGCGTGGAGGGCGGCAGC<br>GGCGGCAGCGGCGGCAGCGGCGGCAGCGGCGGCGTGGACGACATCCAGCTGACCCAG<br>AGCCCCGCCATCATGAGCGCCAGCCCCGGCGAGAAGGTGACCATGACCTGCAGGGCC<br>AGCAGCAGCGTGAGCTACATGAACTGGTACCAGCAGAAGAGCGGCACCAGCCCCAAG<br>AGGTGGATCTACGACACCAGCAAGGTGGCCAGCGGCGTGCCCTACAGGTTCAGCGGC<br>AGCGGCAGCGGCACCAGCTACAGCCTGACCATCAGCAGCATGGAGGCCGAGGACGCC<br>GCCACCTACTACTGCCAGCAGTGGAGCAGCAACCCCCTGACCTTCGGCGCCGGCACC<br>AAGCTGGAGCTGAAGCACCACCATCATCACCACTGAG | 45 |
| SIRP1a-CD3 (LL) | ATGGAGACCGATACCCTGCTCTTGTGGGTTTTGCTTCTTTGGGTGCCAGGATCTACA<br>GGTGATGAAGAAGAATTGCAGATCATCCAACCAGACAAATCCGTACTCGTGGCCGCA<br>GGAGAGACCGCTACCCTCAGATGTACCATCACTTCTCTCTTCCCCGTTGGCCCCATC<br>CAGTGGTTTCGAGGCGCAGGACCAGGACGAGTGCTTATTTACAATCAACGACAGGGC<br>CCATTCCCAAGAGTGACAACAGTATCCGATACCACCAAGCGCAATAATATGGACTTT<br>AGCATTAGAATCGGCAACATAACACCCGCTGACGCCGGTACATACTATTGTATTAAA<br>TTTCGAAAGGGCTCACCAGACGACGTGGAATTTAAGTCAGGGGCCGGAACCGAACTC<br>TCAGTTAGAGCAAAACCTTCTGCTAGCGGCGGCGGCGGCAGCGACATCAAGCTGCAG | 47 |

TABLE 2-continued

Nucleic sequences of exemplary engager molecules

| BiTE | Nucleic Acid Sequence | SEQ ID |
|---|---|---|
| | CAGAGCGGCGCCGAGCTGGCCAGGCCCGGCGCCAGCGTGAAGATGAGCTGCAAGACC<br>AGCGGCTACACCTTCACCAGGTACACCATGCACTGGGTGAAGCAGAGGCCCGGCCAG<br>GGCCTGGAGTGGATCGGCTACATCAACCCCAGCAGGGGCTACACCAACTACAACCAG<br>AAGTTCAAGGACAAGGCCACCCTGACCACCGACAAGAGCAGCAGCACCGCCTACATG<br>CAGCTGAGCAGCCTGACCAGCGAGGACAGCGCCGTGTACTACTGCGCCAGGTACTAC<br>GACGACCACTACTGCCTGGACTACTGGGGCCAGGGCACCACCCTGACCGTGAGCAGC<br>GTGGAGGGCGGCAGCGGCGGCAGCGGCGGCAGCGGCGGCAGCGGCGGCGTGGACGAC<br>ATCCAGCTGACCCAGAGCCCCGCCATCATGAGCGCCAGCCCCGGCGAGAAGGTGACC<br>ATGACCTGCAGGGCCAGCAGCAGCGTGAGCTACATGAACTGGTACCAGCAGAAGAGC<br>GGCACCAGCCCCAAGAGGTGGATCTACGACACCAGCAAGGTGGCCAGCGGCGTGCCC<br>TACAGGTTCAGCGGCAGCGGCAGCGGCACCAGCTACAGCCTGACCATCAGCAGCATG<br>GAGGCCGAGGACGCCGCCACCTACTACTGCCAGCAGTGGAGCAGCAACCCCCTGACC<br>TTCGGCGCCGGCACCAAGCTGGAGCTGAAGCACCACCACCACCACCACTAG | |
| PDL1-<br>CD3 | ATGGAGTTCGGCCTGAGCTGGGTGTTCCTGGTGGCCCTGTTCAGGGGCGTGCAGTGC<br>GACATCAAGCTGCAGCAGAGCGGCGCCGAGCTGGCCAGGCCCGGCGCCAGCGTGAAG<br>ATGAGCTGCAAGACCAGCGGCTACACCTTCACCAGGTACACCATGCACTGGGTGAAG<br>CAGAGGCCCGGCCAGGGCCTGGAGTGGATCGGCTACATCAACCCCAGCAGGGGCTAC<br>ACCAACTACAACCAGAAGTTCAAGGACAAGGCCACCCTGACCACCGACAAGAGCAGC<br>AGCACCGCCTACATGCAGCTGAGCAGCCTGACCAGCGAGGACAGCGCCGTGTACTAC<br>TGCGCCAGGTACTACGACGACCACTACTGCCTGGACTACTGGGGCCAGGGCACCACC<br>CTGACCGTGAGCAGCGTGGAGGGCGGCAGCGGCGGCAGCGGCGGCAGCGGCGGCAGC<br>GGCGGCGTGGACGACATCCAGCTGACCCAGAGCCCCGCCATCATGAGCGCCAGCCCC<br>GGCGAGAAGGTGACCATGACCTGCAGGGCCAGCAGCAGCGTGAGCTACATGAACTGG<br>TACCAGCAGAAGAGCGGCACCAGCCCCAAGAGGTGGATCTACGACACCAGCAAGGTG<br>GCCAGCGGCGTGCCCTACAGGTTCAGCGGCAGCGGCAGCGGCACCAGCTACAGCCTG<br>ACCATCAGCAGCATGGAGGCCGAGGACGCCGCCACCTACTACTGCCAGCAGTGGAGC<br>AGCAACCCCCTGACCTTCGGCGCCGGCACCAAGCTGGAGCTGAAGGGCGGCGGCGGC<br>AGCGATATCCAGATGACACAGAGCCCATCATCTCTGTCTGCAAGCGTAGGAGACCGA<br>GTCACCATTACATGCAGAGCCTCCCAAGACGTTTCCACAGCAGTGGCCTGGTATCAG<br>CAAAAACCTGGTAAGGCGCCCAAGCTTCTCATCTATTCAGCCAGTTTTCTGTATAGC<br>GGCGTTCCCAGCCGATTCTCTGGCTCTGGATCCGGCACGGACTTTACTTTGACAATT<br>TCCTCTCTTCAGCCCGAAGATTTTGCAACCTACTACTGTCAGCAATATCTCTACCAT<br>CCAGCCACATTCGGACAGGGCACCAAAGTCGAAATCAAAAGAGGCGGCGGCGGCAGT<br>GGCGGCGGGGGTTCAGGAGGCGGGGGTTCTGAAGTGCAACTCGTTGAAAGCGGAGGA<br>GGGCTTGTCCAACCTGGCGGGTCACTGCGGTTGAGCTGCGCCGAAGCGGATTCACC<br>TTCTCAGACTCTTGGATCCATTGGGTGCGCCAGGCTCCCGGAAAAGGCTTGGAATGG<br>GTTGCTTGGATTTCACCGTATGCGGTTCCACATACTACGCTGACAGCGTTAAGGGT<br>CGATTCACCATCTCTGCAGATACTTCAAAAAACACAGCCTACCTTCAGATGAATAGT<br>TTGCGCGCCGAGGACACAGCGGTTTATTATTGTGCCCGAAGACATTGGCCCGGCGGT<br>TTCGACTACTGGGGGCAAGGTACGTTGGTGACTGTGAGCGCCCACCACCATCATCAC<br>CACTGA | 49 |
| PDL1-<br>CD3-<br>Fc | ATGGAGTTCGGCCTGAGCTGGGTGTTCCTGGTGGCCCTGTTCAGGGGCGTGCAGTGC<br>GACATCAAGCTGCAGCAGAGCGGCGCCGAGCTGGCCAGGCCCGGCGCCAGCGTGAAG<br>ATGAGCTGCAAGACCAGCGGCTACACCTTCACCAGGTACACCATGCACTGGGTGAAG<br>CAGAGGCCCGGCCAGGGCCTGGAGTGGATCGGCTACATCAACCCCAGCAGGGGCTAC<br>ACCAACTACAACCAGAAGTTCAAGGACAAGGCCACCCTGACCACCGACAAGAGCAGC<br>AGCACCGCCTACATGCAGCTGAGCAGCCTGACCAGCGAGGACAGCGCCGTGTACTAC<br>TGCGCCAGGTACTACGACGACCACTACTGCCTGGACTACTGGGGCCAGGGCACCACC<br>CTGACCGTGAGCAGCGTGGAGGGCGGCAGCGGCGGCAGCGGCGGCAGCGGCGGCAGC<br>GGCGGCGTGGACGACATCCAGCTGACCCAGAGCCCCGCCATCATGAGCGCCAGCCCC<br>GGCGAGAAGGTGACCATGACCTGCAGGGCCAGCAGCAGCGTGAGCTACATGAACTGG<br>TACCAGCAGAAGAGCGGCACCAGCCCCAAGAGGTGGATCTACGACACCAGCAAGGTG<br>GCCAGCGGCGTGCCCTACAGGTTCAGCGGCAGCGGCAGCGGCACCAGCTACAGCCTG<br>ACCATCAGCAGCATGGAGGCCGAGGACGCCGCCACCTACTACTGCCAGCAGTGGAGC<br>AGCAACCCCCTGACCTTCGGCGCCGGCACCAAGCTGGAGCTGAAGGGCGGCGGCGGC<br>AGCGATATCCAGATGACACAGAGCCCATCATCTCTGTCTGCAAGCGTAGGAGACCGA<br>GTCACCATTACATGCAGAGCCTCCCAAGACGTTTCCACAGCAGTGGCCTGGTATCAG<br>CAAAAACCTGGTAAGGCGCCCAAGCTTCTCATCTATTCAGCCAGTTTTCTGTATAGC<br>GGCGTTCCCAGCCGATTCTCTGGCTCTGGATCCGGCACGGACTTTACTTTGACAATT<br>TCCTCTCTTCAGCCCGAAGATTTTGCAACCTACTACTGTCAGCAATATCTCTACCAT<br>CCAGCCACATTCGGACAGGGCACCAAAGTCGAAATCAAAAGAGGCGGCGGCGGCAGT<br>GGCGGCGGGGGTTCAGGAGGCGGGGGTTCTGAAGTGCAACTCGTTGAAAGCGGAGGA<br>GGGCTTGTCCAACCTGGCGGGTCACTGCGGTTGAGCTGCGCCGAAGCGGATTCACC<br>TTCTCAGACTCTTGGATCCATTGGGTGCGCCAGGCTCCCGGAAAAGGCTTGGAATGG<br>GTTGCTTGGATTTCACCGTATGCGGTTCCACATACTACGCTGACAGCGTTAAGGGT<br>CGATTCACCATCTCTGCAGATACTTCAAAAAACACAGCCTACCTTCAGATGAATAGT<br>TTGCGCGCCGAGGACACAGCGGTTTATTATTGTGCCCGAAGACATTGGCCCGGCGGT<br>TTCGACTACTGGGGGCAAGGTACGTTGGTGACTGTGAGCGCCGTAGATGAAGCAAAA<br>TCTTGTGACAAAACCCATACCTGCCCACCATGCCCAGCCCCGAACTTCTTGGCCGA<br>CCCTCTGTCTTCCTTTTCCCTCCGAAGCCCAAGGATACCCTGATGATCAGCCGAACC<br>CCGGAGGTAACATGTGTGGTGGTCGATGTTAGCCATGAGGATCCTGAAGTCAAATTT<br>AACTGGTATGTAGACGGTGTTGAGGTGCACAACGCTAAAACTAAGCCCAGGGAGGAG<br>CAGTACAACTCAACCTATCGCGTCGTATCTGTGCTTACCGTCCTGCATCAAGACTGG<br>CTCAATGGTAAGGAATATAAATGTAAAGTGAGTAACAAGGCACTGCCAGCACCTATC | 51 |

TABLE 2-continued

Nucleic sequences of exemplary engager molecules

| BiTE | Nucleic Acid Sequence | SEQ ID |
|---|---|---|
| | GAAAAAACCATCTCAAAGGCGAAGGGACAGCCCAGGGAACCCCAGGTCTATACTCTG<br>CCACCTTCTCGGGATGAATTGACCAAGAACCAAGTTAGCCTGACATGTCTGGTGAAA<br>GGTTTCTATCCAAGCGATATAGCTGTCGAGTGGGAGTCCAATGGCCAACCTGAGAAC<br>AATTATAAGACCACCCCACCCGTTCTGGACAGCGACGGATCCTTTTTCCTGTACTCA<br>AAACTCACTGTCGATAAATCAAGATGGCAACAAGGCAACGTTTTTAGCTGTAGCGTG<br>ATGCACGAAGCACTTCATAATCACTATACACAGAAGTCACTCTCTCTTTCTCCAGGA<br>CACCACCATCATCACCACTGA | |
| SIRP1α-<br>CD3-<br>PDL1-<br>Fc (SL) | ATGGAAACCGATACACTTCTGTTGTGGGTGCTGCTGCTGTGGGTCCCTGGTTCAACA<br>GGCGATTATCCCTACGATGTGCCCGACTACGCAGGCGCTCAGCCAGCTGATGATATC<br>CAGATGACACAGAGCCCATCATCTCTGTCTGCAAGCGTAGGAGACCGAGTCACCATT<br>ACATGCAGAGCCTCCCAAGACGTTTCCACAGCAGTGGCCTGGTATCAGCAAAAACCT<br>GGTAAGGCGCCCAAGCTTCTCATCTATTCAGCCAGTTTTCTGTATAGCGGCGTTCCC<br>AGCCGATTCTCTGGCTCTGGATCCGGCACGGACTTTACTTTGACAATTTCCTCTCTT<br>CAGCCCGAAGATTTTGCAACCTACTACTGTCAGCAATATCTCTACCATCCAGCCACA<br>TTCGGACAGGGCACCAAAGTCGAAATCAAAGAGGCGGCGGCGGCAGTGGCGGCGGG<br>GGTTCAGGAGGCGGGGGTTCTGAAGTGCAACTCGTTGAAAGCGTAGGAGGGCTTGTC<br>CAACCTGGCGGGTCACTGCGGTTGAGCTGCCCGCAAGCGGATTCACCTTCTCAGAC<br>TCTTGGATCCATTGGGTGCGCCAGGCTCCCGGAAAAGGCTTGGAATGGGTTGCTTGG<br>ATTTCACCGTATGGCGGTTCCACATACTACGCTGACAGCGTTAAGGGTCGATTCACC<br>ATCTCTGCAGATACTTCAAAAAACACAGCCTACCTTCAGATGAATAGTTTGCGCGCC<br>GAGGACACAGCGGTTTATTATTGTGCCCAAGACATTGGCCCGGCGGTTTCGACTAC<br>TGGGGGCAAGGTACGTTGGTGACTGTGAGCGCCGTAGATGAAGCAAATCTTGTGAC<br>AAAACCCATACCTGCCCACCATGCCCAGCCCCAGAACTTCTTGGCGTACCCTCTGTC<br>TTCCTTTTCCCTCCGAAGCCCAAGGATACCCTGATGATCAGCCGAACCCCGGAGGTA<br>ACATGTGTGGTGGTCGATGTTAGCCATGAGGATCCTGAAGTCAAATTTAACTGGTAT<br>GTAGACGGTGTTGAGGTGCACAACGCTAAAACTAAGCCCAGGGAGGAGCAGTACAAC<br>TCAACCTATCGCTCGTATCTGTGCTTACCGTCCTGCATCAAGACTGGCTCAATGGT<br>AAGGAATATAAATGTAAAGTGAGTAACAAGGCACTGCCAGCACCTATCGAAAAAACC<br>ATCTCAAAGGCGAAGGGACAGCCCAGGGAACCCCAGGTCTATACTCTGCAACCTTCT<br>CGGGATGAATTGACCAAGAACCAAGTTAGCCTGACATGTCTGGTGAAAGGTTTCTAT<br>CCAAGCGATATAGCTGTCGAGTGGGAGTCCAATGGCCAACCTGAGAACAATTATAAG<br>ACCACCCCACCCGTTCTGGACAGCGACGGATCCTTTTTCCTGTACTCAAAACTCACT<br>GTCGATAAATCAAGATGGCAACAAGGCAACGTTTTTAGCTGTAGCGTGATGCACGAA<br>GCACTTCATAATCACTATACACAGAAGTCACTCTCTCTTTCTCCAGGAAAGGTTGAC<br>GAACAGAAATTGATATCCGAGGAAGATCTCAATAGGAGGAAGAGAGAAGGCAGGGGG<br>AGCCTTCTCACTTGCGGCGATGTCGAGGAAAATCCGGGGCCTATGGAGACCGATACC<br>CTGCTCTTGTGGGTTTTGCTTCTTTGGGTGCCAGGATCTACAGGTGATGAAGAAGAA<br>TTGCAGATCATCCAACCAGACAAATCCGTACTCGTGGCCGCAGGAGAGACCGCTACC<br>CTCAGATGTACCATCACTTCTCTCTTCCCCGTTGGCCCCATCCAGTGGTTTCGAGGC<br>GCAGGACCAGGACGAGTGCTTATTTACAATCAACGACAGGGCCCATTCCCAAGAGTG<br>ACAACAGTATCCGATACCACCAAGCGCAATAATATGGACTTTAGCATTAGAATCGGC<br>AACATAACACCCGCTGACGCCGGTACATACTATTGTATTAAATTTCGAAAGGGCTCA<br>CCAGACGACGTGGAATTTAAGTCAGGGGCCGGAACCGAACTCTCAGTTAGAGCAAAA<br>CCTTCTGCTAGCGACATCAAGCTGCAGCAGAGCGGCGCCGAGCTGGCCAGGCCCGGC<br>GCCAGCGTGAAGATGAGCTGCAAGACCAGCGGCTACACCTTCACCAGGTACACCATG<br>CACTGGGTGAAGCAGAGGCCCGGCCAGGGCCTGGAGTGGATCGGCTACATCAACCCC<br>AGCAGGGGCTACACCAACTACAACCAGAAGTTCAAGGACAAGGCCACCCTGACCACC<br>GACAAGAGCAGCAGCACCGCCTACATGCAGCTGAGCAGCCTGACCAGCGAGGACAGC<br>GCCGTGTACTACTGCGCCAGGTACTACGACGACCACTACTGCCTGGACTACTGGGGC<br>CAGGGCACCACCCTGACCGTGAGCAGCGTGAGGGCGGCAGCGGCGGCAGCGGCGGC<br>AGCGGCGGCAGCGGCGGCGTGGACGACATCCAGCTGACCCAGAGCCCCGCCATCATG<br>AGCGCCAGCCCCGGCGAGAAGGTGACCATGACCTGCAGGGCCAGCAGCAGCGTGAGC<br>TACATGAACTGGTACCAGCAGAAGAGCGGCACCAGCCCCAAGAGGTGGATCTACGAC<br>ACCAGCAAGGTGGCCAGCGGCGTGCCCTACAGGTTCAGCGGCAGCGGCAGCGGCACC<br>AGCTACAGCCTGACCATCAGCAGCATGGAGGCCGAGGACGCCGCCACCTACTACTGC<br>CAGCAGTGGAGCAGCAACCCCCTGACCTCCGGCGCCGGCACCAAGCTGGAGCTGAAG<br>CACCACCATCATCACCACTGA | 67 |
| SIRP1α-<br>CD3-<br>PDL1-<br>Fc (LL) | ATGGAAACCGATACACTTCTGTTGTGGGTGCTGCTGCTGTGGGTCCCTGGTTCAACA<br>GGCGATTATCCCTACGATGTGCCCGACTACGCAGGCGCTCAGCCAGCTGATGATATC<br>CAGATGACACAGAGCCCATCATCTCTGTCTGCAAGCGTAGGAGACCGAGTCACCATT<br>ACATGCAGAGCCTCCCAAGACGTTTCCACAGCAGTGGCCTGGTATCAGCAAAAACCT<br>GGTAAGGCGCCCAAGCTTCTCATCTATTCAGCCAGTTTTCTGTATAGCGGCGTTCCC<br>AGCCGATTCTCTGGCTCTGGATCCGGCACGGACTTTACTTTGACAATTTCCTCTCTT<br>CAGCCCGAAGATTTTGCAACCTACTACTGTCAGCAATATCTCTACCATCCAGCCACA<br>TTCGGACAGGGCACCAAAGTCGAAATCAAAGAGGCGGCGGCGGCAGTGGCGGCGGG<br>GGTTCAGGAGGCGGGGGTTCTGAAGTGCAACTCGTTGAAAGCGTAGGAGGGCTTGTC<br>CAACCTGGCGGGTCACTGCGGTTGAGCTGCCCGCAAGCGGATTCACCTTCTCAGAC<br>TCTTGGATCCATTGGGTGCGCCAGGCTCCCGGAAAAGGCTTGGAATGGGTTGCTTGG<br>ATTTCACCGTATGGCGGTTCCACATACTACGCTGACAGCGTTAAGGGTCGATTCACC<br>ATCTCTGCAGATACTTCAAAAAACACAGCCTACCTTCAGATGAATAGTTTGCGCGCC<br>GAGGACACAGCGGTTTATTATTGTGCCCAAGACATTGGCCCGGCGGTTTCGACTAC<br>TGGGGGCAAGGTACGTTGGTGACTGTGAGCGCCGTAGATGAAGCAAATCTTGTGAC<br>AAAACCCATACCTGCCCACCATGCCCAGCCCCAGAACTTCTTGGCGTACCCTCTGTC<br>TTCCTTTTCCCTCCGAAGCCCAAGGATACCCTGATGATCAGCCGAACCCCGGAGGTA | 69 |

TABLE 2-continued

Nucleic sequences of exemplary engager molecules

| BiTE | Nucleic Acid Sequence | SEQ ID |
|---|---|---|
|  | ACATGTGGTGGTCGATGTTAGCCATGAGGATCCTGAAGTCAAATTTAACTGGTAT<br>GTAGACGGTGTTGAGGTGCACAACGCTAAAACTAAGCCCAGGGAGGAGCAGTACAAC<br>TCAACCTATCGCGTCGTATCTGTGCTTACCGTCCTGCATCAAGACTGGCTCAATGGT<br>AAGGAATATAAATGTAAAGTGAGTAACAAGGCACTGCCAGCACCTATCGAAAAAACC<br>ATCTCAAAGGCGAAGGGACAGCCCAGGGAACCCCAGGTCTATACTCTGCAACCTTCT<br>CGGGATGAATTGACCAAGAACCAAGTTAGCCTGACATGTCTGGTGAAAGGTTTCTAT<br>CCAAGCGATATAGCTGTCGAGTGGGAGTCCAATGGCCAACCTGAGAACAATTATAAG<br>ACCACCCCACCCGTTCTGGACAGCGACGGATCCTTTTTCCTGTACTCAAAACTCACT<br>GTCGATAAATCAAGATGGCAACAAGGCAACGTTTTTAGCTGTAGCGTGATGCACGAA<br>GCACTTCATAATCACTATACACAGAAGTCACTCTCTCTTTCTCCAGGAAAGGTTGAC<br>GAACAGAAATTGATATCCGAGGAAGATCTCAATAGGAGGAAGAGAGAAGGCAGGGGG<br>AGCCTTCTCACTTGCGGCGATGTCGAGGAAAATCCGGGGCCTATGGAGACCGATACC<br>CTGCTCTTGTGGGTTTTGCTTCTTTGGGTGCCAGGATCTACAGGTGATGAAGAAGAA<br>TTGCAGATCATCCAACCAGACAAATCCGTACTCGTGGCCGCAGGAGAGACCGCTACC<br>CTCAGATGTACCATCACTTCTCTCTTCCCCGTTGGCCCCATCCAGTGGTTTCGAGGC<br>GCAGGACCAGGACGAGTGCTTATTTACAATAACGACAGGGCCCATTCCCAAGAGTG<br>ACAACAGTATCCGATACCACCAAGCGCAATAATATGGACTTTAGCATTAGAATCGGC<br>AACATAACACCCGCTGACGCCGGTACATACTATTGTATTAAATTTCGAAAGGGCTCA<br>CCAGACGACGTGGAATTTAAGTCAGGGGCCGGAACCGAACTCTCAGTTAGAGCAAAA<br>CCTTCTGCTAGCGGCGGCGGCGGCAGCGACATCAAGCTGCAGCAGAGCGGCGCCGAG<br>CTGGCCAGGCCCGGCGCCAGCGTGAAGATGAGCTGCAAGACCAGCGGCTACACCTTC<br>ACCAGGTACACCATGCACTGGGTGAAGCAGAGGCCCGGCCAGGGCCTGGAGTGGATC<br>GGCTACATCAACCCCAGCAGGGGCTACACCAACTACAACCAGAAGTTCAAGGACAAG<br>GCCACCCTGACCACCGACAAGAGCAGCAGCACCGCCTACATGCAGCTGAGCAGCCTG<br>ACCAGCGAGGACAGCGCCGTGTACTACTGCGCCAGGTACTACGGCGACCACTACTGC<br>CTGGACTACTGGGGCCAGGGCACCACCCTGACCGTGAGCAGCGTGGAGGGCGGCAGC<br>GGCGGCAGCGGCGGCAGCGGCGGCAGCGGCGGCGTGGACGACATCCAGCTGACCCAG<br>AGCCCCGCCATCATGAGCGCCAGCCCCGGCGAGAAGGTGACCATGACCTGCAGGGCC<br>AGCAGCAGCGTGAGCTACATGAACTGGTACCAGCAGAAGAGCGGCACCAGCCCCAAG<br>AGGTGGATCTACGACACCAGCAAGGTGGCCAGCGGCGTGCCCTACAGGTTCAGCGGC<br>AGCGGCAGCGGCACCAGCTACAGCCTGACCATCAGCAGCATGGAGGCCGAGGACGCC<br>GCCACCTACTACTGCCAGCAGTGGAGCAGCAACCCCCTGACCTTCGGCGCCGGCACC<br>AAGCTGGAGCTGAAGCACCACCACCACCACCACTAG |  |
| FAP-CD3 | ATGGTTTTGCTTGTGACCAGCCTCCTGCTCTGTGAACTGCCTCATCCTGCATTCCTG<br>TTGATCCCACAGGTGCAGCTCCAGCAGAGTGGCGCAGAGCTCGCTCGCCCAGGCGCT<br>TCTGTGAATCTGAGTTGTAAGGCCTCCGGATATACTTTTACGAACAACGGCATCAAC<br>TGGCTGAAGCAGCGGACCGGCCAGGGCCTGGAGTGGATCGGCGAAATATACCCCCGG<br>TCCACAAACACTCTCTATAACGAGAAGTTTAAGGGCAAAGCAACTCTGACCGCGGAC<br>AGGTCCTCTAACACAGCCTATATGGAGCTGAGAAGCTTGACGAGTGAGGACTCCGCT<br>GTCTATTTTTGCGCCCGAACTCTGACCGCTCCTTTTGCTTTTTGGGGCCAGGGCACG<br>CTCGTGACCGTAAGTGCGGGCTCCACTAGCGGTTCCGGCAAACCTGGCAGCGGAGAA<br>GGCAGCACCAAAGGGCAGATCGTCCTGACGCAGTCTCCAGCCATCATGAGCGCCTCA<br>CCCGGCGAAAAGGTGACCATGACCTGCTCAGCCTCTTCTGGTGTGAATTTCATGCAC<br>TGGTACCAGCAAAAAAGTGGGACCTCCCCTAAAAGGTGGATCTTCGATACCAGCAAA<br>CTGGCTTCTGGCGTTCCCGCAAGGTTTAGCGGCTCTGGTTCCGGCACATCATACAGC<br>CTGACGATCAGCAGCATGGAGGCAGAAGACGCAGCTACCTATTACTGCCAGCAATGG<br>AGCTTTAACCCACCTACTTTCGGAGGAGGAACAAAGCTGGAAATAAAAAGAGGTGGT<br>GGTGGATCAGAGGTGCAGCTGGTGGAGTCTGGGGGAGGCTTGGTGCAGCCTGGAAAG<br>TCCCTGAAACTCTCCTGTGAGGCCTCTGGATTCACCTTCAGCGGCTATGGCATGCAC<br>TGGGTCCGCCAGGCTCCAGGGAGGGGCTGGAGTCGGTCGCATACATTACTAGTAGT<br>AGTATTAATATCAAATATGCTGACGCTGTGAAAGGCCGGTTCACCGTCTCCAGAGAC<br>AATGCCAAGAACTTACTGTTTCTACAAATGAACATTCTCAAGTCTGAGGACACAGCC<br>ATGTACTACTGTGCAAGATTCGACTGGGACAAAAATTACTGGGGCCAAGGAACCATG<br>GTCACCGTCTCCTCAGGTGGTGGTGGATCAGGTGGAGGCGGAAGTGGAGGTGGCGGA<br>TCCGACATCCAGATGACCCAGTCTCCATCATCACTGCCTGCCTCCTGGGAGACAGA<br>GTCACTATCAATTGTCAGGCCAGTCAGGACATTAGCAATTATTTAAACTGGTACCAG<br>CAGAAACCAGGGAAAGCTCCTAAGCTCCTGATCTATTATACAAATAAATTGGCAGAT<br>GGAGTCCCATCAAGGTTCAGTGGCAGTGGTTCTGGGAGAGATTCTTCTTTCACTATC<br>AGCAGCCTGGAATCCGAAGATATTGGATCTTATTACTGTCAACAGTATTATAACTAT<br>CCGTGGACGTTCGGACCTGGCACCAAGCTGGAAATCAAACGGCACCACCATCATCAC<br>CACTGA | 74 |

Additional exemplary embodiments of engager molecules include engager molecules comprising an effector domain comprising an anti-CD3 scFv (e.g., comprised of SEQ ID NOs: 20 and 22) and an activation domain comprising an scFv that binds to a cell surface protein such as CTLA4, TIM3, LAG3, BTLA, KIR, TIGIT, OX40, or GITR. In some embodiments, the oncolytic viruses described herein comprise a bicistronic or multicistronic nucleic acid sequence, wherein a first nucleic acid sequence encodes an engager molecules comprising an effector domain comprising an anti-CD3 scFv (e.g., comprised of SEQ ID NOs: 20 and 22) and an activation domain comprising an scFv that binds to a cell surface protein such as CTLA4, TIM3, LAG3, BTLA, KIR, TIGIT, OX40, CD47, or GITR, and a second nucleic acid sequence encoding a therapeutic molecule such as IL-15 (SEQ ID NO: 24), IL-12 (SEQ ID NOs: 26 and 28), CXCL10 (SEQ ID NO: 30), or MMP9 (SEQ ID NO: 34). In such embodiments, the engager molecule is linked to the therapeutic molecule polypeptide by a T2A self-cleaving peptide linker (SEQ ID NO: 14).

Additional exemplary embodiments of engager molecules include engager molecules comprising an effector domain comprising an anti-CD3 scFv (e.g., comprised of SEQ ID NOs: 20 and 22) and a targeting domain comprising an scFv that binds to SLAMF7 (also known as CD319) or CD27 (either the membrane bound form of CD27 or the soluble form of CD27). In some embodiments, the oncolytic viruses described herein comprise a bicistronic or multicistronic nucleic acid sequence, wherein a first nucleic acid sequence encodes an engager molecules comprising an effector domain comprising an anti-CD3 scFv (e.g., comprised of SEQ ID NOs: 20 and 22) and an antigen-recognition domain comprising an scFv that binds to a target cell antigen such as SLAMF7 or CD27, and a second nucleic acid sequence encoding a therapeutic molecule such as IL-15 (SEQ ID NO: 24), IL-12 (SEQ ID NOs: 26 and 28), CXCL10 (SEQ ID NO: 30), or MMP9 (SEQ ID NO: 34). In such embodiments, the engager molecule is linked to the therapeutic molecule polypeptide by a T2A self-cleaving peptide linker (SEQ ID NO: 14).

Additional cell surface proteins that are suitable for target by the engager molecules described herein are shown below in Table 3. Additional proteins that are suitable for use as therapeutic molecules are show below in Table 4.

TABLE 3

Cell-surface proteins suitable for targeting by engager molecules

| Cell-surface protein | NCBI Reference Sequence (RefSeq) Identifier |
|---|---|
| human SLAMF7 | NP_067004.3 |
| human NKGD2L | NP_079494.1 |
| human CTLA4 | NP_005205.2 |
| human TIM3 | NP_116171.3 |
| human LAG3 | NP_002277.4 |
| human BTLA (isoform 1 and 2, respectively) | NP_001078826.1; NP_861445.3 |
| human KIR | |
| human TIGIT | NP_776160.2 |
| human OX40 | NP_003318.1 |
| human GITR (isoform 1, 2, 3 respectively) | NP_004186.1; NP_683699.1; NP_683700.1 |
| human CD27 | NP_001233.1 |
| human CD40 (isoforms 1-5, respectively) | NP_001241.1; NP_690593.1; NP_001289682.1; NP_001309350.1; NP_001309351.1 |
| human NKGD2L | NP_079494.1 |
| human CD200 | NP_005935.4 |

TABLE 4

Proteins suitable for use as therapeutic molecules

| Molecule | NCBI Reference Sequence (RefSeq) Identifier |
|---|---|
| human TNFα | NP_000585.2 |
| human CX3CL1 | NP_002987.1 |
| human CCR4 | NP_005499.1 |
| human CSF-1 | NP_000748.3 |
| human TGFβ | NP_000651.3 |
| human IL-7 | NP_000871.1 |
| human GM-CSF | NP_000749.2 |

Therapeutic Uses of Oncolytic Viruses

In some embodiments, the present invention provides compositions and methods of use for the prevention, treatment, and/or amelioration of a cancerous disease. In some embodiments, the methods described herein comprise administering an effective amount (e.g., a therapeutically effective amount) of an oncolytic virus described herein to a subject in need thereof, wherein the virus expresses an engager molecule or an engager molecule and a therapeutic molecule.

In some embodiments, compositions and methods of the present invention are useful for all stages and types of cancer, including for minimal residual disease, early solid tumor, advanced solid tumor and/or metastatic solid tumor. In some embodiments, compositions and methods of the present invention are used to treat a variety of solid tumors associated with a number of different cancers. The term "solid tumors" refers to relapsed or refractory tumors as well as metastases (wherever located), other than metastases observed in lymphatic cancer.

Exemplary solid tumors include, but are not limited to, brain and other central nervous system tumors (e.g. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, oligodendroglioma, oligoastrocytoma, astrocytoma, glioblastoma or medulloblastoma or other solid tumor.

In particular embodiments, the solid tumor is a brain tumor. In some instances, the brain tumor includes, but is not limited to, a glioma, in particular ependymoma, oligodendroglioma, oligoastrocytoma, astrocytoma, glioblastoma, or a medulloblastoma.

In some embodiments, compositions and methods of the present invention are used to treat a hematologic cancer. The term "hematologic cancer" refers herein to a cancer of the blood system and includes relapsed or refractory hematologic cancer as well as a metastasized hematologic cancer (wherever located). In some instances, the hematologic cancer is a T-cell malignancy or a B-cell malignancy. Exemplary T-cell malignancies include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

Exemplary B-cell malignancies include, but are not limited to, chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the hematologic cancer is a relapsed or refractory hematologic cancer. In some cases, the hematologic cancer is a metastasized hematologic cancer.

In some embodiments, the oncolytic virus is engineered to produce a high level of expression of the engager molecule and/or the therapeutic polypeptide prior to the death of the virally-infected cell, e.g., within 1, 2, 3, 4, 5, 6, 7, 8, 9, 10, 11, 12, 13, 14, 15, 16, 17, 18, 19, 20, 21, 22, 23 or 24 hours of infection, or within 2, 3, 4, 5, or 6 days of infection. Expression of the engager molecule and/or the therapeutic polypeptide can be determined by methods known in the art, including Western blot, ELISA, immunoprecipitation, or electrophoresis, among others. In general, a "high level of expression" in reference to a therapeutic molecule refers to a level of expression that is greater than the basal level of expression of a corresponding polypeptide in a cell that is not infected with the oncolytic virus Compositions and Routes of Administration In some embodiments, a therapeutically effective amount of an oncolytic virus or compositions thereof are administered to a subject. In accordance with this disclosure, the term "pharmaceutical composition" relates to a composition for administration to an individual. Administration of the compositions described herein can be local or systemic and can be effected by different ways, e.g., by intravenous, subcutaneous, intraperitoneal, intramuscular, topical or intradermal administration. In some embodiments, compositions disclosed herein are administered by any means known in the art. For example, the compositions described herein may be administered to a subject intravenously, intratumorally, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a cream, or in a lipid composition. In particular embodiments, the composition is administered to the individual via infusion or injection. In some embodiments, administration is parenteral, e.g., intravenous. In some embodiments, the oncolytic virus or composition thereof is administered directly to the target site, e.g., by biolistic delivery to an internal or external target site or by catheter to a site in an artery. In particular embodiments, the compositions described herein are administered subcutaneously or intravenously. In some embodiments, the oncolytic viruses or compositions thereof described herein are administered intravenously or intraarterially.

In a preferred embodiment, the compositions described herein are formulated for a particular route of administration, for parenteral, transdermal, intraluminal, intra-arterial, intrathecal, intravenous administration, or for direct injection into a cancer. In some embodiments, the compositions further comprise a pharmaceutically acceptable carrier. "Pharmaceutically or pharmacologically acceptable" refer herein to molecular entities and compositions that do not produce an adverse, allergic or other untoward reaction when administered to an animal, or a human, as appropriate. In some embodiments, the pharmaceutical compositions of the present disclosure further comprise a pharmaceutically acceptable carrier. A "pharmaceutically acceptable carrier" includes any and all solvents, dispersion media, coatings, buffer, stabilizing formulation, antibacterial and antifungal agents, isotonic and absorption delaying agents and the like. Examples of suitable pharmaceutical carriers are well known in the art and include phosphate buffered saline solutions, water, emulsions, such as oil/water emulsions, various types of wetting agents, sterile solutions, etc. Compositions comprising such carriers are formulated by well-known conventional methods. In some embodiments, supplementary active ingredients are also incorporated into the compositions. For human administration, the compositions described herein are met with sterility, pyrogenicity, and general safety and purity standards as required by FDA Office of Biologics standards.

In some embodiments, the compositions described herein comprise a carrier such as a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents known in the art. In many cases, it is preferable to include isotonic agents, for example, sugars or sodium chloride. In some embodiments, prolonged absorption of the injectable compositions is brought about by the use in the compositions of agents delaying absorption, for example, aluminum monostearate and gelatin.

In some embodiments, the oncolytic viruses described herein are formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups are derived from inorganic bases such as, for example, sodium, potassium, ammonium, calcium, or ferric hydroxides, and such organic bases as isopropylamine, trimethylamine, histidine, procaine and the like.

Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In some cases, the form is sterile and is fluid. In some cases, it is stable under the conditions of manufacture and certain storage parameters (e.g. refrigeration and freezing) and is preserved against the contaminating action of microorganisms, such as bacteria and fungi. Aqueous compositions of some embodiments herein include an effective amount of a virus, nucleic acid, therapeutic protein, peptide, construct, stimulator, inhibitor, and the like, dissolved or dispersed in a pharmaceutically acceptable carrier or aqueous medium. Aqueous compositions of vectors expressing any of the foregoing are also contemplated.

In certain embodiments, biological material is extensively dialyzed to remove undesired small molecular weight molecules and/or lyophilized for more ready formulation into a desired vehicle, where appropriate. In some embodiments, the active compounds or constructs are formulated for parenteral administration, e.g., formulated for injection via the intravenous, intramuscular, sub-cutaneous, intralesional, intranasal or intraperitoneal routes. Any route used for vaccination or boost of a subject is used. The preparation of an aqueous composition that contains an active component or ingredient is known to those of skill in the art in light of the present disclosure. Typically, such compositions are prepared as injectables, either as liquid solutions or suspensions; solid forms suitable for use in preparing solutions or suspensions upon the addition of a liquid prior to injection is also prepared; and the preparations are also emulsified.

In some instances, the oncolytic virus is dispersed in a pharmaceutically acceptable formulation for injection. In some embodiments, sterile injectable solutions are prepared by incorporating the active compounds or constructs in the required amount in the appropriate solvent with any of the other ingredients enumerated above, as required, followed by filtered sterilization.

Upon formulation, the compositions described herein are administered in a manner compatible with disease to be treated and the dosage formulation and in such amount as is therapeutically effective. The formulations are easily administered in a variety of dosage forms, such as the type of injectable solutions described above, but also as slow release capsules or microparticles and microspheres and the like.

For parenteral administration in an aqueous solution, for example, the solution is suitably buffered if necessary and the liquid diluent first rendered isotonic with sufficient saline or glucose. These particular aqueous solutions are especially suitable for intravenous, intratumorally, intramuscular, sub-cutaneous and intraperitoneal administration. In this context, sterile aqueous media that is employed is known to those of skill in the art in light of the present disclosure. For example, one dosage is dissolved in 1 mL of isotonic NaCl solution and either added to 1000 mL of hypodermoclysis fluid or injected at the proposed site of infusion.

In addition to the compounds formulated for parenteral administration, such as intravenous, intratumorally, intradermal or intramuscular injection, other pharmaceutically acceptable forms include, e.g., tablets or other solids for oral administration; liposomal formulations; time release capsules; biodegradable and any other form currently used.

In some embodiments, the viruses are encapsulated to inhibit immune recognition and placed at the site of a tumor.

In some instances, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives are also present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the proteinaceous bispecific single chain antibody constructs or nucleic acid molecules or vectors encoding the same (as described in this disclosure), further biologically active agents, depending on the intended use of the pharmaceutical composition.

In some embodiments, tumor-infiltrating virus-producing cells which continuously release vectors are formulated for direct implantation into a tumor in order to increase the viral oncolysis and the transfer efficiency of the therapeutic genes.

Intranasal formulations are known in the art and are described in, for example, U.S. Pat. Nos. 4,476,116; 5,116,817; and 6,391,452. Formulations which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these are found in Remington: The Science and Practice of Pharmacy, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are also present. The nasal dosage form is isotonic with nasal secretions.

For administration by inhalation described herein is in a form as an aerosol, a mist or a powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges of, such as, by way of example only, gelatin for use in an inhaler or insufflator is formulated containing a powder mix of the compound described herein and a suitable powder base such as lactose or starch.

Therapeutically Effective Amounts and Therapeutic Regimens

In some embodiments, the oncolytic viruses and compositions thereof described herein are administered to a subject at therapeutically effective amount. The therapeutically effective amount will depend on the subject to be treated, the state (e.g., general health) of the subject, the protection desired, the disease to be treated, the route of administration, and/or the nature of the virus. In some embodiments, the person responsible for administration (e.g., an attending physician) will determine the appropriate dose for an individual. As is well known in the medical arts, dosages for any one patient depend upon many factors, including the patient's size, weight, body surface area, age, sex, and general health, the particular compound to be administered, the particular disease to be treated, timing and route of administration, and other drugs being administered concurrently. Therefore, it is expected that for each individual patient, even if the viruses that are administered to the population at large, each patient is monitored for the proper dosage for the individual, and such practices of monitoring a patient are routine in the art.

In some embodiments, the therapeutically effective amount of an oncolytic virus described herein is administered in a single dose. In some embodiments of the present invention, the oncolytic viruses or compositions thereof are administered to a subject at a dose ranging from about $1\times10^{+5}$ pfu to about $1\times10^{+15}$ pfu (plaque forming units), about $1\times10^{+8}$ pfu to about $1\times10^{+15}$ pfu, about $1\times10^{+10}$ pfu to about $1\times10^{+15}$ pfu, or about $1\times10^{+8}$ pfu to about $1\times10^{+12}$ pfu. For example, in some embodiments, the oncolytic viruses or compositions thereof are administered to a subject at a dose of about $10^5$, $10^6$, $10^7$, $10^8$, $10^9$, $10^{10}$, $10^{11}$, $10^{12}$, $10^{13}$, $10^{14}$, or $10^{15}$ pfu of virus. In some embodiments, the dose depends, on the age of the subject to which a composition is being administered. For example, a lower dose may be required if the subject is juvenile, and a higher dose may be required if the subject is an adult human subject. In certain embodiments, for example, a juvenile subject receives about $1\times10^{+8}$ pfu and about $1\times10^{+10}$ pfu, while an adult human subject receives a dose between about $1\times10^{+10}$ pfu and about $1\times10^{+12}$ pfu. In some embodiments, the therapeutically effective amount of an oncolytic virus described herein is administered over the course of two or more doses. In some embodiments, the two or more doses are administered simultaneously (e.g., on the same day or over a short period of time) or at appropriate intervals, for example as two, three, four or more sub-doses per day.

In some embodiments, the oncolytic viruses or compositions thereof described herein are administered to a subject once. In some embodiments, the oncolytic viruses or compositions thereof described herein are administered to a subject more than once. For example, a composition disclosed herein may be administered multiple times, including 1, 2, 3, 4, 5, 6, or more times. In some embodiments, a composition disclosed herein may be administered to a subject on a daily or weekly basis for a time period or on a monthly, bi-yearly, or yearly basis depending on need or exposure to a pathogenic organism or to a condition in the subject (e.g. cancer). In particular embodiments, the oncolytic viruses and compositions thereof are formulated in such a way, and administered in such and amount and/or frequency, that they are retained by the subject for extended periods of time.

In some embodiments, the oncolytic viruses or compositions thereof are administered for therapeutic applications or is administered as a maintenance therapy, such as for example, for a patient in remission. In some embodiments, the oncolytic viruses or compositions thereof are administered once every month, once every 2 months, once every 6 months, once a year, twice a year, three times a year, once every two years, once every three years, or once every five years.

In some embodiments wherein a patient's status does improve, the oncolytic viruses or compositions thereof may be administered continuously upon the doctor's discretion. In some embodiments, the dose composition is temporarily reduced and/or administration of the composition is temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In some embodiments, once improvement of a patient's conditions has occurred, a maintenance dose may be administered if necessary. In some embodiments, the dosage and/or the frequency of administration of the composition is reduced, as a function of the symptoms, to a level at which the improved disease, disorder or condition is retained. In some embodiments, patients may require intermittent treatment on a long-term basis upon any recurrence of symptoms.

In some embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it is expressed as the ratio between $LD_{50}$ and $ED_{50}$. Compounds exhibiting high therapeutic indices are preferred. The data obtained from cell culture assays and animal studies are used in formulating a range of dosage for use in human. The dosage of such compounds lies preferably within a range of circulating concentrations that include the $ED_{50}$ with minimal toxicity. The dosage varies within this range depending upon the dosage form employed and the route of administration utilized.

In some instances, tumor antigen expression levels are evaluated to assess the progress of treatment in a patient, to stratify a patient, and/or to modulate a therapeutic regimen. In some instances, assessment of antigen expression levels include the use of immunohistochemistry (HIC) (including semi-quantitative or quantitative IHC) or other antibody-based assays (Western blot, fluorescent immunoassay (FIA), fluorescence in situ hybridization (FISH), radioimmunoassay (RIA), radioimmunoprecipitation (RIP), enzyme-linked immunosorbent assay (ELISA), immunoassay, immunoradiometric assay, fluoroimmunoassay, chemiluminescent assay, bioluminescent assay, gel electrophoresis), or indirectly by quantitating the transcripts for these genes (e.g. by in situ hybridization, nuclease protection, Northern blot, polymerase chain reaction (PCR) including reverse transcriptase PCR (RT-PCR)). In some instances, cells, for example, lymphocytes, are analyzed using FACs technology or paraffin embedded tumor sections using antibodies.

In some instances, antibodies are used to characterize the protein content of target cells through techniques such as immunohistochemistry, ELISAs and Western blotting. In some cases, this provides a screen e.g. for the presence or absence of a subject likely to respond favorably to oncolytic virus therapy and/or a need for co-administering an immune stimulating agent with an oncolytic virus.

In some embodiments, immunohistochemistry is performed on a sample of tissue from a biopsy. In some cases, the sample is examined fresh or frozen. In some instances, antibodies against antigens presented in the cell are added to the sample on a slide and the antibodies bind wherever the antigens are present. In some embodiments, excess antibody is then washed away. In some cases, the antibodies that remain bound to the cell are further labeled by a secondary antibody for visualization under a microscope.

In some embodiments, test samples are obtained from a subject such as for example, from tissue (e.g. tumor biopsy), cerebrospinal fluid (CSF), lymph, blood, plasma, serum, peripheral blood mononuclear cells (PBMCs), lymph fluid, lymphocytes, synovial fluid and urine. In particular embodiments, the test sample is obtained from CSF or tumor tissue. In other particular embodiments, the test sample is obtained from tumor tissue and e.g. the relative number of CD4$^+$ and/or CD8$^+$ cells in the sample is determined and/or the level of one or more Th1 and/or Th2 cytokines in the sample is measured e.g. by immunofluorescent staining of fixed and permeabilized cells from the sample with antibodies against the Th1 and/or Th2 cytokines. In other particular embodiments, the test sample is obtained from blood and e.g. the level of one or more Th1 and/or Th2 cytokines in the sample is measured by ELISA.

Combination Therapy

In some embodiments, the viruses, expression constructs, nucleic acid molecules and/or vectors described herein are administered in combination with another therapeutic agent. In some embodiments, the oncolytic viruses and an additional therapeutic agent are formulated in the same compositions. In such embodiments, the composition may further comprise a pharmaceutically acceptable carrier or excipient. In some embodiments, the oncolytic viruses and an additional therapeutic agent are formulated in separate compositions (e.g., two or more compositions suitable for administration to patient or subject). The disclosure further encompasses co-administration protocols with other cancer therapies, e.g. bispecific antibody constructs, targeted toxins or other compounds, including those which act via immune cells, including T-cell therapy. The clinical regimen for co-administration of the inventive composition(s) encompass(es) co-administration at the same time, before and/or after the administration of the other component. Particular combination therapies include chemotherapy, radiation, surgery, hormone therapy, and/or other types of immunotherapy. In some embodiments, a therapeutically effective amount of a oncolytic virus is administered to a subject in need thereof in combination with an additional therapeutic agent. In some instances, the additional therapeutic agent is a chemotherapeutic agent, a steroid, an immunotherapeutic agent, a targeted therapy, or a combination thereof.

In some embodiments, pharmaceutical compositions are administered in conjunction with an adjuvant therapy. For examples, activating adjuvant treatments are administered prior to, contemporaneous with, or after one or more administrations (e.g., intratumoral injection of the virus). For example, adjuvant therapy includes modulation of Toll-like receptor (TLR) ligands, such as TLR9 activation by DNA molecules comprising CpG sequences, or TLR9 activation (e.g., by RNA ligands), Other adjuvant treatments include agonizing antibodies or other polypeptides (e.g., activation of CD40 or GITR by CD40 Ligand (CD40L) or GITR Ligand (GITRL), respectively). Further, provided are cyclic dinucleotides (e.g., c-di-GMP) that modulate STING. Another activating adjuvant includes interleukins such as IL-33.

In some embodiments, the additional therapeutic agent comprises an agent selected from: bendamustine, bortezomib, lenalidomide, idelalisib (GS-1101), vorinostat, everolimus, panobinostat, temsirolimus, romidepsin, vorinostat, fludarabine, cyclophosphamide, mitoxantrone, pentostatine, prednisone, etoposide, procarbazine, and thalidomide.

In some embodiments, the additional therapeutic agent is a multi-agent therapeutic regimen. In some embodiments the additional therapeutic agent comprises the HyperCVAD regimen (cyclophosphamide, vincristine, doxorubicin, dexamethasone alternating with methotrexate and cytarabine). In some embodiments, the HyperCVAD regimen is administered in combination with rituximab.

In some embodiments the additional therapeutic agent comprises the R-CHOP regiment (rituximab, cyclophosphamide, doxorubicin, vincristine, and prednisone). In some embodiments the additional therapeutic agent comprises the FCR regimen (FCR (fludarabine, cyclophosphamide, rituximab). In some embodiments the additional therapeutic agent comprises the FCMR regimen (fludarabine, cyclophosphamide, mitoxantrone, rituximab). In some embodiments the additional therapeutic agent comprises the FMR regimen (fludarabine, mitoxantrone, rituximab). In some embodiments the additional therapeutic agent comprises the PCR regimen (pentostatin, cyclophosphamide, rituximab). In some embodiments the additional therapeutic agent comprises the PEPC regimen (prednisone, etoposide, procarbazine, cyclophosphamide). In some embodiments the additional therapeutic agent comprises radioimmunotherapy with $^{90}$Y-ibritumomab tiuxetan or $^{131}$I-tositumomab. In some embodiments, the additional therapeutic agent is an autologous stem cell transplant.

In some embodiments, the additional therapeutic agent is selected from: nitrogen mustards such as for example, bendamustine, chlorambucil, chlormethine, cyclophosphamide, ifosfamide, melphalan, prednimustine, trofosfamide; alkyl sulfonates like busulfan, mannosulfan, treosulfan; ethylene imines like carboquone, thiotepa, triaziquone; nitrosoureas like carmustine, fotemustine, lomustine, nimustine, ranimustine, semustine, streptozocin; epoxides such as for example, etoglucid; other alkylating agents such as for example dacarbazine, mitobronitol, pipobroman, temozolomide; folic acid analogues such as for example methotrexate, permetrexed, pralatrexate, raltitrexed; purine analogs such as for example cladribine, clofarabine, fludarabine, mercaptopurine, nelarabine, tioguanine; pyrimidine analogs such as for example azacitidine, capecitabine, carmofur, cytarabine, decitabine, fluorouracil, gemcitabine, tegafur; vinca alkaloids such as for example vinblastine, vincristine, vindesine, vinflunine, vinorelbine; podophyllotoxin derivatives such as for example etoposide, teniposide; colchicine derivatives such as for example demecolcine; taxanes such as for example docetaxel, paclitaxel, paclitaxel poliglumex; other plant alkaloids and natural products such as for example trabectedin; actinomycines such as for example dactinomycin; antracyclines such as for example aclarubicin, daunorubicin, doxorubicin, epirubicin, idarubicin, mitoxantrone, pirarubicin, valrubicin, zorubincin; other cytotoxic antibiotics such as for example bleomycin, ixabepilone, mitomycin, plicamycin; platinum compounds such as for example carboplatin, cisplatin, oxaliplatin, satraplatin; methylhydrazines such as for example procarbazine; sensitizers such as for example aminolevulinic acid, efaproxiral, methyl aminolevulinate, porfimer sodium, temoporfin; protein kinase inhibitors such as for example dasatinib, erlotinib, everolimus, gefitinib, imatinib, lapatinib, nilotinib, pazonanib, sorafenib, sunitinib, temsirolimus; other antineoplastic agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; estrogens such as for example diethylstilbenol, ethinylestradiol, fosfestrol, polyestradiol phosphate; progestogens such as for example gestonorone, medroxyprogesterone, megestrol; gonadotropin releasing hormone analogs such as for example buserelin, goserelin, leuprorelin, triptorelin; anti-estrogens such as for example fulvestrant, tamoxifen, toremifene; anti-androgens such as for example bicalutamide, flutamide, nilutamide, enzyme inhibitors, aminoglutethimide, anastrozole, exemestane, formestane, letrozole, vorozole; other hormone antagonists such as for example abarelix, degarelix; Immunostimulants such as for example histamine dihydrochloride, mifamurtide, pidotimod, plerixafor, roquinimex, thymopentin; immunosuppressants such as for example everolimus, gusperimus, leflunomide, mycophenolic acid, sirolimus; calcineurin inhibitors such as for example ciclosporin, tacrolimus; other immunosuppressants such as for example azathioprine, lenalidomide, methotrexate, thalidomide; and Radiopharmaceuticals such as for example, iobenguane.

In some embodiments, the additional therapeutic agent is selected from: interferons, interleukins, tumor necrosis factors, growth factors, or the like.

In some embodiments, the additional therapeutic agent is selected from: ancestim, filgrastim, lenograstim, molgramostim, pegfilgrastim, sargramostim; Interferons such as for example IFNα natural, IFN α-2a, IFN α-2b, IFN alfacon-1, IFN α-n1, IFN βnatural, IFN β-1a, IFN β-1b, IFN γ, peginterferon α-2a, peginterferon α-2b; interleukins such as for example aldesleukin, oprelvekin; other immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNFα inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; calcineurin inhibitors such as for example ciclosporin, tacrolimus; other immunosuppressants such as for example azathioprine, lenalidomide, methotrexate, thalidomide. In some embodiments, the additional therapeutic agent is selected from: Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

In some embodiments, the additional therapeutic agent is selected from: monoclonal antibodies such as for example alemtuzumab, bevacizumab, catumaxomab, cetuximab, edrecolomab, gemtuzumab, panitumumab, rituximab, trastuzumab; Immunosuppressants, eculizumab, efalizumab, muromab-CD3, natalizumab; TNF alpha Inhibitors such as for example adalimumab, afelimomab, certolizumab pegol, golimumab, infliximab; Interleukin Inhibitors, basiliximab, canakinumab, daclizumab, mepolizumab, tocilizumab, ustekinumab; Radiopharmaceuticals, ibritumomab tiuxetan, tositumomab; additional monoclonal antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

In some embodiments, the additional therapeutic agent is selected from: agents that affect the tumor micro-environment such as cellular signaling network (e.g. phosphatidylinositol 3-kinase (PI3K) signaling pathway, signaling from the B-cell receptor and the IgE receptor). In some embodiments, the additional therapeutic agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, protein kinase inhibitors such as for example dasatinib, erlotinib, everolimus, gefitinib, imatinib, lapatinib, nilotinib, pazonanib, sorafenib, sunitinib, temsirolimus; other angiogenesis inhibitors such as for example GT-111, JI-101, R1530; other kinase inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, R05185426, SAR103168, SCH 727965, SGI-1176, SGX523, SNS-314, TAK-593, TAK-901, TKI258, TLN-232, TTP607, XL147, XL228, XL281R05126766, XL418, XL765.

In some embodiments, the additional therapeutic agent is selected from: inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In some embodiments, the additional therapeutic agent is selected from: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the additional therapeutic agent is selected from: alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

In some embodiments, pharmaceutical compositions are administered in conjunction with an adjuvant therapy. For examples, activating adjuvant treatments are administered prior to, contemporaneous with, or after one or more administrations (e.g., intratumoral injection of the virus). For example, adjuvant therapy includes modulation of Toll-like receptor (TLR) ligands, such as TLR9 activation by DNA molecules comprising CpG sequences, or TLR9 activation (e.g., by RNA ligands). Other adjuvant treatments include agonizing antibodies or other polypeptides (e.g., activation of CD40 or GITR by CD40 Ligand (CD40L) or GITR Ligand (GITRL), respectively). Further, provided are cyclic dinucleotides (e.g., c-di-GMP) that modulate STING. Another activating adjuvant includes interleukins such as IL-33. In some instances, the pharmaceutical compositions described herein are administered in conjunction with an adjuvant therapy.

Kits

In some embodiments, the present invention provides kits comprising one or more oncolytic viruses as described herein, a nucleic acid sequence as described herein, a vector as described herein, and/or a host cell as described herein. In some embodiments, the kits comprise a pharmaceutical composition as described herein above, either alone or in combination with further therapeutic agents to be administered to an individual in need thereof.

In some embodiments, the present invention provides kits for the use of vectors and virus-producing cells according to the invention as drugs in therapeutic methods. In particular, the vectors and virus producing cells according to some embodiments of the invention are used for the therapy or treatment of solid tumors in a subject. In some embodiments, the therapeutic effect is caused by the oncolytic properties of the recombinant vectors and viruses as well as by the use of therapeutic genes.

In some embodiments, the present invention provides kits for use with methods and compositions. Some embodiments concern kits having vaccine compositions of use to reduce onset of or treat subjects having one or more solid tumors. Other embodiments concern kits for making and using molecular constructs described herein. In some instances, kits also include a suitable container, for example, vials, tubes, mini- or microfuge tubes, test tube, flask, bottle, syringe or other container. Where an additional component or agent is provided, the kit contains one or more additional containers into which this agent or component is placed. Kits herein also include a means for containing the constructs, vaccine compositions and any other reagent containers in close confinement for commercial sale. Such containers include injection or blow-molded plastic containers into which the desired vials are retained. Optionally, one or more additional agents such as other anti-viral agents, anti-fungal or anti-bacterial agents are needed for compositions described, for example, for compositions of use as a vaccine.

All publications, patents, and patent applications mentioned in this specification are herein incorporated by reference to the same extent as if each individual publication, patent, or patent application was specifically and individually indicated to be incorporated by reference.

EXAMPLES

The examples below further illustrate the described embodiments without limiting the scope of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1: Preparation of Pseudotyped VSV-G

The following protocol was adopted to prepare an exemplary pseudotyped VSV-G, by combining VSV-Glycoprotein (VSV-GP) with HIV1-gag and rev proteins.

Cell culture and transfection: DNA of the following packaging plasmids was mixed and prepared for transfection into 293T cells: pMDLg/pRRE expressing HIV-1 GAG/POL; pRSV/REV expressing HIV-1 REV; and pMD2.G 5 60 5.8 VSV glycoprotein. The DNA mix was added to 500 µL of pre-warmed Optimem II medium. A working stock of polyethyleneimine transfection reagent (PEI) was prepared at 1 µg/µL in 1×PBS, pH 4.5, and 88 µL of the working stock was added to the mixture, maintaining a 4:1 v/w ratio of PEI:DNA. The mixture was vortexed briefly and left for 5-10 min at room temperature to form a PEI:DNA transfection complex. A total of $2.5 \times 10^6$ low passage (less than P20) 293T cells were seeded per 15 cm dish in 15 mL DMEM supplemented with 10% serum and 1% Pen/Strep. 2 hours prior to transfection, the cell culture medium was aspirated and replaced with 15 mL of fresh pre-warmed growth medium (GM). The transfection complex was then added drop-wise to each 15 cm plate, swirled briefly to mix and incubated for 8 hrs in 10% $CO_2$, 35° C. After 8 hours, the medium was replaced with 10 mL of fresh growth medium containing 25 mM HEPES and 10% serum. The mixture was then incubated for 48 hrs post-transfection.

Virus collection: The medium from each dish was removed, pooled, and filtered through a 0.22 µm low protein binding/fast flow filter unit and stored at 4° C. A 5 mL volume of fresh growth medium was added to each dish and incubated overnight at 4° C. (60-72 hours post transfection). The second lot of medium from each dish was collected, as in the previous step, and pooled with previous media harvest. The plasmid carry-over is removed by digestion with DNASE-I (1 mg/mL stock). A 1 µg/mL solution the viral supernatant, supplemented with 1 µL of 1M $MgCl_2$, was incubated at room temperature for 30 min followed by 2-4 hrs at 4° C. The filtered supernatants can be used directly on cultured cells, or aliquoted and stored at −80° C. The pseudotyped VSV-G viral supernatant can be optionally concentrated and purified.

Example 2: Construction of Pseudotyped VSV-G Expressing a CD28-CA125 Bispecific Antibody Engager Molecule Pseudotyped VSV-G is prepared as described in Example 1 and further processed to express a nucleic acid encoding an engager polypeptide comprising an effector domain comprising an anti-CD28 molecule and a targeting domain comprising an anti-CA125 molecule, and a nucleic acid encoding an anti-PD1 immune modulatory peptide. The resulting oncolytic virus is a pseudotyped oncolytic VSV-G virus encoding a CD28-CA125 engager molecule and an anti-PD1 therapeutic molecule (CD28-CA125-PD1 VSV-G).

Example 3: CD28-CA125-PD1 VSV-G Activates Human T Cells and Exhibits Anti-Tumor Activity Human T cells are infected with the pseudotyped CD28-CA125-PD1 VSV-G virus. 24 hrs to 48 hrs post viral infection, the T cell culture medium is collected and checked for the presence of proinflammatory cytokines. These results will show that T cells are activated by CD28-CA125-PD1 VSV-G, as evidenced by presence of proinflammatory cytokines such as IFN-β and IL-2 in the cell culture supernatant of CD28-CA125-PD1 VSV-G infected human T cells.

EphA2-overexpressing gastric cancer cells, from KATO3 cell line, are infected with pseudotyped CD28-CA125-PD1 VSV-G or non-pseudotyped CD28-CA125-PD1 VSV virus and the cell proliferation is assessed. These results will show that cell proliferation is significantly reduced in cells KATO3 cells infected with pseudotyped CD28-CA125-PD1 VSV-G compared to KATO3 cells infected with non-pseudotyped CD28-CA125-PD1 VSV virus.

Example 4: CD19-CD3, SIRP1α-CD3, and PDL1-CD3-Fc Engager Molecules Specifically Bind to T-Cells Via CD3

The binding of bipartite (CD19-CD3 and SIRP1α-CD3) and triparte (PDL1-CD3-Fc) engager molecules to T cells was assessed. Briefly, 25,000 T cells were stimulated with 200 U/mL IL-2 for 12 days. After 12 days, T cell were incubated with varying concentrations of engager molecules (500, 1000, or 2000 ng/mL for CD19-CD3 and SIRP1α-CD3; neat supernatant for PDL1-CD3-Fc) for 20 minutes at room temperature in triplicate. Cells were then washed twice, followed by staining with an anti-6xHis APC antibody at 500 ng/mL for an additional 20 minutes. Cells were washed again and treated with propidium iodide (PI) to exclude dead cells from further analysis. Stained cells were analyzed by flow cytometry on a BD LSR Fortesa cytometer and the percentage of the cell population positive for staining was set at 2% of the secondary only control.

Figure 19B:
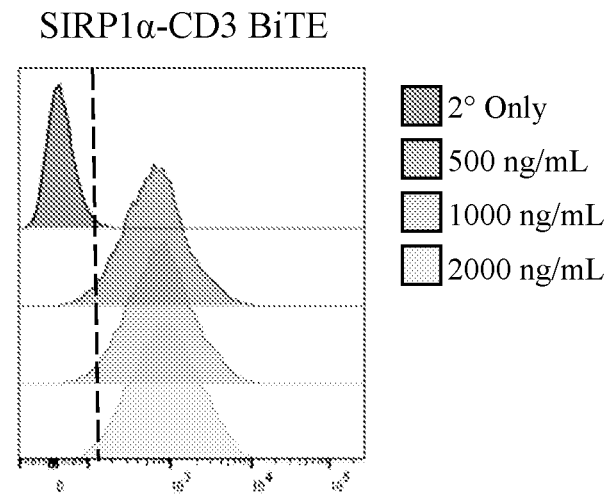
Figure 19C:
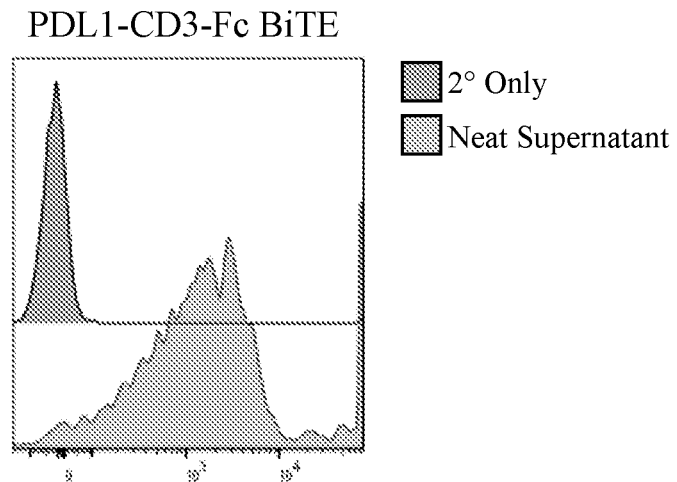

Results for CD19-CD3 (FIG. 19A), SIRP1α-CD3 (FIG. 19B), and PDL1-CD3-Fc (FIG. 19C) show that the CD3 binding moiety of each of these molecules functional binds to CD3-expressing 293F T cells, as indicated by an increase in the percentage of cells that are positive for the engager molecules compared to the secondary antibody alone. In particular, a dose dependent increase in the % positive cells is observed for CD19-CD3 (FIG. 19A), while the SIRP1α-CD3 construct demonstrated maximal binding at all concentrations. The amount of the neat PDL1-CD3-Fc supernatant used resulted in binding of the construct to the majority of T cells (FIG. 19C).

Figure 20:
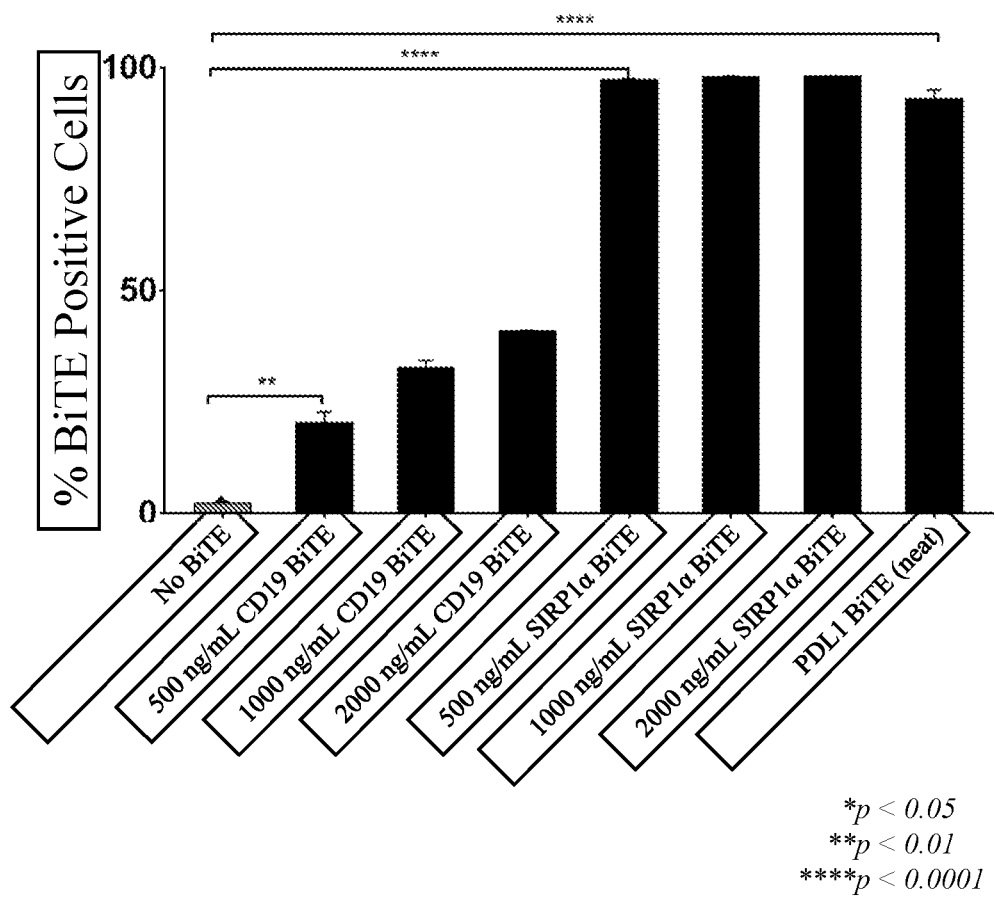
FIG. 20 illustrates the quantification of the T cell engager construct binding shown in FIG. 19.

The results of this experiment are quantified in FIG. 20. In particular, all of the constructs demonstrated a significant increase in the % positive T cells compared to samples where no engager molecule was added.

Figure 21A:
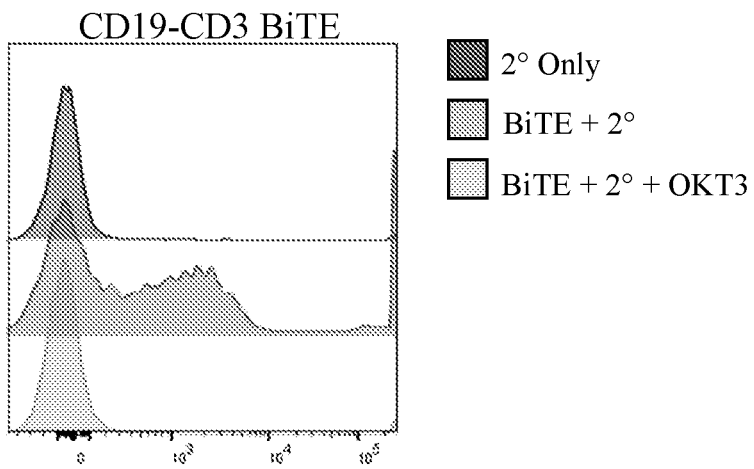
FIG. 21 illustrates the CD3-specific binding of CD19-CD3 BiTE constructs (FIG. 21A), SIRP1α-CD3 BiTE constructs (FIG. 21B), and PDL1-CD3-Fc tripartite T cell engagers (FIG. 21C) through the use of an anti-CD3 antibody, OKT3.
Figure 21B:
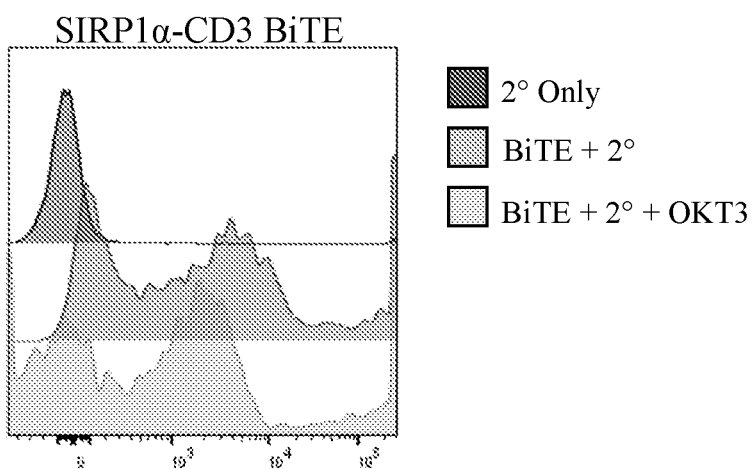
Figure 21C:
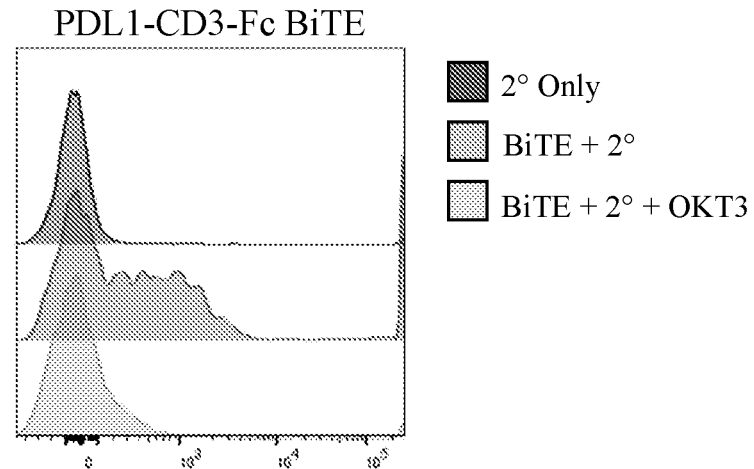

Additional experiments demonstrated that the binding of the CD19-CD3, SIRP1α-CD3, and PDL1-CD3-Fc was mediated by interactions of the anti-CD3 domain of the engager molecules with CD3 expressed by the T cells. Prior to exposure of T cells to the engager molecules, the T cells were incubated with an anti-CD3 monoclonal antibody (OKT3). Preincubation with the OKT3 inhibited binding of the CD19-CD3 engager, and substantially reduced binding of the PDL1-CD3-Fc engager. The lack of inhibition of binding of the SIRP1α-CD3 engager by preincubation with OKT3 (FIG. 21C) is likely due to an incomplete inhibition of CD3 by OKT3 in these samples.

Example 5: SIRP1α-CD3 Constructs Specifically Bind to CD47

Figure 22:
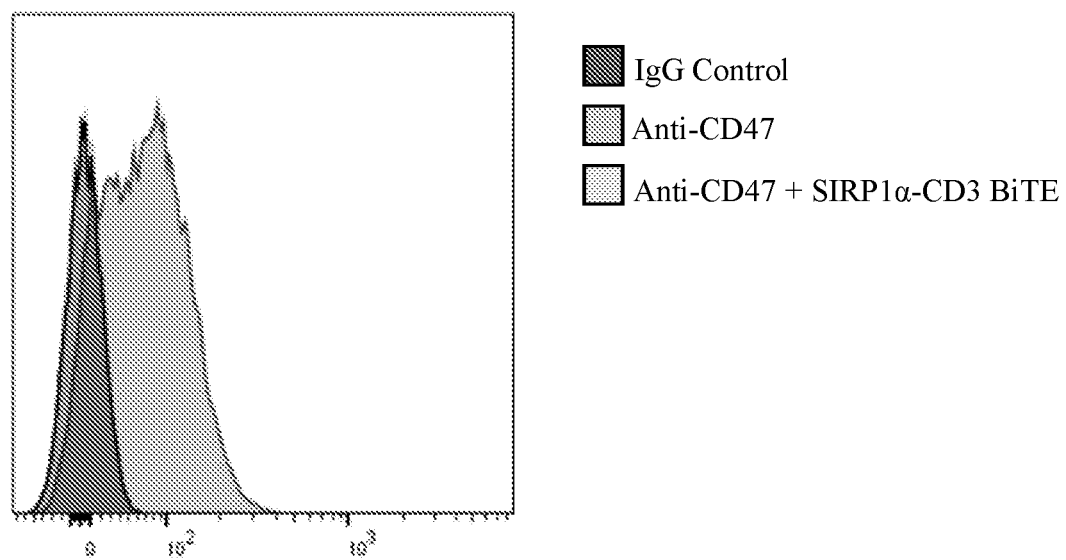
FIG. 22 illustrates the specificity of the CD47-binding SIRP1α arm of a SIRP1α-CD3 BiTE construct.

Experiments were performed to determine the binding specificity of the SIRP1α-CD3 engager constructs. Raji cells were preincubated with SIRP1α-CD3 engagers for 20 min at RT. Cells were then washed and incubated with a fluorescently labelled anti-CD47 monoclonal antibody for 20 min at RT, after which cells were washed and analyzed by flow cytometry. Raji cells that were not preincubated with the SIRP1α-CD3 engager showed significant binding of the anti-CD47 monoclonal antibody (FIG. 22, IgG control histogram vs. the anti-CD47 histogram). Preincubation of Raji cells with the SIRP1α-CD3 engager blocked binding of the anti-CD47 monoclonal antibody (FIG. 22, anti-CD47 histogram vs. anti-CD47+SIRP1α-CD3 hectograph).

Example 6: Binding of SIRP1α-CD3 and CD19-CD3 Engager Molecules to Target Cells

Experiments were performed to determine the ability of SIRP1α-CD3 and CD19-CD3 BiTEs to bind to Raji (CD19$^+$CD47$^+$, FIG. 23), U2OS (CD19$^-$CD47$^+$, FIG. 24), GBM30-luc (CD19$^-$CD47$^+$, FIG. 25), and U251 (CD19$^-$CD47$^+$, FIG. 26) target cell types. For each target cell type, cells were treated with 500 or 1000 ng/mL of either (i) His-tagged soluble SIRP1α; (ii) SIRP1α-CD3 BiTE; or (iii) or CD19-CD3 BiTE. Cells were then stained with a fluorescently labelled anti-His antibody and analyzed by flow cytometry.

Figure 23A:
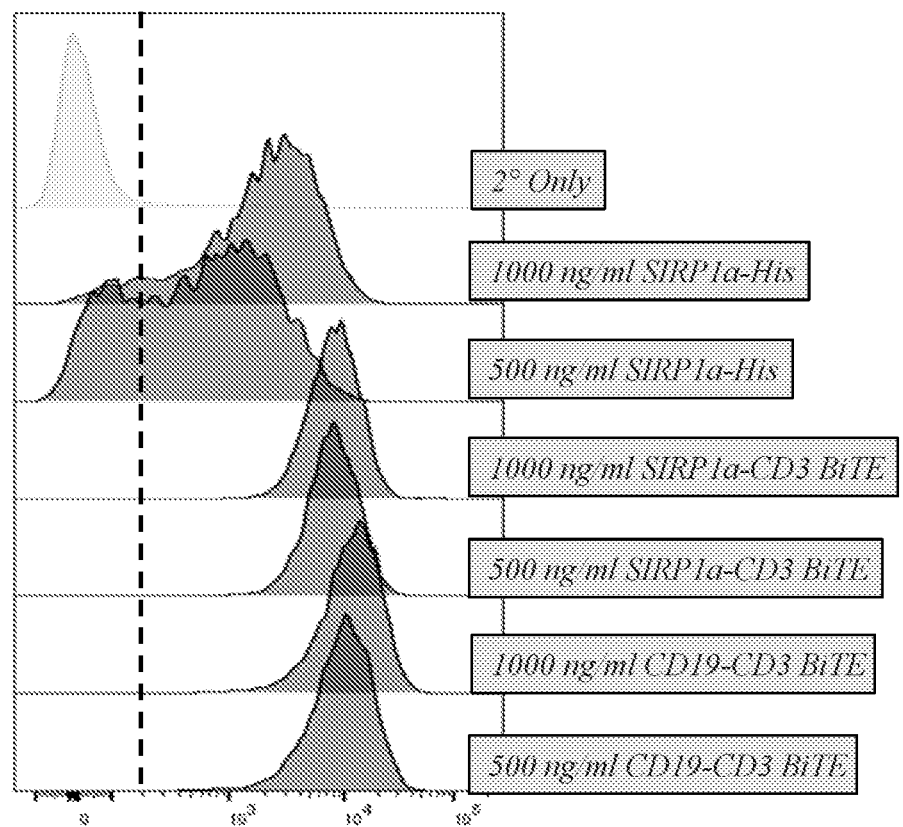
FIG. 23A-FIG. 23B illustrate the binding of CD19-CD3 and SIRP1α-CD3 BiTE constructs (FIG. 23A) to Raji cells (CD19$^+$CD47$^+$). % binding is quantified in FIG. 23B.
Figure 23B:
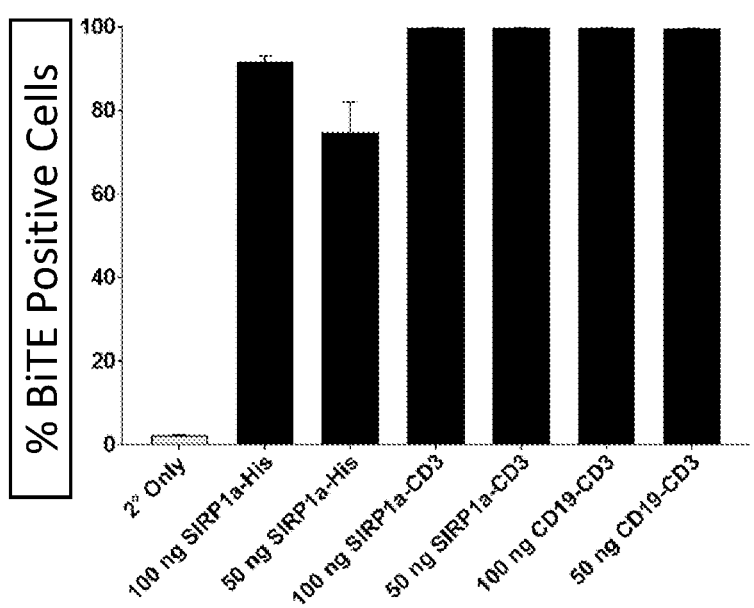

The results of SIRP1α-CD3 and CD19-CD3 binding to CD19$^+$CD47$^+$ Raji cells are shown in FIG. 23. Relative to the negative control Ig (2° only), soluble SIRP1α, SIRP1α-CD3 BiTE, and CD19-CD3 BiTE were able to bind to Raji cells, as indicated by a shift towards the right of the engager histograms compared to the IgG control histogram (FIG. 23A). Quantitation of the binding data showing percentage of BiTE positive cells is show in FIG. 23B.

Figure 24A:
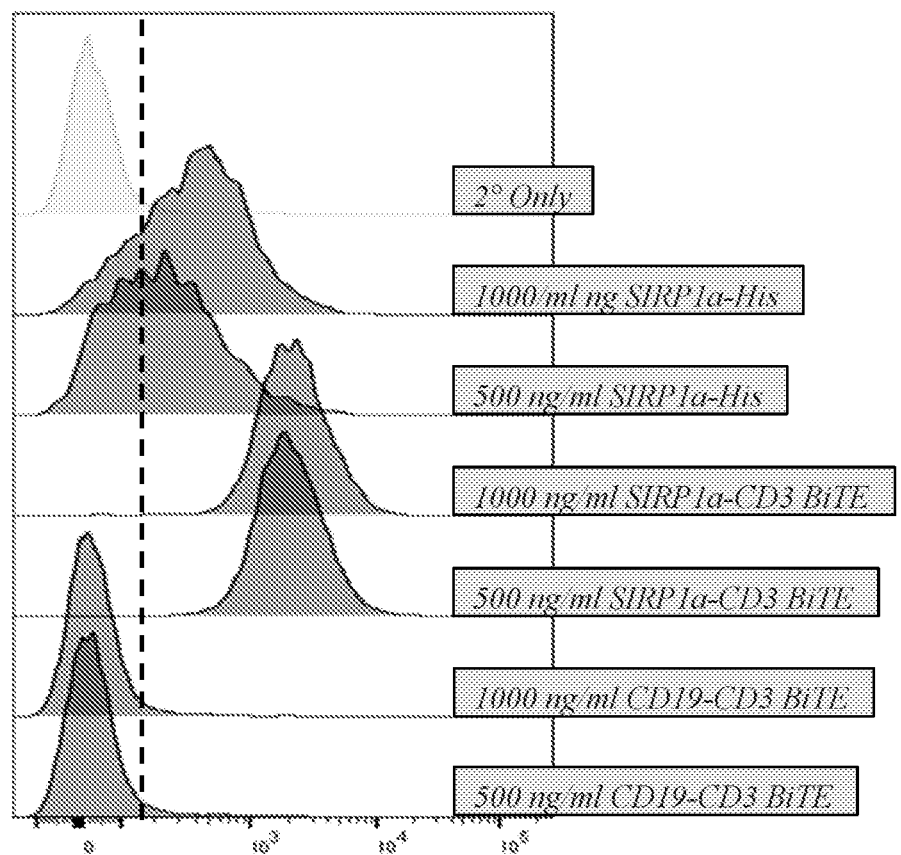
FIG. 24A-FIG. 24B illustrate the binding of CD19-CD3 and SIRP1α-CD3 BiTE constructs (FIG. 24A) to U2OS cells (CD19$^-$CD471. % binding is quantified in FIG. 24B.
Figure 24B:
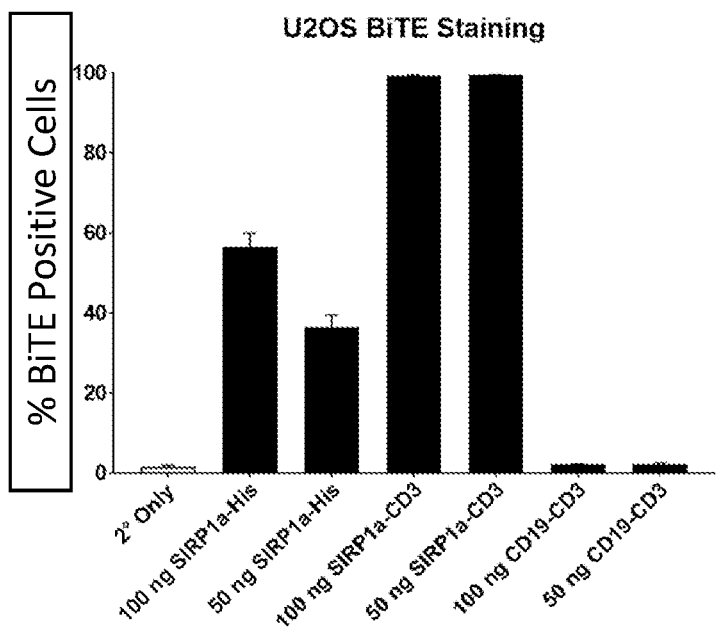

The results of SIRP1α-CD3 and CD19-CD3 binding to CD19$^-$CD47$^+$ U2OS cells are shown in FIG. 24. Relative to the negative control Ig (2° only), soluble SIRP1α, SIRP1α-CD3 BiTE were able to bind to U2OS cells at all concentrations used, as indicated by a shift towards the right of the engager histograms compared to the IgG control histogram (FIG. 24A). CD19-CD3 BiTEs were unable to bind to U2OS cells, which was expected based on the lack of CD19 expression by U2OS cells. Quantitation of these binding data showing percentage of BiTE positive cells is show in FIG. 24B.

Figure 25A:
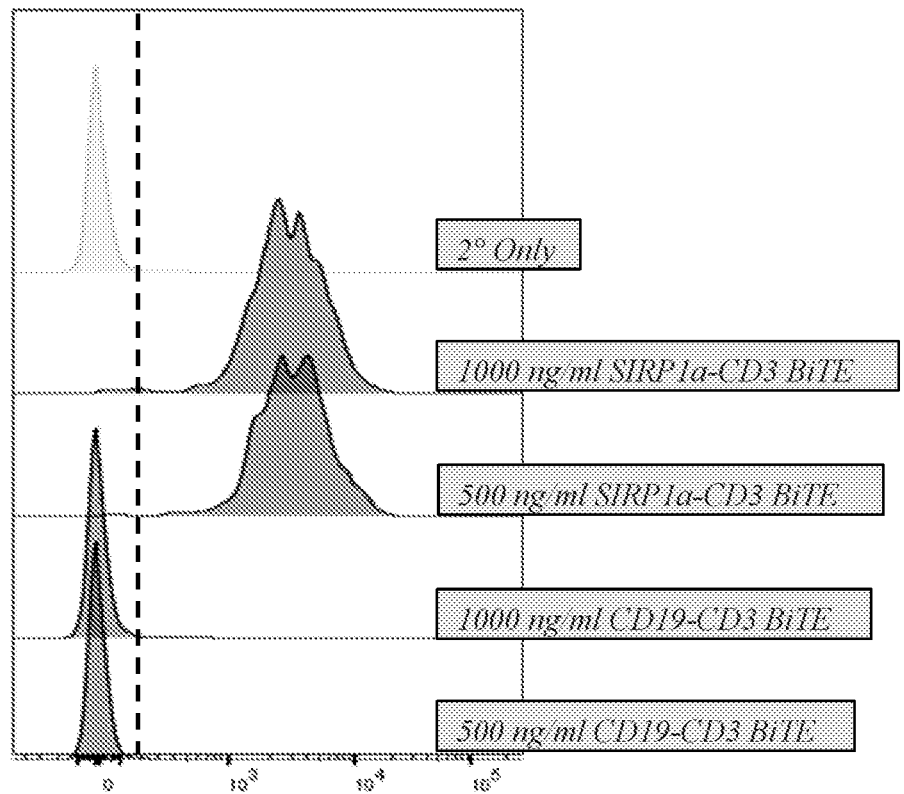
FIG. 25A-FIG. 25B illustrate the binding of CD19-CD3 and SIRP1α-CD3 BiTE constructs (FIG. 25A) to GBM30-luc cells (CD19$^-$CD47$^+$). % binding is quantified in FIG. 25B.
Figure 25B:
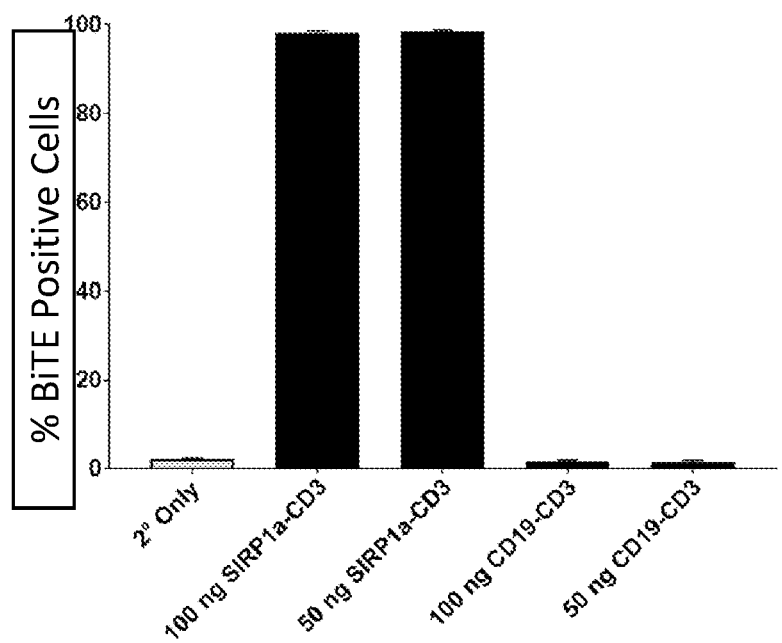

The results of SIRP1α-CD3 and CD19-CD3 binding to CD19$^-$CD47$^+$ GBM30-luc cells are shown in FIG. 25. Relative to the negative control Ig (2° only), SIRP1α-CD3 BiTE were able to bind to GBM30-luc cells at all concentrations used, as indicated by a shift towards the right of the engager histograms compared to the IgG control histogram (FIG. 25A). In contrast, CD19-CD3 BiTEs were unable to bind to GBM30-luc cells, which was expected based on the lack of CD19 expression by GBM30-luc cells. Quantitation of these binding data showing percentage of BiTE positive cells is show in FIG. 25B.

Figure 26A:
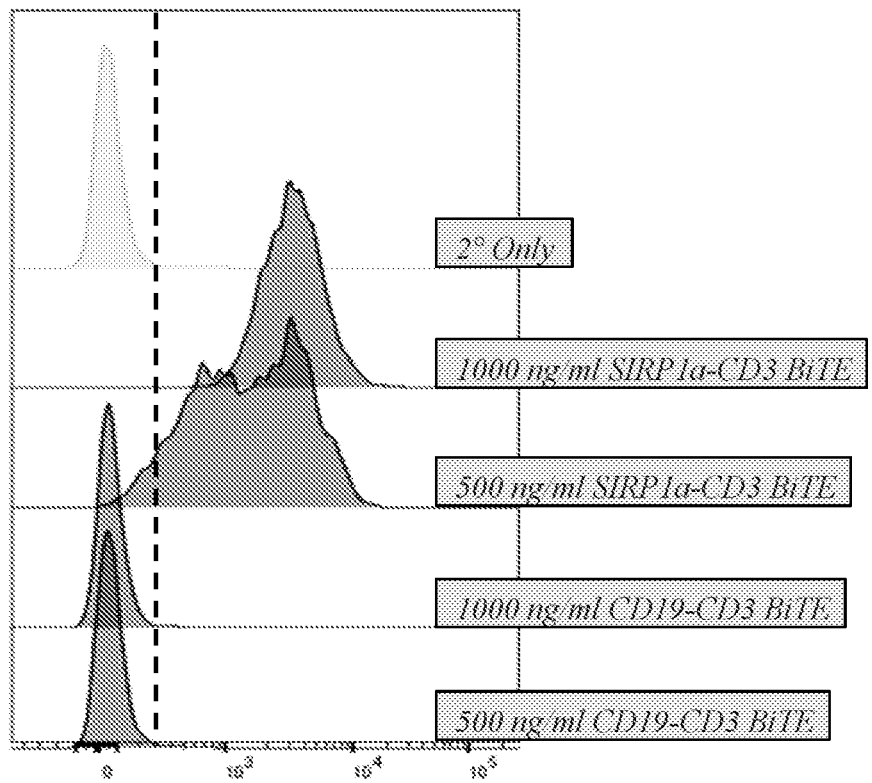
FIG. 26A-FIG. 26B illustrate the binding of CD19-CD3 and SIRP1α-CD3 BiTE constructs (FIG. 26A) to U251 cells (CD19$^-$CD47$^+$). % binding is quantified in FIG. 26B.
Figure 26B:
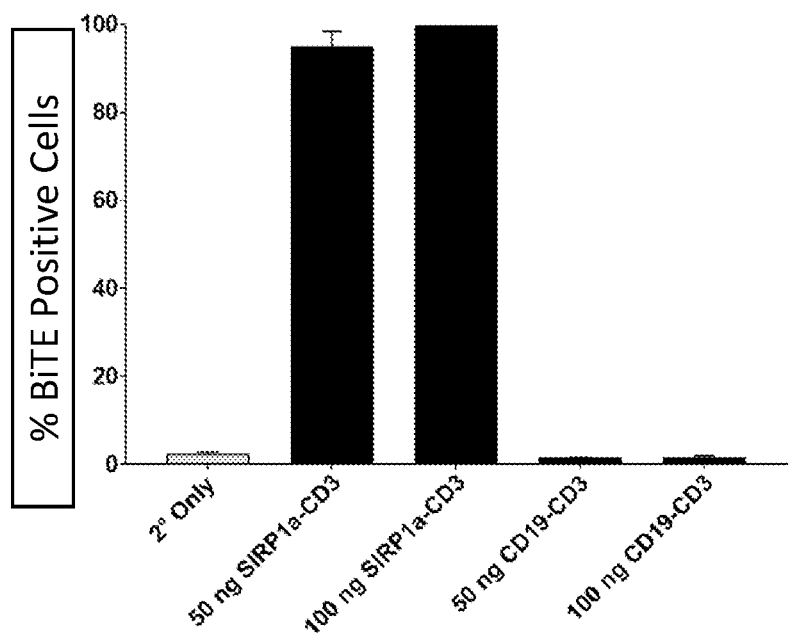

The results of SIRP1α-CD3 and CD19-CD3 binding to CD19$^-$CD47$^+$ U251 cells are shown in FIG. 26. Relative to the negative control Ig (2° only), SIRP1α-CD3 BiTE were able to bind to U251 cells at all concentrations used, as indicated by a shift towards the right of the engager histograms compared to the IgG control histogram (FIG. 26A). In contrast, CD19-CD3 BiTEs were unable to bind to U251 cells, which was expected based on the lack of CD19 expression by U251 cells. Quantitation of these binding data showing percentage of BiTE positive cells is show in FIG. 26B.

Example 7: Binding of PDL1-CD3-Fc TiTEs to U251 Cells is Mediated by CD47, not FcγRs As the PDL1-CD3-Fc TiTE construct comprises 2 domains that are capable of binding to target cells (the anti-PDL1 and the Fc domain) experiments were performed to assess the binding specificity of these constructs. CD19⁻ CD47⁺ U251 cells were treated with 2 µg/mL of a fluorescently labeled anti-PDL1 antibody, an isotype control, or PDL1-CD3-Fc transfection supernatant. Relative to negative control Ig, the PDL1-CD3-Fc TiTE bound to U251 cells (FIG. 27B). To assess whether this observed binding was due to interactions with CD47 or FcγRs expressed by U251 cells, the FcγR expression on U251 cells was determined. Cells were incubated with 2 µg/mL of fluorophore-conjugated anti-CD16/32 (recognizing FcγRIII/FcγRII) or anti-CD64 (recognizing FcγRI) mAbs for 20 min at RT. Cells were then washed and analyzed by flow cytometry using a BD LSR Fortessa cytometer. As shown in FIG. 27C, U251 cells do not express FcγRI, FcγRII, or FcγRIII, indicating the binding of the PDL1-CD3-Fc construct was mediated by interactions with CD47 and not FcγRs.

Figure 28:
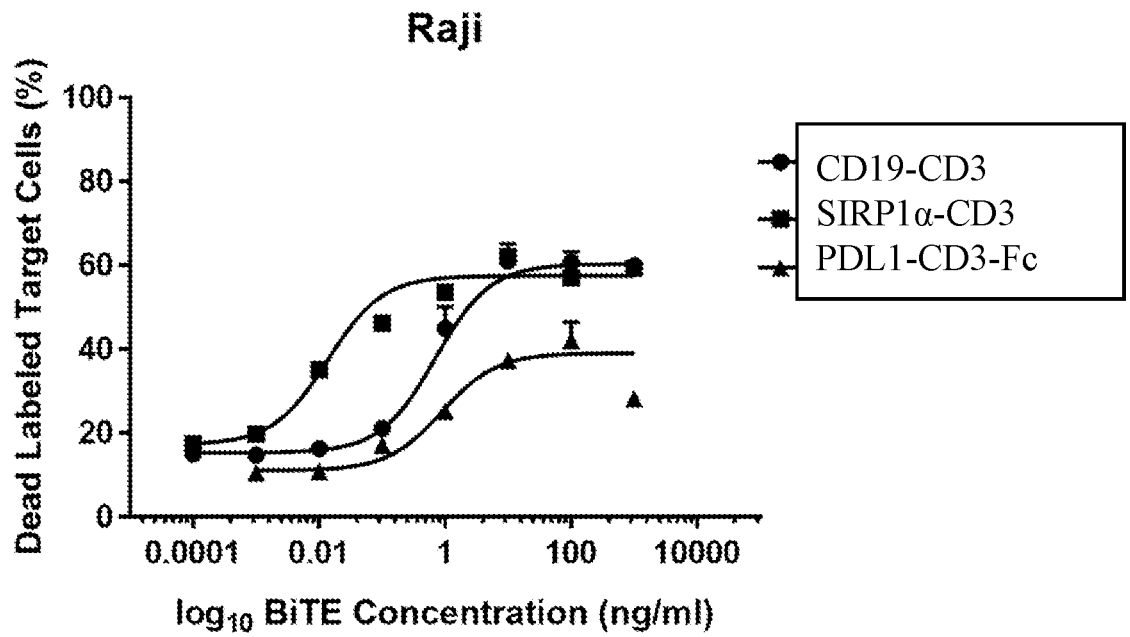
FIG. 28 illustrates CD19-CD3 BiTE, SIRP1α-CD3 BiTE, and PDL1-CD3-Fc tripartite T cell engager-mediated T cell-dependent cytotoxicity (TDCC) of Raji cells.
Figure 30:
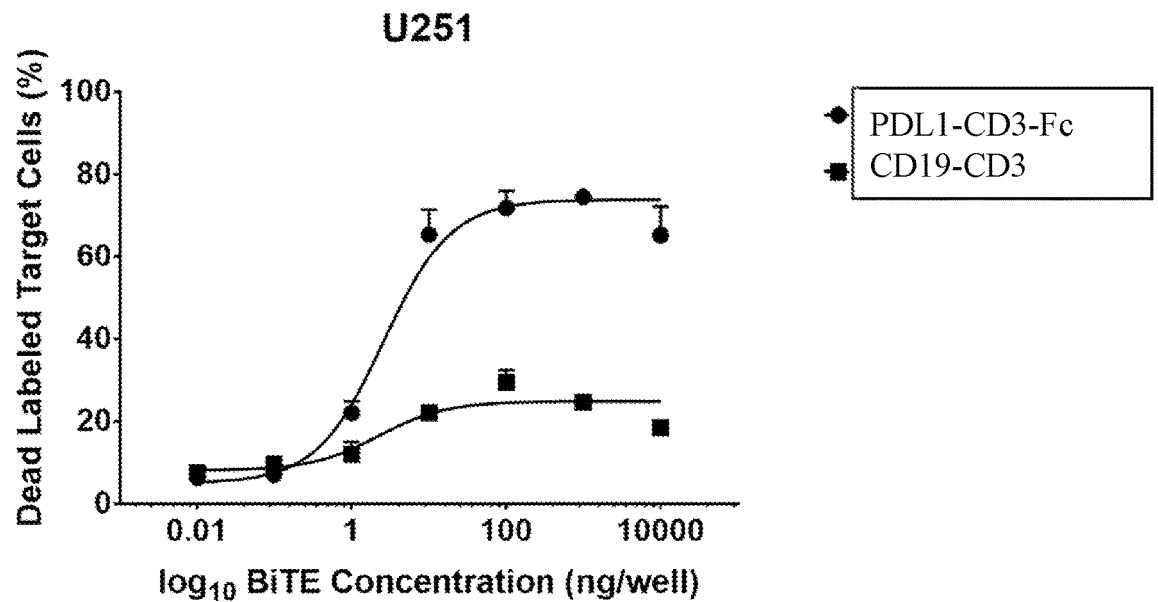
FIG. 30 illustrates CD19-CD3 BiTE and PDL1-CD3-Fc tripartite T cell engager-mediated TDCC of U251 cells.
Figure 31:
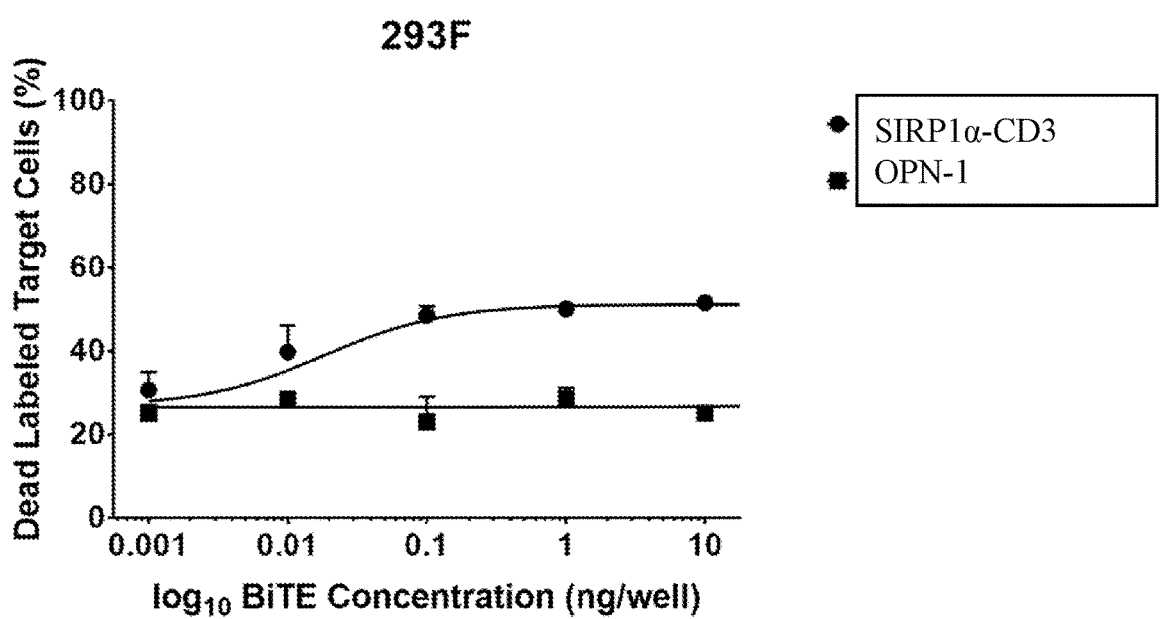
FIG. 31 illustrates SIRP1α-CD3 BiTE-mediated TDCC of 293F cells compared to an osteopontin-fusion control construct.

Example 8: CD19-CD3, SIRP1α-CD3, and PDL1-CD3-Fc Constructs Stimulate CD8+ T Cell-Mediated Killing of Target Cells Experiments were performed to determine the ability of CD19-CD3, SIRP1α-CD3, and PDL1-CD3-Fc constructs to mediate killing of target cells. Briefly, CD8⁺ T cells were stimulated for 8-12 days in the presence of 200 U/mL IL-2 and Dynabeads. Prior to co-culture with target cells, all Dynabeads were removed by magnet and cells were washed to remove IL-2. Raji (FIG. 28), THP1 (FIG. 29), U251 (FIG. 30), and 293F (FIG. 31) target cells were labeled with the fluorescent membrane dye PKH67 green before plating. CD8⁺ effector T cells were then co-cultured with target cells at an effector to target ratio of 1:1 along with 1000 ng/mL CD19-CD3 BiTE, SIRP1α-CD3 BiTEs, or a 1:3 dilution of PDL1-CD3-Fc transfection supernatant. Co-cultures of target and effector cells were incubated for 18 hours, after which they were stained with 7-AAD and live/dead analysis was performed by flow cytometry on a BD LSR Fortesa cytometer.

The results of these experiments indicate that the CD19-CD3, SIRP1α-CD3 and PDL1-CD3-Fc engager constructs were all capable of inducing effector cell-mediated death of Raji target cells (FIG. 28), The $EC_{50}$ for each of the CD19-CD3, SIRP1α-CD3 and PDL1-CD3-Fc engager molecules on Raji cells are shown below in Table 5.

TABLE 5

| EC50 of engager molecules on Raji cells | |
|---|---|
| Engager Molecule | $EC_{50}$ (ng/mL) |
| CD19-CD3 | 0.6997 |
| SIRP1α-CD3 | 0.0137 |
| PDL1-CD3-Fc | 0.8907 |

Figure 29:
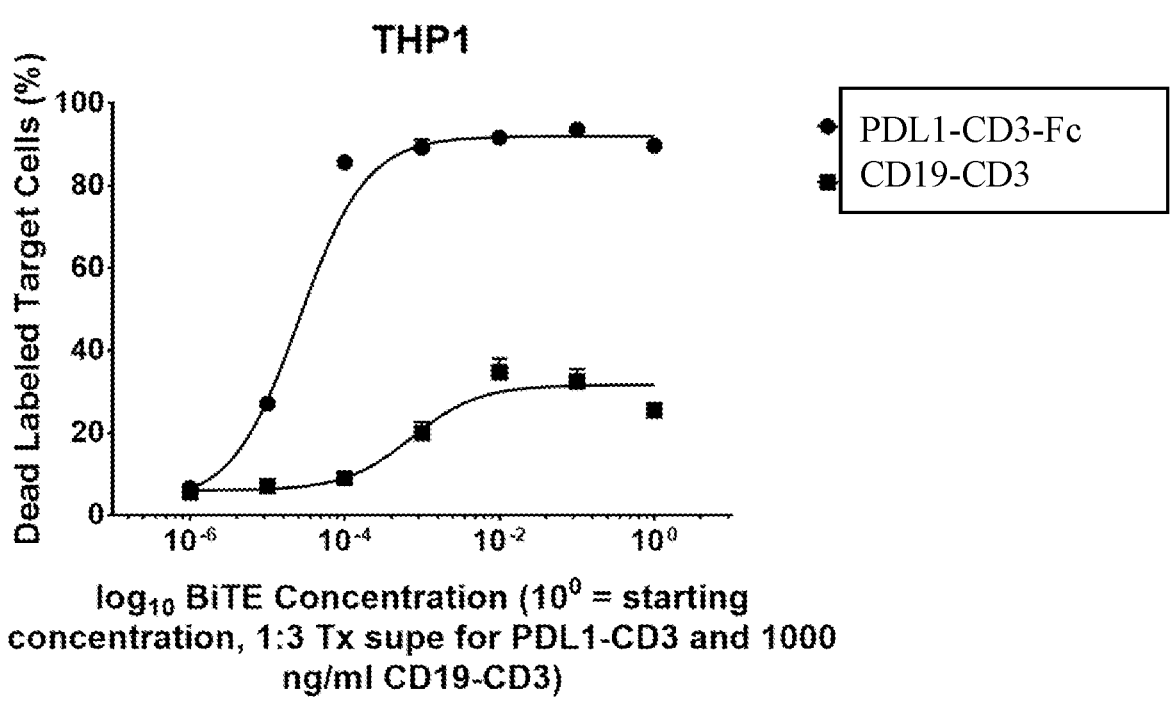
FIG. 29 illustrates CD19-CD3 BiTE and PDL1-CD3-Fc tripartite T cell engager-mediated TDCC of THP1 cells.

The results of these experiments further indicate that the PDL1-CD3-Fc engager constructs, but not the CD19-CD3 constructs, were capable of inducing effector cell-mediated death of THP1 target cells (FIG. 29). This is likely due to the lack of/relatively low expression of CD19 by THP1 cells.

Further, the PDL1-CD3-Fc engager constructs were capable of inducing effector cell-mediated death of U251 target cells (FIG. 30), while the CD19-CD3 constructs did not induce effector cell-mediated death of U251 cells due to a lack of CD19 expression by U251 cells. The $EC_{50}$ for each of the CD19-CD3 and PDL1-CD3-Fc constructs on U251 cells are shown below in Table 6.

TABLE 6

| $EC_{50}$ of engager molecules on U251 cells | |
|---|---|
| Engager Molecule | $EC_{50}$ (ng/mL) |
| CD19-CD3 | 2.247 |
| PDL1-CD3-Fc | 2.611 |

Further, the SIRP1α-CD3 engager constructs were capable of inducing effector cell-mediated death of 293F target cells (FIG. 31), indicated by the increase in cell death in SIRP1α-CD3 containing cultures compared to a control osteopontin-fusion protein (OPN 1). The $EC_{50}$ for SIRP1α-CD3 engager molecules on 293F cells is shown below in Table 7.

TABLE 7

| $EC_{50}$ of SIRP1α-CD3 on 293F cells | |
|---|---|
| Engager Molecule | $EC_{50}$ (ng/mL) |
| SIRP1α-CD3 | 0.0184 |

Example 9: PDL1-CD3-Fc BiTE Enhances Primary NK Cell Killing of U251 Cells

Figure 32:
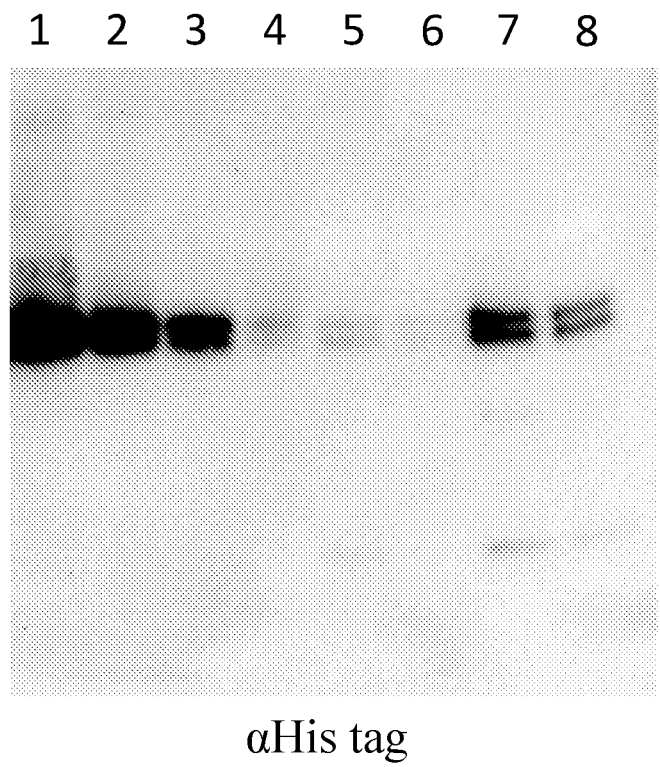
FIG. 32 illustrates expression of SIRP1α-CD3 BiTE constructs from oncolytic-HSV vectors. Expression of SIRP1α-CD3 BiTE constructs with short linkers (Lanes 1-4 and ONCR085 in lanes 5-6, shown in FIG. 5) and SIRP1α-CD3 BiTE constructs with long linkers (ONCR087 in lanes 7-8, shown in FIG. 6) are shown.

Experiments are performed to assess the ability of PDL1-CD3-Fc constructs to induce NK cell-mediated killing of target cells. Briefly, U251 cells are labelled with cell membrane dye PKH67 green, and then seeded and allowed to adhere to wells over night (FIG. 32). Primary NK cells (StemCell Technologies, Inc.) are then added to each well at an effector to target ratio of 1:1, along with varying amounts of virally produced PDL1-CD3-Fc protein. Effector/target cell co-culture are incubated at 37° C. for 6 hours prior to live/dead analysis by 7-AAD staining. Stained cells are analyzed by flow cytometry on a BD LSR Fortesa cytometer.

These results will demonstrate that virally produced PDL1-CD3-Fc compounds are able to stimulate NK cell-mediated death of target cells such as U251.

Example 10: oHSV-Infected Vero Cells Express SIRP-1α-CD3 BiTEs

Figure 33:
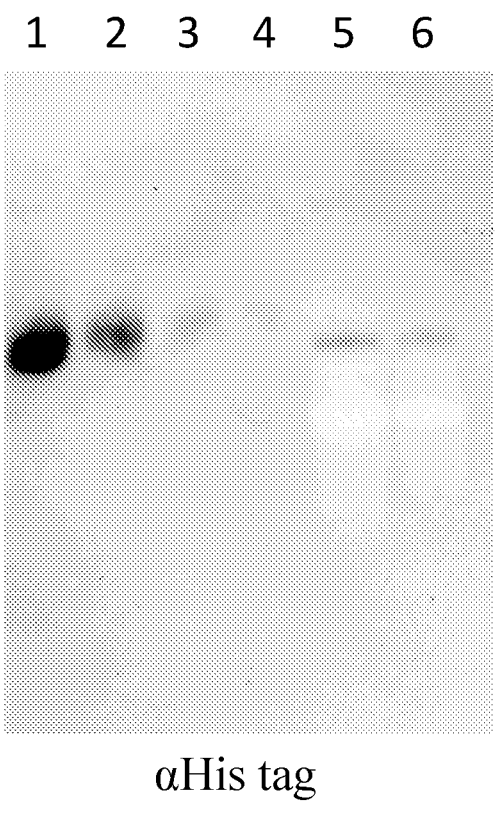
FIG. 33 illustrates expression of PDL1-CD3-Fc BiTE constructs from oncolytic-HSV vectors. Purified PDL1-CD3-Fc BiTE protein is shown in lanes 1-4. Concentrated viral supernatants are shown in lanes 5-6.

To demonstrate that the oncolytic viruses described here are capable or producing the engager molecules, Vero cells were infected with oHSV expressing SIRP1α-CD3 BiTEs (FIG. 32) with either a short linker (SL) (ONCR-085; 2A5B SIRP1α-CD3 (SL) BiTE) or long linker (LL) (ONCR-087; 2A5B SIRP1α-CD3 (LL) BiTE), or with oHSV expressing PDL1-CD3-Fc TiTEs (ONCR-089, FIG. 33). Cells were infected for 3 days, after which supernatants from infected cells were passed through a 100K MWCO ultrafiltration membrane to remove any viral particles. The flowthrough was concentrated with a 10K MWCO ultrafiltration membrane. Concentrated viral supernatants and 100 ng, 50 ng, 25 ng, or 12.5 ng of purified SIRP1α-CD3 or PDL1-CD3-Fc protein were then analyzed by PAGE followed by Western blotting with an anti-6×His detection antibody in order to determine the amount of engager protein present in the viral supernatants.

Figure 35:
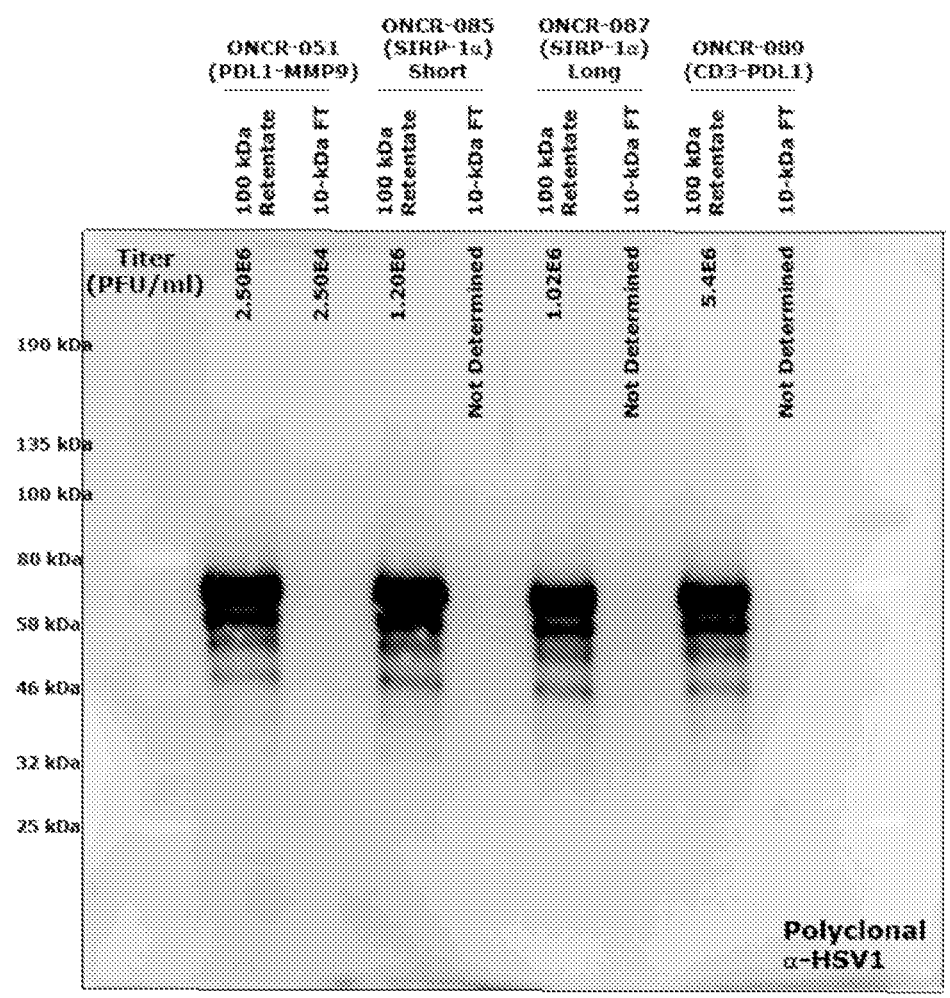
FIG. 35 illustrates that Amicon ultrafiltration effectively removes virus from samples, as determined by Western blotting with polyclonal anti-HSV antibody, and indicated that BiTE-killing is due to the BiTE and not viral infection.

The results demonstrate that cells infected with either ONCR-085 or ONCR-087 produced the SIRP1α-CD3 (SL) and SIRP1α-CD3 (LL) protein, respectively (FIG. 32). Further, cells infected with ONCR-089 produced the PDL1-CD3-Fc protein (FIG. 33). The ability of the 100K and 10K Amicon filtration and concentration steps to remove remaining virus was assessed by Western blot. The workflow for clarifying viral supernatants comprises low-speed centrifugation of the supernatants followed by filtration through a 0.8 μm filter membrane. Supernatant filtrates are then passaged through an Amicon 100 kDa filter to entrain the virus, followed by passage of the filtrate through an Amicon 10 kDa filter to entrain remaining protein. Aliquots of supernatants from virally-infected cells were taken before and after processing with the Amicon filters and the presence of HSV was determined by blotting with an anti-HSV polyclonal antibody. These results show that the ultrafiltration steps used to purify the engager constructs effectively removed virus (FIG. 35). Therefore, any target cell killing observed in the presence of these engager constructs is due to the engager construct itself, and not a result of viral infection of the target cells.

Example 11: Virally-Produced SIRP1α-CD3 and PDL1-CD3-Fc Engager Constructs Induced Effector-Cell Mediated Killing of Target Cells Experiments were performed to assess the ability of virally-produced engager molecules (SIRP1α-CD3 and PDL1-CD3-Fc constructs) to mediate target cell killing. Briefly, SIRP1α-CD3 (SL), SIRP1α-CD3 (LL) and PDL1-CD3-Fc proteins were prepared from Vero cells as described in Example 10. 50 μL of the resulting SIRP1α-CD3 (SL), SIRP1α-CD3 (LL), and PDL1-CD3-Fc engager proteins protein samples were diluted 1:1 in tissue culture media containing 20% FBS. The diluted engager proteins were then incubated with activated CD8+ effector T cells co-cultured with fluorescently labelled U251 target cells at a target to effector ratio of 1:1 for 18 hours. Cell death of U251 cells was assessed by flow cytometry on a BD LSR Fortesa cytometer.

Figure 34A:
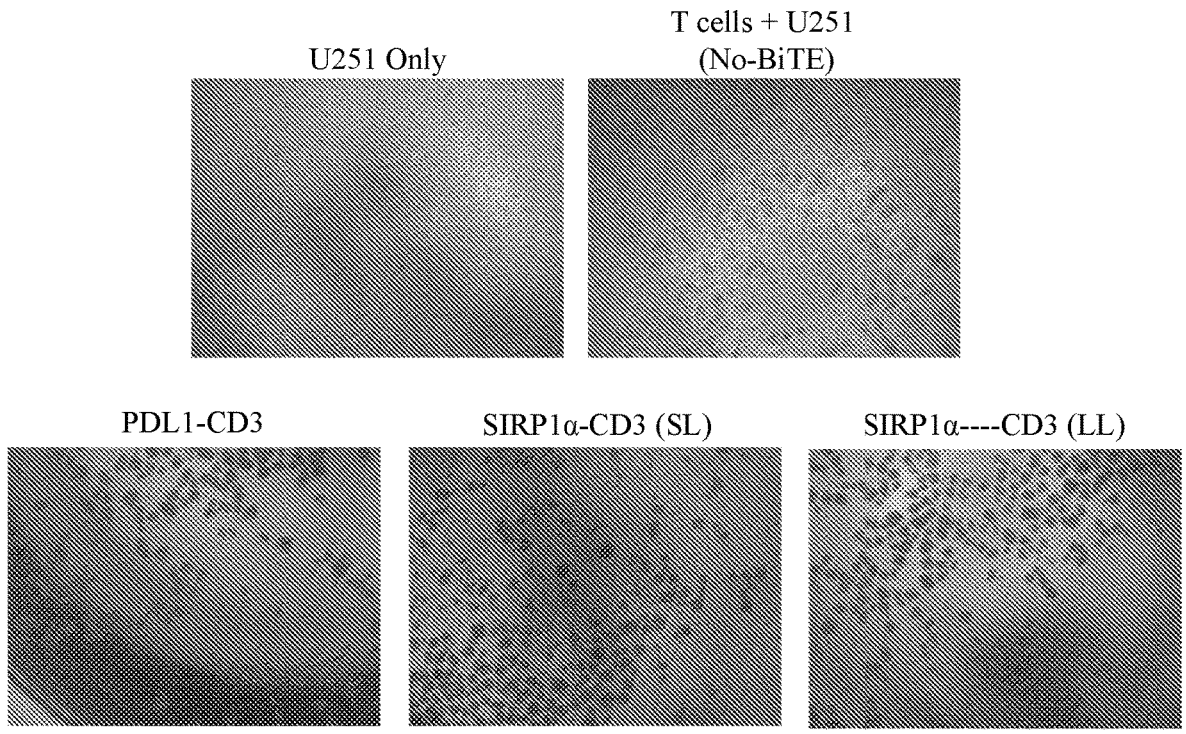
FIG. 34A-FIG. 34B illustrates TDCC of U251 cells by virally produced SIRP1α-CD3, SIRP1α-CD3-LL, and PDL1-CD3-Fc BiTE constructs. Photographs of U251 cell cultures after incubation with the indicated BiTE constructs and CD8+ T cells are shown in FIG. 34A. Activity of virally produced BiTE constructs, measured by % of cell killing and quantified by flow cytometry, is shown in FIG. 34B.
Figure 34B:
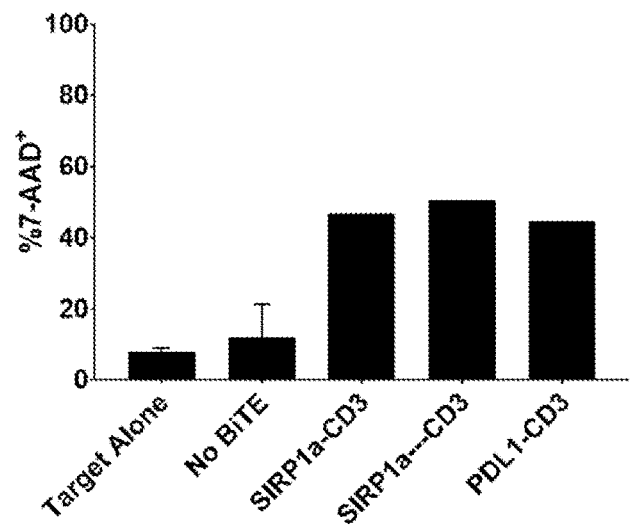

The results of this experiment demonstrate that virally-produced engager constructs direct T-cell mediated killing of U251 target cells (FIG. 34A). These results are quantified in FIG. 34B.

Example 12: Expression of SIRP1α-CD3/PDL1-Fc Compounds from 293 T Cells

Figure 39:
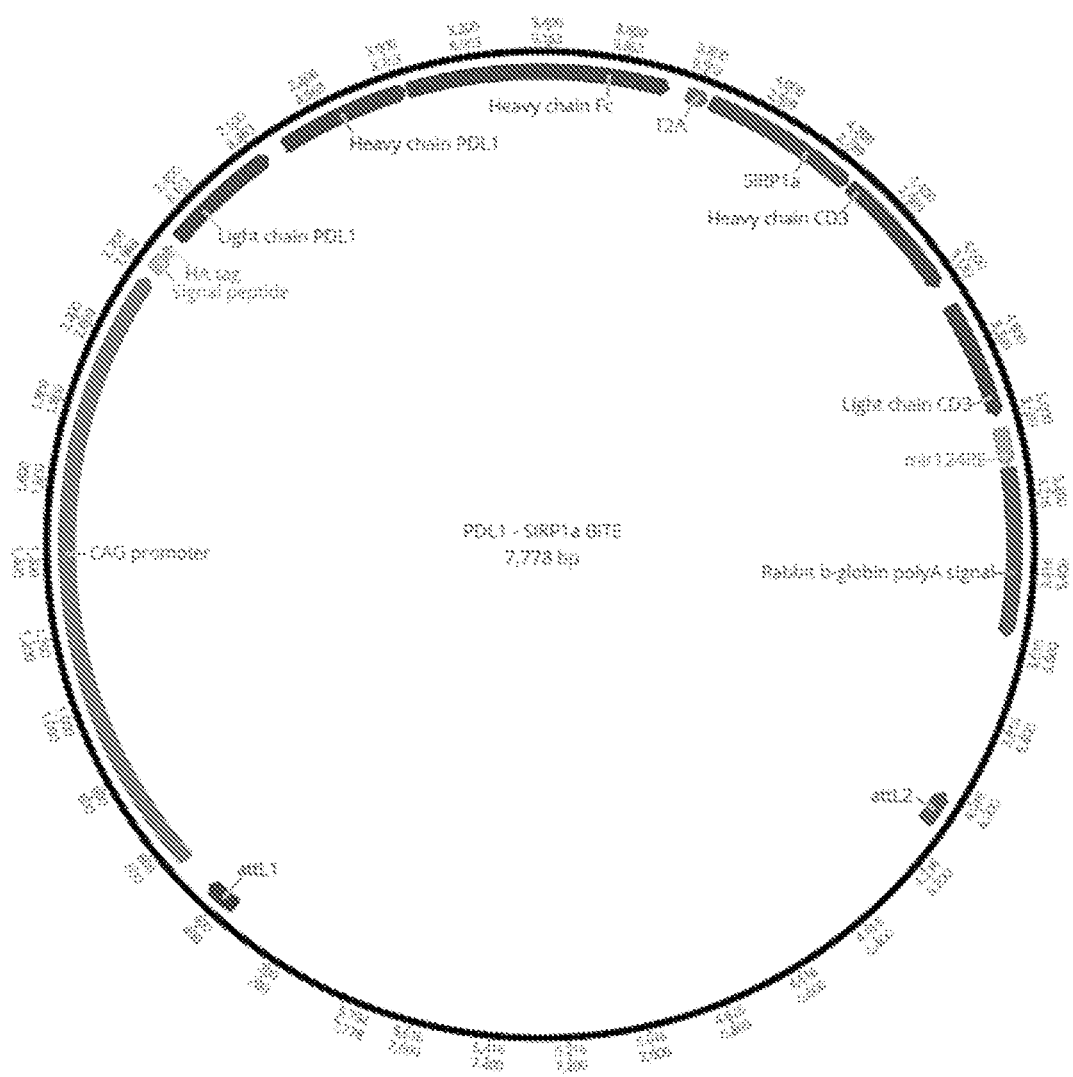
FIG. 39 illustrates a schematic of a SIRP1α-CD3-PDL1-Fc expression plasmid. Two plasmid constructs, one for SIRP1α-CD3-PDL1-Fc (SL) and one for SIRP1α-CD3-PDL1-Fc (LL) were generated.

Two expression plasmids encoding a SIRP1α-CD3 engager molecule and a PDL1-Fc therapeutic molecule were generated. One construct comprised a first gene encoding an HA-tagged PDL1-Fc linked to a second gene encoding a His-tagged SIRP1α-CD3 BiTE. The SIRP1α amino acid sequence was linked to the anti-CD3 scFv by a single amino acid linker (i.e., a short linker) (SIRP1α-CD3/PDL1-Fc (SL), FIG. 37). The other construct comprised a first gene encoding a PDL1-Fc linked to a second gene encoding a SIRP1α-CD3 BiTE. The SIRP1α amino acid sequence was linked to the anti-CD3 scFv by a G4S linker (i.e., a long linker) (SIRP1α-CD3/PDL1-Fc (LL), FIG. 38). The constructs were inserted into a plasmid (FIG. 39) and the resultant SIRP1α-CD3/PDL1-Fc expression plasmids were transfected into 293 Free Style T cells. Four days after plasmid transfection, culture supernatants were collected.

Anti-PDL1-Fc compounds were purified from the culture supernatants using a HiTrap MabSelect SuRe Protein A column HiTrap column (GE Healthcare). Briefly, supernatants from 293 T cells transfected with either the SIRP1α-CD3/PDL1-Fc (LL) or the SIRP1α-CD3/PDL1-Fc (LL) expression plasmids were loaded onto the column to purify the anti-PDL1-Fc compounds by binding of the HA-tag to the column. Flow through was collected for SIRP1α-CD3 BiTE detection by Western Blot using an anti-His antibody (FIG. 40B). Columns were washed with wash buffer (20 mM sodium phosphate, 150 mM NaCl, pH 7.4). Bound anti-PDL1-Fc protein was eluted with IgG elution buffer (pH 2.8, Pierce) and was immediately neutralized with a 1 M Tris-HCl buffer, pH 8.

The anti-PDL1-Fc protein content of different elution fractions then were visualized by Coomassie staining. Briefly, elution fractions were run on a 4%-12% Bis-Tris NuPAGE gel in MOPS buffer at 180 volts for 1 hour. Gels were stained for 1 hour in Simply Blue SafeStain followed by distaining with water. Anti-PDL1-Fc protein content for each elution fraction is show in FIG. 40A. After Coomassie analysis, elution fractions were combined and dialyzed against PBS at 4° C. Total anti-PDL1-Fc protein concentration was then determined by a BCA assay.

Example 13: Isolated PDL1-Fc Proteins Stimulate T Cell-Mediated Death of Target Cells The ability of the anti-PDL1-Fc proteins to induce effector cell-mediated death of target cells was assessed by a PD1/PDL1 blockade assay. A general schematic of the assay is show in FIG. 41A-41B. Briefly, CD8+ T cells were co-cultured with PDL1-expressing target cells (CHO-K1 cells). Varying concentrations of the anti-PDL1-Fc protein isolated as described in Example 12 were then added to the culture. The highest concentration of anti-PDL1-Fc used was 50 μg/mL. 8, 2.5 fold serial dilutions were then performed to generate the remainder of the anti-PDL1-Fc concentrations. Cell death was analyzed by a CytoTox-Glo™ cytotoxicity assay in the presence (FIG. 41B) and absence (FIG. 41A) of the anti-PDL1-Fc. Results are quantified in FIG. 41C. The $EC_{50}$ of the anti-PDL1-Fc is shown in Table 8. These results demonstrate that the anti-PDL1-Fc therapeutic molecules produced from the expression constructs described herein are capable of mediating effector cell-mediated death of target cells.

TABLE 8

| $EC_{50}$ of anti-PDL1-Fc compounds | |
| --- | --- |
| Compound | $EC_{50}$ |
| anti-PDL1-Fc | 0.45 μg/mL |

Example 14: oHSV-Infected Vero Cells Express MMP9 and Anti-PDL1-Fc Therapeutic Molecules In addition to producing the engager molecules as described in Example 10, experiments are performed to demonstrate that the oncolytic viruses described here are capable or producing the MMP9 and anti-PDL1-Fc therapeutic molecules. Vero cells are infected with oHSV expressing SIRP1α-CD3/PDL1-Fc constructs BiTEs (FIG. 37 and FIG. 38) or with oHSV expressing SIRP1α-CD3/MMP9 constructs (FIG. 18A and FIG. 18B). Cells are infected for 3 days, after which supernatants from infected cells are passed through a 100K MWCO ultrafiltration membrane to remove any viral particles. The flowthrough is concentrated with a 10K MWCO ultrafiltration membrane. MMP9 and anti-PDL1-Fc are purified from filtered, concentrated supernatants according to the protocol outlined in Example 11. Protein A-isolated MMP9 and anti-PDL1 fractions are analyzed by PAGE followed by Coomassie staining. SIRP1α-CD3 BiTEs present in the Protein A flow-through are analyzed by Western blotting with an anti-6xHis detection antibody.

The results will demonstrate that cells infected with oHSV vectors encoding either SIRP1α-CD3/PDL1-Fc constructs or SIRP1α-CD3/MMP9 constructs produce the SIRP1α-CD3 (SL) and SIRP1α-CD3 (LL) BiTE protein, MMP9, and anti-PDL1-Fc.

Example 15: Virally-Produced SIRP1α-CD3/MMP9 and SIRP1α-CD3/PDL1-Fc Engager Constructs Induce Effector-Cell Mediated Killing of Target Cells Experiments are performed to assess the ability of virally-produced engager molecules (SIRP1α-CD3) and therapeutic molecules (MMP9 and anti-PDL1-Fc) to mediate target cell killing. Briefly, SIRP1α-CD3 (SL), SIRP1α-CD3 (LL), MMP9, and anti-PDL1-Fc proteins are prepared from Vero cells as described in Example 13. 50 µL of the resulting protein samples are diluted in tissue culture media containing 20% FBS. The diluted proteins are then incubated with activated CD8$^+$ effector T cells or NK effector cells and are co-cultured with fluorescently labelled target cells at a target to effector ratio of 1:1 for 18 hours. Cell death of target cells is assessed by flow cytometry on a BD LSR Fortesa cytometer.

The results of this experiment will demonstrate that virally-produced SIRP1α-CD3 engager constructs and therapeutic molecules MMP9 and anti-PDL1-Fc are able to direct T-cell and/or NK cell mediated killing of target cells.

Example 16: Isolated FAP-CD3 Engager Molecules Bind FAP and T-Cells

The binding of bipartite (FAP-CD3) engager molecules to T cells will be assessed. Briefly, 25,000 T cells are stimulated with 200 U/mL IL-2 for 12 days. After 12 days, T cell are incubated with varying concentrations of engager molecules (500, 1000, or 2000 ng/mL) for 20 minutes at room temperature in triplicate. Cells are then washed twice, followed by staining with an anti-6xHis APC antibody at 500 ng/mL for an additional 20 minutes. Cells are washed again and treated with propidium iodide (PI) to exclude dead cells from further analysis. Stained cells are analyzed by flow cytometry on a BD LSR Fortesa cytometer and the percentage of the cell population positive for staining was set at 2% of the secondary only control.

Assessment of binding of bipartite (FAP-CD3) engager molecules to tumor cells. Briefly, HEK293 stably overexpressing FAB or negative control cells (HEK293) are treated with 500 or 1000 ng/mL of either (i) His-tagged soluble FAP or (ii) His-tagged Fc negative control protein. Cells are stained with a fluorescently labelled anti-His antibody and analyze by flow cytometry.

Example 17: Intravenous Delivery of Retargeted-oHSV Encoding FAP-CD3 Engager Molecules The gD glycoprotein of HSV was modified to mediate viral entry via the EGFR receptor and engineered to encode for FAP-CD3. To test the ability of a retargeted ONCR-virus that encodes FAP-CD3 to induce tumor killing, $5\times10^6$ A431 cells are implanted subcutaneously into the right flank Nude mice. When the flank tumors reach ~100 mm$^3$, mice are injected intravenously with a single dose or ONCR-EGFR-(FAP-CD3) at $1\times10^6$ PFU; $3\times10^6$ PFU; $1\times10^7$ PFU, or vehicle (PBS). Tumor measurements are recorded every 2 to 3 days. Tumor growth inhibition is calculated against vehicle control treated cohort.

Example 18: Intratumoral Delivery of oHSV Encoding FAP-CD3 Engager Molecules Experiments were performed to assess the ability of an oHSV encoding a bipartite FAP-CD3 engager molecule to inhibit tumor growth in vivo. ONCR-148 virus that encodes s can induce tumor growth inhibition in vivo. Briefly, $5\times10^5$ murine colon carcinoma cells expressing fibroblast activation protein (MC38-FAP) were implanted subcutaneously into both flanks of female C57BL/6 mice. When tumors reached a volume of ~100 mm$^3$, mice were divided into experimental groups and injected intratumorally (IT) with $3\times10^6$ PFU of osHSV ONCR-148 (encoding bipartite FAP-CD3) or ONCR-146 (negative control virus encoding bipartite FAP-CD19). Vehicle controls were IT injected with PBS. Dosing was repeated every third day for a total number of 3 doses. Tumor measurements were performed twice weekly using electronic calipers, and tumor volume (TV) was calculated according to the modified ellipsoid formula: TV=½(length×width). Inhibition of tumor growth was determined against vehicle-treated group.

Figure 42:
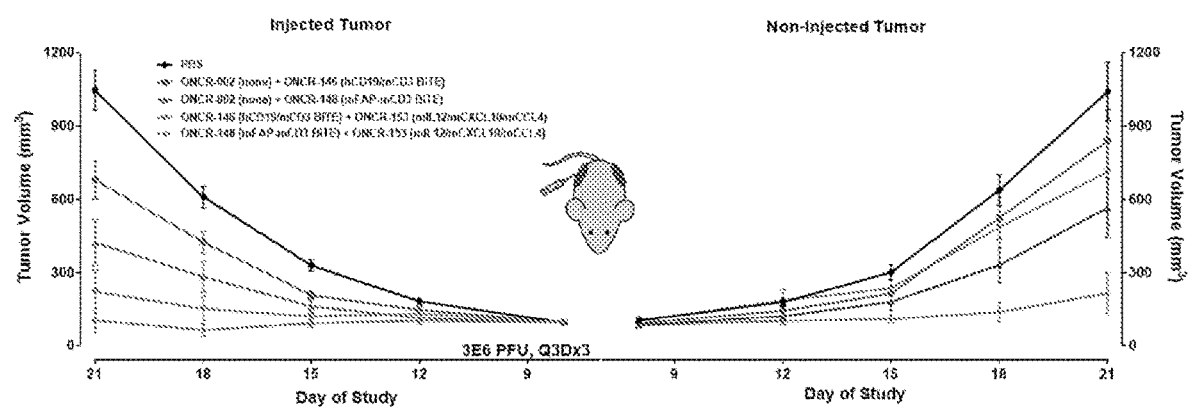
FIG. 42 shows tumor growth inhibition after treatment with oHSV expressing a FAP-CD3 BiTE (ONCR-148) and combined treatment with ONCR-148 and an oHSV expressing CCL4, CXCL10, and IL-12 (ONCR-153).

To assess the effect of FAP-CD3 engager molecule expression by oHSV on tumor growth, mice were divided into experimental groups and injected intratumorally (IT) with $3\times10^6$ PFU of ONCR-148 (oHSV encoding bipartite FAP-CD3) or ONCR-146 (negative control virus encoding bipartite FAP-CD19). As shown in FIG. 42 mice treated with ONCR-148 demonstrated significant tumor growth inhibition in both injected (ipsilateral) and distant (contralateral) tumors.

Additional experiments were performed to determine additional effects of payloads that promote T cell activation and antigen presentation in tumor microenvironment (IL-12, CXCL10, and CCL4) on tumor growth inhibition. Mice were injected IT with vehicle control, $3\times10^6$ PFU/dose ONCR-148 (oHSV encoding bipartite FAP-CD3), $3\times10^6$ PFU/dose ONCR-153 (oHSV encoding IL-12, CXCL10 and CCL4), or a mixture of $1.5\times10^6$ PFU each ONCR-148 and ONCR-153 (for a total viral dose of $3\times10^6$ PFU/dose). Additional control groups were treated with ONCR-146 (negative control virus encoding bipartite FAP-CD19) or ONCR-146 and ONCR-153.

As depicted in FIG. 42, ONCR-148 and ONCR-153, when combined, elicited antitumor effect that was stronger than observed for either virus alone. Combination viral therapy resulted in 90% and 80% tumor growth inhibition in injected (ipsilateral) and distant (contralateral) tumors, respectively.

The invention claimed is:

1. An oncolytic virus comprising a first recombinant nucleic acid encoding an engager polypeptide comprising an effector domain specific for an antigen expressed on an effector cell and a targeting domain specific for an antigen expressed on a target cell, wherein the antigen expressed on the target cell is fibroblast activation protein (FAP), wherein the antigen expressed on the effector cell is CD3, and wherein the engager polypeptide comprises a polypeptide sequence that is at least 90% identical to SEQ ID NO: 75.

2. The oncolytic virus of claim 1, comprising one or more microRNA (miR) target sequences inserted into a locus of one or more genes required for viral replication.

3. The oncolytic virus of claim 2, wherein the one or more miR target sequences is recognized by miR-10b, miR-17, miR-21, miR-106a, miR-125b, miR-145, miR-146a, miR-146b, miR-155, miR-96, miR-182, miR-183, miR-221, miR-222, or miR-1247-5p.

4. The oncolytic virus of claim 2, wherein the one or more miR target sequences is recognized by a plurality of microRNAs selected from miR-10b, miR-17, miR-21, miR-106a, miR-125b, miR-145, miR-146a, miR-146b, miR-155, miR-96, miR-182, miR-183, miR-221, miR-222, and miR-1247-5p.

5. The oncolytic virus of claim 1, wherein the oncolytic virus is derived from herpes simplex virus-1 (HSV-1).

6. The oncolytic virus of claim 1, wherein the oncolytic virus is capable of preferential replication in a tumor cell.

7. The oncolytic virus of claim 1, further comprising a second recombinant nucleic acid encoding an immune modulator polypeptide selected from the group consisting of a cytokine, a costimulatory molecule, an immune checkpoint polypeptide, an anti-angiogenesis factor, and a matrix metalloprotease (MMP).

8. The oncolytic virus of claim 7, wherein the cytokine is selected from IL-15, IL-12, CXCL10, and CCL4.

9. The oncolytic virus of claim 1, wherein the engager polypeptide is a bipartite polypeptide and is comprised of an antibody, an antibody domain, a human immunoglobulin heavy chain variable domain, a dual-variable-domain antibody (DVD-Ig), a Tandab, a diabody, a flexibody, a dock-and-lock antibody, a Scorpion polypeptide, a single chain variable fragment (scFv), a BiTE, a DuoBody, an Fc-engineered IgG, an Fcab, a Mab2, or DART polypeptide.

10. The oncolytic virus of claim 7, wherein the first and second recombinant nucleic acids are expressed from a single promoter sequence.

11. The oncolytic virus of claim 1, wherein the effector cell is a T cell, an NKT cell, an NK cell, or a macrophage.

12. The oncolytic virus of claim 7, wherein the first and second recombinant nucleic acids have a size of 7.2-38 kb.

13. The oncolytic virus of claim 1, further comprising one or more additional recombinant nucleic acid sequences encoding two or more immune modulator polypeptides.

14. The oncolytic virus of claim 13, wherein the two or more immune modulator polypeptides are selected from CCL4, CXCL20, and IL-12.

* * * * *

SEQUENCE LISTING

```
<160> NUMBER OF SEQ ID NOS: 80

<210> SEQ ID NO 1
<211> LENGTH: 57
<212> TYPE: DNA
<213> ORGANISM: Artificial Sequence
<220> FEATURE:
<223> OTHER INFORMATION: Synthesized polynucleotide encoding signal
      peptide

<400> SEQUENCE: 1
atggagttcg gcctgagctg ggtgttcctg gtggccctgt tcagggcgt gcagtgc         57

<210> SEQ ID NO 2
<211> LENGTH: 20
<212> TYPE: PRT
<213> ORGANISM: Artificial Sequence
<220> FEATURE:
<223> OTHER INFORMATION: Synthesized signal peptide sequence

<400> SEQUENCE: 2

Met Glu Phe Gly Leu Ser Trp Val Phe Leu Val Ala Leu Phe Arg Gly
1               5                   10                  15

Val Gln Cys Asp
            20

<210> SEQ ID NO 3
<211> LENGTH: 20
<212> TYPE: PRT
<213> ORGANISM: Artificial Sequence
<220> FEATURE:
<223> OTHER INFORMATION: human GM-CSF leader sequence

<400> SEQUENCE: 3

Met Tyr Arg Met Gln Leu Leu Ser Cys Ile Ala Leu Ser Leu Ala Leu
1               5                   10                  15

Val Thr Asn Ser
            20

<210> SEQ ID NO 4
<211> LENGTH: 20
<212> TYPE: PRT
<213> ORGANISM: Artificial Sequence
<220> FEATURE:
<223> OTHER INFORMATION: Polypeptide sequence of human GM-CSFR leader
      sequence

<400> SEQUENCE: 4

Met Tyr Arg Met Gln Leu Leu Ser Cys Ile Ala Leu Ser Leu Ala Leu
1               5                   10                  15

Val Thr Asn Ser
            20

<210> SEQ ID NO 5
<211> LENGTH: 15
<212> TYPE: DNA
<213> ORGANISM: Artificial Sequence
<220> FEATURE:
<223> OTHER INFORMATION: Synthesized polynucleotide encoding 4GlySer
      linker peptide

<400> SEQUENCE: 5
```

```
ggcggcggcg gcagc                                                          15

<210> SEQ ID NO 6
<211> LENGTH: 5
<212> TYPE: PRT
<213> ORGANISM: Artificial Sequence
<220> FEATURE:
<223> OTHER INFORMATION: Synthesized 4GlySer linker peptide sequence

<400> SEQUENCE: 6

Gly Gly Gly Gly Ser
1               5

<210> SEQ ID NO 7
<211> LENGTH: 45
<212> TYPE: DNA
<213> ORGANISM: Artificial Sequence
<220> FEATURE:
<223> OTHER INFORMATION: Synthesized polynucleotide encoding 3x 4GlySer
      linker peptide

<400> SEQUENCE: 7
ggcggcggcg gcagcggcgg cggcggcagc ggcggcggcg gcagc                         45

<210> SEQ ID NO 8
<211> LENGTH: 15
<212> TYPE: PRT
<213> ORGANISM: Artificial Sequence
<220> FEATURE:
<223> OTHER INFORMATION: Synthesized 3x 4GlySer linker peptide sequence

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 37
<212> TYPE: DNA
<213> ORGANISM: Artificial Sequence
<220> FEATURE:
<223> OTHER INFORMATION: Synthesized polynucleotide encoding 4x 2GlySer
      linker peptide

<400> SEQUENCE: 9
gggcggcagc ggcggcagcg gcggcagcgg cggcagc                                  37

<210> SEQ ID NO 10
<211> LENGTH: 12
<212> TYPE: PRT
<213> ORGANISM: Artificial Sequence
<220> FEATURE:
<223> OTHER INFORMATION: Synthesized 4x 2GlySer linker peptide sequence

<400> SEQUENCE: 10

Gly Gly Ser Gly Gly Ser Gly Gly Ser Gly Gly Ser
1               5                   10

<210> SEQ ID NO 11
<211> LENGTH: 18
<212> TYPE: DNA
<213> ORGANISM: Artificial Sequence
<220> FEATURE:
<223> OTHER INFORMATION: Synthesized polynucleotide encoding 6-His tag

<400> SEQUENCE: 11
caccaccacc accaccac                                                       18
```

<210> SEQ ID NO 12
<211> LENGTH: 6
<212> TYPE: PRT
<213> ORGANISM: Artificial Sequence
<220> FEATURE:
<223> OTHER INFORMATION: Synthesized 6-His tag sequence

<400> SEQUENCE: 12

His His His His His His
1               5

<210> SEQ ID NO 13
<211> LENGTH: 66
<212> TYPE: DNA
<213> ORGANISM: Artificial Sequence
<220> FEATURE:
<223> OTHER INFORMATION: Synthesized polynucleotide encoding T2A linker

<400> SEQUENCE: 13
cgaagaaaac gcgaggggag gggctccctg ctcacctgtg gtgatgtcga agagaaccct     60
gggccg                                                                66

<210> SEQ ID NO 14
<211> LENGTH: 22
<212> TYPE: PRT
<213> ORGANISM: Artificial Sequence
<220> FEATURE:
<223> OTHER INFORMATION: Synthesized T2A linker linker sequence

<400> SEQUENCE: 14

Arg Arg Lys Arg Glu Gly Arg Gly Ser Leu Leu Thr Cys Gly Asp Val
1               5                   10                  15

Glu Glu Asn Pro Gly Pro
            20

<210> SEQ ID NO 15
<211> LENGTH: 333
<212> TYPE: DNA
<213> ORGANISM: Artificial Sequence
<220> FEATURE:
<223> OTHER INFORMATION: Synthesized polynucleotide encoding anti-CD19
      light chain sequence

<400> SEQUENCE: 15
gacatccagc tgacccagag ccccgccagc ctggccgtga gcctgggcca gagggccacc     60
atcagctgca aggccagcca gagcgtggac tacgacggcg acagctacct gaactggtac    120
cagcagatcc ccggccagcc ccccaagctg ctgatctacg acgccagcaa cctggtgagc    180
ggcatccccc ccaggttcag cggcagcggc agcggcaccg acttcaccct gaacatccac    240
cccgtggaga aggtggacgc cgccacctac cactgccagc agagcaccga ggacccctgg    300
accttcggcg gcggcaccaa gctggagatc aag                                 333

<210> SEQ ID NO 16
<211> LENGTH: 111
<212> TYPE: PRT
<213> ORGANISM: Artificial Sequence
<220> FEATURE:
<223> OTHER INFORMATION: Synthesized anti-CD19 light chain sequence

<400> SEQUENCE: 16

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 17
<211> LENGTH: 372
<212> TYPE: DNA
<213> ORGANISM: Artificial Sequence
<220> FEATURE:
<223> OTHER INFORMATION: Synthesized polynucleotide encoding anti-CD19
      heavy chain sequence

<400> SEQUENCE: 17
caggtgcagc tgcagcagag cggcgccgag ctggtgaggc ccggcagcag cgtgaagatc      60
agctgcaagg ccagcggcta cgccttcagc agctactgga tgaactgggt gaagcagagg     120
cccggccagg gcctggagtg gatcggccag atctggcccg gcgacggcga caccaactac     180
aacggcaagt tcaagggcaa ggccaccctg accgccgacg agagcagcag caccgcctac     240
atgcagctga gcagcctggc cagcgaggac agcgccgtgt acttctgcgc caggagggag     300
accaccaccg tgggcaggta ctactacgcc atggactact ggggccaggg caccaccgtg     360
accgtgagca gc                                                        372

<210> SEQ ID NO 18
<211> LENGTH: 124
<212> TYPE: PRT
<213> ORGANISM: Artificial Sequence
<220> FEATURE:
<223> OTHER INFORMATION: Synthesized anti-CD19 heavy chain sequence

<400> SEQUENCE: 18

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
    115                 120

<210> SEQ ID NO 19
<211> LENGTH: 318
<212> TYPE: DNA
<213> ORGANISM: Artificial Sequence
<220> FEATURE:
<223> OTHER INFORMATION: Synthesized polynucleotide encoding anti-CD3
      light chain sequence

<400> SEQUENCE: 19

```
gacatccagc tgacccagag ccccgccatc atgagcgcca gccccggcga gaaggtgacc    60
atgacctgca gggccagcag cagcgtgagc tacatgaact ggtaccagca gaagagcggc   120
accagcccca gaggtggat ctacgacacc agcaaggtgg ccagcggcgt gccctacagg    180
ttcagcggca gcggcagcgg caccagctac agcctgacca tcagcagcat ggaggccgag   240
gacgccgcca cctactactg ccagcagtgg agcagcaacc ccctgacctt cggcgccggc   300
accaagctgg agctgaag                                                 318
```

<210> SEQ ID NO 20
<211> LENGTH: 106
<212> TYPE: PRT
<213> ORGANISM: Artificial Sequence
<220> FEATURE:
<223> OTHER INFORMATION: Synthesized anti-CD3 light chain sequence

<400> SEQUENCE: 20

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 21
<211> LENGTH: 357
<212> TYPE: DNA
<213> ORGANISM: Artificial Sequence
<220> FEATURE:
<223> OTHER INFORMATION: Synthesized polynucleotide encoding anti-CD3
      heavy chain sequence

<400> SEQUENCE: 21

```
gacatcaagc tgcagcagag cggcgccgag ctggccaggc ccggcgccag cgtgaagatg    60
agctgcaaga ccagcggcta caccttcacc aggtacacca tgcactgggt gaagcagagg   120
cccggccagg gcctggagtg gatcggctac atcaacccca gcagggcta caccaactac    180 aaccagaagt tcaaggacaa ggccaccctg accaccgaca gagcagcag caccgcctac   240 atgcagctga gcagcctgac cagcgaggac agcgccgtgt actactgcgc caggtactac   300
gacgaccact actgcctgga ctactggggc cagggcacca ccctgaccgt gagcagc     357
```

<210> SEQ ID NO 22
<211> LENGTH: 119

<212> TYPE: PRT
<213> ORGANISM: Artificial Sequence
<220> FEATURE:
<223> OTHER INFORMATION: Synthesized anti-CD3 heavy chain sequence

<400> SEQUENCE: 22

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 23
<211> LENGTH: 489
<212> TYPE: DNA
<213> ORGANISM: Homo sapiens

<400> SEQUENCE: 23
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca agaatgtga ggaactggag      420 gaaaaaata ttaaagaatt tttgcagagt tttgtacata ttgtccaaat gttcatcaac      480
acttcttag                                                              489

<210> SEQ ID NO 24
<211> LENGTH: 162
<212> TYPE: PRT
<213> ORGANISM: Homo sapiens

<400> SEQUENCE: 24

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
            85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser

<210> SEQ ID NO 25
<211> LENGTH: 987
<212> TYPE: DNA
<213> ORGANISM: Homo sapiens

<400> SEQUENCE: 25
atgtgtcacc agcagttggt catctcttgg tttttccctgg ttttttctggc atctcccctc      60
gtggccatat gggaactgaa gaaagatgtt tatgtcgtag aattggattg gtatccggat     120
gcccctggag aaatggtggt cctcacctgt gacacccctg aagaagatgg tatcacctgg     180
accttggacc agagcagtga ggtcttaggc tctggcaaaa ccctgaccat ccaagtcaaa     240
gagtttggag atgctggcca gtacacctgt cacaaaggag gcgaggttct aagccattcg     300
ctcctgctgc ttcacaaaaa ggaagatgga atttggtcca ctgatatttt aaaggaccag     360
aaagaaccca aaataagac cttctctaaga tgcgaggcca agaattattc tggacgtttc     420
acctgctggt ggctgacgac aatcagtact gatttgacat tcagtgtcaa aagcagcaga     480
ggctcttctg acccccaagg ggtgacgtgc ggagctgcta cactctctgc agagagagtc     540
agaggggaca caaggagta tgagtactca gtggagtgcc aggaggacag tgcctgccca     600
gctgctgagg agagtctgcc cattgaggtc atggtggatg ccgttcacaa gctcaagtat     660
gaaaactaca ccagcagctt cttcatcagg gacatcatca aacctgaccc acccaagaac     720
ttgcagctga agccattaaa gaattctcgg caggtggagg tcagctggga gtaccctgac     780
acctggagta ctccacattc ctacttctcc ctgacattct gcgttcaggt ccagggcaag     840
agcaagagag aaaagaaaga tagagtcttc acggacaaga cctcagccac ggtcatctgc     900
cgcaaaaatg ccagcattag cgtgcgggcc caggaccgct actatagctc atcttggagc     960
gaatgggcat ctgtgccctg cagttag                                         987

<210> SEQ ID NO 26
<211> LENGTH: 329
<212> TYPE: PRT
<213> ORGANISM: Homo sapiens

<400> SEQUENCE: 26

Pro Met Cys His Gln Gln Leu Val Ile Ser Trp Phe Ser Leu Val Phe
1               5                   10                  15

Leu Ala Ser Pro Leu Val Ala Ile Trp Glu Leu Lys Lys Asp Val Tyr
            20                  25                  30

Val Val Glu Leu Asp Trp Tyr Pro Asp Ala Pro Gly Glu Met Val Val
        35                  40                  45

Leu Thr Cys Asp Thr Pro Glu Glu Asp Gly Ile Thr Trp Thr Leu Asp
    50                  55                  60

```
Gln Ser Ser Glu Val Leu Gly Ser Gly Lys Thr Leu Thr Ile Gln Val
 65                  70                  75                  80

Lys Glu Phe Gly Asp Ala Gly Gln Tyr Thr Cys His Lys Gly Gly Glu
             85                  90                  95

Val Leu Ser His Ser Leu Leu Leu Leu His Lys Lys Glu Asp Gly Ile
            100                 105                 110

Trp Ser Thr Asp Ile Leu Lys Asp Gln Lys Glu Pro Lys Asn Lys Thr
        115                 120                 125

Phe Leu Arg Cys Glu Ala Lys Asn Tyr Ser Gly Arg Phe Thr Cys Trp
    130                 135                 140

Trp Leu Thr Thr Ile Ser Thr Asp Leu Thr Phe Ser Val Lys Ser Ser
145                 150                 155                 160

Arg Gly Ser Ser Asp Pro Gln Gly Val Thr Cys Gly Ala Ala Thr Leu
                165                 170                 175

Ser Ala Glu Arg Val Arg Gly Asp Asn Lys Glu Tyr Glu Tyr Ser Val
            180                 185                 190

Glu Cys Gln Glu Asp Ser Ala Cys Pro Ala Ala Glu Glu Ser Leu Pro
        195                 200                 205

Ile Glu Val Met Val Asp Ala Val His Lys Leu Lys Tyr Glu Asn Tyr
    210                 215                 220

Thr Ser Ser Phe Phe Ile Arg Asp Ile Ile Lys Pro Asp Pro Pro Lys
225                 230                 235                 240

Asn Leu Gln Leu Lys Pro Leu Lys Asn Ser Arg Gln Val Glu Val Ser
                245                 250                 255

Trp Glu Tyr Pro Asp Thr Trp Ser Thr Pro His Ser Tyr Phe Ser Leu
            260                 265                 270

Thr Phe Cys Val Gln Val Gln Gly Lys Ser Lys Arg Glu Lys Lys Asp
        275                 280                 285

Arg Val Phe Thr Asp Lys Thr Ser Ala Thr Val Ile Cys Arg Lys Asn
    290                 295                 300

Ala Ser Ile Ser Val Arg Ala Gln Asp Arg Tyr Tyr Ser Ser Ser Trp
305                 310                 315                 320

Ser Glu Trp Ala Ser Val Pro Cys Ser
                325

<210> SEQ ID NO 27
<211> LENGTH: 762
<212> TYPE: DNA
<213> ORGANISM: Homo sapiens

<400> SEQUENCE: 27
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aattttaccc ttgcacttct     300
gaagagattg atcatgaaga tatcacaaaa gataaaacca gcacagtgga ggcctgttta     360
ccattggaat taaccaagaa tgagagttgc ctaaattcca gagagacctc tttcataact     420
aatgggagtt gcctggcctc agaaagacc tcttttatga tggccctgtg ccttagtagt     480
atttatgaag acttgaagat gtaccaggtg gagttcaaga ccatgaatgc aaagcttctg     540
atggatccta agaggcagat ctttctagat caaaacatgc tggcagttat tgatgagctg     600
```

```
atgcaggccc tgaatttcaa cagtgagact gtgccacaaa atcctccct tgaagaaccg    660 gattttata aaactaaaat caagctctgc atacttcttc atgctttcag aattcgggca    720
gtgactattg atagagtgat gagctatctg aatgcttcct ag                      762
```

<210> SEQ ID NO 28
<211> LENGTH: 253
<212> TYPE: PRT
<213> ORGANISM: Homo sapiens

<400> SEQUENCE: 28

```
Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

<210> SEQ ID NO 29
<211> LENGTH: 297
<212> TYPE: DNA
<213> ORGANISM: Homo sapiens

<400> SEQUENCE: 29

```
atgaatcaaa ctgccattct gatttgctgc cttatctttc tgactctaag tggcattcaa    60
ggagtacctc tctctagaac tgtacgctgt acctgcatca gcattagtaa tcaacctgtt   120
aatccaaggt ctttagaaaa acttgaaatt attcctgcaa gccaattttg tccacgtgtt   180
gagatcattg ctacaatgaa aaagaagggt gagaagagat gtctgaatcc agaatcgaag   240
```
gccatcaaga atttactgaa agcagttagc aaggaaaggt ctaaaagatc tccttag    297

<210> SEQ ID NO 30
<211> LENGTH: 98
<212> TYPE: PRT
<213> ORGANISM: Homo sapiens

<400> SEQUENCE: 30

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 31
<211> LENGTH: 426
<212> TYPE: DNA
<213> ORGANISM: Homo sapiens

<400> SEQUENCE: 31
atggagaccg ataccctgct cttgtgggtt ttgcttcttt gggtgccagg atctacaggt    60
gatgaagaag aattgcagat catccaacca gacaaatccg tactcgtggc cgcaggagag   120
accgctaccc tcagatgtac catcacttct ctcttccccg ttggccccat ccagtggttt   180
cgaggcgcag gaccaggacg agtgcttatt acaatcaac gacagggccc attcccaaga   240
gtgacaacag tatccgatac caccaagcgc aataatatgg actttagcat tagaatcggc   300
aacataacac ccgctgacgc cggtacatac tattgtatta aatttcgaaa gggctcacca   360
gacgacgtgg aatttaagtc aggggccgga accgaactct cagttagagc aaaaccttct   420
gctagc                                                             426

<210> SEQ ID NO 32
<211> LENGTH: 142
<212> TYPE: PRT
<213> ORGANISM: Homo sapiens

<400> SEQUENCE: 32

Met Glu Thr Asp Thr Leu Leu Leu Trp Val Leu Leu Leu Trp Val Pro
1               5                   10                  15

Gly Ser Thr Gly Asp Glu Glu Glu Leu Gln Ile Ile Gln Pro Asp Lys
            20                  25                  30

Ser Val Leu Val Ala Ala Gly Glu Thr Ala Thr Leu Arg Cys Thr Ile
        35                  40                  45

Thr Ser Leu Phe Pro Val Gly Pro Ile Gln Trp Phe Arg Gly Ala Gly
    50                  55                  60

Pro Gly Arg Val Leu Ile Tyr Asn Gln Arg Gln Gly Pro Phe Pro Arg
65                  70                  75                  80

Val Thr Thr Val Ser Asp Thr Thr Lys Arg Asn Asn Met Asp Phe Ser
                85                  90                  95

Ile Arg Ile Gly Asn Ile Thr Pro Ala Asp Ala Gly Thr Tyr Tyr Cys
            100                 105                 110

Ile Lys Phe Arg Lys Gly Ser Pro Asp Asp Val Glu Phe Lys Ser Gly
        115                 120                 125

Ala Gly Thr Glu Leu Ser Val Arg Ala Lys Pro Ser Ala Ser
    130                 135                 140

<210> SEQ ID NO 33
<211> LENGTH: 2124
<212> TYPE: DNA
<213> ORGANISM: Homo sapiens

<400> SEQUENCE: 33

```
atgagcctct ggcagcccct ggtcctggtg ctcctggtgc tgggctgctg ctttgctgcc      60
cccagacagc gccagtccac ccttgtgctc ttccctggag acctgagaac caatctcacc     120
gacaggcagc tggcagagga atacctgtac cgctatggtt acactcgggt ggcagagatg     180
cgtggagagt cgaaatctct ggggcctgcg ctgctgcttc tccagaagca actgtccctg     240
cccgagaccg tgagctggag tagcgccacg ctgaaggcca tgcgaacccc acggtgcggg     300
gtcccagacc tgggcagatt ccaaaccttt gagggcgacc tcaagtggca ccaccacaac     360
atcacctatt ggatccaaaa ctactcggaa gacttgccgc gggcggtgat tgacgacgcc     420
tttgcccgcg ccttcgcact gtggagcgcg gtgacgccgc tcaccttcac tcgcgtgtac     480
agccgggacg cagacatcgt catccagttt ggtgtcgcgg agcacggaga cgggtatccc     540
ttcgacggga aggacgggct cctggcacac gcctttcctc ctggccccgg cattcaggga     600
gacgcccatt tcgacgatga cgagttgtgg tccctgggca agggcgtcgt ggttccaact     660
cggtttggaa acgcagatgg cgcggcctgc cacttcccct tcatcttcga gggccgctcc     720
tactctgcct gcaccaccga cggtcgctcc gacggcttgc cctggtgcag taccacggcc     780
aactacgaca ccgacgaccg gtttggcttc tgccccagcg agagactcta cacccgggac     840
ggcaatgctg atgggaaacc ctgccagttt ccattcatct tccaaggcca atcctactcc     900
gcctgcacca cggacggtcg ctccgacggc taccgctggt gcgccaccac cgccaactac     960
gaccgggaca agctcttcgg cttctgcccg acccgagctg actcgacggt gatgggggc    1020 aactcggcgg gggagctgtg cgtcttcccc ttcactttcc tgggtaagga gtactcgacc    1080
tgtaccagcg agggccgcgg agatgggcgc tctctggtgcg ctaccacctc gaactttgac    1140
agcgacaaga gtggggcttt ctgcccggac caaggataca gtttgttcct cgtggcggcg    1200
catgagttcg ccacgcgct gggcttagat cattcctcag tgccggaggc gctcatgtac    1260
cctatgtacc gcttcactga ggggcccccc ttgcataagg acgacgtgaa tggcatccgg    1320
cacctctatg gtcctcgccc tgaacctgag ccacggcctc aaccaccac acaccgcag     1380 cccacggctc ccccgacggt ctgccccacc ggaccccca ctgtccaccc ctcagagcgc    1440
cccacagctg gccccacagg tcccccctca gctggcccca caggtccccc cactgctggc    1500
ccttctacgg ccactactgt gcctttgagt ccggtggacg atgcctgcaa cgtgaacatc    1560
ttcgacgcca tcgcggagat tgggaaccag ctgtatttgt tcaaggatgg aagtactgg    1620 cgattctctg agggcagggg gagccggccg cagggcccct tccttatcgc cgacaagtgg    1680
cccgcgctgc cccgcaagct ggactcggtc tttgaggagc gctctccaa gaagcttttc    1740 ttcttctctg gcgccaggt gtgggtgtac acaggcgcgt cggtgctggg cccgaggcgt    1800
ctggacaagc tgggcctggg agccgacgtg gcccaggtga ccggggccct ccggagtggc    1860
```

```
agggggaaga tgctgctgtt cagcgggcgg cgcctctgga ggttcgacgt gaaggcgcag   1920
atggtggatc cccggagcgc cagcgaggtg gaccggatgt tccccggggt gcctttggac   1980
acgcacgacg tcttccagta ccgagagaaa gcctatttct gccaggaccg cttctactgg   2040
cgcgtgagtt cccggagtga gttgaaccag gtggaccaag tgggctacgt gacctatgac   2100
atcctgcagt gccctgagga ctag                                         2124
```

```
<210> SEQ ID NO 34
<211> LENGTH: 707
<212> TYPE: PRT
<213> ORGANISM: Homo sapiens

<400> SEQUENCE: 34
```

```
Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320
```

-continued

Asp Arg Asp Lys Leu Phe Gly Phe Cys Pro Thr Arg Ala Asp Ser Thr
            325                 330                 335

Val Met Gly Gly Asn Ser Ala Gly Glu Leu Cys Val Phe Pro Phe Thr
        340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
        370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
            405                 410                 415

Ala Leu Met Tyr Pro Met Tyr Arg Phe Thr Glu Gly Pro Pro Leu His
        420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
            485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
            565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
            645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
    690                 695                 700

Pro Glu Asp
705

<210> SEQ ID NO 35
<211> LENGTH: 324
<212> TYPE: DNA

<213> ORGANISM: Artificial Sequence
<220> FEATURE:
<223> OTHER INFORMATION: Synthesized polynucleotide encoding PD-L1 light chain Fv

<400> SEQUENCE: 35

```
gatatccaga tgacacagag cccatcatct ctgtctgcaa gcgtaggaga ccgagtcacc    60
attacatgca gagcctccca agacgtttcc acagcagtgg cctggtatca gcaaaaacct   120
ggtaaggcgc ccaagcttct catctattca gccagttttc tgtatagcgg cgttcccagc   180
cgattctctg gctctggatc cggcacggac tttactttga caatttcctc tcttcagccc   240
gaagattttg caacctacta ctgtcagcaa tatctctacc atccagccac attcggacag   300
ggcaccaaag tcgaaatcaa aaga                                          324
```

<210> SEQ ID NO 36
<211> LENGTH: 108
<212> TYPE: PRT
<213> ORGANISM: Artificial Sequence
<220> FEATURE:
<223> OTHER INFORMATION: Synthesized PD-L1 light chain Fv sequence

<400> SEQUENCE: 36

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys Arg
            100                 105
```

<210> SEQ ID NO 37
<211> LENGTH: 354
<212> TYPE: DNA
<213> ORGANISM: Artificial Sequence
<220> FEATURE:
<223> OTHER INFORMATION: Synthesized polynucleotide encoding PD-L1 heavy chain Fv

<400> SEQUENCE: 37

```
gaagtgcaac tcgttgaaag cggaggaggg cttgtccaac tggcgggtc actgcggttg    60
agctgcgccg caagcggatt caccttctca gactcttgga tccattgggt gcgccaggct   120
cccggaaaag gcttggaatg ggttgcttgg atttcaccgt atggcggttc acatactac    180
gctgacagcg ttaagggtcg attcaccatc tctgcagata cttcaaaaaa cacagcctac   240
cttcagatga atagtttgcg cgccgaggac acagcggttt attattgtgc ccgaagacat   300
tggcccggcg gtttcgacta ctgggggcaa ggtacgttgg tgactgtgag cgcc         354
```

<210> SEQ ID NO 38
<211> LENGTH: 118
<212> TYPE: PRT
<213> ORGANISM: Artificial Sequence
<220> FEATURE:

<223> OTHER INFORMATION: Synthesized PD-L1 heavy chain Fv sequence

<400> SEQUENCE: 38

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ala
        115

<210> SEQ ID NO 39
<211> LENGTH: 699
<212> TYPE: DNA
<213> ORGANISM: Homo sapiens

<400> SEQUENCE: 39
gtagatgaag caaatcttg tgacaaaacc catacctgcc caccatgccc agccccagaa      60
cttcttggcg acccctctgt cttccttttc cctccgaagc caaggatac cctgatgatc     120
agccgaaccc cggaggtaac atgtgtggtg gtcgatgtta gccatgagga tcctgaagtc    180
aaatttaact ggtatgtaga cggtgttgag gtgcacaacg ctaaaactaa gcccagggag    240
gagcagtaca actcaaccta tcgcgtcgta tctgtgctta ccgtcctgca tcaagactgg    300
ctcaatggta aggaatataa atgtaaagtg agtaacaagg cactgccagc acctatcgaa    360
aaaaccatct caaggcgaa gggacagccc agggaacccc aggtctatac tctgccacct    420
tctcgggatg aattgaccaa gaaccaagtt agcctgacat gtctggtgaa aggtttctat    480
ccaagcgata tagctgtcga gtgggagtcc aatggccaac tgagaacaa ttataagacc     540
accccacccg ttctggacag cgacggatcc tttttcctgt actcaaaact cactgtcgat    600
aaaatcaagat ggcaacaagg caacgttttt agctgtagcg tgatgcacga agcacttcat   660
aatcactata cacagaagtc actctctctt tctccagga                           699

<210> SEQ ID NO 40
<211> LENGTH: 233
<212> TYPE: PRT
<213> ORGANISM: Homo sapiens

<400> SEQUENCE: 40

Val Asp Glu Ala Lys Ser Cys Asp Lys Thr His Thr Cys Pro Pro Cys
1               5                   10                  15
Pro Ala Pro Glu Leu Leu Gly Gly Pro Ser Val Phe Leu Phe Pro Pro
            20                  25                  30
Lys Pro Lys Asp Thr Leu Met Ile Ser Arg Thr Pro Glu Val Thr Cys
        35                  40                  45
Val Val Val Asp Val Ser His Glu Asp Pro Glu Val Lys Phe Asn Trp
    50                  55                  60

```
Tyr Val Asp Gly Val Glu Val His Asn Ala Lys Thr Lys Pro Arg Glu
 65                  70                  75                  80

Glu Gln Tyr Asn Ser Thr Tyr Arg Val Val Ser Val Leu Thr Val Leu
                 85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly
225                 230

<210> SEQ ID NO 41
<211> LENGTH: 69
<212> TYPE: DNA
<213> ORGANISM: Homo sapiens

<400> SEQUENCE: 41
gtagatgaag caaatcttg tgacaaaacc catacctgcc caccatgccc agccccagaa      60
cttcttggc                                                             69

<210> SEQ ID NO 42
<211> LENGTH: 23
<212> TYPE: PRT
<213> ORGANISM: Homo sapiens

<400> SEQUENCE: 42

Val Asp Glu Ala Lys Ser Cys Asp Lys Thr His Thr Cys Pro Pro Cys
  1               5                  10                  15

Pro Ala Pro Glu Leu Leu Gly
             20

<210> SEQ ID NO 43
<211> LENGTH: 1572
<212> TYPE: DNA
<213> ORGANISM: Artificial Sequence
<220> FEATURE:
<223> OTHER INFORMATION: Synthesized polynucleotide encoding CD19-CD3
      bi-specific T-cell engager construct

<400> SEQUENCE: 43
atggagttcg gcctgagctg ggtgttcctg gtggccctgt tcaggggcgt gcagtgcgac      60
atccagctga cccagagccc cgccagcctg gccgtgagcc tgggccagag ggccaccatc     120
agctgcaagg ccagccagag cgtggactac gacggcgaca gctacctgaa ctggtaccag     180
cagatccccg gccagccccc caagctgctg atctacgacg ccagcaacct ggtgagcggc     240
```

```
atccccccca ggttcagcgg cagcggcagc ggcaccgact tcaccctgaa catccacccc    300
gtggagaagg tggacgccgc cacctaccac tgccagcaga gcaccgagga ccccctggac    360
ttcggcggcg gcaccaagct ggagatcaag ggcggcggcg gcagcggcgg cggcggcagc    420
ggcggcggcg gcagccaggt gcagctgcag cagagcggcg ccgagctggt gaggcccggc    480
agcagcgtga agatcagctg caaggccagc ggctacgcct tcagcagcta ctggatgaac    540
tgggtgaagc agaggcccgg ccagggcctg gagtggatcg ccagatctg gcccggcgac    600 ggcgacacca actacaacgg caagttcaag ggcaaggcca ccctgaccgc cgacgagagc    660
agcagcaccg cctacatgca gctgagcagc ctggccagcg aggacagcgc cgtgtacttc    720
tgcgccagga gggagaccac caccgtgggc aggtactact acgccatgga ctactggggc    780
cagggcacca ccgtgaccgt gagcagcggc ggcggcggca gcgacatcaa gctgcagcag    840
agcggcgccg agctggccag gcccggcgcc agcgtgaaga tgagctgcaa gaccagcggc    900
tacacctsca ccaggtacac catgcactgg gtgaagcaga ggcccggcca gggcctggag    960
tggatcggct acatcaaccc cagcagggc tacaccaact acaaccagaa gttcaaggac   1020
aaggccaccc tgaccaccga caagagcagc agcaccgcct acatgcagct gagcagcctg   1080
accagcgagg acagcgccgt gtactactgc gccaggtact acgacgacca ctactgcctg   1140
gactactggg gccagggcac caccctgacc gtgagcagcg tggagggcgg cagcggcggc   1200
agcggcggca gcggcggcag cggcggcgtg acgacatcc agctgaccca gagccccgcc   1260
atcatgagcg ccagccccgg cgagaaggtg accatgacct gcagggccag cagcagcgtg   1320
agctacatga actggtacca gcagaagagc ggcaccagcc ccaagaggtg gatctacgac   1380
accagcaagg tggccagcgg cgtgccctac aggttcagcg gcagcggcag cggcaccagc   1440
tacagcctga ccatcagcag catggaggcc gaggacgccg ccacctacta ctgccagcag   1500
tggagcagca acccctgac cttcggcgcc ggcaccaagc tggagctgaa gcaccaccac   1560
caccaccact ag                                                      1572

<210> SEQ ID NO 44
<211> LENGTH: 523
<212> TYPE: PRT
<213> ORGANISM: Artificial Sequence
<220> FEATURE:
<223> OTHER INFORMATION: Synthesized CD19-CD3 bi-specific T-cell
      engager construct

<400> SEQUENCE: 44

Met Glu Phe Gly Leu Ser Trp Val Phe Leu Val Ala Leu Phe Arg Gly
1               5                   10                  15

Val Gln Cys Asp Ile Gln Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Tyr Asp Gly Asp Ser Tyr Leu Asn Trp Tyr Gln Gln Ile Pro Gly
    50                  55                  60

Gln Pro Pro Lys Leu Leu Ile Tyr Asp Ala Ser Asn Leu Val Ser Gly
65                  70                  75                  80

Ile Pro Pro Arg Phe Ser Gly Ser Gly Ser Gly Thr Asp Phe Thr Leu
                85                  90                  95

Asn Ile His Pro Val Glu Lys Val Asp Ala Ala Thr Tyr His Cys Gln
            100                 105                 110

Gln Ser Thr Glu Asp Pro Trp Thr Phe Gly Gly Gly Thr Lys Leu Glu
```

```
            115                 120                 125
Ile Lys Gly Gly Gly Ser Gly Gly Gly Ser Gly Gly Gly
    130                 135                 140

Ser Gln Val Gln Leu Gln Gln Ser Gly Ala Glu Leu Val Arg Pro Gly
145                 150                 155                 160

Ser Ser Val Lys Ile Ser Cys Lys Ala Ser Gly Tyr Ala Phe Ser Ser
                165                 170                 175

Tyr Trp Met Asn Trp Val Lys Gln Arg Pro Gly Gln Gly Leu Glu Trp
            180                 185                 190

Ile Gly Gln Ile Trp Pro Gly Asp Gly Asp Thr Asn Tyr Asn Gly Lys
        195                 200                 205

Phe Lys Gly Lys Ala Thr Leu Thr Ala Asp Glu Ser Ser Ser Thr Ala
    210                 215                 220

Tyr Met Gln Leu Ser Ser Leu Ala Ser Glu Asp Ser Ala Val Tyr Phe
225                 230                 235                 240

Cys Ala Arg Arg Glu Thr Thr Thr Val Gly Arg Tyr Tyr Tyr Ala Met
                245                 250                 255

Asp Tyr Trp Gly Gln Gly Thr Thr Val Thr Val Ser Ser Gly Gly Gly
            260                 265                 270

Gly Ser Asp Ile Lys Leu Gln Gln Ser Gly Ala Glu Leu Ala Arg Pro
        275                 280                 285

Gly Ala Ser Val Lys Met Ser Cys Lys Thr Ser Gly Tyr Thr Phe Thr
    290                 295                 300

Arg Tyr Thr Met His Trp Val Lys Gln Arg Pro Gly Gln Gly Leu Glu
305                 310                 315                 320

Trp Ile Gly Tyr Ile Asn Pro Ser Arg Gly Tyr Thr Asn Tyr Asn Gln
                325                 330                 335

Lys Phe Lys Asp Lys Ala Thr Leu Thr Thr Asp Lys Ser Ser Ser Thr
            340                 345                 350

Ala Tyr Met Gln Leu Ser Ser Leu Thr Ser Glu Asp Ser Ala Val Tyr
        355                 360                 365

Tyr Cys Ala Arg Tyr Tyr Asp Asp His Tyr Cys Leu Asp Tyr Trp Gly
    370                 375                 380

Gln Gly Thr Thr Leu Thr Val Ser Ser Val Glu Gly Gly Ser Gly Gly
385                 390                 395                 400

Ser Gly Gly Ser Gly Gly Ser Gly Gly Val Asp Asp Ile Gln Leu Thr
                405                 410                 415

Gln Ser Pro Ala Ile Met Ser Ala Ser Pro Gly Glu Lys Val Thr Met
            420                 425                 430

Thr Cys Arg Ala Ser Ser Ser Val Ser Tyr Met Asn Trp Tyr Gln Gln
        435                 440                 445

Lys Ser Gly Thr Ser Pro Lys Arg Trp Ile Tyr Asp Thr Ser Lys Val
    450                 455                 460

Ala Ser Gly Val Pro Tyr Arg Phe Ser Gly Ser Gly Ser Gly Thr Ser
465                 470                 475                 480

Tyr Ser Leu Thr Ile Ser Ser Met Glu Ala Glu Asp Ala Ala Thr Tyr
                485                 490                 495

Tyr Cys Gln Gln Trp Ser Ser Asn Pro Leu Thr Phe Gly Ala Gly Thr
            500                 505                 510

Lys Leu Glu Leu Lys His His His His His His
        515                 520

<210> SEQ ID NO 45
```

```
<211> LENGTH: 1177
<212> TYPE: DNA
<213> ORGANISM: Artificial Sequence
<220> FEATURE:
<223> OTHER INFORMATION: Synthesized polynucleotide encoding SIRP1alpha-
      CD3-SL bi-specific T-cell engager construct

<400> SEQUENCE: 45
atggagaccg ataccctgct cttgtgggtt ttgcttcttt gggtgccagg atctacaggt      60
gatgaagaag aattgcagat catccaacca gacaaatccg tactcgtggc cgcaggagag     120
accgctaccc tcagatgtac catcacttct ctcttccccg ttggccccat ccagtggttt     180
cgaggcgcag gaccaggacg agtgcttatt tacaatcaac agacagggccc attcccaaga     240
gtgacaacag tatccgatac caccaagcgc aataatatgg actttagcat tagaatcggc     300
aacataacac ccgctgacgc cggtacatac tattgtatta aatttcgaaa gggctcacca     360
gacgacgtgg aatttaagtc aggggccgga accgaactct cagttagagc aaaaccttct     420
gctagcgaca tcaagctgca gcagagcggg gccgagctgg ccaggcccgg cgccagcgtg     480
aagatgagct gcaagaccag cggctacacc ttcaccaggt acaccatgca ctgggtgaag     540
cagaggcccg gccagggcct ggagtggatc ggctacatca cccccagcag gggctacacc     600
aactacaacc agaagttcaa ggacaaggcc accctgacca ccgacaagag cagcagcacc     660
gcctacatgc agctgagcag cctgaccagc gaggacagcg ccgtgtacta ctgcgccagg     720
tactacgacg accactactg cctggactac tggggccagg gcaccaccct gaccgtgagc     780
agcgtggagg gcggcagcgg cggcagcggc ggcagcggcg gcagcggcgg cgtggacgac     840
atccagctga cccagagccc cgccatcatg agcgccagcc ccggcgagaa ggtgaccatg     900
acctgcaggg ccagcagcag cgtgagctac atgaactggt accagcagaa gagcggcacc     960
agccccaaga ggtggatcta cgacaccagc aaggtggcca gcggcgtgcc ctacaggttc    1020
agcggcagcg gcagcggcac cagctacagc ctgaccatca gcagcatgga ggccgaggac    1080
gccgccacct actactgcca gcagtggagc agcaaccccc tgaccttcgg cgccggcacc    1140
aagctggagc tgaagcacca ccatcatcac cactgag                             1177

<210> SEQ ID NO 46
<211> LENGTH: 391
<212> TYPE: PRT
<213> ORGANISM: Artificial Sequence
<220> FEATURE:
<223> OTHER INFORMATION: Synthesized SIRP1alpha-CD3-SL bi-specific
      T-cell engager construct

<400> SEQUENCE: 46

Met Glu Thr Asp Thr Leu Leu Leu Trp Val Leu Leu Leu Trp Val Pro
1               5                   10                  15

Gly Ser Thr Gly Asp Glu Glu Glu Leu Gln Ile Ile Gln Pro Asp Lys
                20                  25                  30

Ser Val Leu Val Ala Ala Gly Glu Thr Ala Thr Leu Arg Cys Thr Ile
            35                  40                  45

Thr Ser Leu Phe Pro Val Gly Pro Ile Gln Trp Phe Arg Gly Ala Gly
        50                  55                  60

Pro Gly Arg Val Leu Ile Tyr Asn Gln Arg Gln Gly Pro Phe Pro Arg
65                  70                  75                  80

Val Thr Thr Val Ser Asp Thr Thr Lys Arg Asn Asn Met Asp Phe Ser
                85                  90                  95

Ile Arg Ile Gly Asn Ile Thr Pro Ala Asp Ala Gly Thr Tyr Tyr Cys
```

100                 105                 110
Ile Lys Phe Arg Lys Gly Ser Pro Asp Asp Val Glu Phe Lys Ser Gly
                115                 120                 125

Ala Gly Thr Glu Leu Ser Val Arg Ala Lys Pro Ser Ala Ser Asp Ile
130                 135                 140

Lys Leu Gln Gln Ser Gly Ala Glu Leu Ala Arg Pro Gly Ala Ser Val
145                 150                 155                 160

Lys Met Ser Cys Lys Thr Ser Gly Tyr Thr Phe Thr Arg Tyr Thr Met
                165                 170                 175

His Trp Val Lys Gln Arg Pro Gly Gln Gly Leu Glu Trp Ile Gly Tyr
            180                 185                 190

Ile Asn Pro Ser Arg Gly Tyr Thr Asn Tyr Asn Gln Lys Phe Lys Asp
        195                 200                 205

Lys Ala Thr Leu Thr Thr Asp Lys Ser Ser Ser Thr Ala Tyr Met Gln
    210                 215                 220

Leu Ser Ser Leu Thr Ser Glu Asp Ser Ala Val Tyr Tyr Cys Ala Arg
225                 230                 235                 240

Tyr Tyr Asp Asp His Tyr Cys Leu Asp Tyr Trp Gly Gln Gly Thr Thr
                245                 250                 255

Leu Thr Val Ser Ser Val Glu Gly Gly Ser Gly Gly Ser Gly Gly Ser
            260                 265                 270

Gly Gly Ser Gly Gly Val Asp Asp Ile Gln Leu Thr Gln Ser Pro Ala
        275                 280                 285

Ile Met Ser Ala Ser Pro Gly Glu Lys Val Thr Met Thr Cys Arg Ala
    290                 295                 300

Ser Ser Ser Val Ser Tyr Met Asn Trp Tyr Gln Gln Lys Ser Gly Thr
305                 310                 315                 320

Ser Pro Lys Arg Trp Ile Tyr Asp Thr Ser Lys Val Ala Ser Gly Val
                325                 330                 335

Pro Tyr Arg Phe Ser Gly Ser Gly Ser Gly Thr Ser Tyr Ser Leu Thr
            340                 345                 350

Ile Ser Ser Met Glu Ala Glu Asp Ala Ala Thr Tyr Tyr Cys Gln Gln
        355                 360                 365

Trp Ser Ser Asn Pro Leu Thr Phe Gly Ala Gly Thr Lys Leu Glu Leu
    370                 375                 380

Lys His His His His His His
385                 390

<210> SEQ ID NO 47
<211> LENGTH: 1191
<212> TYPE: DNA
<213> ORGANISM: Artificial Sequence
<220> FEATURE:
<223> OTHER INFORMATION: Synthesized polynucleotide encoding SIRP1alpha-
      CD3-LL bi-specific T-cell engager construct

<400> SEQUENCE: 47
atggagaccg ataccctgct cttgtgggtt tgcttctttt gggtgccagg atctacaggt    60
gatgaagaag aattgcagat catccaacca gacaaatccg tactcgtggc cgcaggagag   120
accgctaccc tcagatgtac catcacttct ctcttcccgt tggccccat ccagtggttt    180 cgaggcgcag gaccaggacg agtgcttatt tacaatcaac gacagggccc attcccaaga   240
gtgacaacag tatccgatac caccaagcgc aataatatgg actttagcat tagaatcggc   300
aacataacac ccgctgacgc cggtacatac tattgtatta aatttcgaaa gggctcacca   360

```
gacgacgtgg aatttaagtc aggggccgga accgaactct cagttagagc aaaaccttct    420
gctagcggcg gcggcggcag cgacatcaag ctgcagcaga gcggcgccga gctggccagg    480
cccggcgcca gcgtgaagat gagctgcaag accagcggct acaccttcac caggtacacc    540
atgcactggg tgaagcagag gcccggccag ggcctggagt ggatcggcta catcaacccc    600
agcagggcct acaccaacta caaccagaag ttcaaggaca aggccaccct gaccaccgac    660
aagagcagca gcaccgccta catgcagctg agcagcctga ccagcgagga cagcgccgtg    720
tactactgcg ccaggtacta cgacgaccac tactgcctgg actactgggg ccagggcacc    780
accctgaccg tgagcagcgt ggagggcggc agcggcggca gcggcggcag cggcggcagc    840
ggcggcgtgg acgacatcca gctgacccag agccccgcca tcatgagcgc cagccccggc    900
gagaaggtga ccatgacctg cagggccagc agcagcgtga gctacatgaa ctggtaccag    960
cagaagagcg gcaccagccc caagaggtgg atctacgaca ccagcaaggt ggccagcggc   1020
gtgcccctaca ggttcagcgg cagcggcagc ggcaccagct acagcctgac catcagcagc   1080
atggaggccg aggacgccgc cacctactac tgccagcagt ggagcagcaa ccccctgacc   1140
ttcggcgccg gcaccaagct ggagctgaag caccaccacc accaccacta g            1191

<210> SEQ ID NO 48
<211> LENGTH: 396
<212> TYPE: PRT
<213> ORGANISM: Artificial Sequence
<220> FEATURE:
<223> OTHER INFORMATION: Synthesized SIRP1alpha-CD3-LL bi-specific
      T-cell engager construct

<400> SEQUENCE: 48

Met Glu Thr Asp Thr Leu Leu Leu Trp Val Leu Leu Leu Trp Val Pro
1               5                   10                  15

Gly Ser Thr Gly Asp Glu Glu Leu Gln Ile Ile Gln Pro Asp Lys
            20                  25                  30

Ser Val Leu Val Ala Ala Gly Glu Thr Ala Thr Leu Arg Cys Thr Ile
        35                  40                  45

Thr Ser Leu Phe Pro Val Gly Pro Ile Gln Trp Phe Arg Gly Ala Gly
    50                  55                  60

Pro Gly Arg Val Leu Ile Tyr Asn Gln Arg Gln Gly Pro Phe Pro Arg
65                  70                  75                  80

Val Thr Thr Val Ser Asp Thr Thr Lys Arg Asn Asn Met Asp Phe Ser
                85                  90                  95

Ile Arg Ile Gly Asn Ile Thr Pro Ala Asp Ala Gly Thr Tyr Tyr Cys
            100                 105                 110

Ile Lys Phe Arg Lys Gly Ser Pro Asp Asp Val Glu Phe Lys Ser Gly
        115                 120                 125

Ala Gly Thr Glu Leu Ser Val Arg Ala Lys Pro Ser Ala Ser Gly Gly
    130                 135                 140

Gly Gly Ser Asp Ile Lys Leu Gln Gln Ser Gly Ala Glu Leu Ala Arg
145                 150                 155                 160

Pro Gly Ala Ser Val Lys Met Ser Cys Lys Thr Ser Gly Tyr Thr Phe
                165                 170                 175

Thr Arg Tyr Thr Met His Trp Val Lys Gln Arg Pro Gly Gln Gly Leu
            180                 185                 190

Glu Trp Ile Gly Tyr Ile Asn Pro Ser Arg Gly Tyr Thr Asn Tyr Asn
        195                 200                 205

Gln Lys Phe Lys Asp Lys Ala Thr Leu Thr Thr Asp Lys Ser Ser Ser
```

```
                    210                 215                 220
Thr Ala Tyr Met Gln Leu Ser Ser Leu Thr Ser Glu Asp Ser Ala Val
225                 230                 235                 240

Tyr Tyr Cys Ala Arg Tyr Tyr Asp Asp His Tyr Cys Leu Asp Tyr Trp
                    245                 250                 255

Gly Gln Gly Thr Thr Leu Thr Val Ser Ser Val Glu Gly Ser Gly
                260                 265                 270

Gly Ser Gly Gly Ser Gly Gly Ser Gly Gly Val Asp Asp Ile Gln Leu
            275                 280                 285

Thr Gln Ser Pro Ala Ile Met Ser Ala Ser Pro Gly Glu Lys Val Thr
            290                 295                 300

Met Thr Cys Arg Ala Ser Ser Ser Val Ser Tyr Met Asn Trp Tyr Gln
305                 310                 315                 320

Gln Lys Ser Gly Thr Ser Pro Lys Arg Trp Ile Tyr Asp Thr Ser Lys
                    325                 330                 335

Val Ala Ser Gly Val Pro Tyr Arg Phe Ser Gly Ser Gly Ser Gly Thr
                340                 345                 350

Ser Tyr Ser Leu Thr Ile Ser Ser Met Glu Ala Glu Asp Ala Ala Thr
            355                 360                 365

Tyr Tyr Cys Gln Gln Trp Ser Ser Asn Pro Leu Thr Phe Gly Ala Gly
            370                 375                 380

Thr Lys Leu Glu Leu Lys His His His His His His
385                 390                 395

<210> SEQ ID NO 49
<211> LENGTH: 1545
<212> TYPE: DNA
<213> ORGANISM: Artificial Sequence
<220> FEATURE:
<223> OTHER INFORMATION: Synthesized polynucleotide encoding PDL1-CD3
      bi-specific T-cell engager construct

<400> SEQUENCE: 49
atggagttcg gcctgagctg ggtgttcctg gtggccctgt tcaggggcgt gcagtgcgac      60
atcaagctgc agcagagcgg cgccgagctg gccaggcccg gcgccagcgt gaagatgagc     120
tgcaagacca gcggctacac cttcaccagg tacaccatgc actgggtgaa gcagaggccc     180
ggccagggcc tggagtggat cggctacatc aaccccagca ggggctacac caactacaac     240
cagaagttca aggacaaggc caccctgacc accgacaaga gcagcagcac cgcctacatg     300
cagctgagca gcctgaccag cgaggacagc gccgtgtact actgcgccag gtactacgac     360
gaccactact gcctggacta ctggggccag ggcaccaccc tgaccgtgag cagcgtggag     420
ggcggcagcg gcggcagcgg cggcagcggc ggcagcggcg gcgtggacga catccagctg     480
acccagagcc ccgccatcat gagcgccagc cccggcgaga aggtgaccat gacctgcagg     540
gccagcagca gcgtgagcta catgaactgg taccagcaga gagcggcac cagccccaag     600 aggtggatct acgacaccag caaggtggcc agcggcgtgc cctacaggtt cagcggcagc     660
ggcagcggca ccagctacag cctgaccatc agcagcatgg aggccgagga cgccgccacc     720
tactactgcc agcagtggag cagcaacccc ctgaccttcg gcgccggcac caagctggag     780
ctgaagggcg gcggcggcag cgatatccag atgacacaga gccatcatc tctgtctgca     840 agcgtaggag accagtcac cattacatgc agagcctccc aagacgtttc cacagcagtg     900
gcctggtatc agcaaaaacc tggtaaggcg cccaagcttc tcatctattc agccagtttt     960
ctgtatagcg gcgttccag ccgattctct ggctctggat ccggcacgga ctttactttg    1020
```

```
acaatttcct ctcttcagcc cgaagatttt gcaacctact actgtcagca atatctctac    1080
catccagcca cattcggaca gggcaccaaa gtcgaaatca aaagaggcgg cggcggcagt    1140
ggcggcgggg gttcaggagg cggggggttct gaagtgcaac tcgttgaaag cggaggaggg   1200
cttgtccaac ctggcgggtc actgcggttg agctgcgccg caagcggatt caccttctca    1260
gactcttgga tccattgggt gcgccaggct cccggaaaag gcttggaatg ggttgcttgg    1320
atttcaccgt atggcggttc cacatactac gctgacagcg ttaagggtcg attcaccatc    1380
tctgcagata cttcaaaaaa cacagcctac cttcagatga atagtttgcg cgccgaggac    1440
acagcggttt attattgtgc ccgaagacat tggcccggcg tttcgactac tggggggcaa    1500
ggtacgttgg tgactgtgag cgcccaccac catcatcacc actga                    1545
```

<210> SEQ ID NO 50
<211> LENGTH: 514
<212> TYPE: PRT
<213> ORGANISM: Artificial Sequence
<220> FEATURE:
<223> OTHER INFORMATION: Synthesized PDL1-CD3 bi-specific T-cell
      engager construct

<400> SEQUENCE: 50

```
Met Glu Phe Gly Leu Ser Trp Val Phe Leu Val Ala Leu Phe Arg Gly
1               5                   10                  15

Val Gln Cys Asp Ile Lys Leu Gln Gln Ser Gly Ala Glu Leu Ala Arg
            20                  25                  30

Pro Gly Ala Ser Val Lys Met Ser Cys Lys Thr Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Val Glu Gly Gly Ser Gly
    130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
    210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Gly Gly Gly Gly Ser Asp Ile Gln Met Thr
```

```
            260                 265                 270
Gln Ser Pro Ser Ser Leu Ser Ala Ser Val Gly Asp Arg Val Thr Ile
        275                 280                 285

Thr Cys Arg Ala Ser Gln Asp Val Ser Thr Ala Val Ala Trp Tyr Gln
    290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Tyr Leu Tyr His Pro Ala Thr Phe Gly Gln Gly
        355                 360                 365

Thr Lys Val Glu Ile Lys Arg Gly Gly Gly Gly Ser Gly Gly Gly Gly
    370                 375                 380

Ser Gly Gly Gly Gly Ser Glu Val Gln Leu Val Glu Ser Gly Gly Gly
385                 390                 395                 400

Leu Val Gln Pro Gly Gly Ser Leu Arg Leu Ser Cys Ala Ala Ser Gly
                405                 410                 415

Phe Thr Phe Ser Asp Ser Trp Ile His Trp Val Arg Gln Ala Pro Gly
            420                 425                 430

Lys Gly Leu Glu Trp Val Ala Trp Ile Ser Pro Tyr Gly Gly Ser Thr
        435                 440                 445

Tyr Tyr Ala Asp Ser Val Lys Gly Arg Phe Thr Ile Ser Ala Asp Thr
    450                 455                 460

Ser Lys Asn Thr Ala Tyr Leu Gln Met Asn Ser Leu Arg Ala Glu Asp
465                 470                 475                 480

Thr Ala Val Tyr Tyr Cys Ala Arg Arg His Trp Pro Gly Gly Phe Asp
                485                 490                 495

Tyr Trp Gly Gln Gly Thr Leu Val Thr Val Ser Ala His His His His
            500                 505                 510

His His

<210> SEQ ID NO 51
<211> LENGTH: 2244
<212> TYPE: DNA
<213> ORGANISM: Artificial Sequence
<220> FEATURE:
<223> OTHER INFORMATION: Synthesized polynucleotide encoding PDL1-CD3-
      Fc bi-specific T-cell engager construct

<400> SEQUENCE: 51
atggagttcg gcctgagctg ggtgttcctg gtggccctgt tcaggggcgt gcagtgcgac      60
atcaagctgc agcagagcgg cgccgagctg gccaggcccg gcgccagcgt gaagatgagc     120
tgcaagacca gcggctacac cttcaccagg tacaccatgc actgggtgaa gcagaggccc     180
ggccagggcc tggagtggat cggctacatc aaccccagca gggctacac caactacaac     240 cagaagttca aggacaaggc caccctgacc accgacaaga gcagcagcac cgcctacatg     300
cagctgagca gcctgaccag cgaggacagc gccgtgtact actgcgccag gtactacgac     360
gaccactact gcctggacta ctggggccag ggcaccaccc tgaccgtgag cagcgtggag     420
ggcggcagcg gcggcagcgg cggcagcggc ggcagcggcg gcgtggacga catccagctg     480
acccagagcc ccgccatcat gagcgccagc cccggcgaga aggtgaccat gacctgcagg     540
gccagcagca gcgtgagcta catgaactgg taccagcaga agagcggcac cagccccaag     600
```

-continued

```
aggtggatct acgacaccag caaggtggcc agcggcgtgc cctacaggtt cagcggcagc    660
ggcagcggca ccagctacag cctgaccatc agcagcatgg aggccgagga cgccgccacc    720
tactactgcc agcagtggag cagcaacccc ctgaccttcg gcgccggcac caagctggag    780
ctgaagggcg gcggcggcag cgatatccag atgacacaga gcccatcatc tctgtctgca    840
agcgtaggag accgagtcac cattacatgc agagcctccc aagacgtttc cacagcagtg    900
gcctggtatc agcaaaaacc tggtaaggcg cccaagcttc tcatctattc agccagtttt    960
ctgtatagcg gcgttccagc ccgattctct ggctctggat ccggcacgga ctttactttg   1020
acaatttcct ctcttcagcc cgaagatttt gcaacctact actgtcagca atatctctac   1080
catccagcca cattcggaca gggcaccaaa gtcgaaatca aaagaggcgg cggcggcagt   1140
ggcggcgggg gttcaggagg cggggggttct gaagtgcaac tcgttgaaag cggaggaggg   1200
cttgtccaac tggcgggtc actgcggttg agctgcgccg caagcggatt caccttctca   1260
gactcttgga tccattgggt gcgccaggct cccggaaaag gcttggaatg ggttgcttgg   1320
atttcaccgt atggcggttc cacatactac gctgacagcg ttaagggtcg attcaccatc   1380
tctgcagata cttcaaaaaa cacagcctac cttcagatga atagtttgcg cgccgaggac   1440
acagcggttt attattgtgc ccgaagacat tggcccggcg gtttcgacta ctgggggcaa   1500
ggtacgttgg tgactgtgag cgccgtagat gaagcaaaat cttgtgacaa acccataccc   1560
tgcccaccat gcccagcccc agaacttctt ggcggaccct ctgtcttcct ttcccctccg   1620
aagcccaagg ataccctgat gatcagccga accccggagg taacatgtgt ggtggtcgat   1680
gttagccatg aggatcctga agtcaaattt aactggtatg tagacggtgt tgaggtgcac   1740
aacgctaaaa ctaagcccag ggaggagcag tacaactcaa cctatcgcgt cgtatctgtg   1800
cttaccgtcc tgcatcaaga ctggctcaat ggtaaggaat ataaatgtaa agtgagtaac   1860
aaggcactgc cagcacctat cgaaaaaacc atctcaaagg cgaagggaca gcccagggaa   1920
ccccaggtct atactctgcc accttctcgg gatgaattga ccaagaacca agttagcctg   1980
acatgtctgg tgaaaggttt ctatccaagc gatatagctg tcgagtggga gtccaatggc   2040
caacctgaga acaattataa gaccaccca cccgttctgg acagcgacgg atcctttttc   2100
ctgtactcaa aactcactgt cgataaatca agatggcaac aaggcaacgt ttttagctgt   2160
agcgtgatgc acgaagcact tcataatcac tatacacaga agtcactctc tctttctcca   2220
ggacaccacc atcatcacca ctga                                          2244
```

<210> SEQ ID NO 52
<211> LENGTH: 747
<212> TYPE: PRT
<213> ORGANISM: Artificial Sequence
<220> FEATURE:
<223> OTHER INFORMATION: Synthesized PDL1-CD3-Fc bi-specific T-cell engager construct

<400> SEQUENCE: 52

```
Met Glu Phe Gly Leu Ser Trp Val Phe Leu Val Ala Leu Phe Arg Gly
1               5                   10                  15

Val Gln Cys Asp Ile Lys Leu Gln Gln Ser Gly Ala Glu Leu Ala Arg
            20                  25                  30

Pro Gly Ala Ser Val Lys Met Ser Cys Lys Thr Ser Gly Tyr Thr Phe
        35                  40                  45

Thr Arg Tyr Thr Met His Trp Val Lys Gln Arg Pro Gly Gln Gly Leu
    50                  55                  60
```

-continued

```
Glu Trp Ile Gly Tyr Ile Asn Pro Ser Arg Gly Tyr Thr Asn Tyr Asn
 65                  70                  75                  80

Gln Lys Phe Lys Asp Lys Ala Thr Leu Thr Thr Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Cys Leu Asp Tyr Trp
            115                 120                 125

Gly Gln Gly Thr Thr Leu Thr Val Ser Ser Val Glu Gly Gly Ser Gly
        130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
    210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Gly Gly Gly Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Gln Asp Val Ser Thr Ala Val Ala Trp Tyr Gln
    290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Tyr Leu Tyr His Pro Ala Thr Phe Gly Gln Gly
        355                 360                 365

Thr Lys Val Glu Ile Lys Arg Gly Gly Gly Ser Gly Gly Gly Gly
    370                 375                 380

Ser Gly Gly Gly Ser Glu Val Gln Leu Val Glu Ser Gly Gly Gly
385                 390                 395                 400

Leu Val Gln Pro Gly Gly Ser Leu Arg Leu Ser Cys Ala Ala Ser Gly
                405                 410                 415

Phe Thr Phe Ser Asp Ser Trp Ile His Trp Val Arg Gln Ala Pro Gly
            420                 425                 430

Lys Gly Leu Glu Trp Val Ala Trp Ile Ser Pro Tyr Gly Gly Ser Thr
        435                 440                 445

Tyr Tyr Ala Asp Ser Val Lys Gly Arg Phe Thr Ile Ser Ala Asp Thr
    450                 455                 460

Ser Lys Asn Thr Ala Tyr Leu Gln Met Asn Ser Leu Arg Ala Glu Asp
465                 470                 475                 480
```

-continued

```
Thr Ala Val Tyr Tyr Cys Ala Arg Arg His Trp Pro Gly Gly Phe Asp
            485                 490                 495

Tyr Trp Gly Gln Gly Thr Leu Val Thr Val Ser Ala Val Asp Glu Ala
        500                 505                 510

Lys Ser Cys Asp Lys Thr His Thr Cys Pro Pro Cys Pro Ala Pro Glu
    515                 520                 525

Leu Leu Gly Gly Pro Ser Val Phe Leu Phe Pro Pro Lys Pro Lys Asp
530                 535                 540

Thr Leu Met Ile Ser Arg Thr Pro Glu Val Thr Cys Val Val Val Asp
545                 550                 555                 560

Val Ser His Glu Asp Pro Glu Val Lys Phe Asn Trp Tyr Val Asp Gly
            565                 570                 575

Val Glu Val His Asn Ala Lys Thr Lys Pro Arg Glu Glu Gln Tyr Asn
        580                 585                 590

Ser Thr Tyr Arg Val Val Ser Val Leu Thr Val Leu His Gln Asp Trp
    595                 600                 605

Leu Asn Gly Lys Glu Tyr Lys Cys Lys Val Ser Asn Lys Ala Leu Pro
610                 615                 620

Ala Pro Ile Glu Lys Thr Ile Ser Lys Ala Lys Gly Gln Pro Arg Glu
625                 630                 635                 640

Pro Gln Val Tyr Thr Leu Pro Pro Ser Arg Asp Glu Leu Thr Lys Asn
            645                 650                 655

Gln Val Ser Leu Thr Cys Leu Val Lys Gly Phe Tyr Pro Ser Asp Ile
        660                 665                 670

Ala Val Glu Trp Glu Ser Asn Gly Gln Pro Glu Asn Asn Tyr Lys Thr
    675                 680                 685

Thr Pro Pro Val Leu Asp Ser Asp Gly Ser Phe Phe Leu Tyr Ser Lys
690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
            725                 730                 735

Ser Leu Ser Pro Gly His His His His His His
        740                 745
```

<210> SEQ ID NO 53
<211> LENGTH: 707
<212> TYPE: PRT
<213> ORGANISM: Artificial Sequence
<220> FEATURE:
<223> OTHER INFORMATION: Synthesized CD19-IL15 bi-specific T-cell
      engager construct

<400> SEQUENCE: 53

```
Met Glu Phe Gly Leu Ser Trp Val Phe Leu Val Ala Leu Phe Arg Gly
1               5                   10                  15

Val Gln Cys Asp Ile Gln Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Tyr Asp Gly Asp Ser Tyr Leu Asn Trp Tyr Gln Gln Ile Pro Gly
    50                  55                  60

Gln Pro Pro Lys Leu Leu Ile Tyr Asp Ala Ser Asn Leu Val Ser Gly
65                  70                  75                  80

Ile Pro Pro Arg Phe Ser Gly Ser Gly Ser Gly Thr Asp Phe Thr Leu
            85                  90                  95
```

```
Asn Ile His Pro Val Glu Lys Val Asp Ala Thr Tyr His Cys Gln
            100                 105                 110
Gln Ser Thr Glu Asp Pro Trp Thr Phe Gly Gly Gly Thr Lys Leu Glu
        115                 120                 125
Ile Lys Gly Gly Gly Gly Ser Gly Gly Gly Gly Ser Gly Gly Gly Gly
    130                 135                 140
Ser Gln Val Gln Leu Gln Gln Ser Gly Ala Glu Leu Val Arg Pro Gly
145                 150                 155                 160
Ser Ser Val Lys Ile Ser Cys Lys Ala Ser Gly Tyr Ala Phe Ser Ser
                165                 170                 175
Tyr Trp Met Asn Trp Val Lys Gln Arg Pro Gly Gln Gly Leu Glu Trp
            180                 185                 190
Ile Gly Gln Ile Trp Pro Gly Asp Gly Asp Thr Asn Tyr Asn Gly Lys
        195                 200                 205
Phe Lys Gly Lys Ala Thr Leu Thr Ala Asp Glu Ser Ser Ser Thr Ala
    210                 215                 220
Tyr Met Gln Leu Ser Ser Leu Ala Ser Glu Asp Ser Ala Val Tyr Phe
225                 230                 235                 240
Cys Ala Arg Arg Glu Thr Thr Thr Val Gly Arg Tyr Tyr Tyr Ala Met
                245                 250                 255
Asp Tyr Trp Gly Gln Gly Thr Thr Val Thr Val Ser Ser Gly Gly Gly
            260                 265                 270
Gly Ser Asp Ile Lys Leu Gln Gln Ser Gly Ala Glu Leu Ala Arg Pro
        275                 280                 285
Gly Ala Ser Val Lys Met Ser Cys Lys Thr Ser Gly Tyr Thr Phe Thr
    290                 295                 300
Arg Tyr Thr Met His Trp Val Lys Gln Arg Pro Gly Gln Gly Leu Glu
305                 310                 315                 320
Trp Ile Gly Tyr Ile Asn Pro Ser Arg Gly Tyr Thr Asn Tyr Asn Gln
                325                 330                 335
Lys Phe Lys Asp Lys Ala Thr Leu Thr Thr Asp Lys Ser Ser Ser Thr
            340                 345                 350
Ala Tyr Met Gln Leu Ser Ser Leu Thr Ser Glu Asp Ser Ala Val Tyr
        355                 360                 365
Tyr Cys Ala Arg Tyr Tyr Asp Asp His Tyr Cys Leu Asp Tyr Trp Gly
    370                 375                 380
Gln Gly Thr Thr Leu Thr Val Ser Ser Val Glu Gly Gly Ser Gly Gly
385                 390                 395                 400
Ser Gly Gly Ser Gly Gly Ser Gly Gly Val Asp Asp Ile Gln Leu Thr
                405                 410                 415
Gln Ser Pro Ala Ile Met Ser Ala Ser Pro Gly Glu Lys Val Thr Met
            420                 425                 430
Thr Cys Arg Ala Ser Ser Ser Val Ser Tyr Met Asn Trp Tyr Gln Gln
        435                 440                 445
Lys Ser Gly Thr Ser Pro Lys Arg Trp Ile Tyr Asp Thr Ser Lys Val
    450                 455                 460
Ala Ser Gly Val Pro Tyr Arg Phe Ser Gly Ser Gly Ser Gly Thr Ser
465                 470                 475                 480
Tyr Ser Leu Thr Ile Ser Ser Met Glu Ala Glu Asp Ala Ala Thr Tyr
                485                 490                 495
Tyr Cys Gln Gln Trp Ser Ser Asn Pro Leu Thr Phe Gly Ala Gly Thr
            500                 505                 510
```

Lys Leu Glu Leu Lys His His His His His Arg Arg Lys Arg Glu
            515                 520                 525

Gly Arg Gly Ser Leu Leu Thr Cys Gly Asp Val Glu Glu Asn Pro Gly
    530                 535                 540

Pro Met Arg Ile Ser Lys Pro His Leu Arg Ser Ile Ser Ile Gln Cys
545                 550                 555                 560

Tyr Leu Cys Leu Leu Leu Asn Ser His Phe Leu Thr Glu Ala Gly Ile
                565                 570                 575

His Val Phe Ile Leu Gly Cys Phe Ser Ala Gly Leu Pro Lys Thr Glu
            580                 585                 590

Ala Asn Trp Val Asn Val Ile Ser Asp Leu Lys Lys Ile Glu Asp Leu
            595                 600                 605

Ile Gln Ser Met His Ile Asp Ala Thr Leu Tyr Thr Glu Ser Asp Val
            610                 615                 620

His Pro Ser Cys Lys Val Thr Ala Met Lys Cys Phe Leu Leu Glu Leu
625                 630                 635                 640

Gln Val Ile Ser Leu Glu Ser Gly Asp Ala Ser Ile His Asp Thr Val
                645                 650                 655

Glu Asn Leu Ile Ile Leu Ala Asn Asn Ser Leu Ser Ser Asn Gly Asn
            660                 665                 670

Val Thr Glu Ser Gly Cys Lys Glu Cys Glu Glu Leu Glu Glu Lys Asn
            675                 680                 685

Ile Lys Glu Phe Leu Gln Ser Phe Val His Ile Val Gln Met Phe Ile
            690                 695                 700

Asn Thr Ser
705

<210> SEQ ID NO 54
<211> LENGTH: 1149
<212> TYPE: PRT
<213> ORGANISM: Artificial Sequence
<220> FEATURE:
<223> OTHER INFORMATION: Synthesized CD19-IL12 bi-specific T-cell
      engager construct

<400> SEQUENCE: 54

Met Glu Phe Gly Leu Ser Trp Val Phe Leu Val Ala Leu Phe Arg Gly
1               5                   10                  15

Val Gln Cys Asp Ile Gln Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Tyr Asp Gly Asp Ser Tyr Leu Asn Trp Tyr Gln Gln Ile Pro Gly
    50                  55                  60

Gln Pro Pro Lys Leu Leu Ile Tyr Asp Ala Ser Asn Leu Val Ser Gly
65                  70                  75                  80

Ile Pro Pro Arg Phe Ser Gly Ser Gly Ser Gly Thr Asp Phe Thr Leu
                85                  90                  95

Asn Ile His Pro Val Glu Lys Val Asp Ala Ala Thr Tyr His Cys Gln
            100                 105                 110

Gln Ser Thr Glu Asp Pro Trp Thr Phe Gly Gly Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Gln Ser Gly Ala Glu Leu Val Arg Pro Gly
145                 150                 155                 160

Ser Ser Val Lys Ile Ser Cys Lys Ala Ser Gly Tyr Ala Phe Ser Ser
            165                 170                 175

Tyr Trp Met Asn Trp Val Lys Gln Arg Pro Gly Gln Gly Leu Glu Trp
        180                 185                 190

Ile Gly Gln Ile Trp Pro Gly Asp Gly Asp Thr Asn Tyr Asn Gly Lys
    195                 200                 205

Phe Lys Gly Lys Ala Thr Leu Thr Ala Asp Glu Ser Ser Ser Thr Ala
210                 215                 220

Tyr Met Gln Leu Ser Ser Leu Ala Ser Glu Asp Ser Ala Val Tyr Phe
225                 230                 235                 240

Cys Ala Arg Arg Glu Thr Thr Val Gly Arg Tyr Tyr Tyr Ala Met
            245                 250                 255

Asp Tyr Trp Gly Gln Gly Thr Thr Val Thr Val Ser Ser Gly Gly Gly
        260                 265                 270

Gly Ser Asp Ile Lys Leu Gln Gln Ser Gly Ala Glu Leu Ala Arg Pro
    275                 280                 285

Gly Ala Ser Val Lys Met Ser Cys Lys Thr Ser Gly Tyr Thr Phe Thr
290                 295                 300

Arg Tyr Thr Met His Trp Val Lys Gln Arg Pro Gly Gln Gly Leu Glu
305                 310                 315                 320

Trp Ile Gly Tyr Ile Asn Pro Ser Arg Gly Tyr Thr Asn Tyr Asn Gln
            325                 330                 335

Lys Phe Lys Asp Lys Ala Thr Leu Thr Thr Asp Lys Ser Ser Ser Thr
        340                 345                 350

Ala Tyr Met Gln Leu Ser Ser Leu Thr Ser Glu Asp Ser Ala Val Tyr
    355                 360                 365

Tyr Cys Ala Arg Tyr Tyr Asp Asp His Tyr Cys Leu Asp Tyr Trp Gly
370                 375                 380

Gln Gly Thr Thr Leu Thr Val Ser Ser Val Glu Gly Gly Ser Gly Gly
385                 390                 395                 400

Ser Gly Gly Ser Gly Gly Ser Gly Gly Val Asp Asp Ile Gln Leu Thr
            405                 410                 415

Gln Ser Pro Ala Ile Met Ser Ala Ser Pro Gly Glu Lys Val Thr Met
        420                 425                 430

Thr Cys Arg Ala Ser Ser Ser Val Ser Tyr Met Asn Trp Tyr Gln Gln
    435                 440                 445

Lys Ser Gly Thr Ser Pro Lys Arg Trp Ile Tyr Asp Thr Ser Lys Val
450                 455                 460

Ala Ser Gly Val Pro Tyr Arg Phe Ser Gly Ser Gly Ser Gly Thr Ser
465                 470                 475                 480

Tyr Ser Leu Thr Ile Ser Ser Met Glu Ala Glu Asp Ala Ala Thr Tyr
            485                 490                 495

Tyr Cys Gln Gln Trp Ser Ser Asn Pro Leu Thr Phe Gly Ala Gly Thr
        500                 505                 510

Lys Leu Glu Leu Lys His His His His His His Arg Lys Arg Glu
    515                 520                 525

Gly Arg Gly Ser Leu Leu Thr Cys Gly Asp Val Glu Glu Asn Pro Gly
530                 535                 540

Pro Met Trp Pro Pro Gly Ser Ala Ser Gln Pro Pro Ser Pro Ala
545                 550                 555                 560

Ala Ala Thr Gly Leu His Pro Ala Ala Arg Pro Val Ser Leu Gln Cys
            565                 570                 575

```
Arg Leu Ser Met Cys Pro Ala Arg Ser Leu Leu Val Ala Thr Leu
            580                 585                 590

Val Leu Leu Asp His Leu Ser Leu Ala Arg Asn Leu Pro Val Ala Thr
    595                 600                 605

Pro Asp Pro Gly Met Phe Pro Cys Leu His His Ser Gln Asn Leu Leu
610                 615                 620

Arg Ala Val Ser Asn Met Leu Gln Lys Ala Arg Gln Thr Leu Glu Phe
625                 630                 635                 640

Tyr Pro Cys Thr Ser Glu Glu Ile Asp His Glu Asp Ile Thr Lys Asp
                645                 650                 655

Lys Thr Ser Thr Val Glu Ala Cys Leu Pro Leu Glu Leu Thr Lys Asn
            660                 665                 670

Glu Ser Cys Leu Asn Ser Arg Glu Thr Ser Phe Ile Thr Asn Gly Ser
    675                 680                 685

Cys Leu Ala Ser Arg Lys Thr Ser Phe Met Met Ala Leu Cys Leu Ser
690                 695                 700

Ser Ile Tyr Glu Asp Leu Lys Met Tyr Gln Val Glu Phe Lys Thr Met
705                 710                 715                 720

Asn Ala Lys Leu Leu Met Asp Pro Lys Arg Gln Ile Phe Leu Asp Gln
                725                 730                 735

Asn Met Leu Ala Val Ile Asp Glu Leu Met Gln Ala Leu Asn Phe Asn
            740                 745                 750

Ser Glu Thr Val Pro Gln Lys Ser Ser Leu Glu Glu Pro Asp Phe Tyr
    755                 760                 765

Lys Thr Lys Ile Lys Leu Cys Ile Leu Leu His Ala Phe Arg Ile Arg
770                 775                 780

Ala Val Thr Ile Asp Arg Val Met Ser Tyr Leu Asn Ala Ser Arg Arg
785                 790                 795                 800

Lys Arg Glu Gly Arg Gly Ser Leu Leu Thr Cys Gly Asp Val Glu Glu
                805                 810                 815

Asn Pro Gly Pro Pro Met Cys His Gln Gln Leu Val Ile Ser Trp Phe
            820                 825                 830

Ser Leu Val Phe Leu Ala Ser Pro Leu Val Ala Ile Trp Glu Leu Lys
    835                 840                 845

Lys Asp Val Tyr Val Val Glu Leu Asp Trp Tyr Pro Asp Ala Pro Gly
850                 855                 860

Glu Met Val Val Leu Thr Cys Asp Thr Pro Glu Glu Asp Gly Ile Thr
865                 870                 875                 880

Trp Thr Leu Asp Gln Ser Ser Glu Val Leu Gly Ser Gly Lys Thr Leu
                885                 890                 895

Thr Ile Gln Val Lys Glu Phe Gly Asp Ala Gly Gln Tyr Thr Cys His
            900                 905                 910

Lys Gly Gly Glu Val Leu Ser His Ser Leu Leu Leu Leu His Lys Lys
    915                 920                 925

Glu Asp Gly Ile Trp Ser Thr Asp Ile Leu Lys Asp Gln Lys Glu Pro
930                 935                 940

Lys Asn Lys Thr Phe Leu Arg Cys Glu Ala Lys Asn Tyr Ser Gly Arg
945                 950                 955                 960

Phe Thr Cys Trp Trp Leu Thr Thr Ile Ser Thr Asp Leu Thr Phe Ser
                965                 970                 975

Val Lys Ser Ser Arg Gly Ser Ser Asp Pro Gln Gly Val Thr Cys Gly
            980                 985                 990

Ala Ala Thr Leu Ser Ala Glu Arg  Val Arg Gly Asp Asn  Lys Glu Tyr
```

-continued

```
                995                 1000                1005
Glu Tyr  Ser Val Glu Cys  Gln Glu Asp Ser Ala  Cys Pro Ala Ala
    1010             1015             1020

Glu Glu  Ser Leu Pro Ile  Glu Val Met Val Asp  Ala Val His Lys
    1025             1030             1035

Leu Lys  Tyr Glu Asn Tyr  Thr Ser Ser Phe Phe  Ile Arg Asp Ile
    1040             1045             1050

Ile Lys  Pro Asp Pro Pro  Lys Asn Leu Gln Leu  Lys Pro Leu Lys
    1055             1060             1065

Asn Ser  Arg Gln Val Glu  Val Ser Trp Glu Tyr  Pro Asp Thr Trp
    1070             1075             1080

Ser Thr  Pro His Ser Tyr  Phe Ser Leu Thr Phe  Cys Val Gln Val
    1085             1090             1095

Gln Gly  Lys Ser Lys Arg  Glu Lys Lys Asp Arg  Val Phe Thr Asp
    1100             1105             1110

Lys Thr  Ser Ala Thr Val  Ile Cys Arg Lys Asn  Ala Ser Ile Ser
    1115             1120             1125

Val Arg  Ala Gln Asp Arg  Tyr Tyr Ser Ser Ser  Trp Ser Glu Trp
    1130             1135             1140

Ala Ser  Val Pro Cys Ser
    1145

<210> SEQ ID NO 55
<211> LENGTH: 643
<212> TYPE: PRT
<213> ORGANISM: Artificial Sequence
<220> FEATURE:
<223> OTHER INFORMATION: Synthesized CD19-CXCL10 bi-specific T-cell
      engager construct

<400> SEQUENCE: 55

Met Glu Phe Gly Leu Ser Trp Val Phe Leu Val Ala Leu Phe Arg Gly
1               5                   10                  15

Val Gln Cys Asp Ile Gln Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Tyr Asp Gly Asp Ser Tyr Leu Asn Trp Tyr Gln Gln Ile Pro Gly
    50                  55                  60

Gln Pro Pro Lys Leu Leu Ile Tyr Asp Ala Ser Asn Leu Val Ser Gly
65                  70                  75                  80

Ile Pro Pro Arg Phe Ser Gly Ser Gly Ser Gly Thr Asp Phe Thr Leu
                85                  90                  95

Asn Ile His Pro Val Glu Lys Val Asp Ala Ala Thr Tyr His Cys Gln
            100                 105                 110

Gln Ser Thr Glu Asp Pro Trp Thr Phe Gly Gly Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Gln Ser Gly Ala Glu Leu Val Arg Pro Gly
145                 150                 155                 160

Ser Ser Val Lys Ile Ser Cys Lys Ala Ser Gly Tyr Ala Phe Ser Ser
                165                 170                 175

Tyr Trp Met Asn Trp Val Lys Gln Arg Pro Gly Gln Gly Leu Glu Trp
            180                 185                 190
```

-continued

Ile Gly Gln Ile Trp Pro Gly Asp Gly Asp Thr Asn Tyr Asn Gly Lys
            195                 200                 205

Phe Lys Gly Lys Ala Thr Leu Thr Ala Asp Glu Ser Ser Ser Thr Ala
    210                 215                 220

Tyr Met Gln Leu Ser Ser Leu Ala Ser Glu Asp Ser Ala Val Tyr Phe
225                 230                 235                 240

Cys Ala Arg Arg Glu Thr Thr Thr Val Gly Arg Tyr Tyr Tyr Ala Met
                245                 250                 255

Asp Tyr Trp Gly Gln Gly Thr Thr Val Thr Val Ser Ser Gly Gly Gly
            260                 265                 270

Gly Ser Asp Ile Lys Leu Gln Gln Ser Gly Ala Glu Leu Ala Arg Pro
        275                 280                 285

Gly Ala Ser Val Lys Met Ser Cys Lys Thr Ser Gly Tyr Thr Phe Thr
    290                 295                 300

Arg Tyr Thr Met His Trp Val Lys Gln Arg Pro Gly Gln Gly Leu Glu
305                 310                 315                 320

Trp Ile Gly Tyr Ile Asn Pro Ser Arg Gly Tyr Thr Asn Tyr Asn Gln
                325                 330                 335

Lys Phe Lys Asp Lys Ala Thr Leu Thr Thr Asp Lys Ser Ser Ser Thr
            340                 345                 350

Ala Tyr Met Gln Leu Ser Ser Leu Thr Ser Glu Asp Ser Ala Val Tyr
        355                 360                 365

Tyr Cys Ala Arg Tyr Tyr Asp Asp His Tyr Cys Leu Asp Tyr Trp Gly
    370                 375                 380

Gln Gly Thr Thr Leu Thr Val Ser Ser Val Glu Gly Gly Ser Gly Gly
385                 390                 395                 400

Ser Gly Gly Ser Gly Gly Ser Gly Gly Val Asp Asp Ile Gln Leu Thr
                405                 410                 415

Gln Ser Pro Ala Ile Met Ser Ala Ser Pro Gly Glu Lys Val Thr Met
            420                 425                 430

Thr Cys Arg Ala Ser Ser Ser Val Ser Tyr Met Asn Trp Tyr Gln Gln
        435                 440                 445

Lys Ser Gly Thr Ser Pro Lys Arg Trp Ile Tyr Asp Thr Ser Lys Val
    450                 455                 460

Ala Ser Gly Val Pro Tyr Arg Phe Ser Gly Ser Gly Ser Gly Thr Ser
465                 470                 475                 480

Tyr Ser Leu Thr Ile Ser Ser Met Glu Ala Glu Asp Ala Ala Thr Tyr
                485                 490                 495

Tyr Cys Gln Gln Trp Ser Ser Asn Pro Leu Thr Phe Gly Ala Gly Thr
            500                 505                 510

Lys Leu Glu Leu Lys His His His His His His Arg Arg Lys Arg Glu
        515                 520                 525

Gly Arg Gly Ser Leu Leu Thr Cys Gly Asp Val Glu Glu Asn Pro Gly
    530                 535                 540

Pro Met Asn Gln Thr Ala Ile Leu Ile Cys Cys Leu Ile Phe Leu Thr
545                 550                 555                 560

Leu Ser Gly Ile Gln Gly Val Pro Leu Ser Arg Thr Val Arg Cys Thr
                565                 570                 575

Cys Ile Ser Ile Ser Asn Gln Pro Val Asn Pro Arg Ser Leu Glu Lys
            580                 585                 590

Leu Glu Ile Ile Pro Ala Ser Gln Phe Cys Pro Arg Val Glu Ile Ile
        595                 600                 605

Ala Thr Met Lys Lys Lys Gly Glu Lys Arg Cys Leu Asn Pro Glu Ser

```
                610                 615                 620
Lys Ala Ile Lys Asn Leu Leu Lys Ala Val Ser Lys Glu Arg Ser Lys
625                 630                 635                 640

Arg Ser Pro

<210> SEQ ID NO 56
<211> LENGTH: 575
<212> TYPE: PRT
<213> ORGANISM: Artificial Sequence
<220> FEATURE:
<223> OTHER INFORMATION: Synthesized SIRP1alpha-IL15-SL bi-specific
      T-cell engager construct

<400> SEQUENCE: 56

Met Glu Thr Asp Thr Leu Leu Leu Trp Val Leu Leu Leu Trp Val Pro
1               5                   10                  15

Gly Ser Thr Gly Asp Glu Glu Leu Gln Ile Ile Gln Pro Asp Lys
            20                  25                  30

Ser Val Leu Val Ala Ala Gly Glu Thr Ala Thr Leu Arg Cys Thr Ile
            35                  40                  45

Thr Ser Leu Phe Pro Val Gly Pro Ile Gln Trp Phe Arg Gly Ala Gly
        50                  55                  60

Pro Gly Arg Val Leu Ile Tyr Asn Gln Arg Gln Gly Pro Phe Pro Arg
65              70                  75                  80

Val Thr Thr Val Ser Asp Thr Thr Lys Arg Asn Asn Met Asp Phe Ser
                85                  90                  95

Ile Arg Ile Gly Asn Ile Thr Pro Ala Asp Ala Gly Thr Tyr Tyr Cys
            100                 105                 110

Ile Lys Phe Arg Lys Gly Ser Pro Asp Asp Val Glu Phe Lys Ser Gly
        115                 120                 125

Ala Gly Thr Glu Leu Ser Val Arg Ala Lys Pro Ser Ala Ser Asp Ile
130                 135                 140

Lys Leu Gln Gln Ser Gly Ala Glu Leu Ala Arg Pro Gly Ala Ser Val
145                 150                 155                 160

Lys Met Ser Cys Lys Thr Ser Gly Tyr Thr Phe Thr Arg Tyr Thr Met
                165                 170                 175

His Trp Val Lys Gln Arg Pro Gly Gln Gly Leu Glu Trp Ile Gly Tyr
            180                 185                 190

Ile Asn Pro Ser Arg Gly Tyr Thr Asn Tyr Asn Gln Lys Phe Lys Asp
        195                 200                 205

Lys Ala Thr Leu Thr Thr Asp Lys Ser Ser Ser Thr Ala Tyr Met Gln
210                 215                 220

Leu Ser Ser Leu Thr Ser Glu Asp Ser Ala Val Tyr Tyr Cys Ala Arg
225                 230                 235                 240

Tyr Tyr Asp Asp His Tyr Cys Leu Asp Tyr Trp Gly Gln Gly Thr Thr
                245                 250                 255

Leu Thr Val Ser Ser Val Glu Gly Gly Ser Gly Gly Ser Gly Gly Ser
            260                 265                 270

Gly Gly Ser Gly Gly Val Asp Asp Ile Gln Leu Thr Gln Ser Pro Ala
        275                 280                 285

Ile Met Ser Ala Ser Pro Gly Glu Lys Val Thr Met Thr Cys Arg Ala
        290                 295                 300

Ser Ser Ser Val Ser Tyr Met Asn Trp Tyr Gln Gln Lys Ser Gly Thr
305                 310                 315                 320

Ser Pro Lys Arg Trp Ile Tyr Asp Thr Ser Lys Val Ala Ser Gly Val
```

325                 330                 335
Pro Tyr Arg Phe Ser Gly Ser Gly Ser Gly Thr Ser Tyr Ser Leu Thr
                340                 345                 350
Ile Ser Ser Met Glu Ala Glu Asp Ala Ala Thr Tyr Tyr Cys Gln Gln
                355                 360                 365
Trp Ser Ser Asn Pro Leu Thr Phe Gly Ala Gly Thr Lys Leu Glu Leu
370                 375                 380
Lys His His His His His Arg Arg Lys Arg Glu Gly Arg Gly Ser
385                 390                 395                 400
Leu Leu Thr Cys Gly Asp Val Glu Glu Asn Pro Gly Pro Met Arg Ile
                405                 410                 415
Ser Lys Pro His Leu Arg Ser Ile Ser Ile Gln Cys Tyr Leu Cys Leu
                420                 425                 430
Leu Leu Asn Ser His Phe Leu Thr Glu Ala Gly Ile His Val Phe Ile
                435                 440                 445
Leu Gly Cys Phe Ser Ala Gly Leu Pro Lys Thr Glu Ala Asn Trp Val
450                 455                 460
Asn Val Ile Ser Asp Leu Lys Lys Ile Glu Asp Leu Ile Gln Ser Met
465                 470                 475                 480
His Ile Asp Ala Thr Leu Tyr Thr Glu Ser Asp Val His Pro Ser Cys
                485                 490                 495
Lys Val Thr Ala Met Lys Cys Phe Leu Leu Glu Leu Gln Val Ile Ser
                500                 505                 510
Leu Glu Ser Gly Asp Ala Ser Ile His Asp Thr Val Glu Asn Leu Ile
                515                 520                 525
Ile Leu Ala Asn Asn Ser Leu Ser Ser Asn Gly Asn Val Thr Glu Ser
530                 535                 540
Gly Cys Lys Glu Cys Glu Glu Leu Glu Glu Lys Asn Ile Lys Glu Phe
545                 550                 555                 560
Leu Gln Ser Phe Val His Ile Val Gln Met Phe Ile Asn Thr Ser
                565                 570                 575

<210> SEQ ID NO 57
<211> LENGTH: 580
<212> TYPE: PRT
<213> ORGANISM: Artificial Sequence
<220> FEATURE:
<223> OTHER INFORMATION: Synthesized SIRP1alpha-IL15-LL bi-specific
    T-cell engager construct

<400> SEQUENCE: 57

Met Glu Thr Asp Thr Leu Leu Leu Trp Val Leu Leu Leu Trp Val Pro
1               5                   10                  15
Gly Ser Thr Gly Asp Glu Glu Glu Leu Gln Ile Ile Gln Pro Asp Lys
                20                  25                  30
Ser Val Leu Val Ala Ala Gly Glu Thr Ala Thr Leu Arg Cys Thr Ile
            35                  40                  45
Thr Ser Leu Phe Pro Val Gly Pro Ile Gln Trp Phe Arg Gly Ala Gly
        50                  55                  60
Pro Gly Arg Val Leu Ile Tyr Asn Gln Arg Gln Gly Pro Phe Pro Arg
65                  70                  75                  80
Val Thr Thr Val Ser Asp Thr Thr Lys Arg Asn Asn Met Asp Phe Ser
                85                  90                  95
Ile Arg Ile Gly Asn Ile Thr Pro Ala Asp Ala Gly Thr Tyr Tyr Cys
                100                 105                 110

```
Ile Lys Phe Arg Lys Gly Ser Pro Asp Asp Val Glu Phe Lys Ser Gly
            115                 120                 125

Ala Gly Thr Glu Leu Ser Val Arg Ala Lys Pro Ser Ala Ser Gly Gly
130                 135                 140

Gly Gly Ser Asp Ile Lys Leu Gln Gln Ser Gly Ala Glu Leu Ala Arg
145                 150                 155                 160

Pro Gly Ala Ser Val Lys Met Ser Cys Lys Thr Ser Gly Tyr Thr Phe
                165                 170                 175

Thr Arg Tyr Thr Met His Trp Val Lys Gln Arg Pro Gly Gln Gly Leu
            180                 185                 190

Glu Trp Ile Gly Tyr Ile Asn Pro Ser Arg Gly Tyr Thr Asn Tyr Asn
            195                 200                 205

Gln Lys Phe Lys Asp Lys Ala Thr Leu Thr Thr Asp Lys Ser Ser Ser
        210                 215                 220

Thr Ala Tyr Met Gln Leu Ser Ser Leu Thr Ser Glu Asp Ser Ala Val
225                 230                 235                 240

Tyr Tyr Cys Ala Arg Tyr Tyr Asp Asp His Tyr Cys Leu Asp Tyr Trp
                245                 250                 255

Gly Gln Gly Thr Thr Leu Thr Val Ser Ser Val Glu Gly Gly Ser Gly
            260                 265                 270

Gly Ser Gly Gly Ser Gly Gly Ser Gly Gly Val Asp Asp Ile Gln Leu
        275                 280                 285

Thr Gln Ser Pro Ala Ile Met Ser Ala Ser Pro Gly Glu Lys Val Thr
        290                 295                 300

Met Thr Cys Arg Ala Ser Ser Ser Val Ser Tyr Met Asn Trp Tyr Gln
305                 310                 315                 320

Gln Lys Ser Gly Thr Ser Pro Lys Arg Trp Ile Tyr Asp Thr Ser Lys
                325                 330                 335

Val Ala Ser Gly Val Pro Tyr Arg Phe Ser Gly Ser Gly Ser Gly Thr
            340                 345                 350

Ser Tyr Ser Leu Thr Ile Ser Ser Met Glu Ala Glu Asp Ala Ala Thr
        355                 360                 365

Tyr Tyr Cys Gln Gln Trp Ser Ser Asn Pro Leu Thr Phe Gly Ala Gly
370                 375                 380

Thr Lys Leu Glu Leu Lys His His His His His His Arg Arg Lys Arg
385                 390                 395                 400

Glu Gly Arg Gly Ser Leu Leu Thr Cys Gly Asp Val Glu Glu Asn Pro
                405                 410                 415

Gly Pro Met Arg Ile Ser Lys Pro His Leu Arg Ser Ile Ser Ile Gln
            420                 425                 430

Cys Tyr Leu Cys Leu Leu Leu Asn Ser His Phe Leu Thr Glu Ala Gly
        435                 440                 445

Ile His Val Phe Ile Leu Gly Cys Phe Ser Ala Gly Leu Pro Lys Thr
        450                 455                 460

Glu Ala Asn Trp Val Asn Val Ile Ser Asp Leu Lys Lys Ile Glu Asp
465                 470                 475                 480

Leu Ile Gln Ser Met His Ile Asp Ala Thr Leu Tyr Thr Glu Ser Asp
                485                 490                 495

Val His Pro Ser Cys Lys Val Thr Ala Met Lys Cys Phe Leu Leu Glu
            500                 505                 510

Leu Gln Val Ile Ser Leu Glu Ser Gly Asp Ala Ser Ile His Asp Thr
        515                 520                 525

Val Glu Asn Leu Ile Ile Leu Ala Asn Asn Ser Leu Ser Ser Asn Gly
```

```
                    530               535               540
Asn Val Thr Glu Ser Gly Cys Lys Glu Cys Glu Leu Glu Lys
545               550               555               560

Asn Ile Lys Glu Phe Leu Gln Ser Phe Val His Ile Val Gln Met Phe
                565               570               575

Ile Asn Thr Ser
            580

<210> SEQ ID NO 58
<211> LENGTH: 1017
<212> TYPE: PRT
<213> ORGANISM: Artificial Sequence
<220> FEATURE:
<223> OTHER INFORMATION: Synthesized SIRP1alpha-IL12-SL bi-specific
      T-cell engager construct

<400> SEQUENCE: 58

Met Glu Thr Asp Thr Leu Leu Leu Trp Val Leu Leu Leu Trp Val Pro
1               5                   10                  15

Gly Ser Thr Gly Asp Glu Glu Leu Gln Ile Ile Gln Pro Asp Lys
                20                  25                  30

Ser Val Leu Val Ala Ala Gly Glu Thr Ala Thr Leu Arg Cys Thr Ile
                35                  40                  45

Thr Ser Leu Phe Pro Val Gly Pro Ile Gln Trp Phe Arg Gly Ala Gly
            50                  55                  60

Pro Gly Arg Val Leu Ile Tyr Asn Gln Arg Gln Gly Pro Phe Pro Arg
65              70                  75                  80

Val Thr Thr Val Ser Asp Thr Thr Lys Arg Asn Asn Met Asp Phe Ser
                    85                  90                  95

Ile Arg Ile Gly Asn Ile Thr Pro Ala Asp Ala Gly Thr Tyr Tyr Cys
                100                 105                 110

Ile Lys Phe Arg Lys Gly Ser Pro Asp Asp Val Glu Phe Lys Ser Gly
            115                 120                 125

Ala Gly Thr Glu Leu Ser Val Arg Ala Lys Pro Ser Ala Ser Asp Ile
        130                 135                 140

Lys Leu Gln Gln Ser Gly Ala Glu Leu Ala Arg Pro Gly Ala Ser Val
145                 150                 155                 160

Lys Met Ser Cys Lys Thr Ser Gly Tyr Thr Phe Thr Arg Tyr Thr Met
                165                 170                 175

His Trp Val Lys Gln Arg Pro Gly Gln Gly Leu Glu Trp Ile Gly Tyr
                180                 185                 190

Ile Asn Pro Ser Arg Gly Tyr Thr Asn Tyr Asn Gln Lys Phe Lys Asp
            195                 200                 205

Lys Ala Thr Leu Thr Thr Asp Lys Ser Ser Ser Thr Ala Tyr Met Gln
        210                 215                 220

Leu Ser Ser Leu Thr Ser Glu Asp Ser Ala Val Tyr Tyr Cys Ala Arg
225                 230                 235                 240

Tyr Tyr Asp Asp His Tyr Cys Leu Asp Tyr Trp Gly Gln Gly Thr Thr
                245                 250                 255

Leu Thr Val Ser Ser Val Glu Gly Gly Ser Gly Gly Ser Gly Gly Ser
                260                 265                 270

Gly Gly Ser Gly Gly Val Asp Asp Ile Gln Leu Thr Gln Ser Pro Ala
            275                 280                 285

Ile Met Ser Ala Ser Pro Gly Glu Lys Val Thr Met Thr Cys Arg Ala
        290                 295                 300
```

```
Ser Ser Ser Val Ser Tyr Met Asn Trp Tyr Gln Gln Lys Ser Gly Thr
305                 310                 315                 320

Ser Pro Lys Arg Trp Ile Tyr Asp Thr Ser Lys Val Ala Ser Gly Val
            325                 330                 335

Pro Tyr Arg Phe Ser Gly Ser Gly Ser Gly Thr Ser Tyr Ser Leu Thr
            340                 345                 350

Ile Ser Ser Met Glu Ala Glu Asp Ala Ala Thr Tyr Tyr Cys Gln Gln
        355                 360                 365

Trp Ser Ser Asn Pro Leu Thr Phe Gly Ala Gly Thr Lys Leu Glu Leu
    370                 375                 380

Lys His His His His His His Arg Arg Lys Arg Glu Gly Arg Gly Ser
385                 390                 395                 400

Leu Leu Thr Cys Gly Asp Val Glu Glu Asn Pro Gly Pro Met Trp Pro
            405                 410                 415

Pro Gly Ser Ala Ser Gln Pro Pro Ser Pro Ala Ala Ala Thr Gly
            420                 425                 430

Leu His Pro Ala Ala Arg Pro Val Ser Leu Gln Cys Arg Leu Ser Met
        435                 440                 445

Cys Pro Ala Arg Ser Leu Leu Leu Val Ala Thr Leu Val Leu Leu Asp
450                 455                 460

His Leu Ser Leu Ala Arg Asn Leu Pro Val Ala Thr Pro Asp Pro Gly
465                 470                 475                 480

Met Phe Pro Cys Leu His His Ser Gln Asn Leu Leu Arg Ala Val Ser
            485                 490                 495

Asn Met Leu Gln Lys Ala Arg Gln Thr Leu Glu Phe Tyr Pro Cys Thr
        500                 505                 510

Ser Glu Glu Ile Asp His Glu Asp Ile Thr Lys Asp Lys Thr Ser Thr
        515                 520                 525

Val Glu Ala Cys Leu Pro Leu Glu Leu Thr Lys Asn Glu Ser Cys Leu
        530                 535                 540

Asn Ser Arg Glu Thr Ser Phe Ile Thr Asn Gly Ser Cys Leu Ala Ser
545                 550                 555                 560

Arg Lys Thr Ser Phe Met Met Ala Leu Cys Leu Ser Ser Ile Tyr Glu
            565                 570                 575

Asp Leu Lys Met Tyr Gln Val Glu Phe Lys Thr Met Asn Ala Lys Leu
            580                 585                 590

Leu Met Asp Pro Lys Arg Gln Ile Phe Leu Asp Gln Asn Met Leu Ala
        595                 600                 605

Val Ile Asp Glu Leu Met Gln Ala Leu Asn Phe Asn Ser Glu Thr Val
        610                 615                 620

Pro Gln Lys Ser Ser Leu Glu Glu Pro Asp Phe Tyr Lys Thr Lys Ile
625                 630                 635                 640

Lys Leu Cys Ile Leu Leu His Ala Phe Arg Ile Arg Ala Val Thr Ile
            645                 650                 655

Asp Arg Val Met Ser Tyr Leu Asn Ala Ser Arg Arg Lys Arg Glu Gly
            660                 665                 670

Arg Gly Ser Leu Leu Thr Cys Gly Asp Val Glu Glu Asn Pro Gly Pro
            675                 680                 685

Pro Met Cys His Gln Gln Leu Val Ile Ser Trp Phe Ser Leu Val Phe
            690                 695                 700

Leu Ala Ser Pro Leu Val Ala Ile Trp Glu Leu Lys Lys Asp Val Tyr
705                 710                 715                 720

Val Val Glu Leu Asp Trp Tyr Pro Asp Ala Pro Gly Glu Met Val Val
```

```
                725                 730                 735
Leu Thr Cys Asp Thr Pro Glu Glu Asp Gly Ile Thr Trp Thr Leu Asp
            740                 745                 750

Gln Ser Ser Glu Val Leu Gly Ser Gly Lys Thr Leu Thr Ile Gln Val
        755                 760                 765

Lys Glu Phe Gly Asp Ala Gly Gln Tyr Thr Cys His Lys Gly Gly Glu
    770                 775                 780

Val Leu Ser His Ser Leu Leu Leu His Lys Lys Glu Asp Gly Ile
785                 790                 795                 800

Trp Ser Thr Asp Ile Leu Lys Asp Gln Lys Glu Pro Lys Asn Lys Thr
                805                 810                 815

Phe Leu Arg Cys Glu Ala Lys Asn Tyr Ser Gly Arg Phe Thr Cys Trp
            820                 825                 830

Trp Leu Thr Thr Ile Ser Thr Asp Leu Thr Phe Ser Val Lys Ser Ser
        835                 840                 845

Arg Gly Ser Ser Asp Pro Gln Gly Val Thr Cys Gly Ala Ala Thr Leu
    850                 855                 860

Ser Ala Glu Arg Val Arg Gly Asp Asn Lys Glu Tyr Glu Tyr Ser Val
865                 870                 875                 880

Glu Cys Gln Glu Asp Ser Ala Cys Pro Ala Ala Glu Glu Ser Leu Pro
                885                 890                 895

Ile Glu Val Met Val Asp Ala Val His Lys Leu Lys Tyr Glu Asn Tyr
            900                 905                 910

Thr Ser Ser Phe Phe Ile Arg Asp Ile Ile Lys Pro Asp Pro Pro Lys
        915                 920                 925

Asn Leu Gln Leu Lys Pro Leu Lys Asn Ser Arg Gln Val Glu Val Ser
    930                 935                 940

Trp Glu Tyr Pro Asp Thr Trp Ser Thr Pro His Ser Tyr Phe Ser Leu
945                 950                 955                 960

Thr Phe Cys Val Gln Val Gln Gly Lys Ser Lys Arg Glu Lys Lys Asp
                965                 970                 975

Arg Val Phe Thr Asp Lys Thr Ser Ala Thr Val Ile Cys Arg Lys Asn
            980                 985                 990

Ala Ser Ile Ser Val Arg Ala Gln Asp Arg Tyr Tyr Ser Ser Ser Trp
        995                 1000                1005

Ser Glu Trp Ala Ser Val Pro Cys Ser
    1010                1015

<210> SEQ ID NO 59
<211> LENGTH: 1022
<212> TYPE: PRT
<213> ORGANISM: Artificial Sequence
<220> FEATURE:
<223> OTHER INFORMATION: Synthesized SIRP1alpha-IL12-LL bi-specific
      T-cell engager construct

<400> SEQUENCE: 59

Met Glu Thr Asp Thr Leu Leu Leu Trp Val Leu Leu Leu Trp Val Pro
1               5                   10                  15

Gly Ser Thr Gly Asp Glu Glu Glu Leu Gln Ile Ile Gln Pro Asp Lys
            20                  25                  30

Ser Val Leu Val Ala Ala Gly Glu Thr Ala Thr Leu Arg Cys Thr Ile
        35                  40                  45

Thr Ser Leu Phe Pro Val Gly Pro Ile Gln Trp Phe Arg Gly Ala Gly
    50                  55                  60
```

```
Pro Gly Arg Val Leu Ile Tyr Asn Gln Arg Gln Gly Pro Phe Pro Arg
 65                  70                  75                  80

Val Thr Thr Val Ser Asp Thr Lys Arg Asn Asn Met Asp Phe Ser
                 85                  90                  95

Ile Arg Ile Gly Asn Ile Thr Pro Ala Asp Ala Gly Thr Tyr Tyr Cys
                100                 105                 110

Ile Lys Phe Arg Lys Gly Ser Pro Asp Asp Val Glu Phe Lys Ser Gly
            115                 120                 125

Ala Gly Thr Glu Leu Ser Val Arg Ala Lys Pro Ser Ala Ser Gly Gly
        130                 135                 140

Gly Gly Ser Asp Ile Lys Leu Gln Gln Ser Gly Ala Glu Leu Ala Arg
145                 150                 155                 160

Pro Gly Ala Ser Val Lys Met Ser Cys Lys Thr Ser Gly Tyr Thr Phe
                165                 170                 175

Thr Arg Tyr Thr Met His Trp Val Lys Gln Arg Pro Gly Gln Gly Leu
            180                 185                 190

Glu Trp Ile Gly Tyr Ile Asn Pro Ser Arg Gly Tyr Thr Asn Tyr Asn
        195                 200                 205

Gln Lys Phe Lys Asp Lys Ala Thr Leu Thr Thr Asp Lys Ser Ser Ser
210                 215                 220

Thr Ala Tyr Met Gln Leu Ser Ser Leu Thr Ser Glu Asp Ser Ala Val
225                 230                 235                 240

Tyr Tyr Cys Ala Arg Tyr Tyr Asp Asp His Tyr Cys Leu Asp Tyr Trp
                245                 250                 255

Gly Gln Gly Thr Thr Leu Thr Val Ser Ser Val Glu Gly Gly Ser Gly
            260                 265                 270

Gly Ser Gly Gly Ser Gly Gly Ser Gly Gly Val Asp Asp Ile Gln Leu
        275                 280                 285

Thr Gln Ser Pro Ala Ile Met Ser Ala Ser Pro Gly Glu Lys Val Thr
290                 295                 300

Met Thr Cys Arg Ala Ser Ser Ser Val Ser Tyr Met Asn Trp Tyr Gln
305                 310                 315                 320

Gln Lys Ser Gly Thr Ser Pro Lys Arg Trp Ile Tyr Asp Thr Ser Lys
                325                 330                 335

Val Ala Ser Gly Val Pro Tyr Arg Phe Ser Gly Ser Gly Ser Gly Thr
            340                 345                 350

Ser Tyr Ser Leu Thr Ile Ser Ser Met Glu Ala Glu Asp Ala Ala Thr
        355                 360                 365

Tyr Tyr Cys Gln Gln Trp Ser Ser Asn Pro Leu Thr Phe Gly Ala Gly
370                 375                 380

Thr Lys Leu Glu Leu Lys His His His His His Arg Arg Lys Arg
385                 390                 395                 400

Glu Gly Arg Gly Ser Leu Leu Thr Cys Gly Asp Val Glu Glu Asn Pro
                405                 410                 415

Gly Pro Met Trp Pro Gly Ser Ala Ser Gln Pro Pro Ser Pro
            420                 425                 430

Ala Ala Ala Thr Gly Leu His Pro Ala Ala Arg Pro Val Ser Leu Gln
        435                 440                 445

Cys Arg Leu Ser Met Cys Pro Ala Arg Ser Leu Leu Val Ala Thr
450                 455                 460

Leu Val Leu Leu Asp His Leu Ser Leu Ala Arg Asn Leu Pro Val Ala
465                 470                 475                 480

Thr Pro Asp Pro Gly Met Phe Pro Cys Leu His His Ser Gln Asn Leu
```

-continued

```
                485                 490                 495
Leu Arg Ala Val Ser Asn Met Leu Gln Lys Ala Arg Gln Thr Leu Glu
                500                 505                 510

Phe Tyr Pro Cys Thr Ser Glu Glu Ile Asp His Glu Asp Ile Thr Lys
                515                 520                 525

Asp Lys Thr Ser Thr Val Glu Ala Cys Leu Pro Leu Glu Leu Thr Lys
                530                 535                 540

Asn Glu Ser Cys Leu Asn Ser Arg Glu Thr Ser Phe Ile Thr Asn Gly
545                 550                 555                 560

Ser Cys Leu Ala Ser Arg Lys Thr Ser Phe Met Met Ala Leu Cys Leu
                565                 570                 575

Ser Ser Ile Tyr Glu Asp Leu Lys Met Tyr Gln Val Glu Phe Lys Thr
                580                 585                 590

Met Asn Ala Lys Leu Leu Met Asp Pro Lys Arg Gln Ile Phe Leu Asp
                595                 600                 605

Gln Asn Met Leu Ala Val Ile Asp Glu Leu Met Gln Ala Leu Asn Phe
                610                 615                 620

Asn Ser Glu Thr Val Pro Gln Lys Ser Ser Leu Glu Glu Pro Asp Phe
625                 630                 635                 640

Tyr Lys Thr Lys Ile Lys Leu Cys Ile Leu Leu His Ala Phe Arg Ile
                645                 650                 655

Arg Ala Val Thr Ile Asp Arg Val Met Ser Tyr Leu Asn Ala Ser Arg
                660                 665                 670

Arg Lys Arg Glu Gly Arg Gly Ser Leu Leu Thr Cys Gly Asp Val Glu
                675                 680                 685

Glu Asn Pro Gly Pro Met Cys His Gln Gln Leu Val Ile Ser Trp
690                 695                 700

Phe Ser Leu Val Phe Leu Ala Ser Pro Leu Val Ala Ile Trp Glu Leu
705                 710                 715                 720

Lys Lys Asp Val Tyr Val Val Glu Leu Asp Trp Tyr Pro Asp Ala Pro
                725                 730                 735

Gly Glu Met Val Val Leu Thr Cys Asp Thr Pro Glu Glu Asp Gly Ile
                740                 745                 750

Thr Trp Thr Leu Asp Gln Ser Ser Glu Val Leu Gly Ser Gly Lys Thr
                755                 760                 765

Leu Thr Ile Gln Val Lys Glu Phe Gly Asp Ala Gly Gln Tyr Thr Cys
                770                 775                 780

His Lys Gly Gly Glu Val Leu Ser His Ser Leu Leu Leu Leu His Lys
785                 790                 795                 800

Lys Glu Asp Gly Ile Trp Ser Thr Asp Ile Leu Lys Asp Gln Lys Glu
                805                 810                 815

Pro Lys Asn Lys Thr Phe Leu Arg Cys Glu Ala Lys Asn Tyr Ser Gly
                820                 825                 830

Arg Phe Thr Cys Trp Trp Leu Thr Thr Ile Ser Thr Asp Leu Thr Phe
                835                 840                 845

Ser Val Lys Ser Ser Arg Gly Ser Ser Asp Pro Gln Gly Val Thr Cys
                850                 855                 860

Gly Ala Ala Thr Leu Ser Ala Glu Arg Val Arg Gly Asp Asn Lys Glu
865                 870                 875                 880

Tyr Glu Tyr Ser Val Glu Cys Gln Glu Asp Ser Ala Cys Pro Ala Ala
                885                 890                 895

Glu Glu Ser Leu Pro Ile Glu Val Met Val Asp Ala Val His Lys Leu
                900                 905                 910
```

```
Lys Tyr Glu Asn Tyr Thr Ser Ser Phe Phe Ile Arg Asp Ile Ile Lys
            915                 920                 925

Pro Asp Pro Pro Lys Asn Leu Gln Leu Lys Pro Leu Lys Asn Ser Arg
    930                 935                 940

Gln Val Glu Val Ser Trp Glu Tyr Pro Asp Thr Trp Ser Thr Pro His
945                 950                 955                 960

Ser Tyr Phe Ser Leu Thr Phe Cys Val Gln Val Gln Gly Lys Ser Lys
                965                 970                 975

Arg Glu Lys Lys Asp Arg Val Phe Thr Asp Lys Thr Ser Ala Thr Val
            980                 985                 990

Ile Cys Arg Lys Asn Ala Ser Ile  Ser Val Arg Ala Gln  Asp Arg Tyr
            995                 1000                1005

Tyr Ser  Ser Ser Trp Ser Glu  Trp Ala Ser Val Pro  Cys Ser
    1010                1015                1020
```

<210> SEQ ID NO 60
<211> LENGTH: 511
<212> TYPE: PRT
<213> ORGANISM: Artificial Sequence
<220> FEATURE:
<223> OTHER INFORMATION: Synthesized SIRP1alpha-CXCL10-SL bi-specific
      T-cell engager construct

<400> SEQUENCE: 60

```
Met Glu Thr Asp Thr Leu Leu Leu Trp Val Leu Leu Leu Trp Val Pro
1               5                   10                  15

Gly Ser Thr Gly Asp Glu Glu Leu Gln Ile Ile Gln Pro Asp Lys
            20                  25                  30

Ser Val Leu Val Ala Ala Gly Glu Thr Ala Thr Leu Arg Cys Thr Ile
            35                  40                  45

Thr Ser Leu Phe Pro Val Gly Pro Ile Gln Trp Phe Arg Gly Ala Gly
        50                  55                  60

Pro Gly Arg Val Leu Ile Tyr Asn Gln Arg Gly Pro Phe Pro Arg
65              70                  75                  80

Val Thr Thr Val Ser Asp Thr Thr Lys Arg Asn Asn Met Asp Phe Ser
                85                  90                  95

Ile Arg Ile Gly Asn Ile Thr Pro Ala Asp Ala Gly Thr Tyr Tyr Cys
            100                 105                 110

Ile Lys Phe Arg Lys Gly Ser Pro Asp Asp Val Glu Phe Lys Ser Gly
            115                 120                 125

Ala Gly Thr Glu Leu Ser Val Arg Ala Lys Pro Ser Ala Ser Asp Ile
        130                 135                 140

Lys Leu Gln Gln Ser Gly Ala Glu Leu Ala Arg Pro Gly Ala Ser Val
145                 150                 155                 160

Lys Met Ser Cys Lys Thr Ser Gly Tyr Thr Phe Thr Arg Tyr Thr Met
                165                 170                 175

His Trp Val Lys Gln Arg Pro Gly Gln Gly Leu Glu Trp Ile Gly Tyr
            180                 185                 190

Ile Asn Pro Ser Arg Gly Tyr Thr Asn Tyr Asn Gln Lys Phe Lys Asp
        195                 200                 205

Lys Ala Thr Leu Thr Thr Asp Lys Ser Ser Ser Thr Ala Tyr Met Gln
    210                 215                 220

Leu Ser Ser Leu Thr Ser Glu Asp Ser Ala Val Tyr Tyr Cys Ala Arg
225                 230                 235                 240

Tyr Tyr Asp Asp His Tyr Cys Leu Asp Tyr Trp Gly Gln Gly Thr Thr
```

-continued

```
                245                 250                 255
Leu Thr Val Ser Ser Val Glu Gly Gly Ser Gly Gly Ser Gly Gly Ser
                260                 265                 270

Gly Gly Ser Gly Gly Val Asp Asp Ile Gln Leu Thr Gln Ser Pro Ala
            275                 280                 285

Ile Met Ser Ala Ser Pro Gly Glu Lys Val Thr Met Thr Cys Arg Ala
        290                 295                 300

Ser Ser Ser Val Ser Tyr Met Asn Trp Tyr Gln Gln Lys Ser Gly Thr
305                 310                 315                 320

Ser Pro Lys Arg Trp Ile Tyr Asp Thr Ser Lys Val Ala Ser Gly Val
                325                 330                 335

Pro Tyr Arg Phe Ser Gly Ser Gly Ser Gly Thr Ser Tyr Ser Leu Thr
            340                 345                 350

Ile Ser Ser Met Glu Ala Glu Asp Ala Ala Thr Tyr Tyr Cys Gln Gln
        355                 360                 365

Trp Ser Ser Asn Pro Leu Thr Phe Gly Ala Gly Thr Lys Leu Glu Leu
                370                 375                 380

Lys His His His His His His Arg Arg Lys Arg Glu Gly Arg Gly Ser
385                 390                 395                 400

Leu Leu Thr Cys Gly Asp Val Glu Glu Asn Pro Gly Pro Met Asn Gln
                405                 410                 415

Thr Ala Ile Leu Ile Cys Cys Leu Ile Phe Leu Thr Leu Ser Gly Ile
            420                 425                 430

Gln Gly Val Pro Leu Ser Arg Thr Val Arg Cys Thr Cys Ile Ser Ile
        435                 440                 445

Ser Asn Gln Pro Val Asn Pro Arg Ser Leu Glu Lys Leu Glu Ile Ile
450                 455                 460

Pro Ala Ser Gln Phe Cys Pro Arg Val Glu Ile Ile Ala Thr Met Lys
465                 470                 475                 480

Lys Lys Gly Glu Lys Arg Cys Leu Asn Pro Glu Ser Lys Ala Ile Lys
                485                 490                 495

Asn Leu Leu Lys Ala Val Ser Lys Glu Arg Ser Lys Arg Ser Pro
                500                 505                 510
```

<210> SEQ ID NO 61
<211> LENGTH: 516
<212> TYPE: PRT
<213> ORGANISM: Artificial Sequence
<220> FEATURE:
<223> OTHER INFORMATION: Synthesized SIRP1alpha-CXCL10-LL bi-specific
      T-cell engager construct

<400> SEQUENCE: 61

```
Met Glu Thr Asp Thr Leu Leu Leu Trp Val Leu Leu Leu Trp Val Pro
1               5                   10                  15

Gly Ser Thr Gly Asp Glu Glu Glu Leu Gln Ile Ile Gln Pro Asp Lys
            20                  25                  30

Ser Val Leu Val Ala Ala Gly Glu Thr Ala Thr Leu Arg Cys Thr Ile
        35                  40                  45

Thr Ser Leu Phe Pro Val Gly Pro Ile Gln Trp Phe Arg Gly Ala Gly
    50                  55                  60

Pro Gly Arg Val Leu Ile Tyr Asn Gln Arg Gln Gly Pro Phe Pro Arg
65                  70                  75                  80

Val Thr Thr Val Ser Asp Thr Thr Lys Arg Asn Asn Met Asp Phe Ser
                85                  90                  95
```

```
Ile Arg Ile Gly Asn Ile Thr Pro Ala Asp Ala Gly Thr Tyr Tyr Cys
            100                 105                 110
Ile Lys Phe Arg Lys Gly Ser Pro Asp Asp Val Glu Phe Lys Ser Gly
        115                 120                 125
Ala Gly Thr Glu Leu Ser Val Arg Ala Lys Pro Ser Ala Ser Gly Gly
    130                 135                 140
Gly Gly Ser Asp Ile Lys Leu Gln Gln Ser Gly Ala Glu Leu Ala Arg
145                 150                 155                 160
Pro Gly Ala Ser Val Lys Met Ser Cys Lys Thr Ser Gly Tyr Thr Phe
                165                 170                 175
Thr Arg Tyr Thr Met His Trp Val Lys Gln Arg Pro Gly Gln Gly Leu
            180                 185                 190
Glu Trp Ile Gly Tyr Ile Asn Pro Ser Arg Gly Tyr Thr Asn Tyr Asn
        195                 200                 205
Gln Lys Phe Lys Asp Lys Ala Thr Leu Thr Thr Asp Lys Ser Ser Ser
    210                 215                 220
Thr Ala Tyr Met Gln Leu Ser Ser Leu Thr Ser Glu Asp Ser Ala Val
225                 230                 235                 240
Tyr Tyr Cys Ala Arg Tyr Tyr Asp Asp His Tyr Cys Leu Asp Tyr Trp
                245                 250                 255
Gly Gln Gly Thr Thr Leu Thr Val Ser Ser Val Glu Gly Gly Ser Gly
            260                 265                 270
Gly Ser Gly Gly Ser Gly Gly Ser Gly Gly Val Asp Asp Ile Gln Leu
        275                 280                 285
Thr Gln Ser Pro Ala Ile Met Ser Ala Ser Pro Gly Glu Lys Val Thr
    290                 295                 300
Met Thr Cys Arg Ala Ser Ser Ser Val Ser Tyr Met Asn Trp Tyr Gln
305                 310                 315                 320
Gln Lys Ser Gly Thr Ser Pro Lys Arg Trp Ile Tyr Asp Thr Ser Lys
                325                 330                 335
Val Ala Ser Gly Val Pro Tyr Arg Phe Ser Gly Ser Gly Ser Gly Thr
            340                 345                 350
Ser Tyr Ser Leu Thr Ile Ser Ser Met Glu Ala Glu Asp Ala Ala Thr
        355                 360                 365
Tyr Tyr Cys Gln Gln Trp Ser Ser Asn Pro Leu Thr Phe Gly Ala Gly
    370                 375                 380
Thr Lys Leu Glu Leu Lys His His His His His His Arg Arg Lys Arg
385                 390                 395                 400
Glu Gly Arg Gly Ser Leu Leu Thr Cys Gly Asp Val Glu Glu Asn Pro
                405                 410                 415
Gly Pro Met Asn Gln Thr Ala Ile Leu Ile Cys Cys Leu Ile Phe Leu
            420                 425                 430
Thr Leu Ser Gly Ile Gln Gly Val Pro Leu Ser Arg Thr Val Arg Cys
        435                 440                 445
Thr Cys Ile Ser Ile Ser Asn Gln Pro Val Asn Pro Arg Ser Leu Glu
    450                 455                 460
Lys Leu Glu Ile Ile Pro Ala Ser Gln Phe Cys Pro Arg Val Glu Ile
465                 470                 475                 480
Ile Ala Thr Met Lys Lys Gly Glu Lys Arg Cys Leu Asn Pro Glu
                485                 490                 495
Ser Lys Ala Ile Lys Asn Leu Leu Lys Ala Val Ser Lys Glu Arg Ser
                500                 505                 510
Lys Arg Ser Pro
```

-continued

515

<210> SEQ ID NO 62
<211> LENGTH: 698
<212> TYPE: PRT
<213> ORGANISM: Artificial Sequence
<220> FEATURE:
<223> OTHER INFORMATION: Synthesized PDL1-CD3-IL15 bi-specific T-cell
      engager construct

<400> SEQUENCE: 62

Met Glu Phe Gly Leu Ser Trp Val Phe Leu Val Ala Leu Phe Arg Gly
1               5                   10                  15

Val Gln Cys Asp Ile Lys Leu Gln Gln Ser Gly Ala Glu Leu Ala Arg
            20                  25                  30

Pro Gly Ala Ser Val Lys Met Ser Cys Lys Thr Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Val Glu Gly Gly Ser Gly
    130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
    210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Gly Gly Gly Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Gln Asp Val Ser Thr Ala Val Ala Trp Tyr Gln
    290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Tyr Leu Tyr His Pro Ala Thr Phe Gly Gln Gly
            355                 360                 365

Thr Lys Val Glu Ile Lys Arg Gly Gly Gly Ser Gly Gly Gly Gly
    370                 375                 380

Ser Gly Gly Gly Ser Glu Val Gln Leu Val Glu Ser Gly Gly
385                 390                 395                 400

Leu Val Gln Pro Gly Ser Leu Arg Leu Ser Cys Ala Ala Ser Gly
                405                 410                 415

Phe Thr Phe Ser Asp Ser Trp Ile His Trp Val Arg Gln Ala Pro Gly
            420                 425                 430

Lys Gly Leu Glu Trp Val Ala Trp Ile Ser Pro Tyr Gly Gly Ser Thr
        435                 440                 445

Tyr Tyr Ala Asp Ser Val Lys Gly Arg Phe Thr Ile Ser Ala Asp Thr
    450                 455                 460

Ser Lys Asn Thr Ala Tyr Leu Gln Met Asn Ser Leu Arg Ala Glu Asp
465                 470                 475                 480

Thr Ala Val Tyr Tyr Cys Ala Arg Arg His Trp Pro Gly Gly Phe Asp
                485                 490                 495

Tyr Trp Gly Gln Gly Thr Leu Val Thr Val Ser Ala His His His
            500                 505                 510

His His Arg Arg Lys Arg Glu Gly Arg Gly Ser Leu Leu Thr Cys Gly
        515                 520                 525

Asp Val Glu Glu Asn Pro Gly Pro Met Arg Ile Ser Lys Pro His Leu
    530                 535                 540

Arg Ser Ile Ser Ile Gln Cys Tyr Leu Cys Leu Leu Leu Asn Ser His
545                 550                 555                 560

Phe Leu Thr Glu Ala Gly Ile His Val Phe Ile Leu Gly Cys Phe Ser
                565                 570                 575

Ala Gly Leu Pro Lys Thr Glu Ala Asn Trp Val Asn Val Ile Ser Asp
            580                 585                 590

Leu Lys Lys Ile Glu Asp Leu Ile Gln Ser Met His Ile Asp Ala Thr
        595                 600                 605

Leu Tyr Thr Glu Ser Asp Val His Pro Ser Cys Lys Val Thr Ala Met
    610                 615                 620

Lys Cys Phe Leu Leu Glu Leu Gln Val Ile Ser Leu Glu Ser Gly Asp
625                 630                 635                 640

Ala Ser Ile His Asp Thr Val Glu Asn Leu Ile Ile Leu Ala Asn Asn
                645                 650                 655

Ser Leu Ser Ser Asn Gly Asn Val Thr Glu Ser Gly Cys Lys Glu Cys
            660                 665                 670

Glu Glu Leu Glu Glu Lys Asn Ile Lys Glu Phe Leu Gln Ser Phe Val
        675                 680                 685

His Ile Val Gln Met Phe Ile Asn Thr Ser
    690                 695

<210> SEQ ID NO 63
<211> LENGTH: 1140
<212> TYPE: PRT
<213> ORGANISM: Artificial Sequence
<220> FEATURE:
<223> OTHER INFORMATION: Synthesized PDL1-CD3-IL12 bi-specific T-cell
      engager construct

<400> SEQUENCE: 63

Met Glu Phe Gly Leu Ser Trp Val Phe Leu Val Ala Leu Phe Arg Gly
1               5                   10                  15

```
Val Gln Cys Asp Ile Lys Leu Gln Gln Ser Gly Ala Glu Leu Ala Arg
             20                  25                  30

Pro Gly Ala Ser Val Lys Met Ser Cys Lys Thr Ser Gly Tyr Thr Phe
         35                  40                  45

Thr Arg Tyr Thr Met His Trp Val Lys Gln Arg Pro Gly Gln Gly Leu
     50                  55                  60

Glu Trp Ile Gly Tyr Ile Asn Pro Ser Arg Gly Tyr Thr Asn Tyr Asn
 65                  70                  75                  80

Gln Lys Phe Lys Asp Lys Ala Thr Leu Thr Thr Asp Lys Ser Ser Ser
             85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
            115                 120                 125

Gly Gln Gly Thr Thr Leu Thr Val Ser Ser Val Glu Gly Gly Ser Gly
            130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
            195                 200                 205

Val Ala Ser Gly Val Pro Tyr Arg Phe Ser Gly Ser Gly Ser Gly Thr
            210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Gly Gly Gly Ser Asp Ile Gln Met Thr
            260                 265                 270

Gln Ser Pro Ser Ser Leu Ser Ala Ser Val Gly Asp Arg Val Thr Ile
            275                 280                 285

Thr Cys Arg Ala Ser Gln Asp Val Ser Thr Ala Val Ala Trp Tyr Gln
        290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Tyr Leu Tyr His Pro Ala Thr Phe Gly Gln Gly
            355                 360                 365

Thr Lys Val Glu Ile Lys Arg Gly Gly Gly Gly Ser Gly Gly Gly Gly
            370                 375                 380

Ser Gly Gly Gly Gly Ser Glu Val Gln Leu Val Glu Ser Gly Gly Gly
385                 390                 395                 400

Leu Val Gln Pro Gly Gly Ser Leu Arg Leu Ser Cys Ala Ala Ser Gly
                405                 410                 415

Phe Thr Phe Ser Asp Ser Trp Ile His Trp Val Arg Gln Ala Pro Gly
            420                 425                 430
```

```
Lys Gly Leu Glu Trp Val Ala Trp Ile Ser Pro Tyr Gly Ser Thr
            435                 440                 445
Tyr Tyr Ala Asp Ser Val Lys Gly Arg Phe Thr Ile Ser Ala Asp Thr
    450                 455                 460
Ser Lys Asn Thr Ala Tyr Leu Gln Met Asn Ser Leu Arg Ala Glu Asp
465                 470                 475                 480
Thr Ala Val Tyr Tyr Cys Ala Arg Arg His Trp Pro Gly Gly Phe Asp
                485                 490                 495
Tyr Trp Gly Gln Gly Thr Leu Val Thr Val Ser Ala His His His
            500                 505                 510
His His Arg Arg Lys Arg Glu Gly Arg Gly Ser Leu Leu Thr Cys Gly
    515                 520                 525
Asp Val Glu Glu Asn Pro Gly Pro Met Trp Pro Pro Gly Ser Ala Ser
530                 535                 540
Gln Pro Pro Pro Ser Pro Ala Ala Ala Thr Gly Leu His Pro Ala Ala
545                 550                 555                 560
Arg Pro Val Ser Leu Gln Cys Arg Leu Ser Met Cys Pro Ala Arg Ser
                565                 570                 575
Leu Leu Leu Val Ala Thr Leu Val Leu Leu Asp His Leu Ser Leu Ala
            580                 585                 590
Arg Asn Leu Pro Val Ala Thr Pro Asp Pro Gly Met Phe Pro Cys Leu
    595                 600                 605
His His Ser Gln Asn Leu Leu Arg Ala Val Ser Asn Met Leu Gln Lys
610                 615                 620
Ala Arg Gln Thr Leu Glu Phe Tyr Pro Cys Thr Ser Glu Glu Ile Asp
625                 630                 635                 640
His Glu Asp Ile Thr Lys Asp Lys Thr Ser Thr Val Glu Ala Cys Leu
                645                 650                 655
Pro Leu Glu Leu Thr Lys Asn Glu Ser Cys Leu Asn Ser Arg Glu Thr
            660                 665                 670
Ser Phe Ile Thr Asn Gly Ser Cys Leu Ala Ser Arg Lys Thr Ser Phe
    675                 680                 685
Met Met Ala Leu Cys Leu Ser Ser Ile Tyr Glu Asp Leu Lys Met Tyr
690                 695                 700
Gln Val Glu Phe Lys Thr Met Asn Ala Lys Leu Leu Met Asp Pro Lys
705                 710                 715                 720
Arg Gln Ile Phe Leu Asp Gln Asn Met Leu Ala Val Ile Asp Glu Leu
                725                 730                 735
Met Gln Ala Leu Asn Phe Asn Ser Glu Thr Val Pro Gln Lys Ser Ser
            740                 745                 750
Leu Glu Glu Pro Asp Phe Tyr Lys Thr Lys Ile Lys Leu Cys Ile Leu
    755                 760                 765
Leu His Ala Phe Arg Ile Arg Ala Val Thr Ile Asp Arg Val Met Ser
770                 775                 780
Tyr Leu Asn Ala Ser Arg Arg Lys Arg Glu Gly Arg Gly Ser Leu Leu
785                 790                 795                 800
Thr Cys Gly Asp Val Glu Glu Asn Pro Gly Pro Pro Met Cys His Gln
                805                 810                 815
Gln Leu Val Ile Ser Trp Phe Ser Leu Val Phe Leu Ala Ser Pro Leu
            820                 825                 830
Val Ala Ile Trp Glu Leu Lys Lys Asp Val Tyr Val Glu Leu Asp
    835                 840                 845
Trp Tyr Pro Asp Ala Pro Gly Glu Met Val Val Leu Thr Cys Asp Thr
```

```
                      850                 855                 860
Pro Glu Glu Asp Gly Ile Thr Trp Thr Leu Asp Gln Ser Ser Glu Val
865                 870                 875                 880

Leu Gly Ser Gly Lys Thr Leu Thr Ile Gln Val Lys Glu Phe Gly Asp
                885                 890                 895

Ala Gly Gln Tyr Thr Cys His Lys Gly Gly Glu Val Leu Ser His Ser
                900                 905                 910

Leu Leu Leu Leu His Lys Lys Glu Asp Gly Ile Trp Ser Thr Asp Ile
                915                 920                 925

Leu Lys Asp Gln Lys Glu Pro Lys Asn Lys Thr Phe Leu Arg Cys Glu
            930                 935                 940

Ala Lys Asn Tyr Ser Gly Arg Phe Thr Cys Trp Trp Leu Thr Thr Ile
945                 950                 955                 960

Ser Thr Asp Leu Thr Phe Ser Val Lys Ser Arg Gly Ser Ser Asp
                965                 970                 975

Pro Gln Gly Val Thr Cys Gly Ala Ala Thr Leu Ser Ala Glu Arg Val
                980                 985                 990

Arg Gly Asp Asn Lys Glu Tyr Glu Tyr Ser Val Glu Cys Gln Glu Asp
            995                 1000                1005

Ser Ala Cys Pro Ala Ala Glu Glu Ser Leu Pro Ile Glu Val Met
        1010                1015                1020

Val Asp Ala Val His Lys Leu Lys Tyr Glu Asn Tyr Thr Ser Ser
        1025                1030                1035

Phe Phe Ile Arg Asp Ile Ile Lys Pro Asp Pro Lys Asn Leu
        1040                1045                1050

Gln Leu Lys Pro Leu Lys Asn Ser Arg Gln Val Glu Val Ser Trp
        1055                1060                1065

Glu Tyr Pro Asp Thr Trp Ser Thr Pro His Ser Tyr Phe Ser Leu
        1070                1075                1080

Thr Phe Cys Val Gln Val Gln Gly Lys Ser Lys Arg Glu Lys Lys
        1085                1090                1095

Asp Arg Val Phe Thr Asp Lys Thr Ser Ala Thr Val Ile Cys Arg
        1100                1105                1110

Lys Asn Ala Ser Ile Ser Val Arg Ala Gln Asp Arg Tyr Tyr Ser
        1115                1120                1125

Ser Ser Trp Ser Glu Trp Ala Ser Val Pro Cys Ser
        1130                1135                1140

<210> SEQ ID NO 64
<211> LENGTH: 634
<212> TYPE: PRT
<213> ORGANISM: Artificial Sequence
<220> FEATURE:
<223> OTHER INFORMATION: Synthesized PDL1-CD3-CXCL10 bi-specific T-cell
      engager construct

<400> SEQUENCE: 64

Met Glu Phe Gly Leu Ser Trp Val Phe Leu Val Ala Leu Phe Arg Gly
1               5                   10                  15

Val Gln Cys Asp Ile Lys Leu Gln Gln Ser Gly Ala Glu Leu Ala Arg
            20                  25                  30

Pro Gly Ala Ser Val Lys Met Ser Cys Lys Thr Ser Gly Tyr Thr Phe
        35                  40                  45

Thr Arg Tyr Thr Met His Trp Val Lys Gln Arg Pro Gly Gln Gly Leu
    50                  55                  60
```

```
Glu Trp Ile Gly Tyr Ile Asn Pro Ser Arg Gly Tyr Thr Asn Tyr Asn
 65                  70                  75                  80

Gln Lys Phe Lys Asp Lys Ala Thr Leu Thr Thr Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Val Glu Gly Gly Ser Gly
        130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
            245                 250                 255

Thr Lys Leu Glu Leu Lys Gly Gly Gly Ser Asp Ile Gln Met Thr
        260                 265                 270

Gln Ser Pro Ser Ser Leu Ser Ala Ser Val Gly Asp Arg Val Thr Ile
        275                 280                 285

Thr Cys Arg Ala Ser Gln Asp Val Ser Thr Ala Val Ala Trp Tyr Gln
        290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Tyr Leu Tyr His Pro Ala Thr Phe Gly Gln Gly
        355                 360                 365

Thr Lys Val Glu Ile Lys Arg Gly Gly Gly Gly Ser Gly Gly Gly Gly
        370                 375                 380

Ser Gly Gly Gly Ser Glu Val Gln Leu Val Glu Ser Gly Gly Gly
385                 390                 395                 400

Leu Val Gln Pro Gly Gly Ser Leu Arg Leu Ser Cys Ala Ala Ser Gly
                405                 410                 415

Phe Thr Phe Ser Asp Ser Trp Ile His Trp Val Arg Gln Ala Pro Gly
            420                 425                 430

Lys Gly Leu Glu Trp Val Ala Trp Ile Ser Pro Tyr Gly Gly Ser Thr
        435                 440                 445

Tyr Tyr Ala Asp Ser Val Lys Gly Arg Phe Thr Ile Ser Ala Asp Thr
        450                 455                 460

Ser Lys Asn Thr Ala Tyr Leu Gln Met Asn Ser Leu Arg Ala Glu Asp
465                 470                 475                 480

Thr Ala Val Tyr Tyr Cys Ala Arg Arg His Trp Pro Gly Gly Phe Asp
```

```
                  485                 490                 495
Tyr Trp Gly Gln Gly Thr Leu Val Thr Val Ser Ala His His His
            500                 505                 510
His His Arg Arg Lys Arg Glu Gly Arg Gly Ser Leu Leu Thr Cys Gly
            515                 520                 525
Asp Val Glu Glu Asn Pro Gly Pro Met Asn Gln Thr Ala Ile Leu Ile
            530                 535                 540
Cys Cys Leu Ile Phe Leu Thr Leu Ser Gly Ile Gln Gly Val Pro Leu
545                 550                 555                 560
Ser Arg Thr Val Arg Cys Thr Cys Ile Ser Ile Ser Asn Gln Pro Val
                565                 570                 575
Asn Pro Arg Ser Leu Glu Lys Leu Glu Ile Ile Pro Ala Ser Gln Phe
            580                 585                 590
Cys Pro Arg Val Glu Ile Ile Ala Thr Met Lys Lys Lys Gly Glu Lys
            595                 600                 605
Arg Cys Leu Asn Pro Glu Ser Lys Ala Ile Lys Asn Leu Leu Lys Ala
            610                 615                 620
Val Ser Lys Glu Arg Ser Lys Arg Ser Pro
625                 630
```

```
<210> SEQ ID NO 65
<211> LENGTH: 1120
<212> TYPE: PRT
<213> ORGANISM: Artificial Sequence
<220> FEATURE:
<223> OTHER INFORMATION: Synthesized SIRP1alpha-MMP9-SL bi-specific
      T-cell engager construct

<400> SEQUENCE: 65
```

```
Met Glu Thr Asp Thr Leu Leu Leu Trp Val Leu Leu Leu Trp Val Pro
1               5                   10                  15
Gly Ser Thr Gly Asp Glu Glu Glu Leu Gln Ile Ile Gln Pro Asp Lys
            20                  25                  30
Ser Val Leu Val Ala Ala Gly Glu Thr Ala Thr Leu Arg Cys Thr Ile
        35                  40                  45
Thr Ser Leu Phe Pro Val Gly Pro Ile Gln Trp Phe Arg Gly Ala Gly
    50                  55                  60
Pro Gly Arg Val Leu Ile Tyr Asn Gln Arg Gln Gly Pro Phe Pro Arg
65                  70                  75                  80
Val Thr Thr Val Ser Asp Thr Thr Lys Arg Asn Asn Met Asp Phe Ser
                85                  90                  95
Ile Arg Ile Gly Asn Ile Thr Pro Ala Asp Ala Gly Thr Tyr Tyr Cys
            100                 105                 110
Ile Lys Phe Arg Lys Gly Ser Pro Asp Asp Val Glu Phe Lys Ser Gly
        115                 120                 125
Ala Gly Thr Glu Leu Ser Val Arg Ala Lys Pro Ser Ala Ser Asp Ile
    130                 135                 140
Lys Leu Gln Gln Ser Gly Ala Glu Leu Ala Arg Pro Gly Ala Ser Val
145                 150                 155                 160
Lys Met Ser Cys Lys Thr Ser Gly Tyr Thr Phe Thr Arg Tyr Thr Met
                165                 170                 175
His Trp Val Lys Gln Arg Pro Gly Gln Gly Leu Glu Trp Ile Gly Tyr
            180                 185                 190
Ile Asn Pro Ser Arg Gly Tyr Thr Asn Tyr Asn Gln Lys Phe Lys Asp
        195                 200                 205
```

-continued

```
Lys Ala Thr Leu Thr Thr Asp Lys Ser Ser Thr Ala Tyr Met Gln
210                 215                 220
Leu Ser Ser Leu Thr Ser Glu Asp Ser Ala Val Tyr Tyr Cys Ala Arg
225                 230                 235                 240
Tyr Tyr Asp Asp His Tyr Cys Leu Asp Tyr Trp Gly Gln Gly Thr Thr
            245                 250                 255
Leu Thr Val Ser Ser Val Glu Gly Gly Ser Gly Gly Ser Gly Gly Ser
            260                 265                 270
Gly Gly Ser Gly Gly Val Asp Asp Ile Gln Leu Thr Gln Ser Pro Ala
        275                 280                 285
Ile Met Ser Ala Ser Pro Gly Glu Lys Val Thr Met Thr Cys Arg Ala
    290                 295                 300
Ser Ser Ser Val Ser Tyr Met Asn Trp Tyr Gln Gln Lys Ser Gly Thr
305                 310                 315                 320
Ser Pro Lys Arg Trp Ile Tyr Asp Thr Ser Lys Val Ala Ser Gly Val
            325                 330                 335
Pro Tyr Arg Phe Ser Gly Ser Gly Ser Gly Thr Ser Tyr Ser Leu Thr
            340                 345                 350
Ile Ser Ser Met Glu Ala Glu Asp Ala Ala Thr Tyr Tyr Cys Gln Gln
        355                 360                 365
Trp Ser Ser Asn Pro Leu Thr Phe Gly Ala Gly Thr Lys Leu Glu Leu
    370                 375                 380
Lys His His His His His His Arg Arg Lys Arg Glu Gly Arg Gly Ser
385                 390                 395                 400
Leu Leu Thr Cys Gly Asp Val Glu Glu Asn Pro Gly Pro Met Ser Leu
            405                 410                 415
Trp Gln Pro Leu Val Leu Val Leu Leu Val Leu Gly Cys Cys Phe Ala
            420                 425                 430
Ala Pro Arg Gln Arg Gln Ser Thr Leu Val Leu Phe Pro Gly Asp Leu
        435                 440                 445
Arg Thr Asn Leu Thr Asp Arg Gln Leu Ala Glu Glu Tyr Leu Tyr Arg
    450                 455                 460
Tyr Gly Tyr Thr Arg Val Ala Glu Met Arg Gly Glu Ser Lys Ser Leu
465                 470                 475                 480
Gly Pro Ala Leu Leu Leu Leu Gln Lys Gln Leu Ser Leu Pro Glu Thr
            485                 490                 495
Gly Glu Leu Asp Ser Ala Thr Leu Lys Ala Met Arg Thr Pro Arg Cys
            500                 505                 510
Gly Val Pro Asp Leu Gly Arg Phe Gln Thr Phe Glu Gly Asp Leu Lys
        515                 520                 525
Trp His His His Asn Ile Thr Tyr Trp Ile Gln Asn Tyr Ser Glu Asp
    530                 535                 540
Leu Pro Arg Ala Val Ile Asp Asp Ala Phe Ala Arg Ala Phe Ala Leu
545                 550                 555                 560
Trp Ser Ala Val Thr Pro Leu Thr Phe Thr Arg Val Tyr Ser Arg Asp
            565                 570                 575
Ala Asp Ile Val Ile Gln Phe Gly Val Ala Glu His Gly Asp Gly Tyr
            580                 585                 590
Pro Phe Asp Gly Lys Asp Gly Leu Leu Ala His Ala Phe Pro Pro Gly
        595                 600                 605
Pro Gly Ile Gln Gly Asp Ala His Phe Asp Asp Glu Leu Trp Ser
    610                 615                 620
Leu Gly Lys Gly Val Val Val Pro Thr Arg Phe Gly Asn Ala Asp Gly
```

-continued

```
              625                 630                 635                 640
        Ala Ala Cys His Phe Pro Phe Ile Phe Glu Gly Arg Ser Tyr Ser Ala
                        645                 650                 655
        Cys Thr Thr Asp Gly Arg Ser Asp Gly Leu Pro Trp Cys Ser Thr Thr
                        660                 665                 670
        Ala Asn Tyr Asp Thr Asp Arg Phe Gly Phe Cys Pro Ser Glu Arg
                        675                 680                 685
        Leu Tyr Thr Arg Asp Gly Asn Ala Asp Gly Lys Pro Cys Gln Phe Pro
                690                 695                 700
        Phe Ile Phe Gln Gly Gln Ser Tyr Ser Ala Cys Thr Thr Asp Gly Arg
        705                 710                 715                 720
        Ser Asp Gly Tyr Arg Trp Cys Ala Thr Thr Ala Asn Tyr Asp Arg Asp
                        725                 730                 735
        Lys Leu Phe Gly Phe Cys Pro Thr Arg Ala Asp Ser Thr Val Met Gly
                        740                 745                 750
        Gly Asn Ser Ala Gly Glu Leu Cys Val Phe Pro Phe Thr Phe Leu Gly
                        755                 760                 765
        Lys Glu Tyr Ser Thr Cys Thr Ser Glu Gly Arg Gly Asp Gly Arg Leu
                770                 775                 780
        Trp Cys Ala Thr Thr Ser Asn Phe Asp Ser Asp Lys Lys Trp Gly Phe
        785                 790                 795                 800
        Cys Pro Asp Gln Gly Tyr Ser Leu Phe Leu Val Ala Ala His Glu Phe
                        805                 810                 815
        Gly His Ala Leu Gly Leu Asp His Ser Ser Val Pro Glu Ala Leu Met
                        820                 825                 830
        Tyr Pro Met Tyr Arg Phe Thr Glu Gly Pro Pro Leu His Lys Asp Asp
                        835                 840                 845
        Val Asn Gly Ile Arg His Leu Tyr Gly Pro Arg Pro Glu Pro Glu Pro
                850                 855                 860
        Arg Pro Pro Thr Thr Thr Thr Pro Gln Pro Thr Ala Pro Pro Thr Val
        865                 870                 875                 880
        Cys Pro Thr Gly Pro Pro Thr Val His Pro Ser Glu Arg Pro Thr Ala
                        885                 890                 895
        Gly Pro Thr Gly Pro Pro Ser Ala Gly Pro Thr Gly Pro Pro Thr Ala
                        900                 905                 910
        Gly Pro Ser Thr Ala Thr Thr Val Pro Leu Ser Pro Val Asp Asp Ala
                        915                 920                 925
        Cys Asn Val Asn Ile Phe Asp Ala Ile Ala Glu Ile Gly Asn Gln Leu
                        930                 935                 940
        Tyr Leu Phe Lys Asp Gly Lys Tyr Trp Arg Phe Ser Glu Gly Arg Gly
        945                 950                 955                 960
        Ser Arg Pro Gln Gly Pro Phe Leu Ile Ala Asp Lys Trp Pro Ala Leu
                        965                 970                 975
        Pro Arg Lys Leu Asp Ser Val Phe Glu Glu Pro Leu Ser Lys Lys Leu
                        980                 985                 990
        Phe Phe Phe Ser Gly Arg Gln Val Trp Val Tyr Thr Gly Ala Ser Val
                        995                1000                1005
        Leu Gly Pro Arg Arg Leu Asp Lys Leu Gly Leu Gly Ala Asp Val
                1010                1015                1020
        Ala Gln Val Thr Gly Ala Leu Arg Ser Gly Arg Gly Lys Met Leu
                1025                1030                1035
        Leu Phe Ser Gly Arg Arg Leu Trp Arg Phe Asp Val Lys Ala Gln
                1040                1045                1050
```

```
Met Val Asp Pro Arg Ser Ala Ser Glu Val Asp Arg Met Phe Pro
        1055                1060                1065

Gly Val Pro Leu Asp Thr His Asp Val Phe Gln Tyr Arg Glu Lys
        1070                1075                1080

Ala Tyr Phe Cys Gln Asp Arg Phe Tyr Trp Arg Val Ser Ser Arg
        1085                1090                1095

Ser Glu Leu Asn Gln Val Gln Val Gly Tyr Val Thr Tyr Asp
        1100                1105                1110

Ile Leu Gln Cys Pro Glu Asp
        1115                1120

<210> SEQ ID NO 66
<211> LENGTH: 1125
<212> TYPE: PRT
<213> ORGANISM: Artificial Sequence
<220> FEATURE:
<223> OTHER INFORMATION: Synthesized SIRP1alpha-MMP9-LL bi-specific
      T-cell engager construct

<400> SEQUENCE: 66

Met Glu Thr Asp Thr Leu Leu Leu Trp Val Leu Leu Leu Trp Val Pro
1               5                   10                  15

Gly Ser Thr Gly Asp Glu Glu Leu Gln Ile Ile Gln Pro Asp Lys
            20                  25                  30

Ser Val Leu Val Ala Ala Gly Glu Thr Ala Thr Leu Arg Cys Thr Ile
        35                  40                  45

Thr Ser Leu Phe Pro Val Gly Pro Ile Gln Trp Phe Arg Gly Ala Gly
    50                  55                  60

Pro Gly Arg Val Leu Ile Tyr Asn Gln Arg Gln Gly Pro Phe Pro Arg
65                  70                  75                  80

Val Thr Thr Val Ser Asp Thr Thr Lys Arg Asn Asn Met Asp Phe Ser
                85                  90                  95

Ile Arg Ile Gly Asn Ile Thr Pro Ala Asp Ala Gly Thr Tyr Tyr Cys
            100                 105                 110

Ile Lys Phe Arg Lys Gly Ser Pro Asp Asp Val Glu Phe Lys Ser Gly
        115                 120                 125

Ala Gly Thr Glu Leu Ser Val Arg Ala Lys Pro Ser Ala Ser Gly Gly
    130                 135                 140

Gly Gly Ser Asp Ile Lys Leu Gln Gln Ser Gly Ala Glu Leu Ala Arg
145                 150                 155                 160

Pro Gly Ala Ser Val Lys Met Ser Cys Lys Thr Ser Gly Tyr Thr Phe
                165                 170                 175

Thr Arg Tyr Thr Met His Trp Val Lys Gln Arg Pro Gly Gln Gly Leu
            180                 185                 190

Glu Trp Ile Gly Tyr Ile Asn Pro Ser Arg Gly Tyr Thr Asn Tyr Asn
        195                 200                 205

Gln Lys Phe Lys Asp Lys Ala Thr Leu Thr Thr Asp Lys Ser Ser Ser
    210                 215                 220

Thr Ala Tyr Met Gln Leu Ser Ser Leu Thr Ser Glu Asp Ser Ala Val
225                 230                 235                 240

Tyr Tyr Cys Ala Arg Tyr Tyr Asp Asp His Tyr Cys Leu Asp Tyr Trp
                245                 250                 255

Gly Gln Gly Thr Thr Leu Thr Val Ser Ser Val Glu Gly Gly Ser Gly
            260                 265                 270

Gly Ser Gly Gly Ser Gly Gly Ser Gly Gly Val Asp Asp Ile Gln Leu
```

```
            275                 280                 285
Thr Gln Ser Pro Ala Ile Met Ser Ala Ser Pro Gly Glu Lys Val Thr
290                 295                 300
Met Thr Cys Arg Ala Ser Ser Val Ser Tyr Met Asn Trp Tyr Gln
305                 310                 315                 320
Gln Lys Ser Gly Thr Ser Pro Lys Arg Trp Ile Tyr Asp Thr Ser Lys
                325                 330                 335
Val Ala Ser Gly Val Pro Tyr Arg Phe Ser Gly Ser Gly Ser Gly Thr
                340                 345                 350
Ser Tyr Ser Leu Thr Ile Ser Ser Met Glu Ala Glu Asp Ala Ala Thr
                355                 360                 365
Tyr Tyr Cys Gln Gln Trp Ser Ser Asn Pro Leu Thr Phe Gly Ala Gly
                370                 375                 380
Thr Lys Leu Glu Leu Lys His His His His His His Arg Arg Lys Arg
385                 390                 395                 400
Glu Gly Arg Gly Ser Leu Leu Thr Cys Gly Asp Val Glu Glu Asn Pro
                405                 410                 415
Gly Pro Met Ser Leu Trp Gln Pro Leu Val Leu Val Leu Leu Val Leu
                420                 425                 430
Gly Cys Cys Phe Ala Ala Pro Arg Gln Arg Gln Ser Thr Leu Val Leu
                435                 440                 445
Phe Pro Gly Asp Leu Arg Thr Asn Leu Thr Asp Arg Gln Leu Ala Glu
                450                 455                 460
Glu Tyr Leu Tyr Arg Tyr Gly Tyr Thr Arg Val Ala Glu Met Arg Gly
465                 470                 475                 480
Glu Ser Lys Ser Leu Gly Pro Ala Leu Leu Leu Leu Gln Lys Gln Leu
                485                 490                 495
Ser Leu Pro Glu Thr Gly Glu Leu Asp Ser Ala Thr Leu Lys Ala Met
                500                 505                 510
Arg Thr Pro Arg Cys Gly Val Pro Asp Leu Gly Arg Phe Gln Thr Phe
                515                 520                 525
Glu Gly Asp Leu Lys Trp His His His Asn Ile Thr Tyr Trp Ile Gln
                530                 535                 540
Asn Tyr Ser Glu Asp Leu Pro Arg Ala Val Ile Asp Asp Ala Phe Ala
545                 550                 555                 560
Arg Ala Phe Ala Leu Trp Ser Ala Val Thr Pro Leu Thr Phe Thr Arg
                565                 570                 575
Val Tyr Ser Arg Asp Ala Asp Ile Val Ile Gln Phe Gly Val Ala Glu
                580                 585                 590
His Gly Asp Gly Tyr Pro Phe Asp Gly Lys Asp Gly Leu Leu Ala His
                595                 600                 605
Ala Phe Pro Pro Gly Pro Gly Ile Gln Gly Asp Ala His Phe Asp Asp
                610                 615                 620
Asp Glu Leu Trp Ser Leu Gly Lys Gly Val Val Val Pro Thr Arg Phe
625                 630                 635                 640
Gly Asn Ala Asp Gly Ala Ala Cys His Phe Pro Phe Ile Phe Glu Gly
                645                 650                 655
Arg Ser Tyr Ser Ala Cys Thr Thr Asp Gly Arg Ser Asp Gly Leu Pro
                660                 665                 670
Trp Cys Ser Thr Thr Ala Asn Tyr Asp Thr Asp Arg Phe Gly Phe
                675                 680                 685
Cys Pro Ser Glu Arg Leu Tyr Thr Arg Asp Gly Asn Ala Asp Gly Lys
                690                 695                 700
```

```
Pro Cys Gln Phe Pro Phe Ile Phe Gln Gly Gln Ser Tyr Ser Ala Cys
705                 710                 715                 720

Thr Thr Asp Gly Arg Ser Asp Gly Tyr Arg Trp Cys Ala Thr Thr Ala
            725                 730                 735

Asn Tyr Asp Arg Asp Lys Leu Phe Gly Phe Cys Pro Thr Arg Ala Asp
        740                 745                 750

Ser Thr Val Met Gly Gly Asn Ser Ala Gly Glu Leu Cys Val Phe Pro
    755                 760                 765

Phe Thr Phe Leu Gly Lys Glu Tyr Ser Thr Cys Thr Ser Glu Gly Arg
770                 775                 780

Gly Asp Gly Arg Leu Trp Cys Ala Thr Thr Ser Asn Phe Asp Ser Asp
785                 790                 795                 800

Lys Lys Trp Gly Phe Cys Pro Asp Gln Gly Tyr Ser Leu Phe Leu Val
                805                 810                 815

Ala Ala His Glu Phe Gly His Ala Leu Gly Leu Asp His Ser Ser Val
            820                 825                 830

Pro Glu Ala Leu Met Tyr Pro Met Tyr Arg Phe Thr Glu Gly Pro Pro
        835                 840                 845

Leu His Lys Asp Asp Val Asn Gly Ile Arg His Leu Tyr Gly Pro Arg
    850                 855                 860

Pro Glu Pro Glu Pro Arg Pro Pro Thr Thr Thr Pro Gln Pro Thr
865                 870                 875                 880

Ala Pro Pro Thr Val Cys Pro Thr Gly Pro Pro Thr Val His Pro Ser
                885                 890                 895

Glu Arg Pro Thr Ala Gly Pro Thr Gly Pro Pro Ser Ala Gly Pro Thr
            900                 905                 910

Gly Pro Pro Thr Ala Gly Pro Ser Thr Ala Thr Thr Val Pro Leu Ser
        915                 920                 925

Pro Val Asp Asp Ala Cys Asn Val Asn Ile Phe Asp Ala Ile Ala Glu
    930                 935                 940

Ile Gly Asn Gln Leu Tyr Leu Phe Lys Asp Gly Lys Tyr Trp Arg Phe
945                 950                 955                 960

Ser Glu Gly Arg Gly Ser Arg Pro Gln Gly Pro Phe Leu Ile Ala Asp
                965                 970                 975

Lys Trp Pro Ala Leu Pro Arg Lys Leu Asp Ser Val Phe Glu Glu Pro
            980                 985                 990

Leu Ser Lys Lys Leu Phe Phe Phe Ser Gly Arg Gln Val Trp Val Tyr
        995                 1000                1005

Thr Gly Ala Ser Val Leu Gly Pro Arg Arg Leu Asp Lys Leu Gly
    1010            1015            1020

Leu Gly Ala Asp Val Ala Gln Val Thr Gly Ala Leu Arg Ser Gly
    1025            1030            1035

Arg Gly Lys Met Leu Leu Phe Ser Gly Arg Arg Leu Trp Arg Phe
    1040            1045            1050

Asp Val Lys Ala Gln Met Val Asp Pro Arg Ser Ala Ser Glu Val
    1055            1060            1065

Asp Arg Met Phe Pro Gly Val Pro Leu Asp Thr His Asp Val Phe
    1070            1075            1080

Gln Tyr Arg Glu Lys Ala Tyr Phe Cys Gln Asp Arg Phe Tyr Trp
    1085            1090            1095

Arg Val Ser Ser Arg Ser Glu Leu Asn Gln Val Asp Gln Val Gly
    1100            1105            1110
```

Tyr Val Thr Tyr Asp Ile Leu Gln Cys Pro Glu Asp
    1115               1120               1125

<210> SEQ ID NO 67
<211> LENGTH: 2814
<212> TYPE: DNA
<213> ORGANISM: Artificial Sequence
<220> FEATURE:
<223> OTHER INFORMATION: Synthesized polynucleotide encoding SIRP1alpha-
      PDL1-CD3-Fc-SL bi-specific T-cell engager construct

<400> SEQUENCE: 67

| | | |
|---|---|---|
| atggaaaccg atacacttct gttgtgggtg ctgctgctgt gggtccctgg ttcaacaggc | 60 |
| gattatccct acgatgtgcc cgactacgca ggcgctcagc cagctgatga tatccagatg | 120 |
| acacagagcc catcatctct gtctgcaagc gtaggagacc gagtcaccat acatgcaga | 180 |
| gcctcccaag acgtttccac agcagtggcc tggtatcagc aaaaacctgg taaggcgccc | 240 |
| aagcttctca tctattcagc cagttttctg tatagcggcg ttcccagccg attctctggc | 300 |
| tctggatccg gcacggactt tactttgaca atttcctctc ttcagcccga agattttgca | 360 |
| acctactact gtcagcaata tctctaccat ccagccacat cggacaggg caccaaagtc | 420 |
| gaaatcaaaa gaggcggcgg cggcagtggc ggcggggggtt caggaggcgg gggttctgaa | 480 |
| gtgcaactcg ttgaaagcgt aggagggctt gtccaacctg gcgggtcact gcggttgagc | 540 |
| tgcgccgcaa gcggattcac cttctcagac tcttggatcc attgggtgcg ccaggctccc | 600 |
| ggaaaaggct ggaatgggt tgcttggatt tcaccgtatg gcggttccac atactacgct | 660 |
| gacagcgtta aggtcgatt caccatctct gcagatactt caaaaaacac agcctacctt | 720 |
| cagatgaata gtttgcgcgc cgaggacaca gcggtttatt attgtgccct aagacattgg | 780 |
| cccggcggtt tcgactactg ggggcaaggt acgttggtga ctgtgagcgc cgtagatgaa | 840 |
| gcaaaatctt gtgacaaaac ccataccctgc ccaccatgcc cagccccaga acttcttggc | 900 |
| gtaccctctg tcttccttt ccctccgaag cccaaggata ccctgatgat cagccgaacc | 960 |
| ccggaggtaa catgtgtggt ggtcgatgtt agccatgagg atcctgaagt caaatttaac | 1020 |
| tggtatgtag acggtgttga ggtgcacaac gctaaaacta gcccaggga ggagcagtac | 1080 |
| aactcaaccct atcgcgtcgt atctgtgctt accgtcctgc atcaagactg gctcaatggt | 1140 |
| aaggaatata atgtaaagt gagtaacaag gcactgccag cacctatcga aaaaccatc | 1200 |
| tcaaaggcga agggacagcc cagggaaccc caggtctata ctctgcaacc ttctcgggat | 1260 |
| gaattgacca gaaccaagt tagcctgaca tgtctggtga aggtttctta ccaagcgat | 1320 |
| atagctgtcg agtgggagtc caatggccaa cctgagaaca attataagac cacccaccc | 1380 |
| gttctggaca gcgacggatc ctttttcctg tactcaaaac tcactgtcga taatcaaga | 1440 |
| tggcaacaag gcaacgtttt tagctgtagc gtgatgcacg aagcacttca taatcactat | 1500 |
| acacagaagt cactctctct ttctccagga aaggttgacg aacagaaatt gatatccgag | 1560 |
| gaagatctca ataggaggaa gagagaaggc aggggagcc ttctcacttg cggcgatgtc | 1620 |
| gaggaaaatc cggggcctat ggagaccgat accctgctct tgtgggtttt gcttctttgg | 1680 |
| gtgccaggat ctacaggtga tgaagaagaa ttgcagatca tccaaccaga caaatccgta | 1740 |
| ctcgtggccg caggagagac cgctaccctc agatgtacca tcacttctct cttccccgtt | 1800 |
| ggccccatcc agtggtttcg aggcgcagga ccaggacgag tgcttattta caatcaacga | 1860 |
| cagggcccat tcccaagagt gacaacagta tccgatacca ccaagcgcaa taatatggac | 1920 |
| tttagcatta gaatcggcaa cataacaccc gctgacgccg gtacatacta ttgtattaaa | 1980 |

```
tttcgaaagg gctcaccaga cgacgtggaa tttaagtcag gggccggaac cgaactctca   2040
gttagagcaa aaccttctgc tagcgacatc aagctgcagc agagcggcgc cgagctggcc   2100
aggcccggcg ccagcgtgaa gatgagctgc aagaccagcg gctacacctt caccaggtac   2160
accatgcact gggtgaagca gaggcccggc cagggcctgg agtggatcgg ctacatcaac   2220
cccagcaggg gctacaccaa ctacaaccag aagttcaagg acaaggccac cctgaccacc   2280
gacaagagca gcagcaccgc ctacatgcag ctgagcagcc tgaccagcga ggacagcgcc   2340
gtgtactact gcgccaggta ctacgacgac cactactgcc tggactactg gggccagggc   2400
accaccctga ccgtgagcag cgtggagggc ggcagcggcg gcagcggcgg cagcggcggc   2460
agcggcggcg tggacgacat ccagctgacc cagagccccg ccatcatgag cgccagcccc   2520
ggcgagaagg tgaccatgac ctgcagggcc agcagcagcg tgagctacat gaactggtac   2580
cagcagaaga gcggcaccag ccccaagagg tggatctacg acaccagcaa ggtggccagc   2640
ggcgtgccct acaggttcag cggcagcggc agcggcacca gctacagcct gaccatcagc   2700
agcatggagg ccgaggacgc cgccacctac tactgccagc agtggagcag caacccsctg   2760
acctccggcg ccggcaccaa gctggagctg aagcaccacc atcatcacca ctga         2814
```

<210> SEQ ID NO 68
<211> LENGTH: 937
<212> TYPE: PRT
<213> ORGANISM: Artificial Sequence
<220> FEATURE:
<223> OTHER INFORMATION: Synthesized SIRP1alpha-PDL1-CD3-Fc-SL
      bi-specific T-cell engager construct

<400> SEQUENCE: 68

```
Met Glu Thr Asp Arg Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Asp Asp Ile Gln Met Thr Gln Ser Pro Ser Ser Leu Ser
        35                  40                  45

Ala Ser Val Gly Asp Arg Val Thr Ile Thr Cys Arg Ala Ser Gln Asp
    50                  55                  60

Val Ser Thr Ala Val Ala Trp Tyr Gln Gln Lys Pro Gly Lys Ala Pro
65                  70                  75                  80

Lys Leu Leu Ile Tyr Ser Ala Ser Phe Leu Tyr Ser Gly Val Pro Ser
                85                  90                  95

Arg Phe Ser Gly Ser Gly Ser Gly Thr Asp Phe Thr Leu Thr Ile Ser
            100                 105                 110

Ser Leu Gln Pro Glu Asp Phe Ala Thr Tyr Tyr Cys Gln Gln Tyr Leu
        115                 120                 125

Tyr His Pro Ala Thr Phe Gly Gln Gly Thr Lys Val Glu Ile Lys Arg
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Ala Ala Ser Gly Phe Thr Phe Ser Asp Ser Trp
            180                 185                 190

Ile His Trp Val Arg Gln Ala Pro Gly Lys Gly Leu Glu Trp Val Ala
        195                 200                 205
```

-continued

Trp Ile Ser Pro Tyr Gly Gly Ser Thr Tyr Tyr Ala Asp Ser Val Lys
    210                 215                 220

Gly Arg Phe Thr Ile Ser Ala Asp Thr Ser Lys Asn Thr Ala Tyr Leu
225                 230                 235                 240

Gln Met Asn Ser Leu Arg Ala Glu Asp Thr Ala Val Tyr Tyr Cys Ala
                245                 250                 255

Arg Arg His Trp Pro Gly Gly Phe Asp Tyr Trp Gly Gln Gly Thr Leu
            260                 265                 270

Val Thr Val Ser Ala Val Asp Glu Ala Lys Ser Cys Asp Lys Thr His
        275                 280                 285

Thr Cys Pro Pro Cys Pro Ala Pro Glu Leu Leu Gly Gly Pro Ser Val
    290                 295                 300

Phe Leu Phe Pro Pro Lys Pro Lys Asp Thr Leu Met Ile Ser Arg Thr
305                 310                 315                 320

Pro Glu Val Thr Cys Val Val Asp Val Ser His Glu Asp Pro Glu
                325                 330                 335

Val Lys Phe Asn Trp Tyr Val Asp Gly Val Glu Val His Asn Ala Lys
                340                 345                 350

Thr Lys Pro Arg Glu Glu Gln Tyr Asn Ser Thr Tyr Arg Val Val Ser
            355                 360                 365

Val Leu Thr Val Leu His Gln Asp Trp Leu Asn Gly Lys Glu Tyr Lys
        370                 375                 380

Cys Lys Val Ser Asn Lys Ala Leu Pro Ala Pro Ile Glu Lys Thr Ile
385                 390                 395                 400

Ser Lys Ala Lys Gly Gln Pro Arg Glu Pro Gln Val Tyr Thr Leu Pro
                405                 410                 415

Pro Ser Arg Asp Glu Leu Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys Val
            500                 505                 510

Asp Glu Gln Lys Leu Ile Ser Glu Glu Asp Leu Asn Arg Arg Lys Arg
        515                 520                 525

Glu Gly Arg Gly Ser Leu Leu Thr Cys Gly Asp Val Glu Glu Asn Pro
    530                 535                 540

Gly Pro Met Glu Thr Asp Arg Leu Leu Leu Trp Val Leu Leu Leu Trp
545                 550                 555                 560

Val Pro Gly Ser Thr Gly Asp Glu Glu Leu Gln Ile Ile Gln Pro
                565                 570                 575

Asp Lys Ser Val Leu Val Ala Ala Gly Glu Thr Ala Thr Leu Arg Cys
            580                 585                 590

Thr Ile Thr Ser Leu Phe Pro Val Gly Pro Ile Gln Trp Phe Arg Gly
        595                 600                 605

Ala Gly Pro Gly Arg Val Leu Ile Tyr Asn Gln Arg Gln Gly Pro Phe
    610                 615                 620

Pro Arg Val Thr Thr Val Ser Asp Thr Thr Lys Arg Asn Asn Met Asp

Phe Ser Ile Arg Ile Gly Asn Ile Thr Pro Ala Asp Ala Gly Thr Tyr
625                 630                 635                 640

Tyr Cys Ile Lys Phe Arg Lys Gly Ser Pro Asp Asp Val Glu Phe Lys
            645                 650                 655

Ser Gly Ala Gly Thr Glu Leu Ser Val Arg Ala Lys Pro Ser Ala Ser
660                 665                 670

Asp Ile Lys Leu Gln Gln Ser Gly Ala Glu Leu Ala Arg Pro Gly Ala
    675                 680                 685

Ser Val Lys Met Ser Cys Lys Thr Ser Gly Tyr Thr Phe Thr Arg Tyr
690                 695                 700

Thr Met His Trp Val Lys Gln Arg Pro Gly Gln Gly Leu Glu Trp Ile
705                 710                 715                 720

Gly Tyr Ile Asn Pro Ser Arg Gly Tyr Thr Asn Tyr Asn Gln Lys Phe
            725                 730                 735

Lys Asp Lys Ala Thr Leu Thr Thr Asp Lys Ser Ser Ser Thr Ala Tyr
            740                 745                 750

Met Gln Leu Ser Ser Leu Thr Ser Glu Asp Ser Ala Val Tyr Tyr Cys
    755                 760                 765

Ala Arg Tyr Tyr Asp Asp His Tyr Cys Leu Asp Tyr Trp Gly Gln Gly
770                 775                 780

Thr Thr Leu Thr Val Ser Ser Val Glu Gly Gly Ser Gly Gly Ser Gly
785                 790                 795                 800

Gly Ser Gly Gly Ser Gly Gly Val Asp Asp Ile Gln Leu Thr Gln Ser
            805                 810                 815

Pro Ala Ile Met Ser Ala Ser Pro Gly Glu Lys Val Thr Met Thr Cys
            820                 825                 830

Arg Ala Ser Ser Ser Val Ser Tyr Met Asn Trp Tyr Gln Gln Lys Ser
    835                 840                 845

Gly Thr Ser Pro Lys Arg Trp Ile Tyr Asp Thr Ser Lys Val Ala Ser
850                 855                 860

Gly Val Pro Tyr Arg Phe Ser Gly Ser Gly Ser Gly Thr Ser Tyr Ser
865                 870                 875                 880

Leu Thr Ile Ser Ser Met Glu Ala Glu Asp Ala Ala Thr Tyr Tyr Cys
            885                 890                 895

Gln Gln Trp Ser Ser Asn Pro Leu Thr Phe Gly Ala Gly Thr Lys Leu
            900                 905                 910

Glu Leu Lys His His His His His His
    915                 920                 925

<210> SEQ ID NO 69
<211> LENGTH: 2829
<212> TYPE: DNA
<213> ORGANISM: Artificial Sequence
<220> FEATURE:
<223> OTHER INFORMATION: Synthesized polynucleotide encoding SIRP1alpha-
      PDL1-CD3-Fc-LL bi-specific T-cell engager construct

<400> SEQUENCE: 69
atggaaaccg atacacttct gttgtgggtg ctgctgctgt gggtccctgg ttcaacaggc     60
gattatccct acgatgtgcc cgactacgca ggcgctcagc cagctgatga tatccagatg    120
acacagagcc catcatctct gtctgcaagc gtaggagacc gagtcaccat tacatgcaga    180
gcctcccaag acgtttccac agcagtggcc tggtatcaga aaaacctgg taaggcgccc    240 aagcttctca tctattcagc cagttttctg tatagcggcg ttcccagccg attctctggc    300

-continued

```
tctggatccg gcacggactt tactttgaca atttcctctc ttcagcccga agattttgca    360
acctactact gtcagcaata tctctaccat ccagccacat tcggacaggg caccaaagtc    420
gaaatcaaaa gaggcggcgg cggcagtggc ggcgggggtt caggaggcgg gggttctgaa    480
gtgcaactcg ttgaaagcgt aggagggctt gtccaacctg gcgggtcact gcggttgagc    540
tgcgccgcaa gcggattcac cttctcagac tcttggatcc attgggtgcg ccaggctccc    600
ggaaaaggct tggaatgggt tgcttggatt tcaccgtatg gcggttccac atactacgct    660
gacagcgtta aggtcgatt caccatctct gcagatactt caaaaaacac agcctacctt    720
cagatgaata gtttgcgcgc cgaggacaca gcggtttatt attgtgccct aagacattgg    780
cccggcggtt tcgactactg ggggcaaggt acgttggtga ctgtgagcgc cgtagatgaa    840
gcaaaatctt gtgacaaaac ccatacctgc ccaccatgcc cagccccaga acttcttggc    900
gtaccctctg tcttcctttt ccctccgaag cccaaggata ccctgatgat cagccgaacc    960
ccggaggtaa catgtgtggt ggtcgatgtt agccatgagg atcctgaagt caaatttaac   1020
tggtatgtag acggtgttga ggtgcacaac gctaaaacta gcccaggga ggagcagtac   1080
aactcaacct atcgcgtcgt atctgtgctt accgtcctgc atcaagactg gctcaatggt   1140
aaggaatata atgtaaagt gagtaacaag gcactgccag cacctatcga aaaaaccatc   1200
tcaaaggcga agggacagcc cagggaaccc caggtctata ctctgcaacc ttctcgggat   1260
gaattgacca agaaccaagt tagcctgaca tgtctggtga aaggtttcta tccaagcgat   1320
atagctgtcg agtgggagtc caatggccaa cctgagaaca attataagac cacccccaccc  1380
gttctggaca gcgacggatc cttttttcctg tactcaaaac tcactgtcga taaatcaaga   1440
tggcaacaag gcaacgtttt tagctgtagc gtgatgcacg aagcacttca taatcactat   1500
acacagaagt cactctctct ttctccagga aaggttgacg aacagaaatt gatatccgag   1560
gaagatctca ataggaggaa gagagaaggc aggggggagcc ttctcacttg cggcgatgtc   1620
gaggaaaatc cggggcctat ggagaccgat accctgctct tgtgggtttt gcttctttgg   1680
gtgccaggat ctacaggtga tgaagaagaa ttgcagatca tccaaccaga caaatccgta   1740
ctcgtggccg caggagagac cgctacccctc agatgtacca tcacttctct cttccccgtt   1800
ggccccatcc agtggtttcg aggcgcagga ccaggacgag tgcttattta caatcaacga   1860
cagggcccat tcccaagagt gacaacagta tccgatacca ccaagcgcaa taatatggac   1920
tttagcatta gaatcggcaa cataacaccc gctgacgccg gtacatacta ttgtattaaa   1980
tttcgaaagg gctcaccaga cgacgtgaa tttaagtcag gggccggaac cgaactctca   2040
gttagagcaa aaccttctgc tagcggcggc ggcggcagcg acatcaagct gcagcagagc   2100
ggcgccgagc tggccaggcc cggcgccagc gtgaagatga gctgcaagac cagcggctac   2160
accttcacca ggtacaccat gcactgggtg aagcagaggc ccggccaggg cctggagtgg   2220
atcggctaca tcaaccccag caggggctac accaactaca accagaagtt caaggacaag   2280
gccacccctga ccaccgacaa gagcagcagc accgcctaca tgcagctgag cagcctgacc   2340
agcgaggaca cgccgtgta ctactgcgcc aggtactacg acgaccacta ctgcctggac   2400
tactggggcc agggcaccac cctgaccgtg agcagcgtgg agggcggcag cggcggcagc   2460
ggcggcagcg gcggcagcgg cggcgtggac gacatccagc tgacccagag ccccgccatc   2520
atgagcgcca gccccggcga aaaggtgacc atgacctgca gggccagcag cagcgtgagc   2580
tacatgaact ggtaccagca gaagagcggc accagcccca gaggtggat ctacgacacc   2640
```

-continued

```
agcaaggtgg ccagcggcgt gccctacagg ttcagcggca gcggcagcgg caccagctac    2700
agcctgacca tcagcagcat ggaggccgag gacgccgcca cctactactg ccagcagtgg    2760
agcagcaacc ccctgacctt cggcgccggc accaagctgg agctgaagca ccaccaccac    2820
caccactag                                                            2829
```

<210> SEQ ID NO 70
<211> LENGTH: 942
<212> TYPE: PRT
<213> ORGANISM: Artificial Sequence
<220> FEATURE:
<223> OTHER INFORMATION: Synthesized SIRP1alpha-PDL1-CD3-Fc-LL
      bi-specific T-cell engager construct

<400> SEQUENCE: 70

```
Met Glu Thr Asp Arg Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Asp Asp Ile Gln Met Thr Gln Ser Pro Ser Ser Leu Ser
        35                  40                  45

Ala Ser Val Gly Asp Arg Val Thr Ile Thr Cys Arg Ala Ser Gln Asp
    50                  55                  60

Val Ser Thr Ala Val Ala Trp Tyr Gln Gln Lys Pro Gly Lys Ala Pro
65                  70                  75                  80

Lys Leu Leu Ile Tyr Ser Ala Ser Phe Leu Tyr Ser Gly Val Pro Ser
                85                  90                  95

Arg Phe Ser Gly Ser Gly Ser Gly Thr Asp Phe Thr Leu Thr Ile Ser
            100                 105                 110

Ser Leu Gln Pro Glu Asp Phe Ala Thr Tyr Tyr Cys Gln Gln Tyr Leu
        115                 120                 125

Tyr His Pro Ala Thr Phe Gly Gln Gly Thr Lys Val Glu Ile Lys Arg
    130                 135                 140

Gly Gly Gly Gly Ser Gly Gly Gly Ser Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Ala Ala Ser Gly Phe Thr Phe Ser Asp Ser Trp
            180                 185                 190

Ile His Trp Val Arg Gln Ala Pro Gly Lys Gly Leu Glu Trp Val Ala
        195                 200                 205

Trp Ile Ser Pro Tyr Gly Gly Ser Thr Tyr Tyr Ala Asp Ser Val Lys
    210                 215                 220

Gly Arg Phe Thr Ile Ser Ala Asp Thr Ser Lys Asn Thr Ala Tyr Leu
225                 230                 235                 240

Gln Met Asn Ser Leu Arg Ala Glu Asp Thr Ala Val Tyr Tyr Cys Ala
                245                 250                 255

Arg Arg His Trp Pro Gly Gly Phe Asp Tyr Trp Gly Gln Gly Thr Leu
            260                 265                 270

Val Thr Val Ser Ala Val Asp Glu Ala Lys Ser Cys Asp Lys Thr His
        275                 280                 285

Thr Cys Pro Pro Cys Pro Ala Pro Glu Leu Leu Gly Gly Pro Ser Val
    290                 295                 300

Phe Leu Phe Pro Pro Lys Pro Lys Asp Thr Leu Met Ile Ser Arg Thr
305                 310                 315                 320
```

```
Pro Glu Val Thr Cys Val Val Asp Val Ser His Glu Asp Pro Glu
            325                 330                 335

Val Lys Phe Asn Trp Tyr Val Asp Gly Val Glu Val His Asn Ala Lys
            340                 345                 350

Thr Lys Pro Arg Glu Glu Gln Tyr Asn Ser Thr Tyr Arg Val Val Ser
            355                 360                 365

Val Leu Thr Val Leu His Gln Asp Trp Leu Asn Gly Lys Glu Tyr Lys
            370                 375                 380

Cys Lys Val Ser Asn Lys Ala Leu Pro Ala Pro Ile Glu Lys Thr Ile
385                 390                 395                 400

Ser Lys Ala Lys Gly Gln Pro Arg Glu Pro Gln Val Tyr Thr Leu Pro
            405                 410                 415

Pro Ser Arg Asp Glu Leu Thr Lys Asn Gln Val Ser Leu Thr Cys Leu
            420                 425                 430

Val Lys Gly Phe Tyr Pro Ser Asp Ile Ala Val Glu Trp Glu Ser Asn
            435                 440                 445

Gly Gln Pro Glu Asn Asn Tyr Lys Thr Thr Pro Pro Val Leu Asp Ser
            450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
            485                 490                 495

His Asn His Tyr Thr Gln Lys Ser Leu Ser Leu Ser Pro Gly Lys Val
            500                 505                 510

Asp Glu Gln Lys Leu Ile Ser Glu Glu Asp Leu Asn Arg Arg Lys Arg
            515                 520                 525

Glu Gly Arg Gly Ser Leu Leu Thr Cys Gly Asp Val Glu Glu Asn Pro
            530                 535                 540

Gly Pro Met Glu Thr Asp Arg Leu Leu Leu Trp Val Leu Leu Leu Trp
545                 550                 555                 560

Val Pro Gly Ser Thr Gly Asp Glu Glu Leu Gln Ile Ile Gln Pro
            565                 570                 575

Asp Lys Ser Val Leu Val Ala Ala Gly Glu Thr Ala Thr Leu Arg Cys
            580                 585                 590

Thr Ile Thr Ser Leu Phe Pro Val Gly Pro Ile Gln Trp Phe Arg Gly
            595                 600                 605

Ala Gly Pro Gly Arg Val Leu Ile Tyr Asn Gln Arg Gln Gly Pro Phe
            610                 615                 620

Pro Arg Val Thr Thr Val Ser Asp Thr Thr Lys Arg Asn Asn Met Asp
625                 630                 635                 640

Phe Ser Ile Arg Ile Gly Asn Ile Thr Pro Ala Asp Ala Gly Thr Tyr
            645                 650                 655

Tyr Cys Ile Lys Phe Arg Lys Gly Ser Pro Asp Asp Val Glu Phe Lys
            660                 665                 670

Ser Gly Ala Gly Thr Glu Leu Ser Val Arg Ala Lys Pro Ser Ala Ser
            675                 680                 685

Gly Gly Gly Gly Ser Asp Ile Lys Leu Gln Gln Ser Gly Ala Glu Leu
            690                 695                 700

Ala Arg Pro Gly Ala Ser Val Lys Met Ser Cys Lys Thr Ser Gly Tyr
705                 710                 715                 720

Thr Phe Thr Arg Tyr Thr Met His Trp Val Lys Gln Arg Pro Gly Gln
            725                 730                 735

Gly Leu Glu Trp Ile Gly Tyr Ile Asn Pro Ser Arg Gly Tyr Thr Asn
```

```
                    740                 745                 750
Tyr Asn Gln Lys Phe Lys Asp Lys Ala Thr Leu Thr Thr Asp Lys Ser
                755                 760                 765

Ser Ser Thr Ala Tyr Met Gln Leu Ser Ser Leu Thr Ser Glu Asp Ser
            770                 775                 780

Ala Val Tyr Tyr Cys Ala Arg Tyr Tyr Asp Asp His Tyr Cys Leu Asp
785                 790                 795                 800

Tyr Trp Gly Gln Gly Thr Thr Leu Thr Val Ser Ser Val Glu Gly Gly
                805                 810                 815

Ser Gly Gly Ser Gly Gly Ser Gly Gly Ser Gly Gly Val Asp Asp Ile
            820                 825                 830

Gln Leu Thr Gln Ser Pro Ala Ile Met Ser Ala Ser Pro Gly Glu Lys
                835                 840                 845

Val Thr Met Thr Cys Arg Ala Ser Ser Ser Val Ser Tyr Met Asn Trp
            850                 855                 860

Tyr Gln Gln Lys Ser Gly Thr Ser Pro Lys Arg Trp Ile Tyr Asp Thr
865                 870                 875                 880

Ser Lys Val Ala Ser Gly Val Pro Tyr Arg Phe Ser Gly Ser Gly Ser
                885                 890                 895

Gly Thr Ser Tyr Ser Leu Thr Ile Ser Ser Met Glu Ala Glu Asp Ala
            900                 905                 910

Ala Thr Tyr Tyr Cys Gln Gln Trp Ser Ser Asn Pro Leu Thr Phe Gly
                915                 920                 925

Ala Gly Thr Lys Leu Glu Leu Lys His His His His His His
            930                 935                 940

<210> SEQ ID NO 71
<211> LENGTH: 107
<212> TYPE: PRT
<213> ORGANISM: Artificial Sequence
<220> FEATURE:
<223> OTHER INFORMATION: anti-FAP light chain sequence

<400> SEQUENCE: 71

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Gly Val Asn Phe Met
            20                  25                  30

His Trp Tyr Gln Gln Lys Ser Gly Thr Ser Pro Lys Arg Trp Ile Phe
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Arg
            100                 105

<210> SEQ ID NO 72
<211> LENGTH: 117
<212> TYPE: PRT
<213> ORGANISM: Artificial Sequence
<220> FEATURE:
<223> OTHER INFORMATION: anti-FAP heavy chain sequence

<400> SEQUENCE: 72
```

```
Gln Val Gln Leu Gln Gln Ser Gly Ala Glu Leu Ala Arg Pro Gly Ala
1               5                   10                  15

Ser Val Asn Leu Ser Cys Lys Ala Ser Gly Tyr Thr Phe Thr Asn Asn
            20                  25                  30

Gly Ile Asn Trp Leu Lys Gln Arg Thr Gly Gln Gly Leu Glu Trp Ile
        35                  40                  45

Gly Glu Ile Tyr Pro Arg Ser Thr Asn Thr Leu Tyr Asn Glu Lys Phe
    50                  55                  60

Lys Gly Lys Ala Thr Leu Thr Ala Asp Arg Ser Ser Asn Thr Ala Tyr
65                  70                  75                  80

Met Glu Leu Arg Ser Leu Thr Ser Glu Asp Ser Ala Val Tyr Phe Cys
                85                  90                  95

Ala Arg Thr Leu Thr Ala Pro Phe Ala Phe Trp Gly Gln Gly Thr Leu
            100                 105                 110

Val Thr Val Ser Ala
            115

<210> SEQ ID NO 73
<211> LENGTH: 242
<212> TYPE: PRT
<213> ORGANISM: Artificial Sequence
<220> FEATURE:
<223> OTHER INFORMATION: anti-FAP scFv sequence

<400> SEQUENCE: 73

Gln Val Gln Leu Gln Gln Ser Gly Ala Glu Leu Ala Arg Pro Gly Ala
1               5                   10                  15

Ser Val Asn Leu Ser Cys Lys Ala Ser Gly Tyr Thr Phe Thr Asn Asn
            20                  25                  30

Gly Ile Asn Trp Leu Lys Gln Arg Thr Gly Gln Gly Leu Glu Trp Ile
        35                  40                  45

Gly Glu Ile Tyr Pro Arg Ser Thr Asn Thr Leu Tyr Asn Glu Lys Phe
    50                  55                  60

Lys Gly Lys Ala Thr Leu Thr Ala Asp Arg Ser Ser Asn Thr Ala Tyr
65                  70                  75                  80

Met Glu Leu Arg Ser Leu Thr Ser Glu Asp Ser Ala Val Tyr Phe Cys
                85                  90                  95

Ala Arg Thr Leu Thr Ala Pro Phe Ala Phe Trp Gly Gln Gly Thr Leu
            100                 105                 110

Val Thr Val Ser Ala Gly Ser Thr Gly Ser Gly Lys Pro Gly Ser
            115                 120                 125

Gly Glu Gly Ser Thr Lys Gly Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Gly Val Asn Phe Met His Trp Tyr Gln Gln Lys Ser Gly Thr
            165                 170                 175

Ser Pro Lys Arg Trp Ile Phe Asp Thr Ser Lys Leu Ala Ser Gly Val
            180                 185                 190

Pro Ala Arg Phe Ser Gly Ser Gly Ser Gly Thr Ser Tyr Ser Leu Thr
            195                 200                 205

Ile Ser Ser Met Glu Ala Glu Asp Ala Ala Thr Tyr Tyr Cys Gln Gln
        210                 215                 220

Trp Ser Phe Asn Pro Pro Thr Phe Gly Gly Gly Thr Lys Leu Glu Ile
225                 230                 235                 240
```

Lys Arg

<210> SEQ ID NO 74
<211> LENGTH: 1545
<212> TYPE: DNA
<213> ORGANISM: Artificial Sequence
<220> FEATURE:
<223> OTHER INFORMATION: Synthetic polynucleotide sequence encoding anti-FAP - anti-CD3 BiTE sequence

<400> SEQUENCE: 74

```
atggttttgc ttgtgaccag cctcctgctc tgtgaactgc ctcatcctgc attcctgttg      60
atcccacagg tgcagctcca gcagagtggc gcagagctcg ctcgcccagg cgcttctgtg     120
aatctgagtt gtaaggcctc cggatatact tttacgaaca acggcatcaa ctggctgaag     180
cagcggaccg gccagggcct ggagtggatc ggcgaaatat accccccgtc cacaaacact     240
ctctataacg agaagtttaa gggcaaagca actctgaccg cggacaggtc tctaacaca      300
gcctatatgg agctgagaag cttgacgagt gaggactccg ctgtctattt tgcgcccga     360
actctgaccg ctccttttgc tttttggggc cagggcacgc tcgtgaccgt aagtgcgggc     420
tccactagcg gttccggcaa acctggcagc ggagaaggca gcaccaaagg cagatcgtc      480
ctgacgcagt ctccagccat catgagcgcc tcacccggcg aaaaggtgac catgacctgc     540
tcagcctctt ctggtgtgaa tttcatgcac tggtaccagc aaaaaagtgg acctcccct      600
aaaaggtgga tcttcgatac cagcaaactg gcttctggcg ttcccgcaag gtttagcggc     660
tctggttccg gcacatcata cagcctgacg atcagcagca tggaggcaga agacgcagct     720
acctattact gccagcaatg gagctttaac ccacctactt tcggaggagg aacaaagctg     780
gaaataaaaa gaggtggtgg tggatcgag gtgcagctgg tggagtctgg gggaggcttg     840
gtgcagcctg gaaagtccct gaaactctcc tgtgaggcct ctggattcac cttcagcggc     900
tatggcatgc actgggtccg ccaggctcca gggaggggc tggagtcggt cgcatacatt     960
actagtagta gtattaatat caaatatgct gacgctgtga aggccggtt caccgtctcc    1020
agagacaatg ccaagaactt actgtttcta caaatgaaca ttctcaagtc tgaggacaca    1080
gccatgtact actgtgcaag attcgactgg gacaaaaatt actggggcca aggaaccatg    1140
gtcaccgtct cctcaggtgg tgtggatca ggtggaggcg aagtggagg tggcggatcc    1200
gacatccaga tgacccagtc tccatcatca ctgcctgcct ccctgggaga cagagtcact    1260
atcaattgtc aggccagtca ggacattagc aattatttaa actggtacca gcagaaacca    1320
gggaaagctc ctaagctcct gatctattat acaaataat tggcagatgg agtcccatca    1380
aggttcagtg gcagtggttc tgggagagat tcttctttca ctatcagcag cctggaatcc    1440
gaagatattg gatcttatta ctgtcaacag tattataact atccgtggac gttcggacct    1500
ggcaccaagc tggaaatcaa acggcaccac catcatcacc actga                    1545
```

<210> SEQ ID NO 75
<211> LENGTH: 512
<212> TYPE: PRT
<213> ORGANISM: Artificial Sequence
<220> FEATURE:
<223> OTHER INFORMATION: anti-FAP - anti-Cd3 BiTE sequence

<400> SEQUENCE: 75

```
Met Tyr Arg Met Gln Leu Leu Ser Cys Ile Ala Leu Ser Leu Ala Leu
 1               5                  10                  15

Val Thr Asn Ser Gln Val Gln Leu Gln Gln Ser Gly Ala Glu Leu Ala
```

```
                  20                  25                  30
Arg Pro Gly Ala Ser Val Asn Leu Ser Cys Lys Ala Ser Gly Tyr Thr
                35                  40                  45
Phe Thr Asn Asn Gly Ile Asn Trp Leu Lys Gln Arg Thr Gly Gln Gly
            50                  55                  60
Leu Glu Trp Ile Gly Glu Ile Tyr Pro Arg Ser Thr Asn Thr Leu Tyr
65                  70                  75                  80
Asn Glu Lys Phe Lys Gly Lys Ala Thr Leu Thr Ala Asp Arg Ser Ser
                85                  90                  95
Asn Thr Ala Tyr Met Glu Leu Arg Ser Leu Thr Ser Glu Asp Ser Ala
                100                 105                 110
Val Tyr Phe Cys Ala Arg Thr Leu Thr Ala Pro Phe Ala Phe Trp Gly
                115                 120                 125
Gln Gly Thr Leu Val Thr Val Ser Ala Gly Ser Thr Ser Gly Ser Gly
                130                 135                 140
Lys Pro Gly Ser Gly Glu Gly Ser Thr Lys Gly Gln Ile Val Leu Thr
145                 150                 155                 160
Gln Ser Pro Ala Ile Met Ser Ala Ser Pro Gly Glu Lys Val Thr Met
                165                 170                 175
Thr Cys Ser Ala Ser Ser Gly Val Asn Phe Met His Trp Tyr Gln Gln
                180                 185                 190
Lys Ser Gly Thr Ser Pro Lys Arg Trp Ile Phe Asp Thr Ser Lys Leu
                195                 200                 205
Ala Ser Gly Val Pro Ala Arg Phe Ser Gly Ser Gly Ser Gly Thr Ser
                210                 215                 220
Tyr Ser Leu Thr Ile Ser Ser Met Glu Ala Glu Asp Ala Ala Thr Tyr
225                 230                 235                 240
Tyr Cys Gln Gln Trp Ser Phe Asn Pro Pro Thr Phe Gly Gly Gly Thr
                245                 250                 255
Lys Leu Glu Ile Lys Arg Gly Gly Gly Ser Glu Val Gln Leu Val
                260                 265                 270
Glu Ser Gly Gly Gly Leu Val Gln Pro Gly Lys Ser Leu Lys Leu Ser
                275                 280                 285
Cys Glu Ala Ser Gly Phe Thr Phe Ser Gly Tyr Gly Met His Trp Val
                290                 295                 300
Arg Gln Ala Pro Gly Arg Gly Leu Glu Ser Val Ala Tyr Ile Thr Ser
305                 310                 315                 320
Ser Ser Ile Asn Ile Lys Tyr Ala Asp Ala Val Lys Gly Arg Phe Thr
                325                 330                 335
Val Ser Arg Asp Asn Ala Lys Asn Leu Leu Phe Leu Gln Met Asn Ile
                340                 345                 350
Leu Lys Ser Glu Asp Thr Ala Met Tyr Tyr Cys Ala Arg Phe Asp Trp
                355                 360                 365
Asp Lys Asn Tyr Trp Gly Gln Gly Thr Met Val Thr Val Ser Ser Gly
                370                 375                 380
Gly Gly Gly Ser Gly Gly Gly Gly Ser Gly Gly Gly Gly Ser Asp Ile
385                 390                 395                 400
Gln Met Thr Gln Ser Pro Ser Ser Leu Pro Ala Ser Leu Gly Asp Arg
                405                 410                 415
Val Thr Ile Asn Cys Gln Ala Ser Gln Asp Ile Ser Asn Tyr Leu Asn
                420                 425                 430
Trp Tyr Gln Gln Lys Pro Gly Lys Ala Pro Lys Leu Leu Ile Tyr Tyr
                435                 440                 445
```

```
Thr Asn Lys Leu Ala Asp Gly Val Pro Ser Arg Phe Ser Gly Ser Gly
    450                 455                 460
Ser Gly Arg Asp Ser Ser Phe Thr Ile Ser Ser Leu Glu Ser Glu Asp
465                 470                 475                 480
Ile Gly Ser Tyr Tyr Cys Gln Gln Tyr Tyr Asn Tyr Pro Trp Thr Phe
                485                 490                 495
Gly Pro Gly Thr Lys Leu Glu Ile Lys Arg His His His His His His
            500                 505                 510
```

<210> SEQ ID NO 76
<211> LENGTH: 116
<212> TYPE: PRT
<213> ORGANISM: Artificial Sequence
<220> FEATURE:
<223> OTHER INFORMATION: anti-mouse CD3 heavy chain sequence

<400> SEQUENCE: 76

```
Glu Val Gln Leu Val Glu Ser Gly Gly Leu Val Gln Pro Gly Lys
1               5                   10                  15
Ser Leu Lys Leu Ser Cys Glu Ala Ser Gly Phe Thr Phe Ser Gly Tyr
                20                  25                  30
Gly Met His Trp Val Arg Gln Ala Pro Gly Arg Gly Leu Glu Ser Val
            35                  40                  45
Ala Tyr Ile Thr Ser Ser Ser Ile Asn Ile Lys Tyr Ala Asp Ala Val
    50                  55                  60
Lys Gly Arg Phe Thr Val Ser Arg Asp Asn Ala Lys Asn Leu Leu Phe
65                  70                  75                  80
Leu Gln Met Asn Ile Leu Lys Ser Glu Asp Thr Ala Met Tyr Tyr Cys
                85                  90                  95
Ala Arg Phe Asp Trp Asp Lys Asn Tyr Trp Gly Gln Gly Thr Met Val
            100                 105                 110
Thr Val Ser Ser
        115
```

<210> SEQ ID NO 77
<211> LENGTH: 108
<212> TYPE: PRT
<213> ORGANISM: Artificial Sequence
<220> FEATURE:
<223> OTHER INFORMATION: anti-mouse CD3 light chain

<400> SEQUENCE: 77

```
Asp Ile Gln Met Thr Gln Ser Pro Ser Ser Leu Pro Ala Ser Leu Gly
1               5                   10                  15
Asp Arg Val Thr Ile Asn Cys Gln Ala Ser Gln Asp Ile Ser Asn Tyr
                20                  25                  30
Leu Asn Trp Tyr Gln Gln Lys Pro Gly Lys Ala Pro Lys Leu Leu Ile
            35                  40                  45
Tyr Tyr Thr Asn Lys Leu Ala Asp Gly Val Pro Ser Arg Phe Ser Gly
    50                  55                  60
Ser Gly Ser Gly Arg Asp Ser Ser Phe Thr Ile Ser Ser Leu Glu Ser
65                  70                  75                  80
Glu Asp Ile Gly Ser Tyr Tyr Cys Gln Gln Tyr Tyr Asn Tyr Pro Trp
                85                  90                  95
Thr Phe Gly Pro Gly Thr Lys Leu Glu Ile Lys Arg
            100                 105
```

<210> SEQ ID NO 78
<211> LENGTH: 239
<212> TYPE: PRT
<213> ORGANISM: Artificial Sequence
<220> FEATURE:
<223> OTHER INFORMATION: anti-mouse CD3 scFv

<400> SEQUENCE: 78

```
Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser Gly Gly Gly Ser Gly Gly Gly Ser Gly Gly
        115                 120                 125

Gly Gly Ser Asp Ile Gln Met Thr Gln Ser Pro Ser Ser Leu Pro Ala
    130                 135                 140

Ser Leu Gly Asp Arg Val Thr Ile Asn Cys Gln Ala Ser Gln Asp Ile
145                 150                 155                 160

Ser Asn Tyr Leu Asn Trp Tyr Gln Gln Lys Pro Gly Lys Ala Pro Lys
                165                 170                 175

Leu Leu Ile Tyr Tyr Thr Asn Lys Leu Ala Asp Gly Val Pro Ser Arg
            180                 185                 190

Phe Ser Gly Ser Gly Ser Gly Arg Asp Ser Ser Phe Thr Ile Ser Ser
        195                 200                 205

Leu Glu Ser Glu Asp Ile Gly Ser Tyr Tyr Cys Gln Gln Tyr Tyr Asn
    210                 215                 220

Tyr Pro Trp Thr Phe Gly Pro Gly Thr Lys Leu Glu Ile Lys Arg
225                 230                 235
```

<210> SEQ ID NO 79
<211> LENGTH: 18
<212> TYPE: PRT
<213> ORGANISM: Artificial Sequence
<220> FEATURE:
<223> OTHER INFORMATION: Synthetic linker sequence

<400> SEQUENCE: 79

```
Gly Ser Thr Ser Gly Ser Gly Lys Pro Gly Ser Gly Glu Gly Ser Thr
1               5                   10                  15

Lys Gly
```

<210> SEQ ID NO 80
<211> LENGTH: 92
<212> TYPE: PRT
<213> ORGANISM: Artificial Sequence
<220> FEATURE:
<223> OTHER INFORMATION: CCL4 sequence

<400> SEQUENCE: 80

-continued

```
Met Lys Leu Cys Val Thr Val Leu Ser Leu Leu Met Leu Val Ala Ala
1               5               10              15

Phe Cys Ser Pro Ala Leu Ser Ala Pro Met Gly Ser Asp Pro Pro Thr
            20              25              30

Ala Cys Cys Phe Ser Tyr Thr Ala Arg Lys Leu Pro Arg Asn Phe Val
        35              40              45

Val Asp Tyr Tyr Glu Thr Ser Ser Leu Cys Ser Gln Pro Ala Val Val
    50              55              60

Phe Gln Thr Lys Arg Ser Lys Gln Val Cys Ala Asp Pro Ser Glu Ser
65              70              75              80

Trp Val Gln Glu Tyr Val Tyr Asp Leu Glu Leu Asn
                85              90
```